US011732257B2

(12) United States Patent
van Galen et al.

(10) Patent No.: US 11,732,257 B2
(45) Date of Patent: Aug. 22, 2023

(54) SINGLE CELL SEQUENCING LIBRARIES OF GENOMIC TRANSCRIPT REGIONS OF INTEREST IN PROXIMITY TO BARCODES, AND GENOTYPING OF SAID LIBRARIES

(71) Applicants: Massachusetts Institute of Technology, Cambridge, MA (US); The General Hospital Corporation, Boston, MA (US)

(72) Inventors: Peter van Galen, Boston, MA (US); Volker Hovestadt, Boston, MA (US); Travis Hughes, Cambridge, MA (US); Marc H. Wadsworth, II, Cambridge, MA (US); Bradley Bernstein, Boston, MA (US); Alexander K. Shalek, Cambridge, MA (US); Todd M. Gierahn, Cambridge, MA (US); J. Christopher Love, Cambridge, MA (US); Ang A. Tu, Cambridge, MA (US)

(73) Assignees: Massachusetts Institute of Technology, Cambridge, MA (US); The General Hospital Corporation, Boston, MA (US)

( * ) Notice: Subject to any disclaimer, the term of this patent is extended or adjusted under 35 U.S.C. 154(b) by 532 days.

(21) Appl. No.: 16/758,485

(22) PCT Filed: Oct. 23, 2018

(86) PCT No.: PCT/US2018/057170
§ 371 (c)(1),
(2) Date: Apr. 23, 2020

(87) PCT Pub. No.: WO2019/084055
PCT Pub. Date: May 2, 2019

(65) Prior Publication Data
US 2020/0248175 A1  Aug. 6, 2020

Related U.S. Application Data

(60) Provisional application No. 62/575,667, filed on Oct. 23, 2017.

(51) Int. Cl.
C12P 19/34 (2006.01)
C12N 15/10 (2006.01)
(Continued)

(52) U.S. Cl.
CPC ......... *C12N 15/1065* (2013.01); *C12Q 1/686* (2013.01); *C12Q 1/6886* (2013.01); *C12Q 1/6888* (2013.01); *C12Q 2600/158* (2013.01)

(58) Field of Classification Search
CPC .................................................. C12Q 1/6869
See application file for complete search history.

(56) References Cited

U.S. PATENT DOCUMENTS 5,168,038 A   12/1992  Tecott et al.
5,210,015 A   5/1993   Gelfand et al.
(Continued)

FOREIGN PATENT DOCUMENTS

EP   0 927 258 B1   4/2003
EP   2 047 910 B1   1/2012
(Continued)

OTHER PUBLICATIONS

Gierahn et al., Nature Methods 14(4), 395-398 (Feb. 2017). (Year: 2017).*
(Continued)

*Primary Examiner* — Kenneth R Horlick
(74) *Attorney, Agent, or Firm* — F. Brent Nix, Esq.; Johnson, Marcou, Isaacs & Nix, LLC; Michael B. Scher, Esq.

(57) ABSTRACT

The present invention relates to methods of detecting region(s) of interest in a gene comprising a polyA tail. The (Continued)

region(s) of interest can include gene(s), region(s), mutation(s), deletion(s), insertion(s), indel(s), and/or translocation(s). The region(s) can be greater than or less than 1 kilobases from the polyA tail. Methods can include forming a library of single cell transcripts comprising the region(s) in close proximity to a cell barcode and a unique molecular identifier (UMI). Methods for distinguishing cells by genotype can include amplifying the transcripts using PCR methods and detecting the cell barcode and UMI using single cell sequencing methods. Transcripts can be enriched using tagged region-specific PCR primers. Cell barcodes can be brought into close proximity to the region(s) by circularizing the transcripts. Sequencing of the transcripts can include using primer binding sites added during PCR amplification and library indexes for multiplexed sequencing.

21 Claims, 59 Drawing Sheets

Specification includes a Sequence Listing.

(51) Int. Cl.
    *C12Q 1/686* (2018.01)
    *C12Q 1/6886* (2018.01)
    *C12Q 1/6888* (2018.01)

(56) References Cited

U.S. PATENT DOCUMENTS

| | | |
|---|---|---|
| 5,686,281 A | 11/1997 | Roberts |
| 5,843,728 A | 12/1998 | Seed et al. |
| 5,851,828 A | 12/1998 | Seed et al. |
| 5,906,936 A | 5/1999 | Eshhar et al. |
| 5,912,170 A | 6/1999 | Seed et al. |
| 5,912,172 A | 6/1999 | Eshhar et al. |
| 5,925,517 A | 7/1999 | Tyagi et al. |
| 5,965,443 A | 10/1999 | Reznikoff et al. |
| 6,004,811 A | 12/1999 | Seed et al. |
| 6,040,177 A | 3/2000 | Riddell et al. |
| 6,174,670 B1 | 1/2001 | Wittwer et al. |
| 6,284,240 B1 | 9/2001 | Seed et al. |
| 6,392,013 B1 | 5/2002 | Seed et al. |
| 6,410,014 B1 | 6/2002 | Seed et al. |
| 6,437,109 B1 | 8/2002 | Reznikoff et al. |
| 6,489,458 B2 | 12/2002 | Hackett et al. |
| 6,569,627 B2 | 5/2003 | Wittwer et al. |
| 6,753,162 B1 | 6/2004 | Seed et al. |
| 7,041,481 B2 | 5/2006 | Anderson et al. |
| 7,148,203 B2 | 12/2006 | Hackett et al. |
| 7,160,682 B2 | 1/2007 | Hackett et al. |
| 7,446,190 B2 | 11/2008 | Sadelain et al. |
| 7,708,949 B2 | 5/2010 | Stone et al. |
| 7,741,465 B1 | 6/2010 | Eshhar et al. |
| RE41,780 E | 9/2010 | Brian et al. |
| 7,985,739 B2 | 7/2011 | Kay et al. |
| 8,034,334 B2 | 10/2011 | Dudley et al. |
| 8,088,379 B2 | 1/2012 | Robbins et al. |
| 8,211,422 B2 | 7/2012 | Eshhar et al. |
| 8,227,432 B2 | 7/2012 | Hackett et al. |
| 8,399,645 B2 | 3/2013 | Campana et al. |
| 8,637,307 B2 | 1/2014 | June et al. |
| 8,697,854 B2 | 4/2014 | Schendel et al. |
| 8,906,682 B2 | 12/2014 | June et al. |
| 8,911,993 B2 | 12/2014 | June et al. |
| 8,916,381 B1 | 12/2014 | June et al. |
| 8,975,071 B1 | 3/2015 | June et al. |
| 9,101,584 B2 | 8/2015 | June et al. |
| 9,102,760 B2 | 8/2015 | June et al. |
| 9,102,761 B2 | 8/2015 | June et al. |
| 9,181,527 B2 | 11/2015 | Sentman |
| 9,233,125 B2 | 1/2016 | Davila et al. |
| 11,060,130 B2 | 7/2021 | Rasolonjatovo et al. |
| 2004/0224402 A1 | 11/2004 | Bonyhadi et al. |
| 2005/0172476 A1 | 8/2005 | Stone et al. |
| 2007/0195127 A1 | 8/2007 | Ahn et al. |
| 2007/0269870 A1 | 11/2007 | Church et al. |
| 2008/0003142 A1 | 1/2008 | Link et al. |
| 2008/0014589 A1 | 1/2008 | Link et al. |
| 2010/0002241 A1 | 1/2010 | Hirose |
| 2010/0137163 A1 | 6/2010 | Link et al. |
| 2010/0172803 A1 | 7/2010 | Stone et al. |
| 2012/0219947 A1 | 8/2012 | Yurkovetsky et al. |
| 2012/0244133 A1 | 9/2012 | Rosenberg et al. |
| 2013/0071414 A1 | 3/2013 | Dotti et al. |
| 2015/0368342 A1 | 12/2015 | Wu et al. |
| 2015/0368360 A1 | 12/2015 | Liang et al. |
| 2015/0368719 A1 | 12/2015 | Regev et al. |
| 2016/0017320 A1 | 1/2016 | Wang et al. |
| 2016/0060687 A1 | 3/2016 | Zhu et al. |
| 2016/0060691 A1 | 3/2016 | Giresi et al. |
| 2016/0129109 A1 | 5/2016 | Davila et al. |
| 2016/0146821 A1 | 5/2016 | Vyas et al. |
| 2016/0166613 A1 | 6/2016 | Spencer et al. |
| 2016/0175359 A1 | 6/2016 | Spencer et al. |
| 2016/0208323 A1 | 7/2016 | Bernstein et al. |
| 2017/0183721 A1 | 6/2017 | Zong et al. |
| 2020/0299759 A1* | 9/2020 | Zong ............... C12Q 1/6853 |
| 2020/0339978 A1* | 10/2020 | Bostick ............ C12N 15/1086 |

FOREIGN PATENT DOCUMENTS

| | | |
|---|---|---|
| WO | 92/15322 A1 | 9/1992 |
| WO | 03/020763 A2 | 3/2003 |
| WO | 03/057171 A2 | 7/2003 |
| WO | 2004/002627 A2 | 1/2004 |
| WO | 2004/033685 A1 | 4/2004 |
| WO | 2004/044004 A2 | 5/2004 |
| WO | 2004/074322 A1 | 9/2004 |
| WO | 2005/113595 A2 | 12/2005 |
| WO | 2005/114215 A2 | 12/2005 |
| WO | 2006/000830 A2 | 1/2006 |
| WO | 2006/125962 A1 | 11/2006 |
| WO | 2007/089541 A2 | 8/2007 |
| WO | 2008/038002 A2 | 4/2008 |
| WO | 2008/039818 A2 | 4/2008 |
| WO | 2011/146862 A1 | 11/2011 |
| WO | 2012/048265 A2 | 4/2012 |
| WO | 2012/079000 A1 | 6/2012 |
| WO | 2013/039889 A1 | 3/2013 |
| WO | 2013/040371 A2 | 3/2013 |
| WO | 2013/044225 A1 | 3/2013 |
| WO | 2013/166321 A1 | 11/2013 |
| WO | 2014/011987 A1 | 1/2014 |
| WO | 2014/018863 A1 | 1/2014 |
| WO | 2014/047556 A1 | 3/2014 |
| WO | 2014/047561 A1 | 3/2014 |
| WO | 2014/083173 A1 | 6/2014 |
| WO | 2014/133567 A1 | 9/2014 |
| WO | 2014/133568 A1 | 9/2014 |
| WO | 2014/134165 A1 | 9/2014 |
| WO | 2014/134351 A2 | 9/2014 |
| WO | 2014/143158 A1 | 9/2014 |
| WO | 2014/145631 A1 | 9/2014 |
| WO | 2014/210353 A2 | 12/2014 |
| WO | 2015/050998 A2 | 4/2015 |
| WO | 2015/057834 A1 | 4/2015 |
| WO | 2015/057852 A1 | 4/2015 |
| WO | 2015/120096 A2 | 8/2015 |
| WO | 2015/130968 A2 | 9/2015 |
| WO | 2015/187528 A1 | 12/2015 |
| WO | 2016/000304 A1 | 1/2016 |
| WO | 2016/011210 A2 | 1/2016 |
| WO | 2016/040476 A1 | 3/2016 |
| WO | 2016/070061 A1 | 5/2016 |
| WO | 2016/138488 A2 | 9/2016 |
| WO | 2016/168584 A1 | 10/2016 |
| WO | 2016/191756 A1 | 12/2016 |
| WO | 2017/070395 A1 | 4/2017 |
| WO | 2017/075478 A2 | 5/2017 |

(56) References Cited

FOREIGN PATENT DOCUMENTS

| WO | 2017/139690 A1 | 8/2017 |
|---|---|---|
| WO | 2017/156336 A1 | 9/2017 |
| WO | 2019/084055 A1 | 5/2019 |

OTHER PUBLICATIONS

Massachusetts Institute of Technology, "Notification of the Transmittal of the International Search Report and the Written Opinion of the International Searching Authority, or the Declaration for PCT/US2018/057170", dated Dec. 21, 2018, 15 pages.

Massachusetts Institute of Technology, "International Preliminary Report on Patentability Chapter I received for International PCT Application Serial No. PCT/US2018/057170", dated May 7, 2020, 12 pages.

Cao, et al., "Comprehensive Single Cell Transcriptional Profiling of a Multicellular Organism by Combinatorial Indexing", Available at: BioRxiv https://doi.org/10.1101/104844, Feb. 2, 2017, 35 pages.

Cao, et al., "Comprehensive Single-cell Transcriptional Profiling of a Multicellular Organism", Science, vol. 357, No. 6352, Aug. 18, 2017, 661-667.

Gierahn, et al., "Seq-Well: A Portable, Low-Cost Platform for High-Throughput Single-Cell RNA-Seq of Low-Input Samples", Nature Methods, vol. 14, No. 4, Apr. 2017, 9 pages.

Habib, et al., "Div-Seq: Single-Nucleus RNA-Seq Reveals Dynamics of Rare Adult Newborn Neurons", Science, vol. 353, No. 6302, Aug. 26, 2016, 925-928.

Habib, et al., "Massively Parallel Single-Nucleus RNA-seq with DroNc-seq", Nature Methods, vol. 14, No. 10, Oct. 2017, 18 pages.

Hughes, et al., "Clonal Architecture of Secondary Acute Myeloid Leukemia Defined by Single-Cell Sequencing", PLoS Genetics, vol. 10, Issue 7, Jul. 2014, 12 pages.

Islam, et al., "Quantitative Single-Cell RNA-seq with Unique Molecular Identifiers", Nature Methods, 2014, vol. 11, No. 2, Feb. 2014, 163-166.

Kester, et al., "Single-Cell Transcriptomics Meets Lineage Tracing", Cell Stem Cell, vol. 23, No. 2, Aug. 2, 2018, 166-179.

Kivioja, et al., "Counting Absolute Number of Molecules Using Unique Molecular Identifiers", Nature Methods, vol. 9, 2012, 72-74.

Klein, et al., "Droplet Barcoding for Single-Cell Transcriptomics Applied to Embryonic Stem Cells", Cell, vol. 161, No. 5, May 21, 2015, 1187-1201.

Macosko, et al., "Highly Parallel Genome-Wide Expression Profiling of Individual Cells Using Nanoliter Droplets", Cell, vol. 161, No. 5, May 21, 2015, 1202-1214.

Paguirigan, et al., "Single-Cell Genotyping Demonstrates Complex Clonal Diversity in Acute Myeloid Leukemia", Science Translational Medicine, vol. 7, No. 281, Apr. 1, 2015, 18 pages.

Rosenberg, et al., "Scaling Single Cell Transcriptomics Through Split Pool Barcoding", Available at:Bio Rxiv http://dx.doi.org/10.1101/105163, Feb. 2, 2017, 13 pages.

Vitak, et al., "Sequencing Thousands of Single-Cell Genomes with Combinatorial Indexing", Nature Methods, vol. 14, No. 3, Mar. 2017, 302-308.

Zheng, et al., "Haplotyping Germline and Cancer Genomes with High-Throughput Linked-Read Sequencing", Nature Biotechnology, vol. 34, No. 3, Mar. 2016, 303-311.

Zheng, et al., "Massively Parallel Digital Transcriptional Profiling of Single Cells", Nature Communications, vol. 8, No. 14049, Jan. 16, 2017, 12 pages.

Zilionis, et al., "Single-cell Barcoding and Sequencing Using Droplet Microfluidics", Nature Protocols, vol. 12, No. 1, Jan. 2017, 44-73.

* cited by examiner

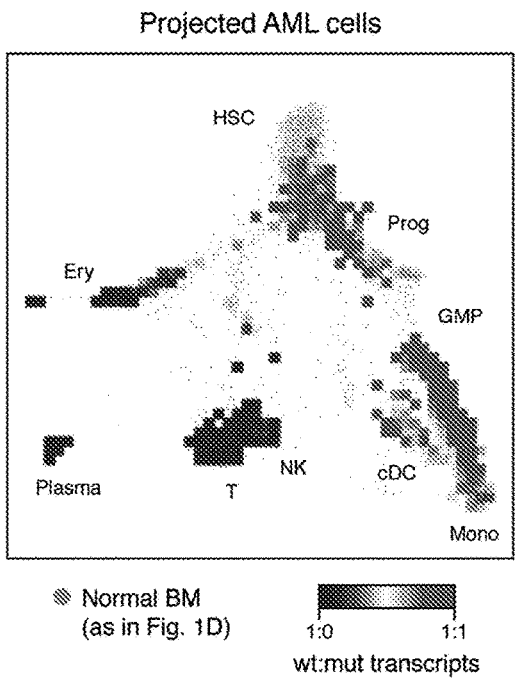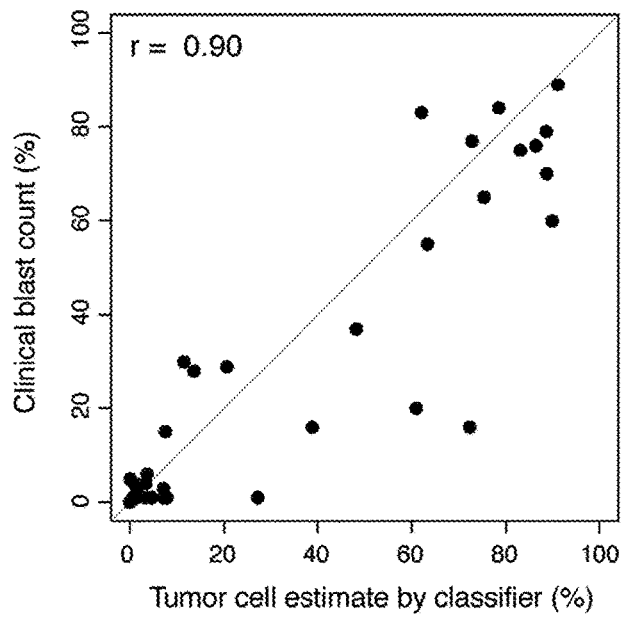
FIG. 19G
FIG. 19H
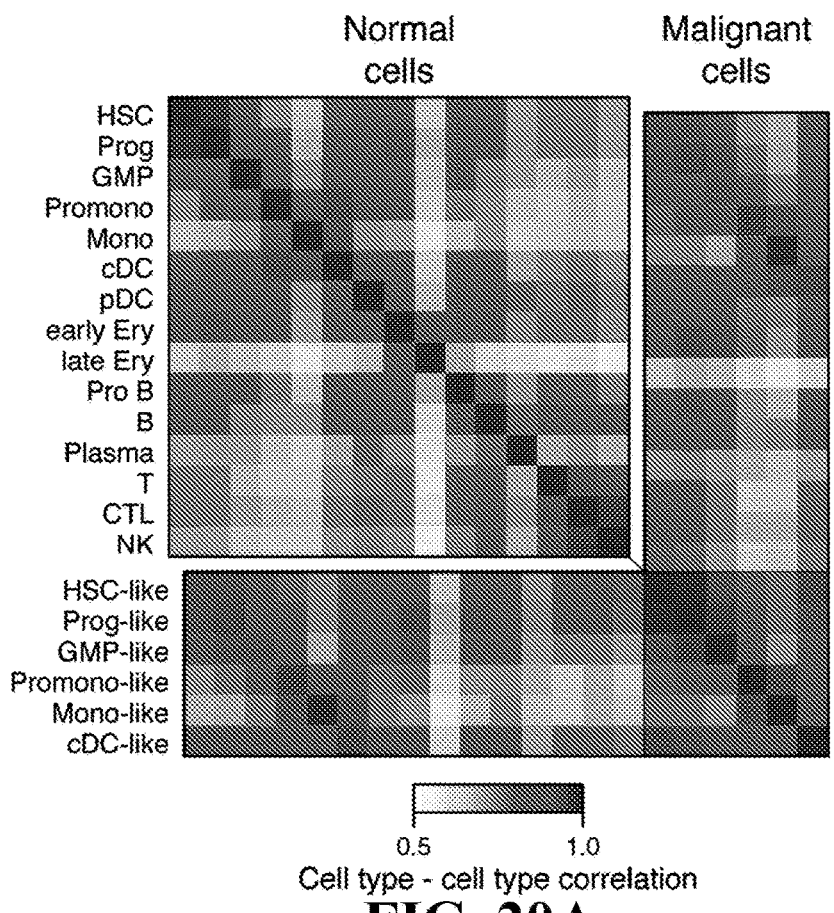
FIG. 20A

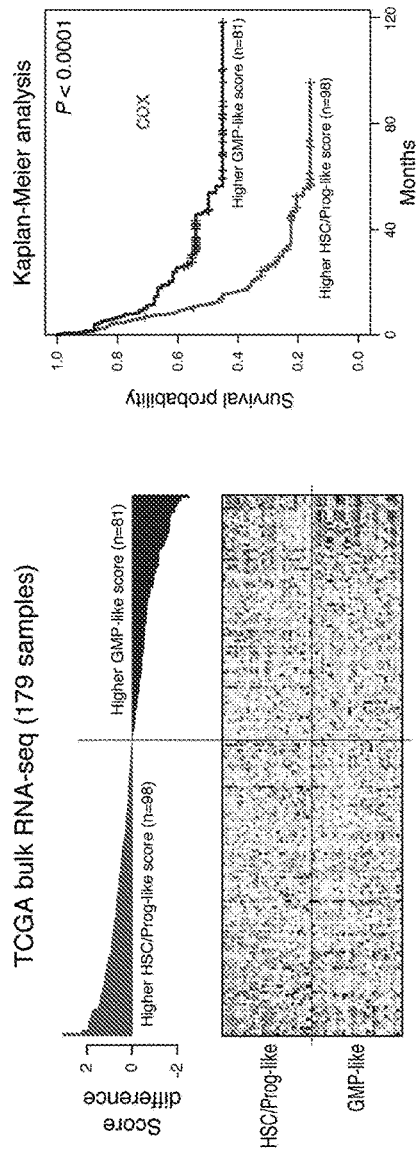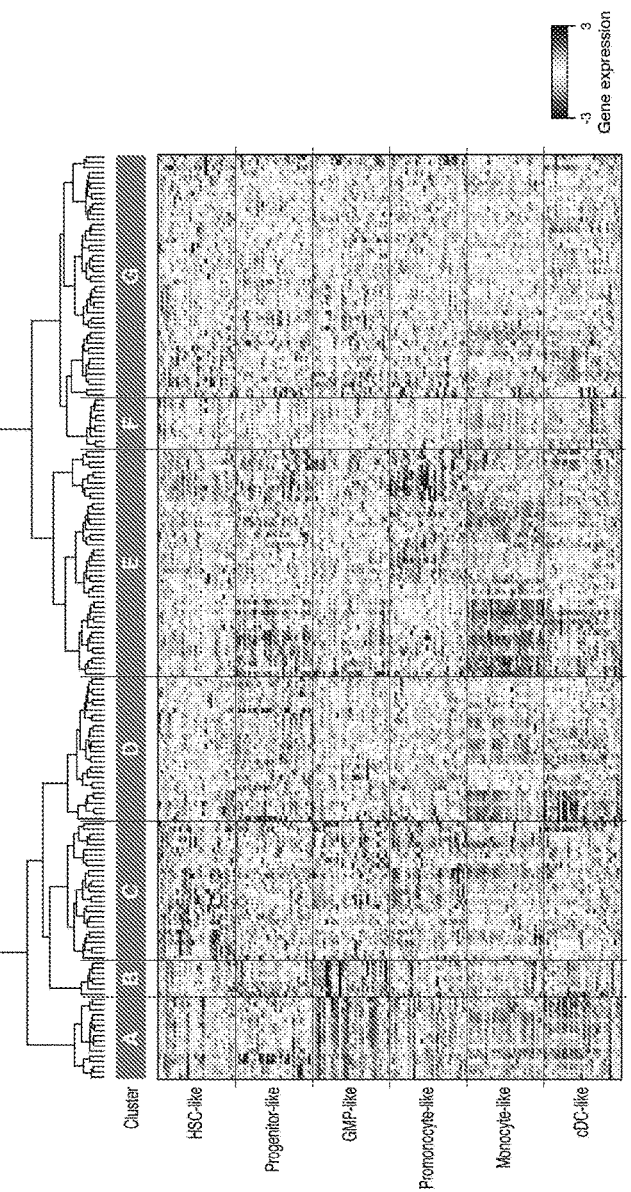
FIG. 21A
FIG. 21B
FIG. 21C

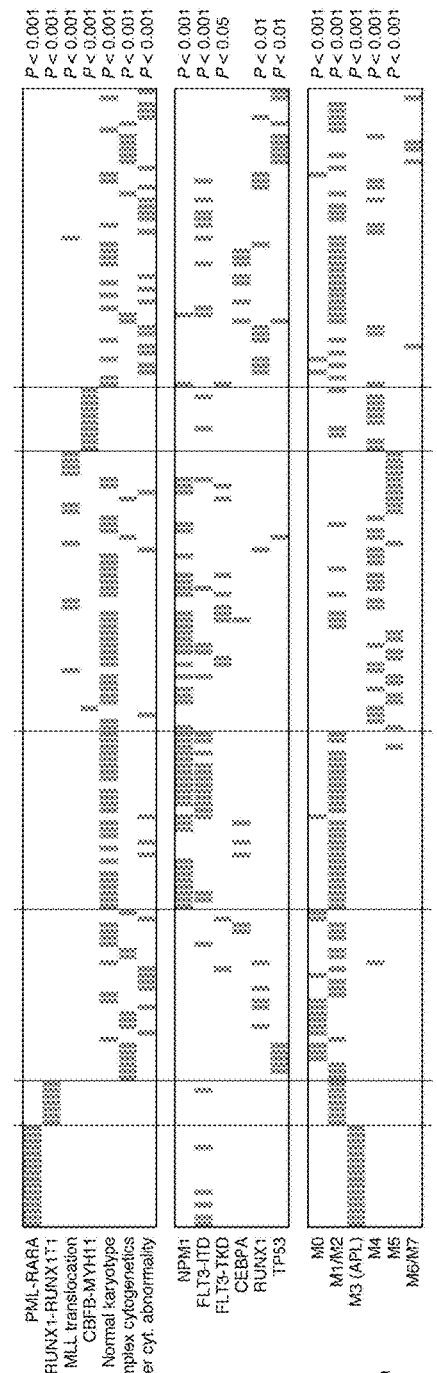
FIG. 21D
FIG. 21E
FIG. 21F
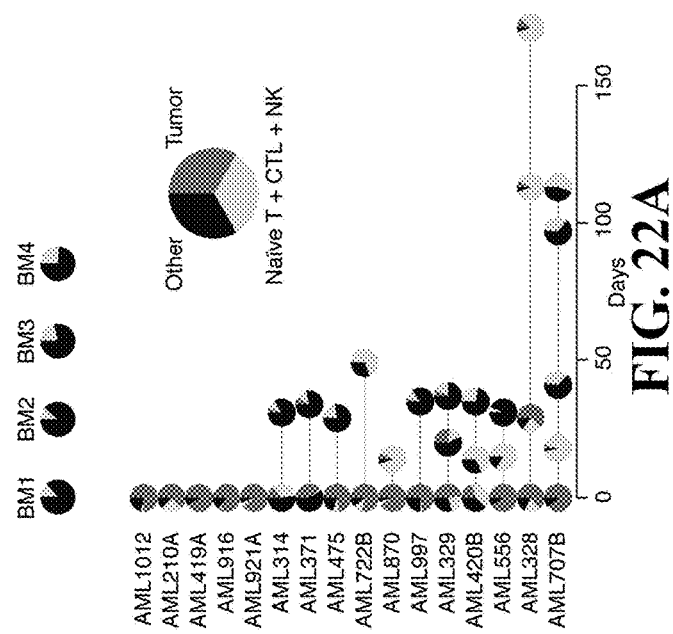
FIG. 22A

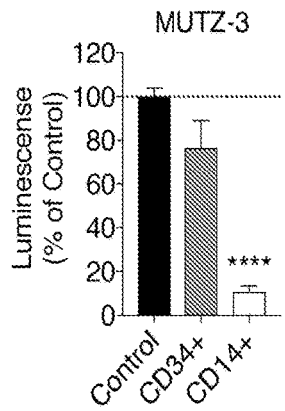
FIG. 23D
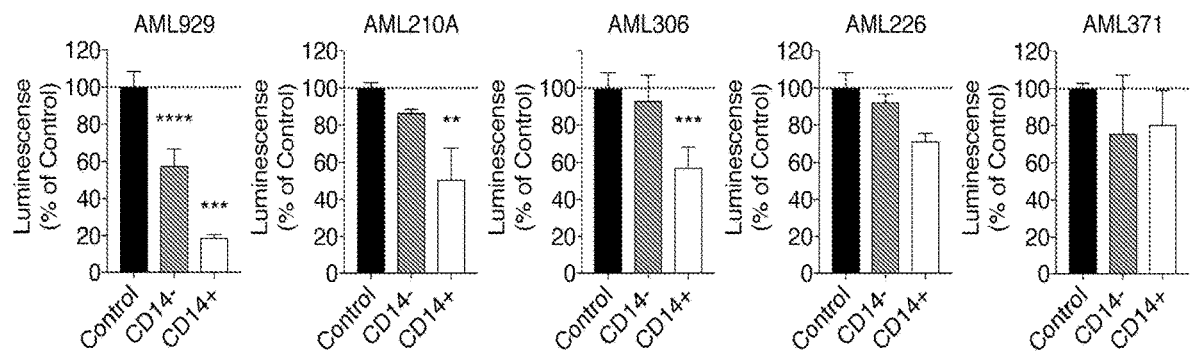
FIG. 23E
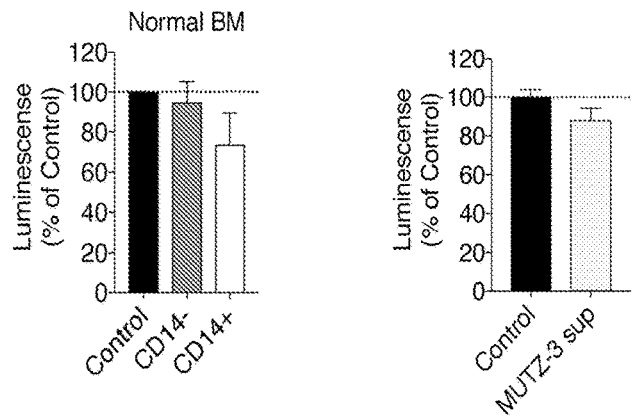
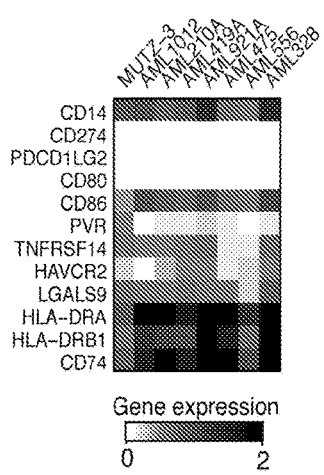
FIG. 23F  FIG. 23G  FIG. 23H

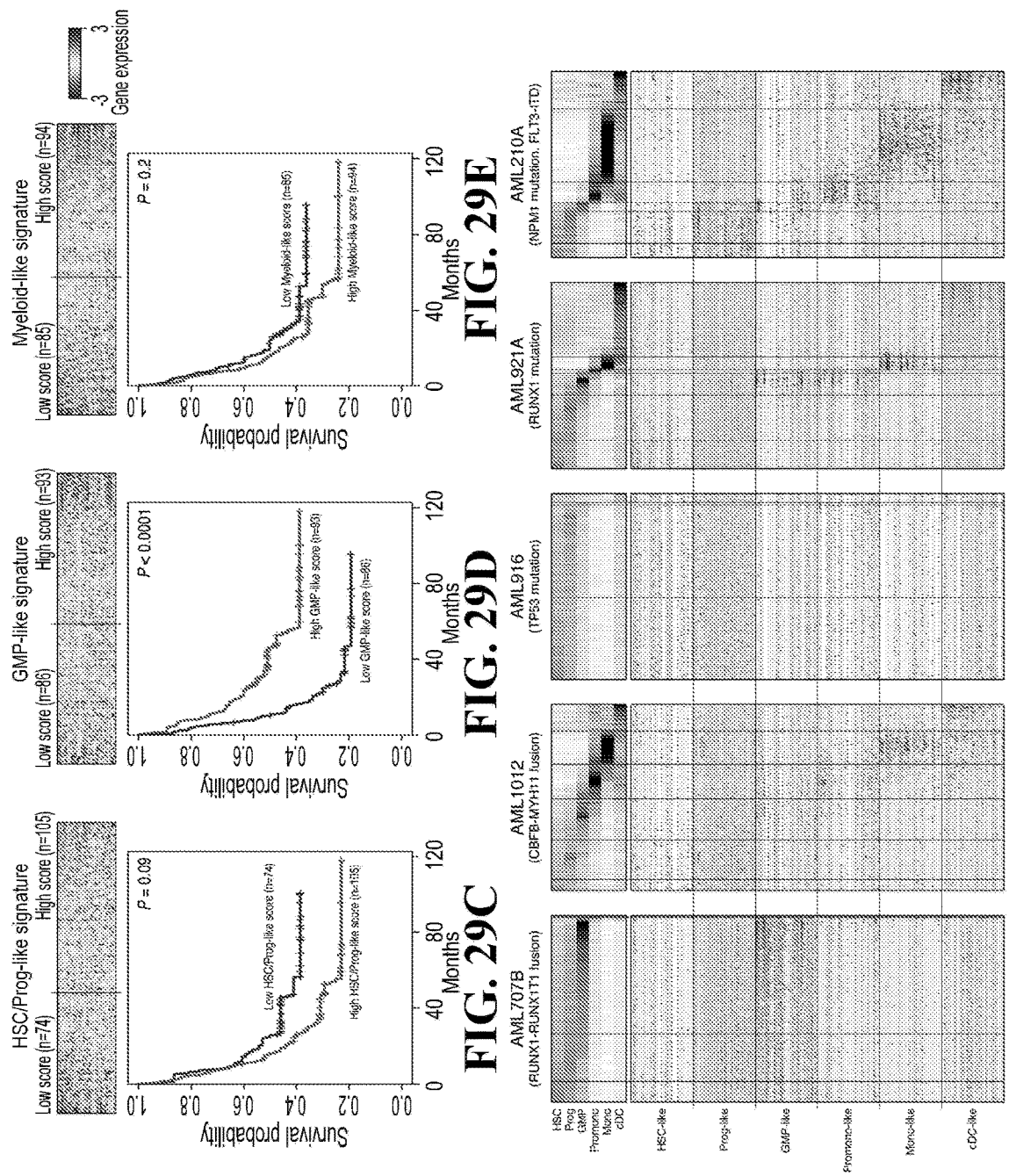

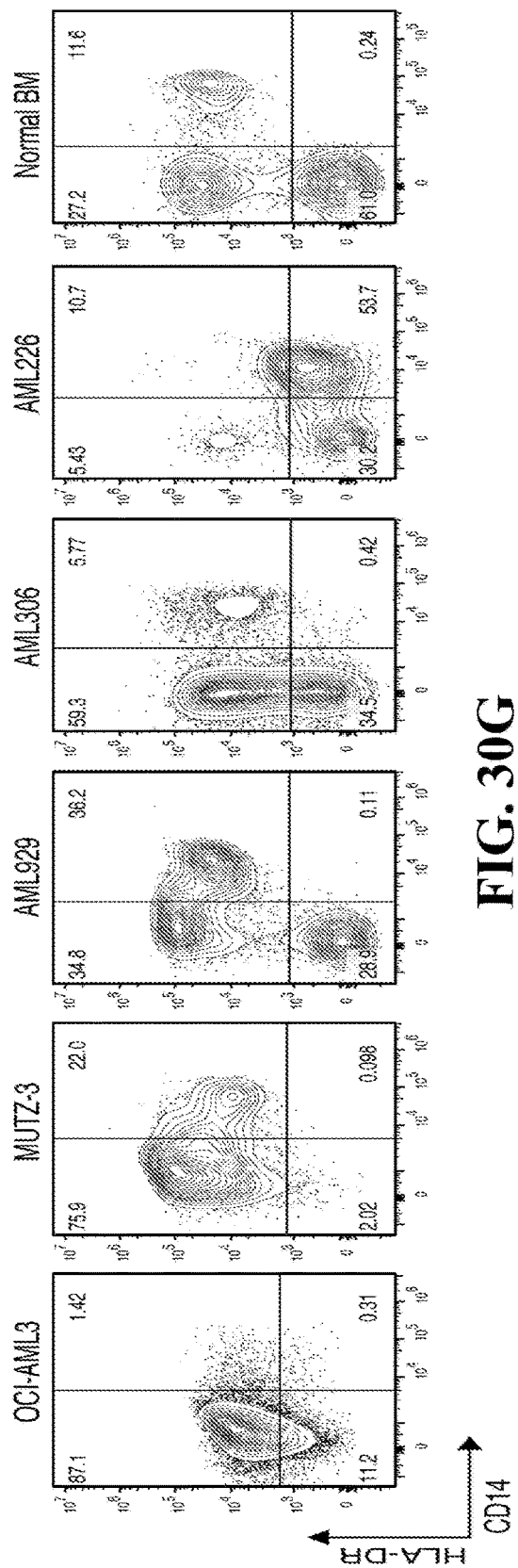
FIG. 30G
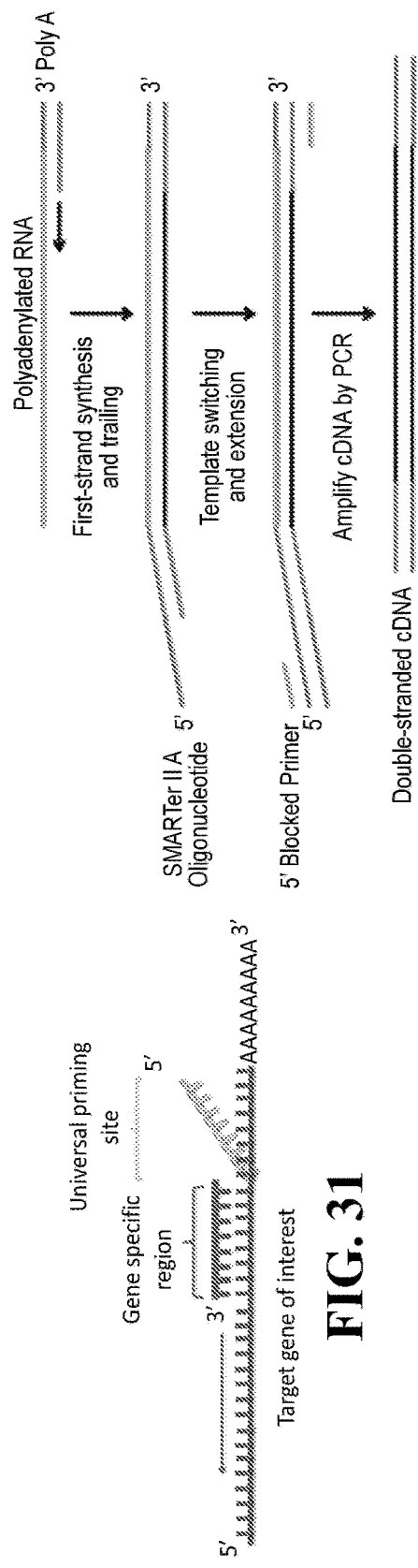
FIG. 32
FIG. 31

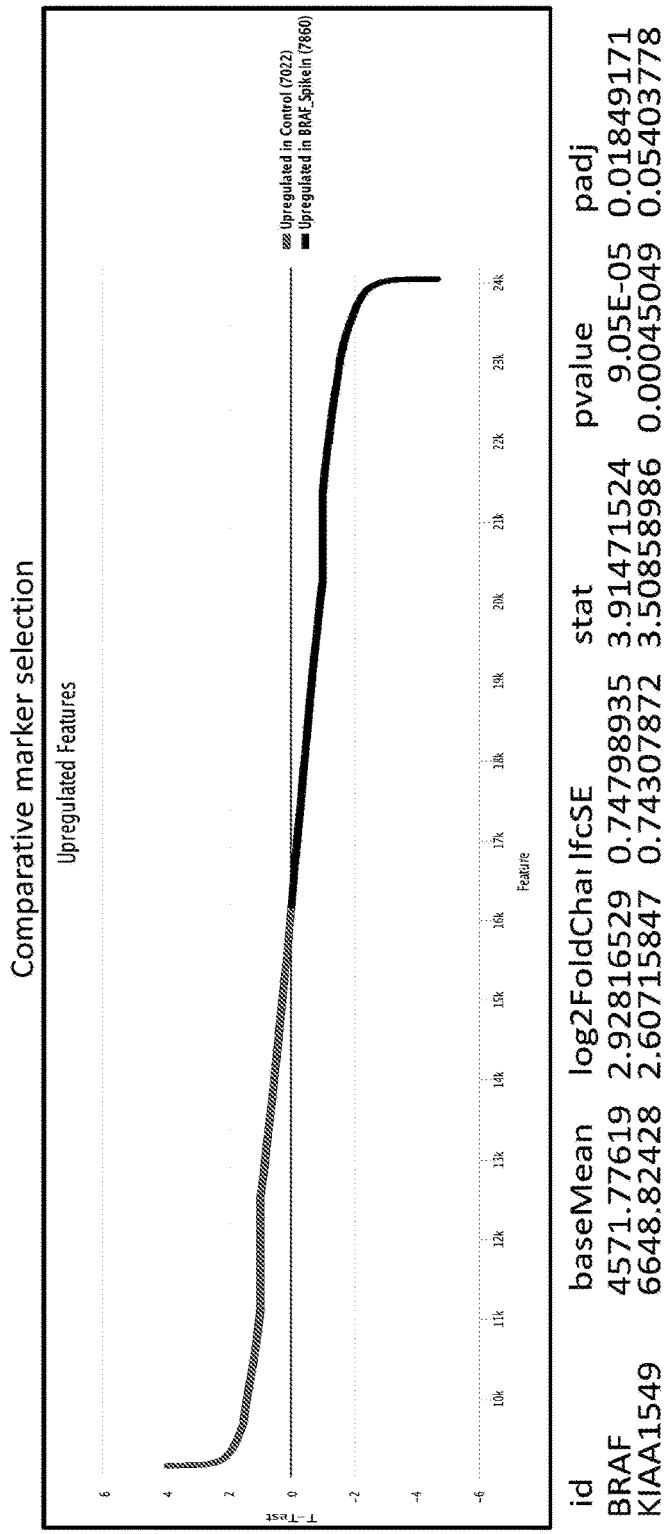
FIG. 36
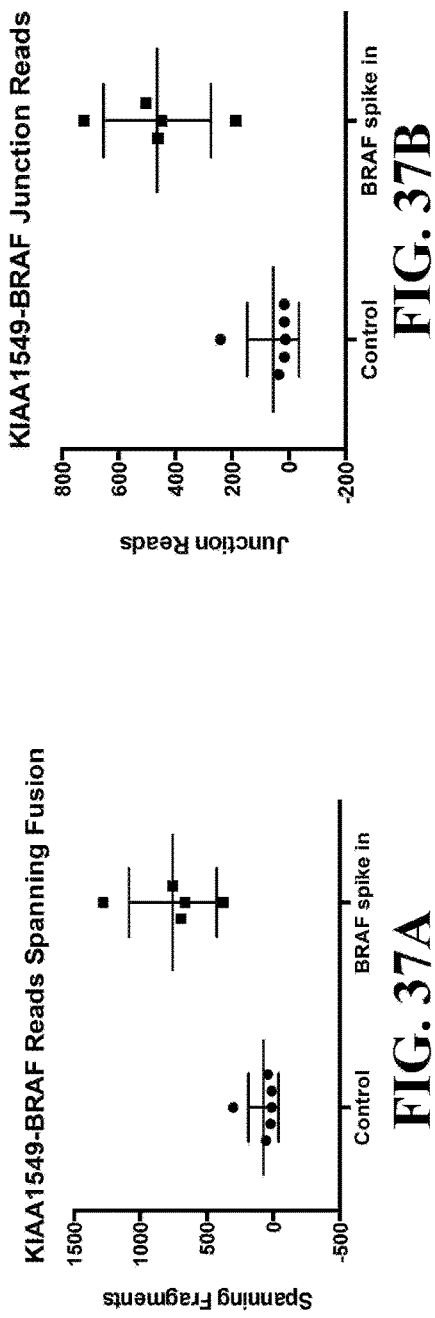
FIG. 37A
FIG. 37B

SINGLE CELL SEQUENCING LIBRARIES OF GENOMIC TRANSCRIPT REGIONS OF INTEREST IN PROXIMITY TO BARCODES, AND GENOTYPING OF SAID LIBRARIES

CROSS REFERENCE TO RELATED APPLICATIONS

This application claims the benefit of U.S. Provisional Application No. 62/575,667, filed Oct. 23, 2017. The entire contents of the above-identified application are hereby fully incorporated herein by reference.

STATEMENT REGARDING FEDERALLY SPONSORED RESEARCH

This invention was made with government support under Grant Nos. GM119419, CA216873, and CA218832 awarded by the National Institutes of Health. The government has certain rights in the invention.

REFERENCE TO AN ELECTRONIC SEQUENCE LISTING

The contents of the electronic sequence listing (BROD_2325WP_ST25.txt"; Size is 16 Kilobytes and created Oct. 16, 2018) is herein incorporated by reference in its entirety.

TECHNICAL FIELD

The subject matter disclosed herein is generally directed to methods of deriving genetic information from RNA-seq libraries. The methods disclosed herein enable an overlay of genetic information (such as cancer driver mutations) onto single-cell transcriptomes and permitting efficient identification, localization, and quantification of certain cells of interest within a population as well as improved low-cost selection and sequencing of any portion of a transcript, including at the 5' end.

BACKGROUND

The impact of high-throughput single-cell RNA-seq technologies is increasingly appreciated by the scientific community, and commercialized platforms are now available that massively parallelize the generation of single cell RNAseq libraries, enabling the creation of RNAseq libraries for $10^4$-$10^5$ cells. All the highly parallelized tools fuse the same cellular DNA barcode to all transcripts isolated from a cell during reverse transcription, creating so-called 3'-barcoded single cell RNAseq libraries derived from random sequencing reads. However, it remains challenging to sequence defined portions of a transcript while maintaining the barcode for single cell identification of the transcript, particularly when the sequence is on the 5' side of the transcripts.

Single cell matched T cell receptor α/β (TCR) and B cell receptor H/L chain (BCR) transcripts for antibody discovery or TCR discovery for use in cellular immunotherapy requires an efficient method of acquiring data from the variable region of TCRs and BCRs. Unfortunately, random sequencing a standard 3'-barcoded library can be a highly inefficient means of acquiring the desired data and if the sequence is in the 5'-end of the transcript, as in the case of the variable region of TCRs and BCRs, the desired sequences may not be extracted. Random sequencing can also suffer from trade-offs in specificity and speed when targeting exact sequences in a transcript. Previous methodologies also make it difficult to unambiguously distinguish tumor cells from normal cells in single-cell RNA-seq datasets from cancer patients and to differentiate malignant clones. One major application of single-cell RNA-seq is the ability for unbiased detection of different cell types in complex tissues. For example, when applied to a cancer patient's tumor, single-cell RNA-seq can unravel the different cell types, including tumor cells with different transcriptional states, stromal cells and immune cells. However, it can be difficult to recognize minority cell populations using standard single-cell RNA-seq techniques.

SUMMARY

In one aspect, the invention provides a library of enriched single cell RNA transcripts comprising a plurality of nucleic acids comprising a cell barcode in close proximity to a desired transcript sequence of interest, the plurality of nucleic acids derived from a 3' barcoded single cell RNA library, wherein at least a subset of the plurality of nucleic acids in the library comprise transcripts of interest that were greater than 1 kb away from the cell barcode in the 3' barcoded single cell RNA library.

In some embodiments, the transcripts may be from a T cell, a T cell, a B cell, or a cancer cell. The transcript of interest may be in a T cell receptor (TCR), a B cell receptor (BCR), CAR-T cell, or an AML, cell. The transcript of interest may be in a variable region of a TCR or BCR.

In some embodiments, close proximity is within 100 bases.

In another aspect, the invention provides a method of distinguishing cells by genotype comprising constructing a library comprising a plurality of nucleic acids wherein each nucleic acid comprises a gene comprising a polyA tail, a unique molecular identifier (UMI) and a cell barcode (cell BC) flanked by sequencing adapters at the 5' and 3' end, amplifying each nucleic acid in the library to create a first PCR product using a tagged 5' primer comprising a binding site for a second PCR product and a sequence complementary to a specific gene of interest and a 3' primer complementary to the adapter sequence at the 3' end of the nucleic acid thereby generating a first PCR product, selectively enriching the first PCR product by binding to the tag introduced by the 5' primer or a targeted 3' capture with a bifunctional bead or targeted capture bead, amplifying the tag-enriched first PCR product with a 5' primer comprising the binding site for the second PCR product and a 3' primer complementary to the adapter sequence at the 3' end of the nucleic acid thereby generating a second PCR product, optionally amplifying the second PCR product with a 5' primer comprising the binding site for a third PCR product and a 3' primer complementary to the adapter sequence at the 3' end of the nucleic acid thereby generating the third PCR product, and determining the genotype of the cell by identifying the UMI and cell BC, thereby distinguishing the cells by genotype.

The method may further comprise size selecting a final product comprising the specific gene of interest. In some embodiments, the sequencing adapters are switching mechanism at 5' end of RNA template (SMART) sequences at the 5' and 3' end.

The binding site for the second PCR product may be an oligomer for a sequencing kit.

In some embodiments, the amplifying the second PCR product is performed to generate a third PCR product. In some embodiments, the method may further comprise sequencing the third PCR product by third generation sequencing. In some embodiments, the method may further comprise sequencing the second PCR product by next generation sequencing. The binding site may be a Next® oligo for Illumina sequencing.

In some embodiments, the 5' primer comprising the binding site for the second PCR product to amplify the first PCR product further comprises a sequence to bind a flow cell. The 5' primer comprising the binding site for the second PCR product to amplify the first PCR product may further comprise a sequence allowing multiple sequencing libraries to be sequenced simultaneously. In some embodiments, the 5' primer comprising the binding site for the second PCR product to amplify the first PCR product further comprises a sequence providing an additional primer binding site. In some embodiments, the 5' primer comprising the binding site for the second PCR product to amplify the first PCR product further comprises a NEXTERA sequence.

The sequence to bind a flow cell may be a P7 sequence and the flow cell may be an Illumina flowcell.

In some embodiments, the sequence allowing multiple sequencing libraries to be sequenced simultaneously may be an INDEX sequence.

In some embodiments, the sequence providing an additional primer binding site may be a custom read1 primer binding site (CR1P) for sequencing.

In some embodiments, the primer complementary to the SMART sequence at the 3' end of the nucleic acid to amplify the first PCR product further comprises a sequence to allow fragments to bind a flowcell. The sequence to allow fragments to bind a flowcell may be a P5 sequence.

In some embodiments, the specific gene of interest comprises a mutation, deletion, insertion, translocation, single nucleotide polymorphism (SNP), splice variant or any combination thereof associated with a particular attribute in the specific gene of interest. The specific gene of interest may be a cancer gene, a tumor protein P53 gene, a KIAA1549: BRAF fusion gene, or an acute myeloid leukemia (AML) gene. The AML, gene may be a DNA methyltransferase gene, optionally wherein the DNA methyltransferase is DNA 5-cytosine methyltransferase 3a (DNMT3A).

In some embodiments, the tagged 5' primer comprises a biotin tag. In some embodiments, the tagged 5' primer and the 3' primer further comprise USER sequences, thereby generating a first PCR product comprising USER sequences, and further comprising treating the first PCR product with a uracil-specific excision reagent ("USER®") enzyme, circularizing the first PCR product by sticky end ligation, and amplifying the tag-enriched circularized PCR product with a 5' primer complementary to gene of interest and having a sequence adapter and a 3' primer having a polyA tail and another sequence adapter thereby generating the second PCR product.

In another aspect, the invention provides a method of distinguishing cells by genotype comprising constructing a library comprising a plurality of nucleic acids wherein each nucleic acid comprises a gene, a unique molecular identifier (UMI) and a cell barcode (cell BC) flanked by sequencing adapters at the 5' and 3' end. Each nucleic acid comprises orientation: 5'-sequencing adapter-cell barcode-UMI-UUUUUUU-mRNA-3'. Each nucleic acid in the library may be amplified to create a whole transcriptome amplified (WTA) RNA by reverse transcription with a primer comprising a sequence adapter, and the reverse transcribed product may be amplified by PCR amplification with primers that bind both sequence adapters and a library barcode and optionally additional sequence adapters may be added to generate a first PCR product. The genotype of the cell may be determined by identifying the UMI and library barcode, thereby distinguishing the cells by genotype.

In some embodiments, the primers for amplifying in step (c) comprise USER sequences, and further comprise treating the first PCR product with USER enzyme, thereby generating a circularized product; and amplifying the circularized product in a second polymerase chain reaction with one or more primers, wherein the one or primers comprise a library barcode and/or additional sequencing adapters.

In some embodiments, the gene comprises a mutation. In some embodiments, the mutation is within 1 kilobase of the polyA tail. In some embodiments, the mutation is anywhere in the gene.

In another aspect, the invention provides a method of identifying a cell genotype comprising constructing a library comprising a plurality of nucleic acids wherein each nucleic acid comprises a gene, a unique molecular identifier (UMI) and a cell barcode (cell BC) flanked by sequencing adapters at the 5' and 3' end, conducting primer extension on the plurality of nucleic acids with one or more tagged 5' primers with each primer comprising a sequence complementary to a desired transcript and a sequence adapter, thereby replicating the one or more desired transcripts and setting a 5' edge of one or more desired transcript sequences in one or more final sequencing constructs; amplifying the replicated one or more desired transcript sequences with universal primers having complementary sequences on 5' ends of the universal primers followed by a deoxy-uracil residue to form an amplicon; and ligating the amplicons by reacting the amplicons with a uracil-specific excision reagent enzyme, thereby cleaving the amplicon at the deoxy-uracil residues resulting in a circularized product.

In some embodiments, one or more PCR amplifications may be performed with primers complementary to the transcript of interest.

In some embodiments, at least two PCR steps may be performed in a nested PCR using two sets of transcript specific primers complementary to a transcript of interest.

In some embodiments, at least one set of the two sets of transcript specific primers comprise adaptor sequences, thereby yielding a final sequencing library of final sequencing constructs. In some embodiments, the last PCR step sets a 3' edge of the transcript sequence of the final construct.

Some embodiments further comprise a sequencing step utilizing primers complementary to the 3' set and 5' set edges of the final sequencing construct. Some embodiments further comprise a sequencing step utilizing a primer binding to a desired location in the final sequencing construct to drive a sequencing read at the desired location in the final sequencing construct.

In some embodiments, the transcript of interest is in a T cell or a B cell. In some embodiments, the transcript of interest is in a T cell receptor, a B cell receptor or a CAR-T cell. In some embodiments, the desired transcript is greater than about 1 kb away from the cell barcode.

In some embodiments, the one or more primers target variable regions. In some embodiments, the one or more tagged 5' primers is a pool of primers. The pool of primers may target all variable regions.

The method may further comprise sequencing the final sequencing library by next generation sequencing or third generation sequencing. The sequencing method may determine SNPs in the single cell.

In yet another aspect, the invention provides a method of stratifying a patient diagnosed with AML as having a higher risk of survival comprising detecting a gene signature of HSC/Progenitor genes and a gene signature comprising GMP signature genes in a tumor sample from a subject with AIL; detecting whether the expression profile contains a relatively higher expression of HCS/Progenitor signature genes than GMP signature genes; and stratifying the patient as having a poorer outcome/lower survival when the HSC/Progenitor gene signature is relatively higher expression.

The GMP signature genes may comprise PRTN3, MPO, CALR, CLEC5A, ELANE, POU4F1, TRH, TSPOAP1, CEBPE, LINC01835, NUCB2, CSF3R, RUNX1T1, CD38, PLPPR3, IGFBP2, PRRT4, SNHG5, FABP5, LOC100419170, CLEC11A, SERPINB1, AZU1, FBN2, HNRNPDL, HSPB1, RNA5-8S, THSD7A, C12orf57, FGFR1, LPO, MGST1, C1QTNF4, HMGN1, SIPA1L2, DDOST, PTGIR, GATM, VAMP8, FAM46A, VAMP5, STAR, ANKRD18A, TM7SF3, CCND1, ROBO1, GFI1, DEFA4, CERS6; and the HSC signature genes may comprise SPINK2, ANGPT1, GUCY1A3, FAM30A, MMRN1, TPT1, GAS5, RAB27B, TPM4, MSI2, GCSAML, SOCS2, EEF1A1, NRIP1, HOPX, CD34, TFPI, TPSD1, PDZRN4, PCNP, PTPRCAP, FLT3, SMIM24, SELENOP, DAPK1, SMYD3, ADGRG6, PIM1, MECOM, CEP70, XIRP2, SPAG6, TAPT1-AS1, GNA15, DSE, TPSAB1, TPSB2, H2AFY, SCHIP1, LINC02470, NPR3, KMT2A, CD200, MACF1, GBP4, ABCC1, PROM1, TMEM70, FAM110A, TMEM123.

In yet another aspect, the invention provides a method of detecting malignant AML cells in a sample, comprising selecting HSC/Prog-like cells in the sample, detecting downregulated expression of one or more genes comprising MSI2, MEIS1 and EGR1 relative to a normal HSC/Prog-like.cell; and detecting upregulated expression of one or more GMP and cell cycles genes such as AZU1, TOP2A, MKI67 and CENPF relative to a normal HSC/Prog-like.cell; wherein the detecting of the upregulated and downregulated genes in the sample is indicative of a malignant AML cell.

These and other aspects, objects, features, and advantages of the example embodiments will become apparent to those having ordinary skill in the art upon consideration of the following detailed description of illustrated example embodiments.

BRIEF DESCRIPTION OF THE DRAWINGS

An understanding of the features and advantages of the present invention will be obtained by reference to the following detailed description that sets forth illustrative embodiments, in which the principles of the invention may be utilized, and the accompanying drawings of which:

FIG. 1A illustrates how mutations may be detected from PCR-based methods such as Drop-Seq and Seq-Well. FIG. 1B illustrates how mutations may be detected from IVT-based methods such as InDrop and 1Cell.

FIG. 17B. Heatmap shows the expression of xxx selected cell type-specific genes (rows) across 6,195 single cells ordered by the BackSPIN-defined clusters (columns). FIG. 17C. Stacked barplots show the frequencies of BackSPIN-defined cell types in five normal BMs. BM5 was sorted for indicated markers prior to scRNA-seq, and is enriched for primitive cells. FIG. 17D. K-nearest-neighbor (KNN) visualization of single-cell transcriptomes (points), with similar cells positioned closer together. Points are color-coded by cell type annotations defined in (17A).

(FIG. 18C) or 4,438 cells from AML707B (FIG. 18D) at successive collections. Each plot shows cells from the indicated time point (red) and cells from the other time points (gray) for that patient. t-SNE plots and H&E stains for the same time points (below) depict marrows predominated by AML cells at presentation (Day 0), hypocellular marrows with T-cells after chemotherapy (Day 15-18), followed by repopulating hematopoiesis (Day 31-41). H&E scale bar is 50 μm.

FIG. 19A-H shows classifier distinguishes normal from malignant cells by transcriptomic and genotypic data. FIG. 19A. Illustration depicts procedures for acquiring transcriptional and genotypic information from single cells. Nanowell plates and beads with barcoded adaptors are used to generate whole transcriptome amplification (WTA) product wherein each transcript cDNA is appended to a unique molecular identifier (UMI), a cell-specific barcode (CB), and a primer binding site (SMART). This WTA product is then split and used as starting material for transposase (Tn5)-mediated scRNA-seq library generation (left) and targeted readout of driver mutations (right). The single-cell genotyping reaction utilizes a panel of 1-6 biotinylated PCR primers that are complementary to sequences just upstream of known mutational sites in AML driver genes. Amplification products generated by these primers are purified using streptavidin beads, yielding a sequencing library comprised of these target loci appended to the same CBs and UMIs as in the scRNA-seq data. See FIG. 25A for a detailed overview of single-cell genotyping. FIG. 19B. Bubble plot depicts the frequency with which single-cell genotyping detects the indicated mutational sites, and is thus able to assign the transcript as wild-type or mutant. Detection is more efficient for mutational sites in highly expressed genes (e.g. NPM1) and close to the 3' polyA signal. FIG. 19C. Scatter plot compares variant allele frequencies (VAF) derived from gold standard targeted DNA sequencing data (y-axis) or inferred from single-cell genotyping data (x-axis). Each point corresponds to a specific mutational site in a specific AML aspirate (seven examples corresponding to a range of variant allele frequencies are highlighted). FIG. 19D-19E. t-SNE plots show cells from AML556 in FIG. 19D and cells from AML 707B in FIG. 19E (clustered as in FIG. 18C-F). Colored points indicate cells for which wild-type (blue) or mutant (red) transcripts were detected by single-cell genotyping. FIG. 19F. Schematic shows data inputs and outputs for the machine learning classifiers used to distinguish malignant from normal cell types. Classifier 1 compared transcriptomes of AML cells with detected driver mutations to 15 normal BM cell types, and thereby identified 6 malignant cell types. Classifier 2 combined this knowledge of 15 normal and 6 malignant cell types with the single-cell transcriptomic and genotypic data to definitively assign all cells as either malignant or normal. FIG. 19G. KNN graph (as in FIG. 17D) shows single-cell transcriptomes of normal BM cells (gray). Cells from AML samples in which wild-type or mutant transcripts were detected in the single-cell genotyping assay were projected onto this graph according to their similarity to the normal cells. The ratio between wild-type and mutant transcripts in these AML cells is shown in blue/red squares. Definitive malignant cells (red) project along the HSC-myeloid differentiation axis. FIG. 19H. Scatter plot compares clinical blast counts (y-axis) to the fraction of cells classified as malignant by scRNA-seq, genotyping and machine learning (x-axis). Each point corresponds to a specific AML BM aspirate.

FIG. 20A-20F characterizes intra-tumoral heterogeneity of malignant AML cells FIG. 20A. Heatmap shows correlation between cell types (rows and columns) from normal BM donors and AML patients. The six malignant cell types distinguished by the classifier are highly correlated to normal counterparts, and were named accordingly (HSC-like, progenitor-like, GMP-like, promonocyte-like, monocyte-like and conventional dendritic cell-like (cDC-like). FIG. 20B. Heatmaps show prediction scores for the indicated cell types (rows) for all malignant cells (columns) from four representative tumors (prediction scores calculated by the first random forest classifier). Cells in which wild-type and/or mutant transcripts were detected, or that express cell cycle signature genes are indicated below. AML916 harbors a single p53 mutant allele, which accounts for the lack of wild-type transcripts. The other tumors are heterozygous for the queried mutations. The detected mutations confirm the malignant origins of these varied cell types. FIG. 20C. KNN graph (as in FIG. 17D) shows single-cell transcriptomes of normal BM cells (gray). Malignant cells from AML samples were projected onto this graph according to their similarity to the normal cells. The density of projected cells (red) conveys the distinct cell type compositions of these tumors. FIG. 20D. Flow cytometry plots show expression of myeloid differentiation markers (CD11b and CD14) in viable cells from four AML patients. FIG. 20E. Heatmaps show pairwise correlations between 90 genes (rows and columns) from the HSC/Progenitor, GMP and myeloid signatures. Heat reflects correlations of expression values over all HSC-myeloid normal BM cells (top) or malignant AML cells (bottom). The distinction between HSC/progenitor and GMP signatures evident in normal cells is lost in malignant cells. FIG. 20F. Heatmap shows expression of signature genes (rows) in normal BM cells (left, columns) or malignant AML cells (right, columns). For normal BM, all cells along the HSC-myeloid axis are shown. For AML, all malignant cells at diagnosis are shown. Cells are ordered by their classifier prediction scores (shown on top). Expression of cell cycle genes is also indicated. Unlike normal cells, primitive AML cells concurrently express HSC/progenitor and GMP programs. This finding is consistent with myeloid priming of AML progenitors and may relate to their combined self-renewal and proliferative properties.

FIG. 21A-21F AML cellular hierarchies predict outcome and correlate to genetics FIG. 21A. Gene signatures for HSC/Progenitor-like and GMP-like cells were applied to bulk RNA-seq profiles from TCGA. Barplot depicts the difference between these scores in 179 AMLs. Each bar represents one patient. Bottom: heatmap shows expression of the 60 genes in these signatures (rows) across the 179 AMLs (columns). FIG. 21B. Kaplan-Meier curves show the survival of 179 AML patients from the TCGA bulk expression cohort that were stratified by the signature scores in A. Patients with higher HSC/progenitor scores have significantly worse outcomes. FIG. 21C. Heatmap shows expression of 180 signature genes for the six malignant cell types (rows) in 179 AMLs (columns). Unbiased clustering revealed seven patient groups with different inferred cell type abundances (FIG. 21A-FIG. 21G). FIG. 21D-FIG. 21F. Charts indicate chromosomal translocations or aberrations (FIG. 21D), gene mutations (FIG. 21E) and FAB subtypes (FIG. 21F) for the 179 AMLs clustered in (FIG. 21C). A striking correspondence between cell type compositions and tumor genetics is evident.

FIG. 22A-22G T-cell signatures altered in AML patients FIG. 22A. Overview depicts the proportions of cells annotated as malignant or T/NK for normal BMs and AMLs collected at indicated time points as in FIG. 2A. AML annotations are based on the random forest classifier and normal BM annotations are based on BackSPIN cluster analysis (FIG. 17A; the same results were obtained when basing normal BM annotations on the random forest classifier). FIG. 22B. KNN graphs show combined visualization of transcriptomes for all 10,153 T- and NK cells identified in normal BMs and AMLs. Cells (points) are color-coded by their annotation as naïve T-cell, CTL or NK cell. Differentially expressed marker genes are listed. Indicated subset of cells deviates from the main populations due to cell cycle gene expression. FIG. 22C. Boxplots show the proportions of cells from normal BM or AMLs annotated as T-cells (left) or CTLs (right) per scRNA-seq. Data is shown as median±quartiles for 4 normal BMs and 16 AMLs at diagnosis. FIG. 22D. Pie charts show relative proportions of CTL, naïve T-cell and NK cell annotations in scRNA-seq data for normal BMs and AMLs at diagnosis. Shown are all samples for which ≥50 T/NK cells were identified. FIG. 22E. Representative IHC stains for T-cells (CD3$^+$) and CTLs (CD8$^+$) in normal BM and AML. H & E stains are also shown. Scale bar is 50 µm. IHC images were used to quantify T-cells and CTLs in normal BMs and AMLs (see panel 22F). FIG. 22F. Boxplots show the numbers of T-cells and CTLs relative to all cells identified in IHC stains. Data shown as median±quartiles for 15 normal BMs and 15 AMLs. FIG. 22G. Pie charts show relative numbers of CTLs (CD8$^+$), Tregs (CD25$^+$FOXP3$^+$) and other T-cells, per IHC stains. Charts show the mean for 15 normal donors and 15 AMLs. AMLs have fewer T-cells and CTLs, but relatively greater numbers of Tregs, compared to normal BM. * $P<0.05$,  $P<0.01$, * $P<0.001$, **** $P<0.0001$.

FIG. 23A-23H Differentiated AML cells suppress T-cell activation in vitro. FIG. 23A. Top: KNN graph (as in FIG. 1D) shows single-cell transcriptomes of normal BM cells (gray). AML lines OCI-AML3 and MUTZ-3 were profiled by scRNA-seq, and single cells were projected onto the KNN graph according to their similarity to the normal BM cells. The density of projected cells is shown in red. MUTZ-3 comprises a more heterogeneous mixture of cells that map to different cell types along the myeloid differentiation axis. Bottom: flow cytometry plots support presence of primitive (CD34$^+$) and monocyte-like (CD14$^+$) cells in MUTZ-3. FIG. 23B. Barplot shows T-cell activation (luminescence) after stimulation with CD28 beads in vitro. The assay was performed in the absence (Control) or presence of OCI-AML3 or MUTZ-3 AML cells. MUTZ-3 cells inhibit T-cell activation. Data shown as mean±SD of n≥3 experiments. FIG. 23C. Barplot shows T-cell activation assay as in B, performed in the presence of increasing numbers of MUTZ-3 cells (mean±SD of n=3 experiments). FIG. 23D. Barplot shows T-cell activation assay performed in the presence of 100,000 sorted CD34$^+$ or CD14$^+$ MUTZ-3 cells (mean±SD of n=3 experiments). FIG. 23E. Barplots show T-cell activation assay performed in the presence of 100,000 sorted CD14$^-$ or CD14$^+$ cells from primary AMLs (n≥3 technical replicates each). FIG. 23F. Barplot shows T-cell activation assay performed in the presence of 100,000 sorted CD14$^-$ or CD14$^+$ cells from normal BMs (6 biological replicates). FIG. 23G. Barplot shows T-cell activation assay performed in the presence of MUTZ-3 conditioned medium (mean±SD of n=3 experiments). FIG. 23H. Heatmap shows expression of CD14 and selected genes implicated in immunosuppression (Austin et al., 2016; Wykes and Lewin, 2018) in monocyte-like cells from MUTZ-3 or primary AMLs. Data represent an average over all tumors with >50 monocyte-like cells. * $P<0.05$,  $P<0.01$, * $P<0.001$, **** $P<0.0001$. Significance is only indicated when T-cell activation was reduced >1.5-fold compared to Control.

FIG. 24A-24H Single-cell profiling of normal BM cells FIG. 24A. Workflow shows the collection and processing of BM aspirates from healthy donors and AML patients for scRNA-seq. FIG. 24B. Flow cytometry plots show gating strategy to sort CD34$^+$ and CD34$^+$ CD38-populations from healthy BM5 donor cells. Post-sort analysis showed purity of 95-96% (not shown). FIG. 24C. Heatmap shows the expression of the 1,435 most variable genes (rows) in 6,915 cells (columns), that were used for BackSPIN clustering. Cells are ordered as in FIG. 17B, clusters are separated by vertical lines. Sample of origin is indicated below the heatmap. FIG. 24D. Barplot shows the number of cells for each BackSPIN cluster. The order of bars corresponds to the order of rows in FIG. 17A. Colors indicate cell types as in FIG. 17C. For every cell type, more than 60 cells were identified and every cell type was identified in three or more donors. FIG. 24E. KNN visualization (as in FIG. 17D) shows single-cell transcriptomes of normal BM cells. Cells from different flow cytometry gating strategies or unsorted cells are shown in red (indicated on top), whereas all other cells are shown in gray. As expected, sorted CD34$^+$ cells are mostly restricted to HSC and Progenitor cell populations, whereas sorted CD34$^+$ CD38$^-$ cells are mostly restricted to the HSC population. FIG. 24F. tSNE visualization shows single-cell transcriptomes of normal BM cells (points). Similar cells are positioned closer together, and cells are color-coded by their BackSPIN classification as in FIG. 17C-D. The t-SNE algorithm provides an alternative method to visualize similarities of normal BM cells, which is in agreement with the KNN visualization (FIG. 17D). FIG. 24G. KNN visualization (as in FIG. 17D) is overlaid with the relative expression levels of MSI2, MPO, and MNDA. These plots exemplify gradual changes in cell type-specific marker genes. FIG. 24H. KNN visualization (as in FIG. 17D) is overlaid with signature scores for genes associated with cycling cells. Cycling cells are mostly present in the differentiating erythroid lineage, in progenitor B cells, and in intermediate myeloid populations, but not in undifferentiated HSCs, differentiated monocytes and differentiated lymphoid cell types.

FIG. 25B. Stacked bar plots show the numbers wild-type and mutant of transcripts that were detected in two normal BM samples. The single-cell genotyping protocol was carried out using normal BM3 and BM4 WTA as starting material, with biotinylated mutation-specific primers directed at the IDH2.419G (R140) and DNMT3A.2645G (R882) mutational hotspots. As expected, we detected only wild-type transcripts in these healthy individuals. FIG. 25C-FIG. 25D. Stacked bar plots show the numbers of wild-type and mutant transcripts that were detected using single-cell genotyping in AML556 and AML707B. For AML556, three single-cell genotyping reactions were carried out (one for each time point), each with a mixture of six biotinylated mutation-specific primers. For AML707B, five single-cell genotyping reactions were carried out (one for each time point, results from D97 and D113 are pooled), each with a mixture of three biotinylated mutation-specific primers. For both patients, colors indicate the targeted mutational sites and clinical blast counts are shown between parentheses for each time point. Both patients went into clinical remission, during which time few or no mutant transcripts were detected.

FIG. 26A. Heatmap depicting results of a 5-fold cross-validation of the first Random forest classifier comprising 15 classes corresponding to the cell types identified in normal BM. Cells that fall on the diagonal are classified according to their annotation (87.9% of cells). Cells that do not fall on the diagonal are mis-classified as a different cell type (12.1%). Most mis-classified cells are classified as a related cell type within the same linage (8.3%), or are mis-classified between HSC/Prog and early Erythroid or GMP (2.8%). Only 1.14% of cells do not fall within these categories and are misclassified between lineages. FIG. 26B. KNN visualization (as in FIG. 1D) shows single-cell transcriptomes of normal BM cells. The color of each cell indicates its prediction score from the cross-validation of the first Random forest classifier for each of the 15 cell types. FIG. 26C. KNN visualization (as in FIG. 17D) shows single-cell transcriptomes of normal BM cells in gray. Peripheral blood mononuclear cells (PBMCs) were projected onto this graph according to their similarity of prediction scores. The density of PBMCs is shown in red squares. PBMCs were analyzed using Seq-Well scRNA-seq in a previous study (Gierahn et al., 2017). Cell types in the blood mostly correspond to differentiated cell types in the BM, such as B, T and NK lymphocytes, conventional dendritic cells, and monocytes. FIG. 26D. Barplot of AML cells with detected driver mutations classified in 15 categories by the first Random forest classifier. The majority of cells with mutations fall within six cell types along the HSC to myeloid differentiation axis. These cells were therefore used to define six malignant cell types, and included in the second Random forest classifier. FIG. 26E. Heatmap depicting results of a 5-fold cross-validation of the second RF classifier comprising 15 classes from the normal BM (identical to the first classifier), and an additional six classes of malignant cell types from AML patient cells for which driver mutations were detected. This classifier is used for distinguishing malignant from normal cells in AML patient samples. The sensitivity of detecting malignant cells (true positive rate) is 95.2%. The specificity of detecting malignant cells (true negative rate) is 99.7%, indicating that malignant cells are more often classified as normal cells than vice versa. FIG. 26F. Heatmap shows correlation between cell types from normal BM donors and normal (non-malignant) cell types from AML patients, as classified by the Random forest classifier (rows and columns). Non-malignant cell types from healthy donors are highly correlated to non-malignant cell types from AML patients. The number of cells for each cell type are indicated in the barplot on the right. FIG. 26G. Barplot shows the fraction of cells for which transcripts from chromosome Y were detected in classified malignant vs. non-malignant cells from AML707B. Loss of chromosome Y in tumor cells was reported by clinical cytogenetics in 19 out of 20 assessed cells. FIG. 26H. Barplot shows the fraction of cells for which the RUNX1-RUNX1T1 fusion was detected by matching unique molecular identifiers (UMIs) associated with reads mapping to both fusion partners. This strategy identified many more fusion transcripts compared to using only reads that cover the fusion junction itself. The fusion transcript is detected much more frequently in cells classified as malignant than in cells classified as normal. FIG. 26I. Barplot shows the fraction of malignant cells for which either allele of a heterozygous SNP located in the 3'UTR of ACTB is detected. ACTB is located on chromosome 7, which is present in only one copy in the malignant cells of this patient. Because of this, only one of the alleles is detected in the single cells classified as malignant. FIG. 26J. Barplot shows plasma cells as a fraction of all cells that were captured in normal BM and AML aspirates at diagnosis (Day 0). AML556 and AML420B were co-diagnosed with plasma cell neoplasms (Table 3), which is reflected in the scRNA-seq data by a higher fraction of plasma cells.

FIG. 27B. Overview depicts classification of all 30,712 cells from all AML patients. Top heatmap shows prediction scores for each of the 15 cell types as calculated by the first Random forest classifier. Cells are separated into normal cells (n=16, 090), malignant cells (n=13,489), and unclear cells (n=1, 133) according to the refined classification of the second Random forest classifier. Cells in which wild-type and/or mutant transcripts were detected, or that express cell cycle signature genes are indicated below. The bottom panel shows the sample of origin for each cell. FIG. 27C. Barplots summarizing the number of cells (left) and the number of wild-type and mutant transcripts detected (right) for each normal cell type (e.g. HSC) and malignant cell type (e.g. HSC-like) profiled in all normal BM and AML patient samples.

FIG. 28A. Top: Heatmaps show prediction scores for the indicated cell types (rows) for all malignant cells (columns) from eight tumors. The prediction scores were calculated by the first random forest classifier. Cells that express cell cycle signature genes are indicated below. Bottom: KNN graphs (as in FIG. 1D) show single-cell transcriptomes of normal BM cells (gray). Malignant cells from AML samples at diagnosis were projected onto this graph according to their similarity to the normal cells. The density of projected cells (red) conveys the distinct cell type compositions of these tumors. FIG. 28B. Scatter plot shows correlation between the percent of differentiated myeloid cells by flow cytometry (CD11b$^+$) and by single-cell RNA-sequencing (promonocyte, monocyte and cDC). Every point represents one of seven patients for which flow cytometry data was available. FIG. 28C. Scatter plots show the correlation of gene expression values to Random forest prediction scores in HSC-to-myeloid cells from normal BM samples. Every point represents one gene. Correlation coefficients for different cell types are compared in different panels. Signature genes, i.e. genes that highly correlate to prediction scores of HSC/Prog, GMP, and myeloid cell types (top panels), are indicated in red, blue, and green. For example, MSI2 expression in single cells is highly correlated to the HSC prediction scores, but not to the GMP prediction scores. Prediction scores for HSC/progenitors and promonocytes/monocytes/cDCs were combined for this analysis, since similar genes were highly correlated to their respective prediction scores (bottom panels). FIG. 28D. Heatmaps show the pairwise correlation of the correlation coefficients displayed in FIG. 28C between individual cell types. Top panel: In cells from normal BM samples, transcriptional profiles of HSC/progenitors and promonocytes/monocytes/cDCs are more similar to each other and are therefore combined in this analysis. Bottom panel: A similar analysis in cells from AML patients (correlating gene expression values to prediction scores in malignant cells) also shows that transcriptional profiles of HSC/progenitors and promonocytes/monocytes/cDCs are more similar to each other. Additionally, transcriptional profiles between HSC/Prog and GMPs are more alike in AML than in normal BM. See also FIG. 30A.

FIG. 29A-29F AML cell states predict outcome FIG. 29A. Scatter plots show the correlation of gene expression values to Random forest prediction scores in malignant cells from AML patients. This analysis was performed to generate six signatures for the malignant cell types (e.g. HSC-like signature). In comparison to cells from normal BM (FIG. 28C-D), HSC/Progenitor and GMP expression programs are more alike, and signature genes for each malignant cell type are also positively correlated to the other cell type. This is not the case for GMP and myeloid expression programs, which are very distinct. FIG. 29B. Kaplan-Meier curves show the survival of 163 AML patients from the TCGA bulk expression cohort that were stratified according to higher HSC/Prog-like score or higher GMP-like score, excluding patients with acute promyelocytic leukemia (APL). FIG. 29C-E. Top: heatmap shows expression of signature genes (rows) in 179 AML patients from the TCGA bulk expression cohort (columns). Bottom: Kaplan-Meier curves show the survival of AML patients that were stratified according to the heatmaps shown on top. Patients with a high HSC/Prog-like signature score showed a trend towards poor survival, and patients with a high GMP-like signature score showed significantly improved survival. However, the best result was obtained when combining these signatures (FIG. 21A). The lack of an association between the differentiated cell signature and outcome underscores the importance of primitive cells for disease progression. FIG. 29F. Top: Heatmaps show prediction scores for the indicated cell types (rows) for all malignant cells (columns) from five representative patients. Prediction scores were calculated by the first Random forest classifier. These heatmaps are also shown in FIGS. 20C and 28A. Bottom: Heatmaps show gene expression levels of malignant cell type-specific signature genes (180 genes). Cells are in the same ordering as in the top panel. Genes are in the same ordering as in FIG. 21C. Prototypic genetic alterations are indicated below the sample label. In general, the abundance of different malignant cell types in the single-cell data is in good agreement with the estimated abundance in bulk cohort samples with the same characterizing genetic alterations.

FIG. 30A-30G Differentiated AML cells suppress T-cell activation in vitro FIG. 30A. Top: heatmaps show RF prediction scores of cells (columns) for six primary tumor cell types (rows). Bottom: heatmaps show expression of genes (rows) in cells from the cell lines (columns). For every tumor cell type, we show expression of the top 20 most correlated genes in primary AML scRNA-seq. Cell cycle bar indicates expression of cell cycle genes (note that monocyte-like MUTZ-3 cells are post-mitotic). FIG. 30B. Left: Barplot shows the number of wells with sorted MUTZ-3 cells that generated new cultures. One-hundred or ten CD34$^+$ or CD14$^+$ cells were deposited in 96-well plate wells using flow cytometry. Positive wells were read out after 14 days. Right: Limiting dilution analysis of the results shown on top. For CD34$^+$ cells, 1/22 are estimated to display culture-initiation potential (95% confidence interval: 1/15-1/32). For CD14$^+$ cells, no estimate was possible (1/infinite). FIG. 30C. Images show upper left, negative control with no AML cells or beads, upper right, negative control with no beads, bottom left, positive control, not AML cells, and bottom right panel, co-culture of TCR/CD3 Effector cells, beads and AML cells; FIG. 30D. Flow cytometry plots show the purity of CD34$^+$ and CD14$^+$ cells that were sorted using magnetic columns. Although the purity did not reach the standards of populations sorted using flow cytometry, magnetic sorting improved performance in subsequent T-cell activation assays, potentially by inflicting less damage on the cells. FIG. 30E. Bar plots show the VAF of AML driver mutations in bulk (original clinical report) and sorted CD14+ AML cells as assessed by targeted DNA sequencing. FIG. 30F. Bar chart shows bulk RNA-seq signal in Jurkat cells for two positive control genes (GAPDH and CD3D) and four genes that have been implicated in immunosuppressive interactions (Austin et al., 2016; Wykes and Lewin, 2018). Tracks were visualized using the Integrative Genomics Viewer (IGV) and Jurkat RNA-seq data from ENCODE (Consortium, 2012). The absence of endogenous BTLA, CTLA4 and TIGIT expression in Jurkat cells is further supported by previous reports (Carreno et al., 2000; Jutz et al., 2017). FIG. 30G. Flow cytometry plots show OCI-AML3, first panel on far left, MUTZ-3, second panel, AML929, third panel, AML306, fourth panel, AML226, fifth panel and normal bone marrow (BM), sixth panel, far right.

FIG. 31 depicts the gene specific priming of adapter sequences approach used in the current methods, including the chimeric gene specific/universal adapter primer.

FIG. 32 is a schematic depicting the updated ultra low input cDNA synthesis process of the current methods. (Adapted from Trombetta et al. 2014).

FIG. 36 is a comparative marker selection showing increased BRAF and KIAA1549 expression after gene specific priming.

FIG. 37A-37B shows BRAF spike in increased reads spanning KIAA1549-BRAF fusion, FIG. 37A charts KIAA1549-BRAF Reads spanning fusion, FIG. 37B charts KIAA1549-BRAF Junction reads.

FIG. 38 shows STAR Fusion detector identified KIAA1549-BRAF, with called fusion in 6/7 samples with primer spike in.

Figure 1A:
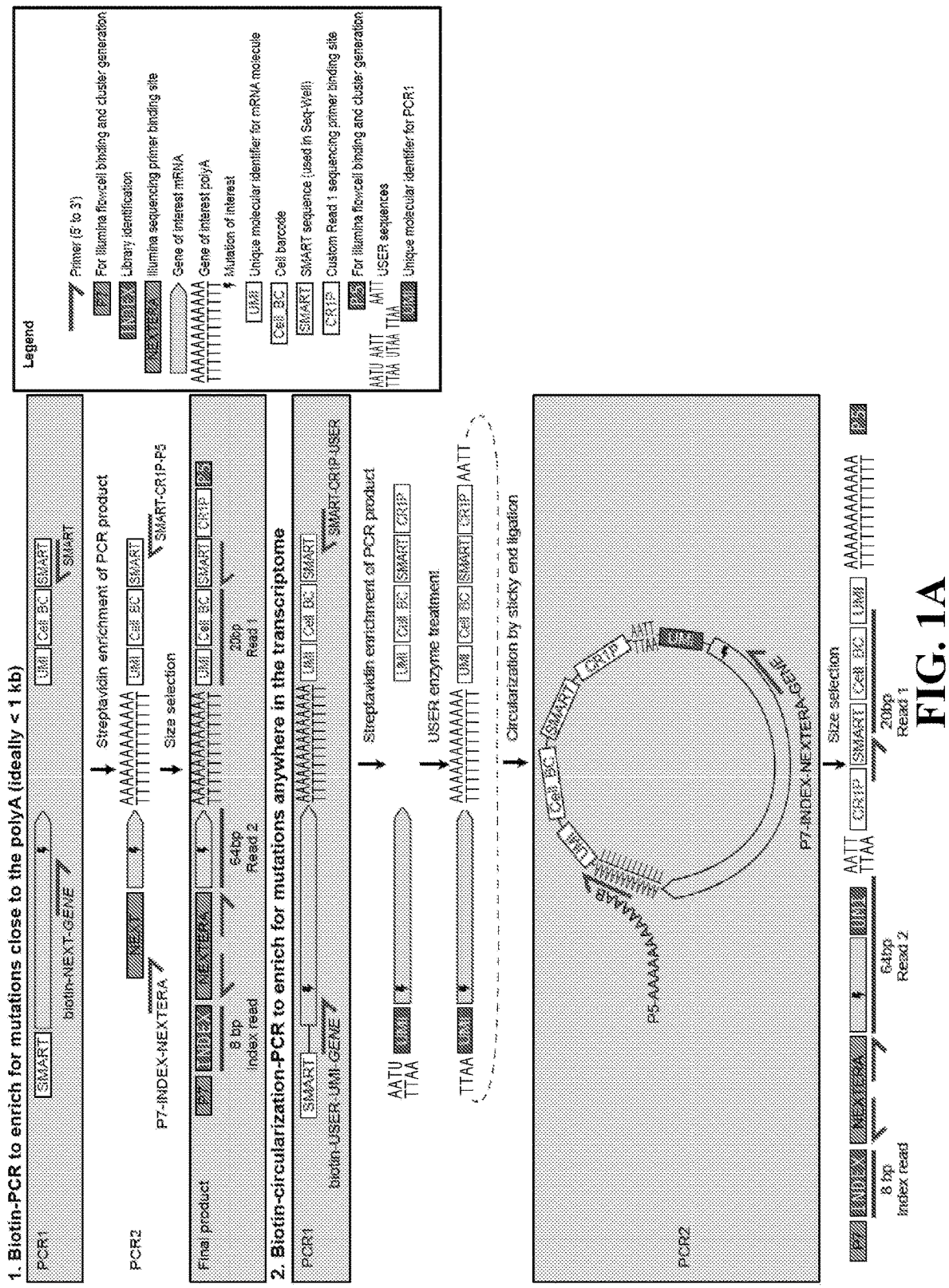
FIGS. 1A and 1B depict non-limiting graphical summaries of the PCR-based approach described herein to amplify genetic region(s) of interest.

The figures herein are for illustrative purposes only and are not necessarily drawn to scale.

DETAILED DESCRIPTION OF THE EXAMPLE EMBODIMENTS

General Definitions

Unless defined otherwise, technical and scientific terms used herein have the same meaning as commonly understood by one of ordinary skill in the art to which this disclosure pertains. Definitions of common terms and techniques in molecular biology may be found in Molecular Cloning: A Laboratory Manual, $2^{nd}$ edition (1989) (Sambrook, Fritsch, and Maniatis); Molecular Cloning: A Laboratory Manual, $4^{th}$ edition (2012) (Green and Sambrook); Current Protocols in Molecular Biology (1987) (F. M. Ausubel et al. eds.); the series Methods in Enzymology (Academic Press, Inc.): PCR 2: A Practical Approach (1995) (M. J. MacPherson, B. D. Hames, and G. R. Taylor eds.): Antibodies, A Laboratory Manual (1988) (Harlow and Lane, eds.): Antibodies, A Laboratory Manual, $2^{nd}$ edition 2013 (E. A. Greenfield ed.); Animal Cell Culture (1987) (R. I. Freshney, ed.); Benjamin Lewin, Genes IX, published by Jones and Bartlett, 2008 (ISBN 0763752223); Kendrew et al. (eds.), The Encyclopedia of Molecular Biology, published by Blackwell Science Ltd., 1994 (ISBN 0632021829); Robert A. Meyers (ed.). Molecular Biology and Biotechnology: a Comprehensive Desk Reference, published by VCH Publishers, Inc., 1995 (ISBN 9780471185710); Singleton et al., Dictionary of Microbiology and Molecular Biology $2^{nd}$ ed., J. Wiley & Sons (New York, N.Y. 1994), March, Advanced Organic Chemistry Reactions, Mechanisms and Structure $4^{th}$ ed., John Wiley & Sons (New York, N.Y. 1992); and Marten H. Hofker and Jan van Deursen, Transgenic Mouse Methods and Protocols, $2^{nd}$ edition (2011).

As used herein, the singular forms "a" "an", and "the" include both singular and plural referents unless the context clearly dictates otherwise.

The term "optional" or "optionally" means that the subsequent described event, circumstance or substituent may or may not occur, and that the description includes instances where the event or circumstance occurs and instances where it does not.

The recitation of numerical ranges by endpoints includes all numbers and fractions subsumed within the respective ranges, as well as the recited endpoints.

The terms "about" or "approximately" as used herein when referring to a measurable value such as a parameter, an amount, a temporal duration, and the like, are meant to encompass variations of and from the specified value, such as variations of +/−10% or less, +/−5% or less, +/−1% or less, and +/−0.1% or less of and from the specified value, insofar such variations are appropriate to perform in the disclosed invention. It is to be understood that the value to which the modifier "about" or "approximately" refers is itself also specifically, and preferably, disclosed.

As used herein, a "biological sample" may contain whole cells and/or live cells and/or cell debris. The biological sample may contain (or be derived from) a "bodily fluid". The present invention encompasses embodiments wherein the bodily fluid is selected from amniotic fluid, aqueous humour, vitreous humour, bile, blood serum, breast milk, cerebrospinal fluid, cerumen (earwax), chyle, chyme, endolymph, perilymph, exudates, feces, female ejaculate, gastric acid, gastric juice, lymph, mucus (including nasal drainage and phlegm), pericardial fluid, peritoneal fluid, pleural fluid, pus, rheum, saliva, sebum (skin oil), semen, sputum, synovial fluid, sweat, tears, urine, vaginal secretion, vomit and mixtures of one or more thereof. Biological samples include cell cultures, bodily fluids, cell cultures from bodily fluids. Bodily fluids may be obtained from a mammal organism, for example by puncture, or other collecting or sampling procedures.

The terms "subject," "individual," and "patient" are used interchangeably herein to refer to a vertebrate, preferably a mammal, more preferably a human. Mammals include, but are not limited to, murines, simians, humans, farm animals, sport animals, and pets. Tissues, cells and their progeny of a biological entity obtained in vivo or cultured in vitro are also encompassed.

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s). Reference throughout this specification to "one embodiment", "an embodiment," "an example embodiment," means that a particular feature, structure or characteristic described in connection with the embodiment is included in at least one embodiment of the present invention. Thus, appearances of the phrases "in one embodiment," "in an embodiment," or "an example embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention. For example, in the appended claims, any of the claimed embodiments can be used in any combination.

All publications, published patent documents, and patent applications cited herein are hereby incorporated by reference to the same extent as though each individual publication, published patent document, or patent application was specifically and individually indicated as being incorporated by reference.

Overview

Embodiments disclosed herein provide single-cell genotyping strategies to amplify nucleic acid targets of interest, including mutations in conjunction with cell barcodes. The methods disclosed herein allow matching of genotyping information to single-cell transcriptomes, utilizing whole transcriptome amplification libraries. As such, the methods disclosed herein enable an overlay of genetic information (such as cancer driver mutations) onto single-cell transcriptomes and concomitant identification of cells of interest within a larger population, including identification of even rare cells of interest by their genotype.

Embodiments disclosed herein include methods that enable single cell matched transcripts from a 3'-barcoded library when sequences of interest are located in the 5' end of the transcript. In some embodiments, the methods provide a more efficient manner of acquiring data from the variable region of T cell receptor α/β (TCR) and B cell receptor H/L chain (BCR) transcripts.

Enriched RNA Transcript Libraries

In an embodiment, the present invention provides a library of enriched single cell RNA transcripts comprising a plurality of nucleic acids comprising a cell barcode in close proximity to a desired transcript sequence of interest, the plurality of nucleic acids derived from a 3'barcoded single cell RNA library, wherein at least a subset of the plurality of nucleic acids in the library comprise transcripts of interest that are greater than 1 kb away from the cell barcode in the 3' barcoded single cell RNA library.

In some embodiments, the subset comprises transcript of interest wherein at least 1%, at least 5%, at least 10%, at least 20%, at least 25%, at least 30%, at least 35%, at least 40%, at least 45%, at least 50%, at least 55%, at least 60%, at least 65%, at least 70%, at least at least 80%, at least 90%, substantially all, or all of the transcripts in the 3' barcoded single cell RNA library are greater than 1kb away from the cell barcode.

In one aspect, a new library of desired transcripts is provided, particularly from the 5' side of transcripts, or portions of transcript distant from the 3' cell barcode of 3' barcoded single cell libraries such as, for example, a SeqWell library. The generated library contains desired transcripts, often enriched from low copy single cell sequencing, or from portions of a transcript that may be difficult to obtain in typical single-cell sequencing methods, while maintaining single cell identity. In some embodiments, the libraries contain variable regions of single cell matched T cell receptor α/β (TCR) or B cell receptor H/L chain (BCR) transcripts. In some embodiments, the library contains transcripts that are distant from the 3' cell barcode, in some instances the library contains transcripts greater than about 1 kb away from the 3' end of the transcript. The enriched libraries can be comprised of enrichment of transcripts containing gene mutations located anywhere in the genome.

A "library" or "fragment library" is a collection of nucleic acid molecules derived from one or more nucleic acid samples, in which fragments of nucleic acid have been modified, generally by incorporating terminal adapter sequences comprising one or more primer binding sites and identifiable sequence tags.

Single-Cell Library

A library of enriched single cell RNA transcripts is provided and may comprise a plurality of nucleic acids comprising a cell barcode and unique molecular identifier in close proximity to a desired transcript of interest, the plurality of nucleic acids derived from a 3'barcoded single cell RNA library, wherein at least a subset of the plurality of nucleic acids in the library comprise transcripts of interest that were greater than 1 kb away from the cell barcode in the 3' barcoded single cell RNA library.

Plurality of Nucleic Acids

The library provides a plurality of nucleic acids comprising a cell barcode, and a desired transcript of interest. In certain embodiments, the nucleic acids may further comprise a unique molecular identifier.

A nucleic acid molecule refers to any nucleic acid containing molecule, including but not limited to, DNA or RNA. The term encompasses sequences that include any of the known base analogs of DNA and RNA and may be from any source. Oligonucleotide or polynucleotide, which are generally used synonymously, mean a linear polymer of natural or modified nucleoside monomers linked by phosphodiester bonds or analogs thereof. The term "oligonucleotide" usually refers to a shorter polymer, e.g., comprising from about 3 to about 100 monomers, and the term "polynucleotide" usually refers to longer polymers, e.g., comprising from about 100 monomers to many thousands of monomers, e.g., 10,000 monomers, or more. Oligonucleotides comprising probes or primers usually have lengths in the range of from 12 to 60 nucleotides, and more usually, from 18 to 40 nucleotides. Oligonucleotides and polynucleotides may be natural or synthetic. Oligonucleotides and polynucleotides include deoxyribonucleosides, ribonucleosides, and non-natural analogs thereof, such as anomeric forms thereof, peptide nucleic acids (PNAs), and the like, provided that they are capable of specifically binding to a target genome by way of a regular pattern of monomer-to-monomer interactions, such as Watson-Crick type of base pairing, base stacking, Hoogsteen or reverse Hoogsteen types of base pairing, or the like.

Cell Barcode (cell BC) and Unique Molecular Identifier (UMI)

The present invention may encompass incorporation of a unique molecular identifier (UMI) (see, e.g., Kivioja et al., 2012, Nat. Methods. 9 (1): 72-4 and Islam et al., 2014, Nat.

Methods. 11 (2): 163-6) a unique cell barcode (cell BC) into the library, or both. The cell barcode as used herein refers to a short sequence of nucleotides (for example, DNA or RNA) that is used as an identifier for an associated molecule, such as a target molecule and/or target nucleic acid, or as an identifier of the source of an associated molecule, such as a cell-of-origin. A barcode may also refer to any unique, non-naturally occurring, nucleic acid sequence that may be used to identify the originating source of a nucleic acid fragment. Although it is not necessary to understand the mechanism of an invention, it is believed that the barcode sequence provides a high-quality individual read of a barcode associated with a single cell, a viral vector, labeling ligand (e.g., an aptamer), protein, shRNA, sgRNA or cDNA such that multiple species can be sequenced together.

Barcoding may be performed based on any of the compositions or methods disclosed in patent publication WO 2014047561 A1, Compositions and methods for labeling of agents, incorporated herein in its entirety. In certain embodiments barcoding uses an error correcting scheme (T. K. Moon, Error Correction Coding: Mathematical Methods and Algorithms (Wiley, New York, ed. 1, 2005)). Not being bound by a theory, amplified sequences from single cells can be sequenced together and resolved based on the barcode associated with each cell.

In preferred embodiments, sequencing is performed using unique molecular identifiers (UMI). The term "unique molecular identifiers" (UMI) as used herein refers to a sequencing linker or a subtype of nucleic acid barcode used in a method that uses molecular tags to detect and quantify unique amplified products. A UMI is used to distinguish effects through a single clone from multiple clones. The term "clone" as used herein may refer to a single mRNA or target nucleic acid to be sequenced. The UMI may also be used to determine the number of transcripts that gave rise to an amplified product, or in the case of target barcodes as described herein, the number of binding events. In preferred embodiments, the amplification is by PCR or multiple displacement amplification (MDA).

In certain embodiments, an UMI with a random sequence of between 4 and 20 base pairs is added to a template, which is amplified and sequenced. In preferred embodiments, the UMI is added to the 5' end of the template. Sequencing allows for high resolution reads, enabling accurate detection of true variants. As used herein, a "true variant" will be present in every amplified product originating from the original clone as identified by aligning all products with a UMI. Each clone amplified will have a different random UMI that will indicate that the amplified product originated from that clone. Background caused by the fidelity of the amplification process can be eliminated because true variants will be present in all amplified products and background representing random error will only be present in single amplification products (See e.g., Islam S. et al., 2014. Nature Methods No: 11, 163-166). Not being bound by a theory, the UMI's are designed such that assignment to the original can take place despite up to 4-7 errors during amplification or sequencing. Not being bound by a theory, an UMI may be used to discriminate between true barcode sequences.

Unique molecular identifiers can be used, for example, to normalize samples for variable amplification efficiency. For example, in various embodiments, featuring a solid or semisolid support (for example a hydrogel bead), to which nucleic acid barcodes (for example a plurality of barcodes sharing the same sequence) are attached, each of the barcodes may be further coupled to a unique molecular identifier, such that every barcode on the particular solid or semisolid support receives a distinct unique molecule identifier. A unique molecular identifier can then be, for example, transferred to a target molecule with the associated barcode, such that the target molecule receives not only a nucleic acid barcode, but also an identifier unique among the identifiers originating from that solid or semisolid support.

A nucleic acid barcode or UMI can have a length of at least, for example, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, or 100 nucleotides, and can be in single- or double-stranded form. Target molecule and/or target nucleic acids can be labeled with multiple nucleic acid barcodes in combinatorial fashion, such as a nucleic acid barcode concatemer. Typically, a nucleic acid barcode is used to identify a target molecule and/or target nucleic acid as being from a particular discrete volume, having a particular physical property (for example, affinity, length, sequence, etc.), or having been subject to certain treatment conditions. Target molecule and/or target nucleic acid can be associated with multiple nucleic acid barcodes to provide information about all of these features (and more). Each member of a given population of UMIs, on the other hand, is typically associated with (for example, covalently bound to or a component of the same molecule as) individual members of a particular set of identical, specific (for example, discreet volume-, physical property-, or treatment condition-specific) nucleic acid barcodes. Thus, for example, each member of a set of origin-specific nucleic acid barcodes, or other nucleic acid identifier or connector oligonucleotide, having identical or matched barcode sequences, may be associated with (for example, covalently bound to or a component of the same molecule as) a distinct or different UMI.

As disclosed herein, unique nucleic acid identifiers are used to label the target molecules and/or target nucleic acids, for example origin-specific barcodes and the like. The nucleic acid identifiers, nucleic acid barcodes, can include a short sequence of nucleotides that can be used as an identifier for an associated molecule, location, or condition. In certain embodiments, the nucleic acid identifier further includes one or more unique molecular identifiers and/or barcode receiving adapters. A nucleic acid identifier can have a length of about, for example, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, or 100 base pairs (bp) or nucleotides (nt). In certain embodiments, a nucleic acid identifier can be constructed in combinatorial fashion by combining randomly selected indices (for example, about 1, 2, 3, 4, 5, 6, 7, 8, 9, or 10 indexes). Each such index is a short sequence of nucleotides (for example, DNA, RNA, or a combination thereof) having a distinct sequence. An index can have a length of about, for example, 4, 5, 6, 7, 8, 9, 10, 11, 12, 13, 14, 15, 16, 17, 18, 19, 20, 21, 22, 23, 24, or 25 bp or nt. Nucleic acid identifiers can be generated, for example, by split-pool synthesis methods, such as those described, for example, in International Patent Publication Nos. WO 2014/047556 and WO 2014/143158, each of which is incorporated by reference herein in its entirety.

One or more nucleic acid identifiers (for example a nucleic acid barcode) can be attached, or "tagged," to a target molecule. This attachment can be direct (for example, covalent or noncovalent binding of the nucleic acid identifier to the target molecule) or indirect (for example, via an additional molecule). Such indirect attachments may, for example, include a barcode bound to a specific-binding agent that recognizes a target molecule. In certain embodiments, a barcode is attached to protein G and the target molecule is an antibody or antibody fragment. Attachment of a barcode to target molecules (for example, proteins and other biomolecules) can be performed using standard methods well known in the art. For example, barcodes can be linked via cysteine residues (for example, C-terminal cysteine residues). In other examples, barcodes can be chemically introduced into polypeptides (for example, antibodies) via a variety of functional groups on the polypeptide using appropriate group-specific reagents (see for example www.drmr.com/abcon). In certain embodiments, barcode tagging can occur via a barcode receiving adapter associate with (for example, attached to) a target molecule, as described herein.

Target molecules can be optionally labeled with multiple barcodes in combinatorial fashion (for example, using multiple barcodes bound to one or more specific binding agents that specifically recognizing the target molecule), thus greatly expanding the number of unique identifiers possible within a particular barcode pool. In certain embodiments, barcodes are added to a growing barcode concatemer attached to a target molecule, for example, one at a time. In other embodiments, multiple barcodes are assembled prior to attachment to a target molecule. Compositions and methods for concatemerization of multiple barcodes are described, for example, in International Patent Publication No. WO 2014/047561, which is incorporated herein by reference in its entirety.

In some embodiments, a nucleic acid identifier (for example, a nucleic acid barcode) may be attached to sequences that allow for amplification and sequencing (for example, SBS3 and P5 elements for Illumina sequencing). In certain embodiments, a nucleic acid barcode can further include a hybridization site for a primer (for example, a single-stranded DNA primer) attached to the end of the barcode. For example, an origin-specific barcode may be a nucleic acid including a barcode and a hybridization site for a specific primer. In particular embodiments, a set of origin-specific barcodes includes a unique primer specific barcode made, for example, using a randomized oligo type NNNNNNNNNNNN.

A nucleic acid identifier can further include a unique molecular identifier and/or additional barcodes specific to, for example, a common support to which one or more of the nucleic acid identifiers are attached. Thus, a pool of target molecules can be added, for example, to a discrete volume containing multiple solid or semisolid supports (for example, beads) representing distinct treatment conditions (and/or, for example, one or more additional solid or semisolid support can be added to the discreet volume sequentially after introduction of the target molecule pool), such that the precise combination of conditions to which a given target molecule was exposed can be subsequently determined by sequencing the unique molecular identifiers associated with it.

Labeled target molecules and/or target nucleic acids associated origin-specific nucleic acid barcodes (optionally in combination with other nucleic acid barcodes as described herein) can be amplified by methods known in the art, such as polymerase chain reaction (PCR). For example, the nucleic acid barcode can contain universal primer recognition sequences that can be bound by a PCR primer for PCR amplification and subsequent high-throughput sequencing. In certain embodiments, the nucleic acid barcode includes or is linked to sequencing adapters (for example, universal primer recognition sequences) such that the barcode and sequencing adapter elements are both coupled to the target molecule. In particular examples, the sequence of the origin specific barcode is amplified, for example using PCR. In some embodiments, an origin-specific barcode further comprises a sequencing adaptor. In some embodiments, an origin-specific barcode further comprises universal priming sites. A nucleic acid barcode (or a concatemer thereof), a target nucleic acid molecule (for example, a DNA or RNA molecule), a nucleic acid encoding a target peptide or polypeptide, and/or a nucleic acid encoding a specific binding agent may be optionally sequenced by any method known in the art, for example, methods of high-throughput sequencing, also known as next generation sequencing or deep sequencing. A nucleic acid target molecule labeled with a barcode (for example, an origin-specific barcode) can be sequenced with the barcode to produce a single read and/or contig containing the sequence, or portions thereof, of both the target molecule and the barcode. Exemplary next generation sequencing technologies include, for example, Illumina sequencing, Ion Torrent sequencing, 454 sequencing, SOLiD sequencing, and nanopore sequencing amongst others. In some embodiments, the sequence of labeled target molecules is determined by non-sequencing based methods. For example, variable length probes or primers can be used to distinguish barcodes (for example, origin-specific barcodes) labeling distinct target molecules by, for example, the length of the barcodes, the length of target nucleic acids, or the length of nucleic acids encoding target polypeptides. In other instances, barcodes can include sequences identifying, for example, the type of molecule for a particular target molecule (for example, polypeptide, nucleic acid, small molecule, or lipid). For example, in a pool of labeled target molecules containing multiple types of target molecules, polypeptide target molecules can receive one identifying sequence, while target nucleic acid molecules can receive a different identifying sequence. Such identifying sequences can be used to selectively amplify barcodes labeling particular types of target molecules, for example, by using PCR primers specific to identifying sequences specific to particular types of target molecules. For example, barcodes labeling polypeptide target molecules can be selectively amplified from a pool, thereby retrieving only the barcodes from the polypeptide subset of the target molecule pool.

A nucleic acid barcode can be sequenced, for example, after cleavage, to determine the presence, quantity, or other feature of the target molecule. In certain embodiments, a nucleic acid barcode can be further attached to a further nucleic acid barcode. For example, a nucleic acid barcode can be cleaved from a specific-binding agent after the specific-binding agent binds to a target molecule or a tag (for example, an encoded polypeptide identifier element cleaved from a target molecule), and then the nucleic acid barcode can be ligated to an origin-specific barcode. The resultant nucleic acid barcode concatemer can be pooled with other such concatemers and sequenced. The sequencing reads can be used to identify which target molecules were originally present in which discrete volumes.

Barcodes Reversibly Coupled to Solid Substrate

In some embodiments, the origin-specific barcodes can be reversibly coupled to a solid or semisolid substrate. In some embodiments, the origin-specific barcodes further comprise a nucleic acid capture sequence that specifically binds to the target nucleic acids and/or a specific binding agent that specifically binds to the target molecules. In specific embodiments, the origin-specific barcodes include two or more populations of origin-specific barcodes, wherein a first population comprises the nucleic acid capture sequence and a second population comprises the specific binding agent that specifically binds to the target molecules. In some examples, the first population of origin-specific barcodes further comprises a target nucleic acid barcode, wherein the target nucleic acid barcode identifies the population as one that labels nucleic acids. In some examples, the second population of origin-specific barcodes further comprises a target molecule barcode, wherein the target molecule barcode identifies the population as one that labels target molecules.

Barcode with Cleavage Sites

A nucleic acid barcode may be cleavable from a specific binding agent, for example, after the specific binding agent has bound to a target molecule. In some embodiments, the origin-specific barcode further comprises one or more cleavage sites. In some examples, at least one cleavage site is oriented such that cleavage at that site releases the origin-specific barcode from a substrate, such as a bead, for example a hydrogel bead, to which it is coupled. In some examples, at least one cleavage site is oriented such that the cleavage at the site releases the origin-specific barcode from the target molecule specific binding agent. In some examples, a cleavage site is an enzymatic cleavage site, such an endonuclease site present in a specific nucleic acid sequence. In other embodiments, a cleavage site is a peptide cleavage site, such that a particular enzyme can cleave the amino acid sequence. In still other embodiments, a cleavage site is a site of chemical cleavage.

Barcode Adapters

In some embodiments, the target molecule is attached to an origin-specific barcode receiving adapter, such as a nucleic acid. In some examples, the origin-specific barcode receiving adapter comprises an overhang and the origin-specific barcode comprises a sequence capable of hybridizing to the overhang. A barcode receiving adapter is a molecule configured to accept or receive a nucleic acid barcode, such as an origin-specific nucleic acid barcode. For example, a barcode receiving adapter can include a single-stranded nucleic acid sequence (for example, an overhang) capable of hybridizing to a given barcode (for example, an origin-specific barcode), for example, via a sequence complementary to a portion or the entirety of the nucleic acid barcode. In certain embodiments, this portion of the barcode is a standard sequence held constant between individual barcodes. The hybridization couples the barcode receiving adapter to the barcode. In some embodiments, the barcode receiving adapter may be associated with (for example, attached to) a target molecule. As such, the barcode receiving adapter may serve as the means through which an origin-specific barcode is attached to a target molecule. A barcode receiving adapter can be attached to a target molecule according to methods known in the art. For example, a barcode receiving adapter can be attached to a polypeptide target molecule at a cysteine residue (for example, a C-terminal cysteine residue). A barcode receiving adapter can be used to identify a particular condition related to one or more target molecules, such as a cell of origin or a discreet volume of origin. For example, a target molecule can be a cell surface protein expressed by a cell, which receives a cell-specific barcode receiving adapter. The barcode receiving adapter can be conjugated to one or more barcodes as the cell is exposed to one or more conditions, such that the original cell of origin for the target molecule, as well as each condition to which the cell was exposed, can be subsequently determined by identifying the sequence of the barcode receiving adapter/barcode concatemer.

Barcode with Capture Moiety

In some embodiments, an origin-specific barcode further includes a capture moiety, covalently or non-covalently linked. Thus, in some embodiments the origin-specific barcode, and anything bound or attached thereto, that include a capture moiety are captured with a specific binding agent that specifically binds the capture moiety. In some embodiments, the capture moiety is adsorbed or otherwise captured on a surface. In specific embodiments, a targeting probe is labeled with biotin, for instance by incorporation of biotin-16-UTP during in vitro transcription, allowing later capture by streptavidin. Other means for labeling, capturing, and detecting an origin-specific barcode include: incorporation of aminoallyl-labeled nucleotides, incorporation of sulfhydryl-labeled nucleotides, incorporation of allyl- or azide-containing nucleotides, and many other methods described in Bioconjugate Techniques ($2^{nd}$ Ed), Greg T. Hermanson, Elsevier (2008), which is specifically incorporated herein by reference. In some embodiments, the targeting probes are covalently coupled to a solid support or other capture device prior to contacting the sample, using methods such as incorporation of aminoallyl-labeled nucleotides followed by 1-Ethyl-3-(3-dimethylaminopropyl)carbodiimide (EDC) coupling to a carboxy-activated solid support, or other methods described in Bioconjugate Techniques. In some embodiments, the specific binding agent has been immobilized for example on a solid support, thereby isolating the origin-specific barcode.

Other Barcoding Embodiments

DNA barcoding is also a taxonomic method that uses a short genetic marker in an organism's DNA to identify it as belonging to a particular species. It differs from molecular phylogeny in that the main goal is not to determine classification but to identify an unknown sample in terms of a known classification. Kress et al., "Use of DNA barcodes to identify flowering plants" Proc. Natl. Acad. Sci. U.S.A. 102(23):8369-8374 (2005). Barcodes are sometimes used in an effort to identify unknown species or assess whether species should be combined or separated. Koch H., "Combining morphology and DNA barcoding resolves the taxonomy of Western Malagasy Liotrigona Moure, 1961" African Invertebrates 51(2): 413-421 (2010); and Seberg et al., "How many loci does it take to DNA barcode a crocus?" PLoS One 4(2):e4598 (2009). Barcoding has been used, for example, for identifying plant leaves even when flowers or fruit are not available, identifying the diet of an animal based on stomach contents or feces, and/or identifying products in commerce (for example, herbal supplements or wood). Soininen et al., "Analysing diet of small herbivores: the efficiency of DNA barcoding coupled with high-throughput pyrosequencing for deciphering the composition of complex plant mixtures" Frontiers in Zoology 6:16 (2009).

It has been suggested that a desirable locus for DNA barcoding should be standardized so that large databases of sequences for that locus can be developed. Most of the taxa of interest have loci that are sequencable without species-specific PCR primers. CBOL Plant Working Group, "A DNA barcode for land plants" PNAS 106(31):12794-12797 (2009). Further, these putative barcode loci are believed short enough to be easily sequenced with current technology. Kress et al., "DNA barcodes: Genes, genomics, and bioinformatics" PNAS 105(8):2761-2762 (2008). Consequently, these loci would provide a large variation between species in combination with a relatively small amount of variation within a species. Lahaye et al., "DNA barcoding the floras of biodiversity hotspots" Proc Natl Acad Sci USA 105(8): 2923-2928 (2008).

DNA barcoding is based on a relatively simple concept. For example, most eukaryote cells contain mitochondria, and mitochondrial DNA (mtDNA) has a relatively fast mutation rate, which results in significant variation in mtDNA sequences between species and, in principle, a comparatively small variance within species. A 648-bp region of the mitochondrial cytochrome c oxidase subunit 1 (CO1) gene was proposed as a potential 'barcode'. As of 2009, databases of CO1 sequences included at least 620,000 specimens from over 58,000 species of animals, larger than databases available for any other gene. Ausubel, J., "A botanical macroscope" Proceedings of the National Academy of Sciences 106(31):12569 (2009).

Software for DNA barcoding requires integration of a field information management system (FIMS), laboratory information management system (LIMS), sequence analysis tools, workflow tracking to connect field data and laboratory data, database submission tools and pipeline automation for scaling up to eco-system scale projects. Geneious Pro can be used for the sequence analysis components, and the two plugins made freely available through the Moorea Biocode Project, the Biocode LIMS and Genbank Submission plugins handle integration with the FIMS, the LIMS, workflow tracking and database submission.

Additionally, other barcoding designs and tools have been described (see e.g., Birrell et al., (2001) Proc. Natl Acad. Sci. USA 98, 12608-12613; Giaever, et al., (2002) Nature 418, 387-391; Winzeler et al., (1999) Science 285, 901-906; and Xu et al., (2009) Proc Natl Acad Sci USA. February 17; 106(7):2289-94).

Unique Molecular Identifiers are short (usually 4-10 bp) random barcodes added to transcripts during reverse-transcription. They enable sequencing reads to be assigned to individual transcript molecules and thus the removal of amplification noise and biases from RNA-seq data. Since the number of unique barcodes (4N, N-length of UMI) is much smaller than the total number of molecules per cell (~106), each barcode will typically be assigned to multiple transcripts. Hence, to identify unique molecules both barcode and mapping location (transcript) must be used. UMI-sequencing typically consists of paired-end reads where one read from each pair captures the cell and UMI barcodes while the other read consists of exonic sequence from the transcript. UMI-sequencing typically consists of paired-end reads where one read from each pair captures the cell and UMI barcodes while the other read consists of exonic sequence from the transcript.

In some embodiments, the nucleic acids of the library are flanked by switching mechanism at 5' end of RNA templates (SMART). SMART is a technology that allows the efficient incorporation of known sequences at both ends of cDNA during first strand synthesis, without adaptor ligation. The presence of these known sequences is crucial for a number of downstream applications including amplification, RACE, and library construction. While a wide variety of technologies can be employed to take advantage of these known sequences, the simplicity and efficiency of the single-step SMART process permits unparalleled sensitivity and ensures that full-length cDNA is generated and amplified. (see, e.g., Zhu et al., 2001, Biotechniques. 30 (4): 892-7.

After processing the reads from a UMI experiment, the following conventions are often used: 1. The UMI is added to the read name of the other paired read. 2. Reads are sorted into separate files by cell barcode. For extremely large, shallow datasets, a cell barcode may be added to the read name as well to reduce the number of files. A cell barcode indicates the cell from which mRNA is captured (e.g., Drop-Seq or Seq-Well).

Sequencing Adapters

As used herein, sequence adapters or sequencing adapters or adapters include primers that may include additional sequences involved in for example, but not limited to, flowcell binding, cluster generation, library generation, sequencing primers, sequences for Seq-Well, and/or custom read sequencing primers. Universal primer recognition sequences.

The present invention may encompass incorporation of SMART sequences into the library. Switching mechanism at 5' end of RNA template (SMART) is a technology that allows the efficient incorporation of known sequences at both ends of cDNA during first strand synthesis, without adaptor ligation. The presence of these known sequences is crucial for a number of downstream applications including amplification, RACE, and library construction. While a wide variety of technologies can be employed to take advantage of these known sequences, the simplicity and efficiency of the single-step SMART process permits unparalleled sensitivity and ensures that full-length cDNA is generated and amplified. (see, e.g., Zhu et al., 2001, Biotechniques. 30 (4): 892-7.

A pooled set of nucleic acids that are tagged refer to a plurality of nucleic acid molecules that results from incorporating an identifiable sequence tag into a pool of sample-tagged nucleic acids, by any of various methods. In some embodiments, the tag serves instead as a minimal sequence adapter for adding nucleic acids onto sample-tagged nucleic acids, rendering the pool compatible with a particular DNA sequencing platform or amplification strategy.

3' Barcoded Single Cell RNA Library

The 3' barcoded single cell RNA library includes a plurality of nucleic acids, each nucleic acid including a gene of interest, a unique molecular identifier (UMI) and a cell barcode (cell BC). The cell barcode is located on the 3' end of the transcript. As the single cell RNA library comprises a cell barcode on the 3' end of the transcripts, at least a subset of the library from the 3' barcoded single cell RNA library contains a transcript of interest at least 1 kb away from the 3' end of the transcript. The 5' side of transcripts are typically underrepresented in standard 3' barcoded libraries.

In a preferred embodiment, each nucleic acid sequence is flanked by switching mechanism at 5' end of RNA template (SMART) sequences at the 5' end and 3' end, that is, in this embodiment, an exemplary nucleic acid in the library would be 5' SMART-genetic region of interest-UMI-Cell BC-SMART 3'.

Multiple technologies have been described that massively parallelize the generation of single cell RNA seq libraries that can be used in the present disclosure. As used herein, RNA-seq methods refer to high-throughput single-cell RNA-sequencing protocols. RNA-seq includes, but is not limited to, Drop-seq, Seq-Well, InDrop and 1Cell Bio. RNA-seq methods also include, but are not limited to, smart-seq2, TruSeq, CEL-Seq, STRT, ChIRP-Seq, GRO-Seq, CLIP-Seq, Quartz-Seq, or any other similar method known in the art (see, e.g., "Sequencing Methods Review" Illumina® Technology, Sequencing Methods Review available at illumina.com.

In certain embodiments, the invention involves plate based single cell RNA sequencing (see, e.g., Picelli, S. et al., 2014, "Full-length RNA-seq from single cells using Smart-seq2" Nature protocols 9, 171-181, doi:10.1038/nprot.2014.006).

Drop-sequence methods or Drop-seq are contemplated for the present invention. Cells come in different types, sub-types and activity states, which are classify based on their shape, location, function, or molecular profiles, such as the set of RNAs that they express. RNA profiling is in principle particularly informative, as cells express thousands of different RNAs. Approaches that measure for example the level of every type of RNA have until recently been applied to "homogenized" samples—in which the contents of all the cells are mixed together. Methods to profile the RNA content of tens and hundreds of thousands of individual human cells have been recently developed, including from brain tissues, quickly and inexpensively. To do so, special microfluidic devices have been developed to encapsulate each cell in an individual drop, associate the RNA of each cell with a 'cell barcode' unique to that cell/drop, measure the expression level of each RNA with sequencing, and then use the cell barcodes to determine which cell each RNA molecule came from. See, e.g., methods of Macosko et al., 2015, Cell 161, 1202-1214 and Klein et al., 2015, Cell 161, 1187-1201 are contemplated for the present invention.

In certain embodiments, the invention involves high-throughput single-cell RNA-seq and/or targeted nucleic acid profiling (for example, sequencing, quantitative reverse transcription polymerase chain reaction, and the like) where the RNAs from different cells are tagged individually, allowing a single library to be created while retaining the cell identity of each read. In this regard reference is made to Macosko et al., 2015, "Highly Parallel Genome-wide Expression Profiling of Individual Cells Using Nanoliter Droplets" Cell 161, 1202-1214; International patent application number PCT/US2015/049178, published as WO2016/040476 on Mar. 17, 2016; Klein et al., 2015, "Droplet Barcoding for Single-Cell Transcriptomics Applied to Embryonic Stem Cells" Cell 161, 1187-1201; International patent application number PCT/US2016/027734, published as WO2016168584A1 on Oct. 20, 2016; Zheng, et al., 2016, "Haplotyping germline and cancer genomes with high-throughput linked-read sequencing" Nature Biotechnology 34, 303-311; Zheng, et al., 2017, "Massively parallel digital transcriptional profiling of single cells" Nat. Commun. 8, 14049 doi: 10.1038/ncomms14049; International patent publication number WO2014210353A2; Zilionis, et al., 2017, "Single-cell barcoding and sequencing using droplet microfluidics" Nat Protoc. January; 12(1):44-73; Cao et al., 2017, "Comprehensive single cell transcriptional profiling of a multicellular organism by combinatorial indexing" bioRxiv preprint first posted online Feb. 2, 2017, doi: dx.doi.org/10.1101/104844; Rosenberg et al., 2017, "Scaling single cell transcriptomics through split pool barcoding" bioRxiv preprint first posted online Feb. 2, 2017, doi: dx.doi.org/10.1101/105163; Vitak, et al., "Sequencing thousands of single-cell genomes with combinatorial indexing" Nature Methods, 14(3):302-308, 2017; Cao, et al., Comprehensive single-cell transcriptional profiling of a multicellular organism. Science, 357(6352):661-667, 2017; and Gierahn et al., "Seq-Well: portable, low-cost RNA sequencing of single cells at high throughput" Nature Methods 14, 395-398 (2017), all the contents and disclosure of each of which are herein incorporated by reference in their entirety.

In certain embodiments, the invention involves single nucleus RNA sequencing. In this regard reference is made to Swiech et al., 2014, "In vivo interrogation of gene function in the mammalian brain using CRISPR-Cas9" Nature Biotechnology Vol. 33, pp. 102-106; Habib et al., 2016, "Div-Seq: Single-nucleus RNA-Seq reveals dynamics of rare adult newborn neurons" Science, Vol. 353, Issue 6302, pp. 925-928; Habib et al., 2017, "Massively parallel single-nucleus RNA-seq with DroNc-seq" Nat Methods. 2017 October; 14(10):955-958; and International patent application number PCT/US2016/059239, published as WO2017164936 on Sep. 28, 2017, which are herein incorporated by reference in their entirety.

Microfluidics involves micro-scale devices that handle small volumes of fluids. Because microfluidics may accurately and reproducibly control and dispense small fluid volumes, in particular volumes less than 1 µl, application of microfluidics provides significant cost-savings. The use of microfluidics technology reduces cycle times, shortens time-to-results, and increases throughput. Furthermore, incorporation of microfluidics technology enhances system integration and automation. Microfluidic reactions are generally conducted in microdroplets or microwells. The ability to conduct reactions in microdroplets depends on being able to merge different sample fluids and different microdroplets. See, e.g., US Patent Publication No. 20120219947. See also international patent application serial no. PCT/US2014/058637 for disclosure regarding a microfluidic laboratory on a chip.

Droplet/microwell microfluidics offers significant advantages for performing high-throughput screens and sensitive assays. Droplets allow sample volumes to be significantly reduced, leading to concomitant reductions in cost. Manipulation and measurement at kilohertz speeds enable up to 108 discrete biological entities (including, but not limited to, individual cells or organelles) to be screened in a single day. Compartmentalization in droplets increases assay sensitivity by increasing the effective concentration of rare species and decreasing the time required to reach detection thresholds. Droplet microfluidics combines these powerful features to enable currently inaccessible high-throughput screening applications, including single-cell and single-molecule assays. See, e.g., Guo et al., Lab Chip, 2012,12, 2146-2155.

Drop-Sequence methods and apparatus provides a high-throughput single-cell RNA-Seq and/or targeted nucleic acid profiling (for example, sequencing, quantitative reverse transcription polymerase chain reaction, and the like) where the RNAs from different cells are tagged individually, allowing a single library to be created while retaining the cell identity of each read. A combination of molecular barcoding and emulsion-based microfluidics to isolate, lyse, barcode, and prepare nucleic acids from individual cells in high-throughput is used. Microfluidic devices (for example, fabricated in polydimethylsiloxane), sub-nanoliter reverse emulsion droplets. These droplets are used to co-encapsulate nucleic acids with a barcoded capture bead. Each bead, for example, is uniquely barcoded so that each drop and its contents are distinguishable. The nucleic acids may come from any source known in the art, such as for example, those which come from a single cell, a pair of cells, a cellular lysate, or a solution. The cell is lysed as it is encapsulated in the droplet. To load single cells and barcoded beads into these droplets with Poisson statistics, 100,000 to 10 million such beads are needed to barcode ~10,000-100,000 cells.

InDrop™, also known as in-drop seq, involves a high-throughput droplet-microfluidic approach for barcoding the RNA from thousands of individual cells for subsequent analysis by next-generation sequencing (see, e.g., Klein et al., Cell 161(5), pp 1187-1201, 21 May 2015). Specifically, in in-drop seq, one may use a high diversity library of barcoded primers to uniquely tag all DNA that originated from the same single cell. Alternatively, one may perform all steps in drop.

Well-based biological analysis or Seq-Well is also contemplated for the present invention. The well-based biological analysis platform, also referred to as Seq-well, facilitates the creation of barcoded single-cell sequencing libraries from thousands of single cells using a device that contains 100,000 40-micron wells. Importantly, single beads can be loaded into each microwell with a low frequency of duplicates due to size exclusion (average bead diameter 35 µm). By using a microwell array, loading efficiency is greatly increased compared to drop-seq, which requires poisson loading of beads to avoid duplication at the expense of increased cell input requirements. Seq-well, however, is capable of capturing nearly 100% of cells applied to the surface of the device.

Seq-well is a methodology which allows attachment of a porous membrane to a container in conditions which are benign to living cells. Combined with arrays of picoliter-scale volume containers made, for example, in PDMS, the platform provides the creation of hundreds of thousands of isolated dialysis chambers which can be used for many different applications. The platform also provides single cell lysis procedures for single cell RNA-seq, whole genome amplification or proteome capture; highly multiplexed single cell nucleic acid preparation (~100× increase over current approaches); highly parallel growth of clonal bacterial populations thus providing synthetic biology applications as well as basic recombinant protein expression; selection of bacterial that have increased secretion of a recombinant product possible product could also be small molecule metabolite which could have considerable utility in chemical industry and biofuels; retention of cells during multiple microengraving events; long term capture of secreted products from single cells; and screening of cellular events. Principles of the present methodology allow for addition and subtraction of materials from the containers, which has not previously been available on the present scale in other modalities.

Seq-Well also enables stable attachment (through multiple established chemistries) of porous membranes to PDMS nanowell devices in conditions that do not affect cells. Based on requirements for downstream assays, amines are functionalized to the PDMS device and oxidized to the membrane with plasma. With regard to general cell culture uses, the PDMS is amine functionalized by air plasma treatment followed by submersion in an aqueous solution of poly (lysine) followed by baking at 80° C. For processes that require robust denaturing conditions, the amine must be covalently linked to the surface. This is accomplished by treating the PDMS with air plasma, followed by submersion in an ethanol solution of amine-silane, followed by baking at 80° C., followed by submersion in 0.2% phenylene diisothiocyanate (PDITC) DMF/pyridine solution, followed by baking, followed by submersion in chitosan or poly (lysine) solution. For functionalization of the membrane for protein capture, membrane can be amine-silanized using vapor deposition and then treated in solution with NHS-biotin or NHS-maleimide to turn the amine groups into the crosslinking species.

After functionalization, the device is loaded with cells (bacterial, mammalian or yeast) in compatible buffers. The cell-laden device is then brought in contact with the functionalized membrane using a clamping device. A plain glass slide is placed on top of the membrane in the clamp to provide force for bringing the two surfaces together. After an hour incubation, as one hour is a preferred time span, the clamp is opened and the glass slide is removed. The device can then be submerged in any aqueous buffer for days without the membrane detaching, enabling repetitive measurements of the cells without any cell loss. The covalently-linked membrane is stable in many harsh buffers including guanidine hydrochloride which can be used to robustly lyse cells. If the pore size of the membrane is small, the products from the lysed cells will be retained in each well. The lysing buffer can be washed out and replaced with a different buffer which allows binding of biomolecules to probes preloaded in the wells. The membrane can then be removed, enabling addition of enzymes to reverse transcribe or amplify nucleic acids captured in the wells after lysis. Importantly, the chemistry enables removal of one membrane and replacement with a membrane with a different pore size to enable integration of multiple activities on the same array.

As discussed, while the platform has been optimized for the generation of individually barcoded single-cell sequencing libraries following confinement of cells and mRNA capture beads (Macosko, et al. Cell. 2015 May 21; 161(5): 1202-1214), it is capable of multiple levels of data acquisition. The platform is compatible with other assays and measurements performed with the same array. For example, profiling of human antibody responses by integrated single-cell analysis is discussed with regard to measuring levels of cell surface proteins (Ogunniyi, A. O., B. A. Thomas, T. J. Politano, N. Varadarajan, E. Landais, P. Poignard, B. D. Walker, D. S. Kwon, and J. C. Love, "Profiling Human Antibody Responses by Integrated Single-Cell Analysis" Vaccine, 32(24), 2866-2873.) The authors demonstrate a complete characterization of the antigen-specific B cells induced during infections or following vaccination, which enables and informs one of skill in the art how interventions shape protective humoral responses. Specifically, this disclosure combines single-cell profiling with on-chip image cytometry, microengraving, and single-cell RT-PCR.

The invention provides a method for creating a single-cell sequencing library comprising: merging one uniquely barcoded mRNA capture microbead with a single-cell in an emulsion droplet having a diameter of 75-125 µm; lysing the cell to make its RNA accessible for capturing by hybridization onto RNA capture microbead; performing a reverse transcription either inside or outside the emulsion droplet to convert the cell's mRNA to a first strand cDNA that is covalently linked to the mRNA capture microbead; pooling the cDNA-attached microbeads from all cells; and preparing and sequencing a single composite RNA-Seq library.

The invention provides a method for preparing uniquely barcoded mRNA capture microbeads, which has a unique barcode and diameter suitable for microfluidic devices comprising: 1) performing reverse phosphoramidite synthesis on the surface of the bead in a pool-and-split fashion, such that in each cycle of synthesis the beads are split into four reactions with one of the four canonical nucleotides (T, C, G, or A) or unique oligonucleotides of length two or more bases; 2) repeating this process a large number of times, at least two, and optimally more than twelve, such that, in the latter, there are more than 16 million unique barcodes on the surface of each bead in the pool. (See http://www.ncbi.nlm.nih.gov/pmc/articles/PMC206447)

In another embodiment, the invention encompasses making beads specific to the panel of desired mutations or mutations plus mRNA and a capture of both. In one embodiment, one or more mutation hot spots may be near the 3' end.

Generally, the invention provides a method for preparing a large number of beads, particles, microbeads, nanoparticles, or the like with unique nucleic acid barcodes comprising performing polynucleotide synthesis on the surface of the beads in a pool-and-split fashion such that in each cycle of synthesis the beads are split into subsets that are subjected to different chemical reactions; and then repeating this split-pool process in two or more cycles, to produce a combinatorially large number of distinct nucleic acid barcodes. Invention further provides performing a polynucleotide synthesis wherein the synthesis may be any type of synthesis known to one of skill in the art for "building" polynucleotide sequences in a step-wise fashion. Examples include, but are not limited to, reverse direction synthesis with phosphoramidite chemistry or forward direction synthesis with phosphoramidite chemistry. Previous and well-known methods synthesize the oligonucleotides separately then "glue" the entire desired sequence onto the bead enzymatically. Applicants present a complexed bead and a novel process for producing these beads where nucleotides are chemically built onto the bead material in a high-throughput manner. Moreover, Applicants generally describe delivering a "packet" of beads which allows one to deliver millions of sequences into separate compartments and then screen all at once.

The invention further provides an apparatus for creating a single-cell sequencing library via a microfluidic system, comprising: an oil-surfactant inlet comprising a filter and a carrier fluid channel, wherein said carrier fluid channel further comprises a resistor; an inlet for an analyte comprising a filter and a carrier fluid channel, wherein said carrier fluid channel further comprises a resistor; an inlet for mRNA capture microbeads and lysis reagent comprising a filter and a carrier fluid channel, wherein said carrier fluid channel further comprises a resistor; said carrier fluid channels have a carrier fluid flowing therein at an adjustable or predetermined flow rate; wherein each said carrier fluid channels merge at a junction; and said junction being connected to a mixer, which contains an outlet for drops.

A mixture comprising a plurality of microbeads adorned with combinations of the following elements: bead-specific oligonucleotide barcodes created by the discussed methods; additional oligonucleotide barcode sequences which vary among the oligonucleotides on an individual bead and can therefore be used to differentiate or help identify those individual oligonucleotide molecules; additional oligonucleotide sequences that create substrates for downstream molecular-biological reactions, such as oligo-dT (for reverse transcription of mature mRNAs), specific sequences (for capturing specific portions of the transcriptome, or priming for DNA polymerases and similar enzymes), or random sequences (for priming throughout the transcriptome or genome). In an embodiment, the individual oligonucleotide molecules on the surface of any individual microbead contain all three of these elements, and the third element includes both oligo-dT and a primer sequence.

Examples of the labeling substance which may be employed include labeling substances known to those skilled in the art, such as fluorescent dyes, enzymes, coenzymes, chemiluminescent substances, and radioactive substances. Specific examples include radioisotopes (e.g., 32P, 14C, 125I, 3H, and 131I), fluorescein, rhodamine, dansyl chloride, umbelliferone, luciferase, peroxidase, alkaline phosphatase, β-galactosidase, p-glucosidase, horseradish peroxidase, glucoamylase, lysozyme, saccharide oxidase, microperoxidase, biotin, and ruthenium. In the case where biotin is employed as a labeling substance, preferably, after addition of a biotin-labeled antibody, streptavidin bound to an enzyme (e.g., peroxidase) is further added.

Advantageously, the label is a fluorescent label. Examples of fluorescent labels include, but are not limited to, Atto dyes, 4-acetamido-4'-isothiocyanatostilbene-2,2'disulfonic acid; acridine and derivatives: acridine, acridine isothiocyanate; 5-(2'-aminoethyl)aminonaphthalene-1-sulfonic acid (EDANS); 4-amino-N-[3-vinylsulfonyl)phenyl]naphthalimide-3,5 disulfonate; N-(4-anilino-1-naphthyl)maleimide; anthranilamide; BODIPY; Brilliant Yellow; coumarin and derivatives; coumarin, 7-amino-4-methylcoumarin (AMC, Coumarin 120), 7-amino-4-trifluoromethylcouluarin (Coumaran 151); cyanine dyes; cyanosine; 4',6-diaminidino-2-phenylindole (DAPI); 5'5"-dibromopyrogallol-sulfonaphthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansylchloride); 4-dimethylaminophenylazophenyl-4'-isothiocyanate (DABITC); eosin and derivatives; eosin, eosin isothiocyanate, erythrosin and derivatives; erythrosin B, erythrosin, isothiocyanate; ethidium; fluorescein and derivatives; 5-carboxyfluorescein (FAM), 5-(4,6-dichlorotriazin-2-yl)amino-fluorescein (DTAF), 2',7'-dimethoxy-4'5'-dichloro-6-carboxyfluorescein, fluorescein, fluorescein isothiocyanate, QFITC, (XRITC); fluorescamine; IR144; IR1446; Malachite Green isothiocyanate; 4-methylumbelliferoneortho cresolphthalein; nitrotyrosine; pararosaniline; Phenol Red; B-phycoerythrin; o-phthaldialdehyde; pyrene and derivatives: pyrene, pyrene butyrate, succinimidyl 1-pyrene; butyrate quantum dots; Reactive Red 4 (Cibacron™ Brilliant Red 3B-A) rhodamine and derivatives: 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red); N,N,N',N' tetramethyl-6-carboxyrhodamine (TAMRA); tetramethyl rhodamine; tetramethyl rhodamine isothiocyanate (TRITC); riboflavin; rosolic acid; terbium chelate derivatives; Cy3; Cy5; Cy5.5; Cy7; IRD 700; IRD 800; La Jolta Blue; phthalo cyanine; and naphthalo cyanine.

The fluorescent label may be a fluorescent protein, such as blue fluorescent protein, cyan fluorescent protein, green fluorescent protein, red fluorescent protein, yellow fluorescent protein or any photoconvertible protein. Colormetric labeling, bioluminescent labeling and/or chemiluminescent labeling may further accomplish labeling. Labeling further may include energy transfer between molecules in the hybridization complex by perturbation analysis, quenching, or electron transport between donor and acceptor molecules, the latter of which may be facilitated by double stranded match hybridization complexes. The fluorescent label may be a perylene or a terylene. In the alternative, the fluorescent label may be a fluorescent bar code.

In an advantageous embodiment, the label may be light sensitive, wherein the label is light-activated and/or light cleaves the one or more linkers to release the molecular cargo. The light-activated molecular cargo may be a major light-harvesting complex (LHCII). In another embodiment, the fluorescent label may induce free radical formation.

The invention discussed herein enables high throughput and high resolution delivery of reagents to individual emulsion droplets that may contain cells, organelles, nucleic acids, proteins, etc. through the use of monodisperse aqueous droplets that are generated by a microfluidic device as a water-in-oil emulsion. The droplets are carried in a flowing oil phase and stabilized by a surfactant. In one aspect single cells or single organelles or single molecules (proteins, RNA, DNA) are encapsulated into uniform droplets from an aqueous solution/dispersion. In a related aspect, multiple cells or multiple molecules may take the place of single cells or single molecules. The aqueous droplets of volume ranging from 1 pL to 10 nL work as individual reactors. Disclosed embodiments provide 104 to 105 single cells in droplets which can be processed and analyzed in a single run.

To utilize microdroplets for rapid large-scale chemical screening or complex biological library identification, different species of microdroplets, each containing the specific chemical compounds or biological probes cells or molecular barcodes of interest, have to be generated and combined at the preferred conditions, e.g., mixing ratio, concentration, and order of combination.

Each species of droplet is introduced at a confluence point in a main microfluidic channel from separate inlet microfluidic channels. Preferably, droplet volumes are chosen by design such that one species is larger than others and moves at a different speed, usually slower than the other species, in the carrier fluid, as disclosed in U.S. Publication No. US 2007/0195127 and International Publication No. WO 2007/089541, each of which are incorporated herein by reference in their entirety. The channel width and length is selected such that faster species of droplets catch up to the slowest species. Size constraints of the channel prevent the faster moving droplets from passing the slower moving droplets resulting in a train of droplets entering a merge zone. Multi-step chemical reactions, biochemical reactions, or assay detection chemistries often require a fixed reaction time before species of different type are added to a reaction. Multi-step reactions are achieved by repeating the process multiple times with a second, third or more confluence points each with a separate merge point. Highly efficient and precise reactions and analysis of reactions are achieved when the frequencies of droplets from the inlet channels are matched to an optimized ratio and the volumes of the species are matched to provide optimized reaction conditions in the combined droplets.

Fluidic droplets may be screened or sorted within a fluidic system of the invention by altering the flow of the liquid containing the droplets. For instance, in one set of embodiments, a fluidic droplet may be steered or sorted by directing the liquid surrounding the fluidic droplet into a first channel, a second channel, etc. In another set of embodiments, pressure within a fluidic system, for example, within different channels or within different portions of a channel, can be controlled to direct the flow of fluidic droplets. For example, a droplet can be directed toward a channel junction including multiple options for further direction of flow (e.g., directed toward a branch, or fork, in a channel defining optional downstream flow channels). Pressure within one or more of the optional downstream flow channels can be controlled to direct the droplet selectively into one of the channels, and changes in pressure can be effected on the order of the time required for successive droplets to reach the junction, such that the downstream flow path of each successive droplet can be independently controlled. In one arrangement, the expansion and/or contraction of liquid reservoirs may be used to steer or sort a fluidic droplet into a channel, e.g., by causing directed movement of the liquid containing the fluidic droplet. In another embodiment, the expansion and/or contraction of the liquid reservoir may be combined with other flow-controlling devices and methods, e.g., as discussed herein. Non-limiting examples of devices able to cause the expansion and/or contraction of a liquid reservoir include pistons.

Key elements for using microfluidic channels to process droplets include: (1) producing droplet of the correct volume, (2) producing droplets at the correct frequency and (3) bringing together a first stream of sample droplets with a second stream of sample droplets in such a way that the frequency of the first stream of sample droplets matches the frequency of the second stream of sample droplets. Preferably, bringing together a stream of sample droplets with a stream of premade library droplets in such a way that the frequency of the library droplets matches the frequency of the sample droplets.

Methods for producing droplets of a uniform volume at a regular frequency are well known in the art. One method is to generate droplets using hydrodynamic focusing of a dispersed phase fluid and immiscible carrier fluid, such as disclosed in U.S. Publication No. US 2005/0172476 and International Publication No. WO 2004/002627. It is desirable for one of the species introduced at the confluence to be a pre-made library of droplets where the library contains a plurality of reaction conditions, e.g., a library may contain plurality of different compounds at a range of concentrations encapsulated as separate library elements for screening their effect on cells or enzymes, alternatively a library could be composed of a plurality of different primer pairs encapsulated as different library elements for targeted amplification of a collection of loci, alternatively a library could contain a plurality of different antibody species encapsulated as different library elements to perform a plurality of binding assays. The introduction of a library of reaction conditions onto a substrate is achieved by pushing a premade collection of library droplets out of a vial with a drive fluid. The drive fluid is a continuous fluid. The drive fluid may comprise the same substance as the carrier fluid (e.g., a fluorocarbon oil). For example, if a library consists of ten pico-liter droplets is driven into an inlet channel on a microfluidic substrate with a drive fluid at a rate of 10,000 pico-liters per second, then nominally the frequency at which the droplets are expected to enter the confluence point is 1000 per second. However, in practice droplets pack with oil between them that slowly drains. Over time the carrier fluid drains from the library droplets and the number density of the droplets (number/mL) increases. Hence, a simple fixed rate of infusion for the drive fluid does not provide a uniform rate of introduction of the droplets into the microfluidic channel in the substrate. Moreover, library-to-library variations in the mean library droplet volume result in a shift in the frequency of droplet introduction at the confluence point. Thus, the lack of uniformity of droplets that results from sample variation and oil drainage provides another problem to be solved. For example if the nominal droplet volume is expected to be 10 pico-liters in the library, but varies from 9 to 11 pico-liters from library-to-library then a 10,000 pico-liter/second infusion rate will nominally produce a range in frequencies from 900 to 1,100 droplet per second. In short, sample to sample variation in the composition of dispersed phase for droplets made on chip, a tendency for the number density of library droplets to increase over time and library-to-library variations in mean droplet volume severely limit the extent to which frequencies of droplets may be reliably matched at a confluence by simply using fixed infusion rates. In addition, these limitations also have an impact on the extent to which volumes may be reproducibly combined. Combined with typical variations in pump flow rate precision and variations in channel dimensions, systems are severely limited without a means to compensate on a run-to-run basis. The foregoing facts not only illustrate a problem to be solved, but also demonstrate a need for a method of instantaneous regulation of microfluidic control over microdroplets within a microfluidic channel.

Combinations of surfactant(s) and oils must be developed to facilitate generation, storage, and manipulation of droplets to maintain the unique chemical/biochemical/biological environment within each droplet of a diverse library. Therefore, the surfactant and oil combination must (1) stabilize droplets against uncontrolled coalescence during the drop forming process and subsequent collection and storage, (2) minimize transport of any droplet contents to the oil phase and/or between droplets, and (3) maintain chemical and biological inertness with contents of each droplet (e.g., no adsorption or reaction of encapsulated contents at the oil-water interface, and no adverse effects on biological or chemical constituents in the droplets). In addition to the requirements on the droplet library function and stability, the surfactant-in-oil solution must be coupled with the fluid physics and materials associated with the platform. Specifically, the oil solution must not swell, dissolve, or degrade the materials used to construct the microfluidic chip, and the physical properties of the oil (e.g., viscosity, boiling point, etc.) must be suited for the flow and operating conditions of the platform.

Droplets formed in oil without surfactant are not stable to permit coalescence, so surfactants must be dissolved in the oil that is used as the continuous phase for the emulsion library. Surfactant molecules are amphiphilic—part of the molecule is oil soluble, and part of the molecule is water soluble. When a water-oil interface is formed at the nozzle of a microfluidic chip for example in the inlet module discussed herein, surfactant molecules that are dissolved in the oil phase adsorb to the interface. The hydrophilic portion of the molecule resides inside the droplet and the fluorophilic portion of the molecule decorates the exterior of the droplet. The surface tension of a droplet is reduced when the interface is populated with surfactant, so the stability of an emulsion is improved. In addition to stabilizing the droplets against coalescence, the surfactant should be inert to the contents of each droplet and the surfactant should not promote transport of encapsulated components to the oil or other droplets.

A droplet library may be made up of a number of library elements that are pooled together in a single collection (see, e.g., US Patent Publication No. 2010002241). Libraries may vary in complexity from a single library element to 1015 library elements or more. Each library element may be one or more given components at a fixed concentration. The element may be, but is not limited to, cells, organelles, virus, bacteria, yeast, beads, amino acids, proteins, polypeptides, nucleic acids, polynucleotides or small molecule chemical compounds. The element may contain an identifier such as a label. The terms "droplet library" or "droplet libraries" are also referred to herein as an "emulsion library" or "emulsion libraries." These terms are used interchangeably throughout the specification.

A cell library element may include, but is not limited to, hybridomas, B-cells, primary cells, cultured cell lines, cancer cells, stem cells, cells obtained from tissue, or any other cell type. Cellular library elements are prepared by encapsulating a number of cells from one to hundreds of thousands in individual droplets. The number of cells encapsulated is usually given by Poisson statistics from the number density of cells and volume of the droplet. However, in some cases the number deviates from Poisson statistics as discussed in Edd et al., "Controlled encapsulation of single-cells into monodisperse picolitre drops." Lab Chip, 8(8): 1262-1264, 2008. The discrete nature of cells allows for libraries to be prepared in mass with a plurality of cellular variants all present in a single starting media and then that media is broken up into individual droplet capsules that contain at most one cell. These individual droplets capsules are then combined or pooled to form a library consisting of unique library elements. Cell division subsequent to, or in some embodiments following, encapsulation produces a clonal library element.

A bead based library element may contain one or more beads, of a given type and may also contain other reagents, such as antibodies, enzymes or other proteins. In the case where all library elements contain different types of beads, but the same surrounding media, the library elements may all be prepared from a single starting fluid or have a variety of starting fluids. In the case of cellular libraries prepared in mass from a collection of variants, such as genomically modified, yeast or bacteria cells, the library elements will be prepared from a variety of starting fluids.

Often it is desirable to have exactly one cell per droplet with only a few droplets containing more than one cell when starting with a plurality of cells or yeast or bacteria, engineered to produce variants on a protein. In some cases, variations from Poisson statistics may be achieved to provide an enhanced loading of droplets such that there are more droplets with exactly one cell per droplet and few exceptions of empty droplets or droplets containing more than one cell.

Examples of droplet libraries are collections of droplets that have different contents, ranging from beads, cells, small molecules, DNA, primers, antibodies. Smaller droplets may be in the order of femtoliter (fL) volume drops, which are especially contemplated with the droplet dispensors. The volume may range from about 5 to about 600 fL. The larger droplets range in size from roughly 0.5 micron to 500 micron in diameter, which corresponds to about 1 pico liter to 1 nano liter. However, droplets may be as small as 5 microns and as large as 500 microns. Preferably, the droplets are at less than 100 microns, about 1 micron to about 100 microns in diameter. The most preferred size is about 20 to 40 microns in diameter (10 to 100 picoliters). The preferred properties examined of droplet libraries include osmotic pressure balance, uniform size, and size ranges.

The droplets comprised within the emulsion libraries of the present invention may be contained within an immiscible oil which may comprise at least one fluorosurfactant. In some embodiments, the fluorosurfactant comprised within immiscible fluorocarbon oil is a block copolymer consisting of one or more perfluorinated polyether (PFPE) blocks and one or more polyethylene glycol (PEG) blocks. In other embodiments, the fluorosurfactant is a triblock copolymer consisting of a PEG center block covalently bound to two PFPE blocks by amide linking groups. The presence of the fluorosurfactant (similar to uniform size of the droplets in the library) is critical to maintain the stability and integrity of the droplets and is also essential for the subsequent use of the droplets within the library for the various biological and chemical assays discussed herein. Fluids (e.g., aqueous fluids, immiscible oils, etc.) and other surfactants that may be utilized in the droplet libraries of the present invention are discussed in greater detail herein.

The present invention provides an emulsion library which may comprise a plurality of aqueous droplets within an immiscible oil (e.g., fluorocarbon oil) which may comprise at least one fluorosurfactant, wherein each droplet is uniform in size and may comprise the same aqueous fluid and may comprise a different library element. The present invention also provides a method for forming the emulsion library which may comprise providing a single aqueous fluid which may comprise different library elements, encapsulating each library element into an aqueous droplet within an immiscible fluorocarbon oil which may comprise at least one fluoro-surfactant, wherein each droplet is uniform in size and may comprise the same aqueous fluid and may comprise a different library element, and pooling the aqueous droplets within an immiscible fluorocarbon oil which may comprise at least one fluorosurfactant, thereby forming an emulsion library.

For example, in one type of emulsion library, all different types of elements (e.g., cells or beads), may be pooled in a single source contained in the same medium. After the initial pooling, the cells or beads are then encapsulated in droplets to generate a library of droplets wherein each droplet with a different type of bead or cell is a different library element. The dilution of the initial solution enables the encapsulation process. In some embodiments, the droplets formed will either contain a single cell or bead or will not contain anything, i.e., be empty. In other embodiments, the droplets formed will contain multiple copies of a library element. The cells or beads being encapsulated are generally variants on the same type of cell or bead. In one example, the cells may comprise cancer cells of a tissue biopsy, and each cell type is encapsulated to be screened for genomic data or against different drug therapies. Another example is that 1011 or 1015 different type of bacteria; each having a different plasmid spliced therein, are encapsulated. One example is a bacterial library where each library element grows into a clonal population that secretes a variant on an enzyme.

In another example, the emulsion library may comprise a plurality of aqueous droplets within an immiscible fluorocarbon oil, wherein a single molecule may be encapsulated, such that there is a single molecule contained within a droplet for every 20-60 droplets produced (e.g., 20, 25, 30, 35, 40, 45, 50, 55, 60 droplets, or any integer in between). Single molecules may be encapsulated by diluting the solution containing the molecules to such a low concentration that the encapsulation of single molecules is enabled. In one specific example, a LacZ plasmid DNA was encapsulated at a concentration of 20 fM after two hours of incubation such that there was about one gene in 40 droplets, where 10 µm droplets were made at 10 kHz per second. Formation of these libraries rely on limiting dilutions.

Methods of the invention involve forming sample droplets. The droplets are aqueous droplets that are surrounded by an immiscible carrier fluid. Methods of forming such droplets are shown for example in Link et al. (U.S. patent application numbers 2008/0014589, 2008/0003142, and 2010/0137163), Stone et al. (U.S. Pat. No. 7,708,949 and U.S. patent application number 2010/0172803), Anderson et al. (U.S. Pat. No. 7,041,481 and which reissued as RE41, 780) and European publication number EP2047910 to Raindance Technologies Inc. The content of each of which is incorporated by reference herein in its entirety.

In certain embodiments, the carrier fluid may contain one or more additives, such as agents which reduce surface tensions (surfactants). Surfactants can include Tween, Span, fluorosurfactants, and other agents that are soluble in oil relative to water. In some applications, performance is improved by adding a second surfactant to the sample fluid. Surfactants can aid in controlling or optimizing droplet size, flow and uniformity, for example by reducing the shear force needed to extrude or inject droplets into an intersecting channel. This can affect droplet volume and periodicity, or the rate or frequency at which droplets break off into an intersecting channel. Furthermore, the surfactant can serve to stabilize aqueous emulsions in fluorinated oils from coalescing.

In certain embodiments, the droplets may be surrounded by a surfactant which stabilizes the droplets by reducing the surface tension at the aqueous oil interface. Preferred surfactants that may be added to the carrier fluid include, but are not limited to, surfactants such as sorbitan-based carboxylic acid esters (e.g., the "Span" surfactants, Fluka Chemika), including sorbitan monolaurate (Span 20), sorbitan monopalmitate (Span 40), sorbitan monostearate (Span 60) and sorbitan monooleate (Span 80), and perfluorinated polyethers (e.g., DuPont Krytox 157 FSL, FSM, and/or FSH). Other non-limiting examples of non-ionic surfactants which may be used include polyoxyethylenated alkylphenols (for example, nonyl-, p-dodecyl-, and dinonylphenols), polyoxyethylenated straight chain alcohols, polyoxyethylenated polyoxypropylene glycols, polyoxyethylenated mercaptans, long chain carboxylic acid esters (for example, glyceryl and polyglyceryl esters of natural fatty acids, propylene glycol, sorbitol, polyoxyethylenated sorbitol esters, polyoxyethylene glycol esters, etc.) and alkanolamines (e.g., diethanolamine-fatty acid condensates and isopropanolamine-fatty acid condensates).

By incorporating a plurality of unique tags into the additional droplets and joining the tags to a solid support designed to be specific to the primary droplet, the conditions that the primary droplet is exposed to may be encoded and recorded. For example, nucleic acid tags can be sequentially ligated to create a sequence reflecting conditions and order of same. Alternatively, the tags can be added independently appended to solid support. Non-limiting examples of a dynamic labeling system that may be used to bioinformatically record information can be found at US Provisional Patent Application entitled "Compositions and Methods for Unique Labeling of Agents" filed Sep. 21, 2012 and Nov. 29, 2012. In this way, two or more droplets may be exposed to a variety of different conditions, where each time a droplet is exposed to a condition, a nucleic acid encoding the condition is added to the droplet each ligated together or to a unique solid support associated with the droplet such that, even if the droplets with different histories are later combined, the conditions of each of the droplets are remain available through the different nucleic acids. Non-limiting examples of methods to evaluate response to exposure to a plurality of conditions can be found at US Provisional Patent Application entitled "Systems and Methods for Droplet Tagging" filed Sep. 21, 2012.

Applications of the disclosed device may include use for the dynamic generation of molecular barcodes (e.g., DNA oligonucleotides, fluorophores, etc.) either independent from or in concert with the controlled delivery of various compounds of interest (drugs, small molecules, siRNA, CRISPR guide RNAs, reagents, etc.). For example, unique molecular barcodes can be created in one array of nozzles while individual compounds or combinations of compounds can be generated by another nozzle array. Barcodes/compounds of interest can then be merged with cell-containing droplets. An electronic record in the form of a computer log file is kept to associate the barcode delivered with the downstream reagent(s) delivered. This methodology makes it possible to efficiently screen a large population of cells for applications such as single-cell drug screening, controlled perturbation of regulatory pathways, etc. The device and techniques of the disclosed invention facilitate efforts to perform studies that require data resolution at the single cell (or single molecule) level and in a cost effective manner. Disclosed embodiments provide a high throughput and high resolution delivery of reagents to individual emulsion droplets that may contain cells, nucleic acids, proteins, etc. through the use of monodisperse aqueous droplets that are generated one by one in a microfluidic chip as a water-in-oil emulsion. Hence, the invention proves advantageous over prior art systems by being able to dynamically track individual cells and droplet treatments/combinations during life cycle experiments. Additional advantages of the disclosed invention provide an ability to create a library of emulsion droplets on demand with the further capability of manipulating the droplets through the disclosed process(es). Disclosed embodiments may, thereby, provide dynamic tracking of the droplets and create a history of droplet deployment and application in a single cell based environment.

Droplet generation and deployment is produced via a dynamic indexing strategy and in a controlled fashion in accordance with disclosed embodiments of the present invention. Disclosed embodiments of the microfluidic device discussed herein provides the capability of microdroplets that be processed, analyzed and sorted at a highly efficient rate of several thousand droplets per second, providing a powerful platform which allows rapid screening of millions of distinct compounds, biological probes, proteins or cells either in cellular models of biological mechanisms of disease, or in biochemical, or pharmacological assays.

The term "tagmentation" refers to a step in the Assay for Transposase Accessible Chromatin using sequencing (ATAC-seq) as described. (See, Buenrostro, J. D., Giresi, P. G., Zaba, L. C., Chang, H. Y., Greenleaf, W. J., Transposition of native chromatin for fast and sensitive epigenomic profiling of open chromatin, DNA-binding proteins and nucleosome position. Nature methods 2013; 10 (12): 1213-1218). Specifically, a hyperactive Tn5 transposase loaded in vitro with adapters for high-throughput DNA sequencing, can simultaneously fragment and tag a genome with sequencing adapters. In one embodiment the adapters are compatible with the methods described herein.

In certain embodiments, tagmentation is used to introduce adaptor sequences to genomic DNA in regions of accessible chromatin (e.g., between individual nucleosomes) (see, e.g., US20160208323A1; US20160060691A1; WO2017156336A1; and Cusanovich, D. A., Daza, R., Adey, A., Pliner, H., Christiansen, L., Gunderson, K. L., Steemers, F. J., Trapnell, C. & Shendure, J. Multiplex single-cell profiling of chromatin accessibility by combinatorial cellular indexing. Science. 2015 May 22; 348(6237):910-4. doi: 10.1126/science.aab1601. Epub 2015 May 7). In certain embodiments, tagmentation is applied to bulk samples or to single cells in discrete volumes.

The 3' barcoded libraries can be used in the methods as described herein to provide enriched libraries containing transcripts of interest that are not as abundant or accessible in the original single cell RNAseq libraries. Other Seq-Well embodiments that may be used with the current invention are described in PCT Application No. PCT/US2018/057173, entitled "Functionalized Solid Support" filed on Oct. 23, 2018.

Transcript of Interest

A transcript of interest may also be referred to interchangeably as a gene of interest or target sequence. Target sequence can refer to any polynucleotide, such as DNA or RNA polynucleotides. In some embodiments, a target sequence is derived from the nucleus or cytoplasm of a cell, and may include nucleic acids in or from mitochondrial, organelles, vesicles, liposomes or particles present within the cell and subjected to a single cell sequencing metho, retaining identification of the source cell or subcellular organelle.

A gene of interest may comprise, for example, a mutation, deletion, insertion, translocation, single nucleotide polymorphism (SNP), splice variant or any combination thereof associated with a particular attribute in a gene of interest. In another embodiment, the gene of interest may be a cancer gene. In another embodiment, the gene of interest is a mutated cancer gene, such as a somatic mutation.

Any gene, region or mutation of interest and to identify cells containing specific genes, regions or mutations, deletions, insertions, indels, or translocations of interest can be included in the libraries. A gene of interest may be, for example, a cancer gene, in particular a mutation in a cancer gene. The mutation may be one or more somatic mutations found in cancer and may be listed, for example, in the Catalogue Of Somatic Mutations In Cancer (COSMIC) database (see, e.g., http://cancer.sanger.ac.uk/cosmic/).

In some instances, the mutation is located anywhere in the gene. In some instances, the desired transcript can be greater than about 1 kb away from the cell barcode of the nucleic acid of the libraries as described here. The gene of interest may comprise a SNP.

As the methods herein can be designed to distinguish SNPs within a population, the methods may be used to distinguish pathogenic strains that differ by a single SNP or detect certain disease specific SNPs, such as but not limited to, disease associated SNPs, such as without limitation cancer associated SNPs.

The gene of interest, transcript of interest, in some instances comprises a mutation. Mutation within 1 kilobase of the polyA tail of an mRNA in the library.

In some instances, the library can include a transcript of interest, or desired transcript is in a T cell or a B cell. In some instances, the transcript of interest is in a T cell receptor, a B cell receptor or a CAR-T cell. In some instances, the transcript of interest is in variable regions of a sequence, all variable regions of, for example a T cell receptor α/β.

The transcript of interest may derive from a cell. In some embodiments a T cell, or a B cell. In some embodiments a TCR, A BCR, or a CAR-T cell. In some instances, the methods target variable regions of a transcript of interest. In some instances, the gene of interest is in a cancer cell. In some instances, it is an AML cell. In some instances, the cell can be characterized by the highly expressed genes comprised with in a cell, and may be characterized as a GMP like cell, HSC/progenitor like cell or a myeloid cell.

In another embodiment, the specific gene of interest may be a tumor protein P53 gene. Specific mutations include, but are not limited to, positions P152R and/or Q144P in the tumor protein P53 gene.

In one embodiment, the specific gene of interest may be an acute myeloid leukemia (AML) gene, such as a DNA methyltransferase gene, such as DNA 5-cytosine methyltransferase 3a (DNMT3A). DNMT3A mutations were most commonly seen in acute myeloid leukaemia (AML) where they occurred in just over 25% of cases sequenced. These mutations most often occur at position R882 in the protein and this mutation may cause loss of function. In another embodiment, a mutation may also occur at position L637Q in the DNMT3A gene.

AML genes of interest may comprise any gene of interest in Table 2. In some instances, the gene of interest is PRTN3, MPO, CALR, CLEC5A, ELANE, POU4F1, TRH, TSPOAP1, CEBPE, LINC01835, NUCB2, CSF3R, RUNX1T1, CD38, PLPPR3, IGFBP2, PRRT4, SNHG5, FABP5, LOC100419170, CLEC11A, SERPINB1, AZU1, FBN2, HNRNPDL, HSPB1, RNA5-8S, THSD7A, C12orf57, FGFR1, LPO, MGST1, C1QTNF4, HMGN1, SIPA1L2, DDOST, PTGIR, GATM, VAMP8, FAM46A, VAMP5, STAR, ANKRD18A, TM7SF3, CCND1, ROBO1, GFI1, DEFA4, CERS6; SPINK2, ANGPT1, GUCY1A3, FAM30A, MMRN1, TPT1, GAS5, RAB27B, TPM4, MSI2, GCSAML, SOCS2, EEF1A1, NRIP1, HOPX, CD34, TFPI, TPSD1, PDZRN4, PCNP, PTPRCAP, FLT3, SMIM24, SELENOP, DAPK1, SMYD3, ADGRG6, PIM1, MECOM, CEP70, XIRP2, SPAG6, TAPT1-AS1, GNA15, DSE, TPSAB1, TPSB2, H2AFY, SCHIP1, LINC02470, NPR3, KMT2A, CD200, MACF1, GBP4, ABCC1, PROM1, TMEM70, FAM110A, TMEM123.

Method of Distinguishing Cells by Genotype

In an embodiment, the present invention relates to a method of distinguishing cells by genotype by enriching libraries for transcripts of interest which may comprise a PCR-based method, for example: constructing a library comprising a plurality of nucleic acids wherein each nucleic acid may comprise a gene, a unique molecular identifier (UMI) and a cell barcode (cell BC) flanked by switching mechanism at 5' end of RNA template (SMART) sequences at the 5' and 3' end, amplifying each nucleic acid in the library to create a first PCR product using a tagged 5' primer which may comprise a binding site for a second PCR product and a sequence complementary to a specific gene of interest and a 3' SMART primer complementary to the SMART sequence at the 3' end of the nucleic acid thereby generating a first PCR product, selective enrichment of the first PCR product by binding to the tag introduced by the 5' primer or a targeted 3' capture with a bifunctional bead or targeted capture bead, amplifying the tag-enriched first PCR product with a 5' primer which may comprise the binding site for the second PCR product and a 3' SMART primer complementary to the SMART sequence at the 3' end of the nucleic acid thereby generating the second PCR product, size-selecting a final product comprising the specific gene of interest and determining the genotype of the cell by identifying the UMI and cell BC. Specific sequences can be used to uniquely enable Next Generation Sequencing (NGS) or third-generation sequencing can also be performed by using specific sequences to uniquely enable NGS or third-generation sequencing. Advantageously, the methods allow for determination of expressed DNA sequences, such as mutations, translocations, insertions/deletions (indels), etc.

Constructing a Library

The methods disclosed herein include a first step of constructing a library, the library includes a plurality of nucleic acids, each nucleic acid including a gene of interest, a unique molecular identifier (UMI) and a cell barcode (cell BC). In a preferred embodiment, each nucleic acid sequence is flanked by switching mechanism at 5' end of RNA template (SMART) sequences at the 5' end and 3' end, that is, in this embodiment, an exemplary nucleic acid in the library would be 5' SMART-genetic region of interest-UMI-Cell BC-SMART 3'. The libraries can be constructed preferably from any single cell sequencing technique, in some preferred embodiments, an mRNA sequencing protocol, in some embodiments, SMART-Seq. Any single cell sequencing protocol can be used, as described elsewhere herein, to construct the library. In some preferred embodiments, the protocol provides 3' barcoded nucleic acids that are subjected to further steps in the method embodiments disclosed herein.

Amplification

Once a library is constructed, an amplifying step is conducted. The amplifying of each nucleic acid in the library can be performed to create first PCR product. In one preferred embodiment, a PCR-amplification based approach is utilized to derive genetic information from single-cell RNA-seq libraries. However, other amplification techniques can be utilized that amplify the library of nucleic acid sequences, with primers designed in accordance with further desired further processing or sequencing techniques, as described herein.

In one particular embodiment, when the libraries are flanked with SMART sequences on both ends, the vast majority of the first PCR product would be amplification of the entire library.

Alternatively, or in addition to and prior to a PCR amplification step, a step of reverse transcription can be performed. In some embodiments, amplifying each nucleic acid in the library to create a whole transcriptome amplified (WTA) RNA by reverse transcription with a primer comprising a sequence adapter. In some embodiments, In certain embodiments, the amplified RNA comprises the orientation: 5'-sequencing adapter-cell barcode-UMI-UUUUUUU-mRNA-3'. In some embodiments, PCR amplification is then conducted of the reverse transcribed products with primers that bind both sequence adapters and adding a library barcode and optionally additional sequence adapters, with subsequent determination of the genotype of the cell by the methods described herein. This particular method can further comprise use of PCR amplification with one or more primers binding both sequence adapters, wherein the one or more primers comprise sequences allowing for circularization of a first PCR product and subsequent circularizing and a second polymerase chain reaction amplification with one or more primers, wherein the one or primers comprise a library barcode and/or additional sequencing adapters.

In some embodiments, any suitable RNA or DNA amplification technique may be used. In certain example embodiments, the RNA or DNA amplification is an isothermal amplification. In certain example embodiments, the isothermal amplification may be nucleic-acid sequenced-based amplification (NASBA), recombinase polymerase amplification (RPA), loop-mediated isothermal amplification (LAMP), strand displacement amplification (SDA), helicase-dependent amplification (HDA), or nicking enzyme amplification reaction (NEAR). In certain example embodiments, non-isothermal amplification methods may be used which include, but are not limited to, PCR, multiple displacement amplification (MDA), rolling circle amplification (RCA), ligase chain reaction (LCR), or ramification amplification method (RAM).

In specific embodiments, the amplification reaction mixture may further comprise primers, capable of hybridizing to a target nucleic acid strand. The term "hybridization" refers to binding of an oligonucleotide primer to a region of the single-stranded nucleic acid template under the conditions in which primer binds only specifically to its complementary sequence on one of the template strands, not other regions in the template. The specificity of hybridization may be influenced by the length of the oligonucleotide primer, the temperature in which the hybridization reaction is performed, the ionic strength, and the pH. The term "primer" refers to a single stranded nucleic acid capable of binding to a single stranded region on a target nucleic acid to facilitate polymerase dependent replication of the target nucleic acid strand. Nucleic acid(s) that are "complementary" or "complement(s)" are those that are capable of base-pairing according to the standard Watson-Crick, Hoogsteen or reverse Hoogsteen binding complementarity rules.

"PCR" (polymerase chain reaction) refers to a reaction for the in vitro amplification of specific DNA sequences by the simultaneous primer extension of complementary strands of DNA. In other words, PCR is a reaction for making multiple copies or replicates of a target nucleic acid flanked by primer binding sites, such reaction comprising one or more repetitions of the following steps: (i) denaturing the target nucleic acid, (ii) annealing primers to the primer binding sites, and (iii) extending the primers by a nucleic acid polymerase in the presence of nucleoside triphosphates. Usually, the reaction is cycled through different temperatures optimized for each step in a thermal cycler instrument. Particular temperatures, durations at each step, and rates of change between steps depend on many factors well-known to those of ordinary skill in the art, e.g., exemplified by the references: McPherson et al., editors, PCR: A Practical Approach and PCR2: A Practical Approach (IRL Press, Oxford, 1991 and 1995, respectively). For example, in a conventional PCR using Taq DNA polymerase, a double stranded target nucleic acid may be denatured at a temperature greater than 90° C., primers annealed at a temperature in the range 50-75° C., and primers extended at a temperature in the range 72-78° C.

PCR encompasses derivative forms of the reaction, including but not limited to, RT-PCR, real-time PCR, nested PCR, quantitative PCR, multiplexed PCR, and the like. Reaction volumes range from a few hundred nanoliters, e.g., 200 nL, to a few hundred microliters, e.g., 200 microliters. "Reverse transcription PCR," or "RT-PCR," means a PCR that is preceded by a reverse transcription reaction that converts a target RNA to a complementary single stranded DNA, which is then amplified, e.g., Tecott et al., U.S. Pat. No. 5,168,038. "Real-time PCR" means a PCR for which the amount of reaction product, i.e., amplicon, is monitored as the reaction proceeds. There are many forms of real-time PCR that differ mainly in the detection chemistries used for monitoring the reaction product, e.g., Gelfand et al., U.S. Pat. No. 5,210,015 ("Tagman"); Wittwer et al., U.S. Pat. Nos. 6,174,670 and 6,569,627 (intercalating dyes); Tyagi et al., U.S. Pat. No. 5,925,517 (molecular beacons). Detection chemistries for real-time PCR are reviewed in Mackay et al., Nucleic Acids Research, 30:1292-1305 (2002). "Nested PCR" means a two-stage PCR wherein the amplicon of a first PCR becomes the sample for a second PCR using a new set of primers, at least one of which binds to an interior location of the first amplicon. As used herein, "initial primers" in reference to a nested amplification reaction mean the primers used to generate a first amplicon, and "secondary primers" mean the one or more primers used to generate a second, or nested, amplicon. "Multiplexed PCR" means a PCR wherein multiple target sequences (or a single target sequence and one or more reference sequences) are simultaneously carried out in the same reaction mixture (see, e.g., Bernard et al., Anal. Biochem., 273:221-228, 1999 (two-color real-time PCR)). Usually, distinct sets of primers are employed for each sequence being amplified. "Quantitative PCR" means a PCR designed to measure the abundance of one or more specific target sequences in a sample or specimen. Quantitative PCR includes both absolute quantitation and relative quantitation of such target sequences. Techniques for quantitative PCR are well-known to those of ordinary skill in the art, as exemplified in the following references: Freeman et al. (Biotechniques, 26:112-126, 1999; Becker-Andre et al. (Nucleic Acids Research, 17:9437-9447, 1989; Zimmerman et al. (Biotechniques, 21:268-279, 1996; Diviacco et al. (Gene, 122:3013-3020, 1992; Becker-Andre et al., (Nucleic Acids Research, 17:9437-9446, 1989); and the like.

Primers

"Primer" includes an oligonucleotide, either natural or synthetic, that is capable, upon forming a duplex with a polynucleotide template, of acting as a point of initiation of nucleic acid synthesis and being extended from its 3' end along the template so that an extended duplex is formed. The sequence of nucleotides added during the extension process are determined by the sequence of the template polynucleotide. Usually primers are extended by a DNA polymerase. Primers usually have a length in the range of between 3 to 36 nucleotides, from 5 to 24 nucleotides, or from 14 to 36 nucleotides. In certain aspects, primers are universal primers or non-universal primers. Pairs of primers can flank a sequence of interest or a set of sequences of interest. Primers and probes can be degenerate in sequence. In certain aspects, primers bind adjacent to the target sequence, whether it is the sequence to be captured for analysis, or a tag that it to be copied.

In specific embodiments, the amplification reaction mixture may further comprise a first primer and optionally second primer. The first and second primer may comprise a portion that is complementary to a first portion of the target nucleic acid and a second primer comprising a portion that is complementary to a second portion of the target nucleic acid. The first and second primer may be referred to as a primer pair. In some embodiments, the first or second primer may comprise an RNA polymerase promoter.

In specific embodiments, the amplification reaction mixture may further comprise a polymerase. Subsequent to melting and hybridization with a primer, the nucleic acid is subjected to a polymerization step. A DNA polymerase is selected if the nucleic acid to be amplified is DNA. When the initial target is RNA, a reverse transcriptase may first be used to copy the RNA target into a cDNA molecule and the cDNA is then further amplified by a selected DNA polymerase. The DNA polymerase acts on the target nucleic acid to extend the primers hybridized to the nucleic acid templates in the presence of four dNTPs to form primer extension products complementary to the nucleotide sequence on the nucleic acid template.

In some instances, the primer is tagged, in one preferred embodiment, the tagged primer is a 5' biotinylated primer, typically used with a gene specific sequence in the primer, targeting a gene, mutation, or SNP of interest. In some instances then, a first PCR product is generated by amplifying sequences with a biotinylated 5' primer comprising a binding site for a second PCR product and a sequence complementary to a specific gene of interest and a 3' SMART primer complementary to the SMART sequence at the 3' end of the nucleic acid to generate a first PCR product. The binding site for the second PCR product may be a partial Illumina sequencing primer binding site or an oligomer for sequencing kit, such as a NEBNext® oligos for Illumina® sequencing (see, e.g., neb.com For library preparation for next generation sequencing, Illumina library preparation). However, oligomers for other sequencing kits can be used in the methods described herein, allowing for versatile end use products. Advantageously, nanopore sequencing can also be performed with the methods disclosed herein, with binding sites tailored for such end uses.

Figure 1B:
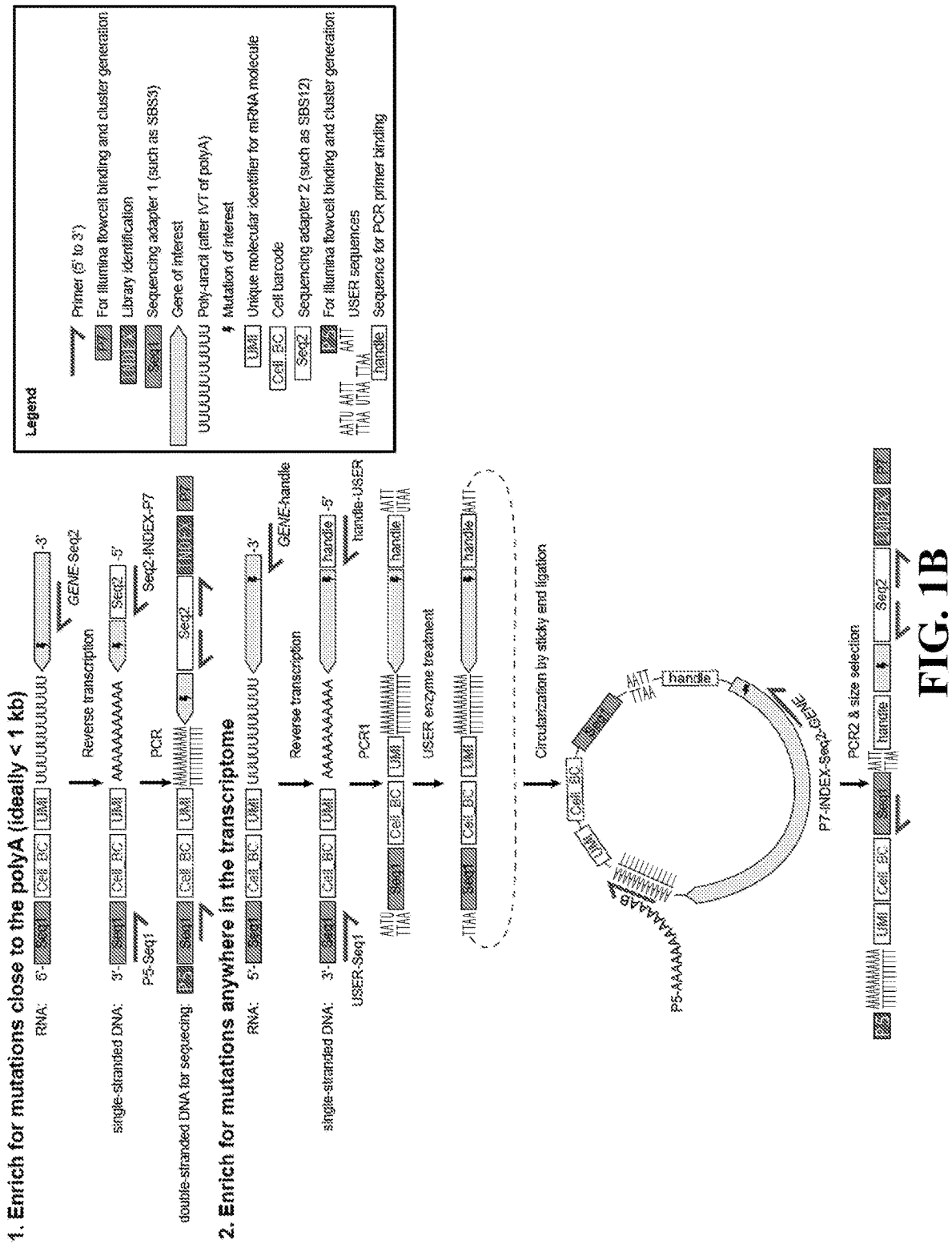

The 5' primer comprising the binding site for the second PCR product to amplify the first PCR product may further comprise a sequence to bind a flow cell, a sequence allowing multiple sequencing libraries to be sequenced simultaneously and/or a sequence providing an additional primer binding site. The sequence to bind a flow cell may be a P7 sequence and the flow cell may be an Illumina® flowcell. In some embodiments where a reverse transcription and subsequent circularization is performed, as shown in FIG. 1B, P5 and P7 are used in primers of a second PCR amplication and size selection. FIGS. 1A and 1B provide certain exemplary embodiments when next generation sequencing is used, but one of skill in the art can adjust the primers based on desired end material when more is needed for example for nanopore sequencing, and for end use, when next generation sequencing is or is not used.

In another embodiment, the SMART primer complementary to the SMART sequence at the 3' end of the nucleic acid to amplify the first PCR product may further comprise a sequence to allow fragments to bind a flowcell. The sequence to allow fragments to bind a flowcell may be a P5 sequence.

Regardless of the library construction method, submitted libraries may consist of a sequence of interest flanked on either side by adapter constructs. On each end, these adapter constructs may have flow cell binding sites, P5 and P7, which allow the library fragment to attach to the flow cell surface. The P5 and P7 regions of single-stranded library fragments anneal to their complementary oligos on the flowcell surface. The flow cell oligos act as primers and a strand complementary to the library fragment is synthesized. The original strand is washed away, leaving behind fragment copies that are covalently bonded to the flowcell surface in a mixture of orientations. 1,000 copies of each fragment are generated by bridge amplification, creating clusters. Bridge amplification can be performed by methods known in the art, for example, as described in U.S. Pat. No. 7,972,820 and U.S. application Ser. No. 15/316,470. For simplification, the figures diagramming the methods show only one copy (out of 1,000) in each cluster, and only two clusters (out of 30-50 million). The P5 region is cleaved, resulting in clusters containing only fragments which are attached by the P7 region. This ensures that all copies are sequenced in the same direction. The sequencing primer anneals to the P5 end of the fragment, and begins the sequencing by synthesis process. Index reads are only performed when a sample is barcoded. When Read 1 is finished, everything from Read 1 is removed and an index primer is added, which anneals at the P7 end of the fragment and sequences the barcode. Everything is stripped from the template, which forms clusters by bridge amplification as in Read 1. This leaves behind fragment copies that are covalently bonded to the flowcell surface in a mixture of orientations. This time, P7 is cut instead of P5, resulting in clusters containing only fragments which are attached by the P5 region. This ensures that all copies are sequences in the same direction (opposite Read 1). The sequencing primer anneals to the P7 region and sequences the other end of the template.

In another embodiment, the sequence allowing multiple sequencing libraries to be sequenced simultaneously may be an INDEX sequence. The INDEX allows multiple sequencing libraries to be sequenced simultaneously (and demultiplexed using Illumina's bcl2fastq command). See, e.g., https://support.illumina.com for exemplary INDEX sequences.

In another embodiment, the 5' primer comprising the binding site for the second PCR product to amplify the first PCR product may further comprise a NEXTERA sequence. See, support.illumina.com and U.S. Pat. Nos. 5,965,443, and 6,437,109 and European Patent No. 0927258, for exemplary NEXTERA sequences.

In another embodiment, the sequence providing an additional primer binding site may be a custom read1 primer binding site (CR1P) for sequencing. CR1P is a Custom Read1 Primer binding site that is used for Drop-Seq and Seq-Well library sequencing. CR1P may comprise the sequence: GCCTGTCCGCGGAAGCAGTGGTAT-CAACGCAGAGTAC (SEQ ID NO: 1, see also Table 4 CR1P) (see e.g., Gierahn et al., Nature Methods 14, 395-398 (2017).

In an exemplary embodiment, several primer designs are presented in FIG. 1.

Biotin-NEXT-GENE-for: Biotinylation enables purification of the desired product following the first PCR reaction. NEXT creates a binding site for the second PCR product as well as a partial primer binding site for standard Illumina sequencing kits. NEXT may be any sequence that allows targeted enrichment and then select addition of sequencing handles. GENE is a sequence complementary to the WTA, designed to amplify a specific region of interest (in some embodiments, an exon).

SMART-rev: The SMART sequence is used in Drop-seq and Seq-Well to generate WTA libraries. Because the polyT-unique molecular identifier-unique cellular barcode (polyT-UMI-CB) sequence is followed by the SMART sequence, and the template switching oligo (TSO) also contains the SMART sequence, WTA libraries have the SMART sequence as a PCR binding site on both the 5' and the 3' end.

P7-INDEX-NEXTERA: The P7 sequence allows fragments to bind the Illumina flowcell. The INDEX allows multiple sequencing libraries to be sequenced simultaneously (and demultiplexed using Illumina's bcl2fastq command). The NEXTERA sequence provides a primer binding site for Illumina's standard Read2 sequencing primer mix.

SMART-CR1P-P5: The SMART sequence is the same as in SMART-rev. CR1P is a Custom Read1 Primer binding site that is used for Drop-Seq and Seq-Well library sequencing. The P5 sequence allows fragments to bind the Illumina flowcell. Note that the primer design can be easily modified for compatibility with additional single-cell RNA-seq technologies (SMART) or sequencing technologies (NEXTERA, CR1P).

Gene specific primers may be mixed for simultaneous detection of multiple mutations. Libraries may also be mixed for simultaneous detection of mutations in multiple samples. Mixed primers sometimes may not always detect multiple mutations in the same gene as only the shortest fragment in some instances will be detected. The 5' primer comprising the binding site for the second PCR product to amplify the first PCR product further comprises a sequence allowing multiple sequencing libraries to be sequenced simultaneously.

Enrichment

Nucleic acid enrichment reduces the complexity of a large nucleic acid sample, such as a genomic DNA sample, cDNA library or mRNA library, to facilitate further processing and genetic analysis. In certain example embodiments, the enrichment step is optional.

The method also provides for biotin enrichment of the first PCR product. Biotinylation of the primer to amplify the gene, region or mutation of interest from the library allows for the purification of the PCR product of interest. Because the libraries are flanked with SMART sequences on both ends, the vast majority of the first PCR product would be amplification of the entire library. In some embodiments, without the biotinylated primer, enrichment of the gene, region or mutation of interest would be insufficient to efficiently and confidently call genetic mutations. Biotin enrichment may be accomplished by streptavidin binding of the biotinylated first PCR product. The streptavidin bead kilobaseBINDER kit (Thermo Fisher Cat #60101) allows for isolation of large biotinylated DNA fragments. However, as described herein, other embodiments of the methods disclosed herein do not require an enrichment step and may advantageously be used without biotinylated primers.

Second Amplification

A second step of amplifying may be performed, in a preferred embodiment, a second PCR step is performed. However, in some embodiments, other methods of amplification can be utilized, as discussed herein.

In one embodiment, amplifying the tag-enriched first PCR product with a 5' primer comprising the binding site for the second PCR product and a 3' SMART primer complementary to the SMART sequence at the 3' end of the nucleic acid thereby generating the second PCR product, the SMART primer complementary to the SMART sequence at the 3' end of the nucleic acid to amplify the first PCR product further comprises a sequence to allow fragments to bind a flowcell. In an embodiment, one of the PCR primers for the second PCR amplification comprises a sequence to allow fragments to bind a flowcell is a P5 sequence, with the second primer comprising a barcoded oligos that can be used for library indexing. In some instances the primers comprise a deoxyuracil residue that can be incorporated in the first PCR product such that the first PCR product can be treated with a uracil-specific excision reagent.

In some embodiment, as discussed herein, comprises treating the first PCR product with a uracil-specific excision reagent ("USER®") enzyme, circularizing the first PCR product by sticky end ligation, and amplifying the tag-enriched circularized PCR product with a 5' primer complementary to gene of interest and having a sequence adapter and a 3' primer having a polyA tail and another sequence adapter thereby generating the second PCR product.

Optionally, additional amplification steps can be performed, including a third or fourth amplification. In some embodiments, amplification is performed by PCR, and can be utilized when additional material is needed for further manipulation of the libraries, including, for example third generation sequencing. Other amplification methods as described elsewhere herein, can be used with appropriate primers selected according to the amplification methods used, and the final library content desired.

Determining Genotype

Determining the genotype of the cell may be accomplished by identifying the UMI and cell BC, thereby distinguishing the cells by genotype, or expressed DNA sequences, such as mutations, translocations, insertions/deletions (indels), etc. In one embodiment, the nucleic acids comprise a tag that is a molecule that can be affinity selected such as, but not limited to, a small protein, peptide, nucleic acid. Advantageously, the tag is a biotin tag. The enriched libraries provided by the methods may be further distinguished or manipulated, including by subjecting to sequencing.

In addition to next-generation sequencing, long read/third-generation sequencing is also contemplated for use in the presently disclosed subject matter. Third-generation sequencing reads nucleotide sequences at the single molecule level. In some embodiments, third-generation sequencing is used when long reads are desired, and can be used, in some instances, instead of next-generation sequencing technologies in desired applications. In particular embodiments, nanopore sequencing or single molecule real time sequencing (SMRT) is used for third-generation sequencing. Nanopore technology libraries are generated by end-repair and sequencing adapter ligation, and, as such, allows for versatility in the sequencing adapters utilized in the PCR reaction. Accordingly, in some instances, when nanopore sequencing is utilized, the 'sequencing adapters' in the first PCR reaction is any adapter that allows for a second PCR with common primers. Exemplary nanopore technology that can be used for long reads can be found, for example, using Oxford Nanopore technology, available at nanoporetech.com. Long-read sequencing can also utilize SMRT sequencing which enables single-molecule resolution through the use of nucleotides uniquely labeled with a fluorophore, and observing a single DNA polymerase molecule while synthesizing a complementary DNA in a replication reaction to allow for single molecule resolution. tallows production of a natural DNA strand using the labeled nucleotides. In some instances, when third-generation sequencing will be used, additional amplification can be performed to generate sufficient material.

Distinguishing Cells by Genotype

A method of distinguishing cells by genotype may, in some embodiments comprise constructing a library as discussed herein that comprises a plurality of nucleic acids wherein each nucleic acid comprises a gene, a unique molecular identifier (UMI) and a cell barcode (cell BC) flanked by sequencing adapters at the 5' and 3' end. In particular embodiments, each nucleic acid comprises the orientation: 5'-sequencing adapter-cell barcode-UMI-UUUUUUU-mRNA-3'. Amplifying each nucleic acid in the library to create a whole transcriptome amplified (WTA) RNA by reverse transcription can be performed with a primer comprising a sequence adapter to provide a reverse transcribed product. The steps provide amplifying the reverse transcribed product by PCR amplification with primers that bind both sequence adapters and adding a library barcode and optionally additional sequence adapters to generate a first PCR product. The genotype of the cell can be performed as discussed elsewhere, including identifying the UMI and library barcode, thereby distinguishing the cells by genotype.

Reverse Transcribing

In specific embodiments, the amplification reaction mixture may further comprise a polymerase. Subsequent to melting and hybridization with a primer, the nucleic acid is subjected to a polymerization step. A DNA polymerase is selected if the nucleic acid to be amplified is DNA. When the initial target is RNA, a reverse transcriptase may first be used to copy the RNA target into a cDNA molecule and the cDNA is then further amplified by a selected DNA polymerase. The DNA polymerase acts on the target nucleic acid to extend the primers hybridized to the nucleic acid templates in the presence of four dNTPs to form primer extension products complementary to the nucleotide sequence on the nucleic acid template.

Optionally Treating with USER Enzyme and Amplifying

In some embodiments, the primers for amplifying in in a first PCR amplification comprise USER sequences, and further comprising treating the first PCR product with USER enzyme, thereby generating a circularized product.

The steps include cleaving the dU residue by addition of a uracil-specific excision reagent ("USER®") enzyme/T4 ligase to generate long complementary sticky ends to mediate efficient circularization and ligation, which now places the barcode and the 5' edge of the transcript sequence set in the primer extension in close proximity, thereby bringing the cell barcode within 100 bases of any desired sequence in the transcript.

Following treating with USER enzyme, the step of amplifying the circularized product in a second polymerase chain reaction with one or more primers, wherein the one or primers comprise a library barcode and/or additional sequencing adapters can be conducted.

In some embodiments, the method can then include more than one PCR steps with transcript specific primers, that can include adaptor sequences, and preferably uses nested PCR reactions where the final PCR reaction sets the 3' edge of the transcript sequence of the final sequencing construct. The final sequencing library can be utilized in several ways, including sequencing of the transcript sequence, or at some desired location in the transcript sequence.

Circularization without Enrichment

In one embodiment, the methods disclosed herein provide a protocol that eliminates need for enrichment in a scalable process. An exemplary embodiment can provide for amplification of all variable regions of a T-cell receptor. The methods described herein can advantageously be used for the amplification of regions not well characterized in RNA seq libraries. The steps include providing an RNAseq library, in some preferred embodiments, a SeqWell library. The starting library comprises a plurality of nucleic acids with each nucleic acid comprising a gene, a unique molecular identifier (UMI) and a cell barcode (cell BC) flanked by universal sequences.

In an embodiment, the method comprises conducting primer extension on a nucleic acid in the library with one or more 5' primers with each primer comprising a sequence complementary to a desired transcript and the universal sequence of the nucleic acid, thereby replicating one or more desired transcripts and setting a 5' edge of one or more desired transcript sequences in one or more final sequencing constructs; amplifying the replicated one or more desired transcript sequences with universal primers having complementary sequences on 5' ends of the universal primers followed by a deoxy-uracil residue to form an amplicon; and ligating the amplicons by reacting the amplicons with a uracil-specific excision reagent enzyme, thereby cleaving the amplicon at the deoxy-uracil residues resulting in sticky ends that mediate circularization.

Additional steps of amplifying by PCR may be performed. In these instances, primers complementary to a transcript of interest. In some preferred embodiments, at least two PCR steps are performed in a nested PCR using two sets of transcript specific primers complementary to a transcript of interest. As described previously, the primers may comprise adaptor sequences. In one embodiment, at least one set of the two sets of transcript specific primers comprise adaptor sequences, thereby yielding a final sequencing library of final sequencing constructs. In an embodiment, the last PCR step sets a 3' edge of the transcript sequence of the final construct. In some embodiments, the sequencing step utilizes primers complementary to the 3' set and 5' set edges of the final sequencing construct. The sequencing step can utilize a primer binding to a desired location in the final sequencing construct to drive a sequencing read at the desired location in the final sequencing construct, as described elsewhere herein.

The embodiments disclosed herein method works particularly well for libraries where a subset of the transcripts of interest are more than 1 kb away from the cell barcode. Particularly, variable regions of T-cell receptors can be used in the current methods. Accordingly, the transcript of interest can be in a T cell or a B cell, in some embodiments, in a T cell receptor, a B cell receptor or a CAR-T cell. Advantageously, the embodiment can comprise use of a pool of primers that, in an embodiment targeting variable regions, may target all variable regions. The sequencing method may also determine SNPs in the single cell.

Methods for AML Characterization, Diagnosis and Treatment

Methods of using the enriched libraries provided herein include the ability to stratify a patient diagnosed with AML as having a higher or lower chance of survival. In some embodiments, a patient may be determined to have a poorer outcome or lower survival rate based on the detection of certain gene signatures in a tumor sample from the patient with AML.

The stratification of patients into higher or lower survivability is important for the determination of treatment protocols, and methods herein contemplate a step of administering a treatment protocol based on the stratification disclosed herein. For a patient stratified as lower survival or poorer outcome, treatment modalities beyond the general standard of care may be indicated.

Induction therapy with cytarabine and an anthracycline remains a standard of care in AML. The standard combination is the 7+3, with a 7-day continuous infusion of cytarabine at the dosage of 100 or 200 mg/m2 per day on days 1 to 7 and daunorubicin at 60 mg/m2 per day on days 1 to 3.

In some instances, allogeneic hematopoietic stem cell transplantation (HSCT) is utilized, although it is an intensive treatment. Thus, if patient is stratified as higher change of survivability, foregoing HSCT may be recommended or indicated. For patients stratified as at risk of lower survivability, more aggressive approaches may be used.

For example, a dose-dense approach to increasing induction intensity relies on systematic administration of a second sequence of chemotherapy starting earlier than normal after the completion of the first sequence (generally between day 7 and day 14), or use of higher doses of daunorubicin during induction may aid in achieving remission. Alternatively, or in addition, a third drug may be added to the standard of care including the addition of Gemtuzumab ozogamicin (GO) or purine analogs to intensive chemotherapy. Moreover, enrollment in clinical trials including use of new targeted agents may be considered, including considering a standard of care for poorer outcomes to consider novel therapeutic strategies at the outset.

Other methods of treatment may include modulating the gene signatures utilized for stratification.

Use of Signature Genes

As used herein a "signature" may encompass any gene or genes, protein or proteins, or epigenetic element(s) whose expression profile or whose occurrence is associated with a specific cell type, subtype, or cell state of a specific cell type or subtype within a population of cells. For ease of discussion, when discussing gene expression, any of gene or genes, protein or proteins, or epigenetic element(s) may be substituted. As used herein, the terms "signature", "expression profile", or "expression program" may be used interchangeably. It is to be understood that also when referring to proteins (e.g. differentially expressed proteins), such may fall within the definition of "gene" signature. Levels of expression or activity or prevalence may be compared between different cells in order to characterize or identify for instance signatures specific for cell (sub)populations. Increased or decreased expression or activity or prevalence of signature genes may be compared between different cells in order to characterize or identify for instance specific cell (sub)populations. The detection of a signature in single cells may be used to identify and quantitate for instance specific cell (sub)populations. A signature may include a gene or genes, protein or proteins, or epigenetic element(s) whose expression or occurrence is specific to a cell (sub)population, such that expression or occurrence is exclusive to the cell (sub)population. A gene signature as used herein, may thus refer to any set of up- and down-regulated genes that are representative of a cell type or subtype. A gene signature as used herein, may also refer to any set of up- and downregulated genes between different cells or cell (sub)populations derived from a gene-expression profile. For example, a gene signature may comprise a list of genes differentially expressed in a distinction of interest.

The signature as defined herein (being it a gene signature, protein signature or other genetic or epigenetic signature) can be used to indicate the presence of a cell type, a subtype of the cell type, the state of the microenvironment of a population of cells, a particular cell type population or subpopulation, and/or the overall status of the entire cell (sub)population. Furthermore, the signature may be indicative of cells within a population of cells in vivo. The signature may also be used to suggest for instance particular therapies, or to follow up treatment, or to suggest ways to modulate immune systems. The signatures of the present invention may be discovered by analysis of expression profiles of single-cells within a population of cells from isolated samples (e.g. blood samples), thus allowing the discovery of novel cell subtypes or cell states that were previously invisible or unrecognized. The presence of subtypes or cell states may be determined by subtype specific or cell state specific signatures. The presence of these specific cell (sub)types or cell states may be determined by applying the signature genes to bulk sequencing data in a sample. Not being bound by a theory the signatures of the present invention may be microenvironment specific, such as their expression in a particular spatio-temporal context. Not being bound by a theory, signatures as discussed herein are specific to a particular pathological context. Not being bound by a theory, a combination of cell subtypes having a particular signature may indicate an outcome. Not being bound by a theory, the signatures can be used to deconvolute the network of cells present in a particular pathological condition. Not being bound by a theory the presence of specific cells and cell subtypes are indicative of a particular response to treatment, such as including increased or decreased susceptibility to treatment. The signature may indicate the presence of one particular cell type. In one embodiment, the novel signatures are used to detect multiple cell states or hierarchies that occur in subpopulations of cancer cells that are linked to particular pathological condition (e.g. cancer grade), or linked to a particular outcome or progression of the disease, or linked to a particular response to treatment of the disease.

The signature according to certain embodiments of the present invention may comprise or consist of one or more genes, proteins and/or epigenetic elements, such as for instance 1, 2, 3, 4, 5, 6, 7, 8, 9, 10 or more. In certain embodiments, the signature may comprise or consist of two or more genes, proteins and/or epigenetic elements, such as for instance 2, 3, 4, 5, 6, 7, 8, 9, 10 or more. In certain embodiments, the signature may comprise or consist of three or more genes, proteins and/or epigenetic elements, such as for instance 3, 4, 5, 6, 7, 8, 9, 10 or more. In certain embodiments, the signature may comprise or consist of four or more genes, proteins and/or epigenetic elements, such as for instance 4, 5, 6, 7, 8, 9, 10 or more. In certain embodiments, the signature may comprise or consist of five or more genes, proteins and/or epigenetic elements, such as for instance 5, 6, 7, 8, 9, 10 or more. In certain embodiments, the signature may comprise or consist of six or more genes, proteins and/or epigenetic elements, such as for instance 6, 7, 8, 9, 10 or more. In certain embodiments, the signature may comprise or consist of seven or more genes, proteins and/or epigenetic elements, such as for instance 7, 8, 9, 10 or more. In certain embodiments, the signature may comprise or consist of eight or more genes, proteins and/or epigenetic elements, such as for instance 8, 9, 10 or more. In certain embodiments, the signature may comprise or consist of nine or more genes, proteins and/or epigenetic elements, such as for instance 9, 10 or more. In certain embodiments, the signature may comprise or consist of ten or more genes, proteins and/or epigenetic elements, such as for instance 10, 11, 12, 13, 14, 15, or more. It is to be understood that a signature according to the invention may for instance also include genes or proteins as well as epigenetic elements combined.

In certain embodiments, a signature is characterized as being specific for a particular tumor cell or tumor cell (sub)population if it is upregulated or only present, detected or detectable in that particular tumor cell or tumor cell (sub)population, or alternatively is downregulated or only absent, or undetectable in that particular tumor cell or tumor cell (sub)population. In this context, a signature consists of one or more differentially expressed genes/proteins or differential epigenetic elements when comparing different cells or cell (sub)populations, including comparing different tumor cells or tumor cell (sub)populations, as well as comparing tumor cells or tumor cell (sub)populations with non-tumor cells or non-tumor cell (sub)populations. It is to be understood that "differentially expressed" genes/proteins include genes/proteins which are up- or down-regulated as well as genes/proteins which are turned on or off. When referring to up- or down-regulation, in certain embodiments, such up- or down-regulation is preferably at least two-fold, such as two-fold, three-fold, four-fold, five-fold, or more, such as for instance at least ten-fold, at least 20-fold, at least 30-fold, at least 40-fold, at least 50-fold, or more. Alternatively, or in addition, differential expression may be determined based on common statistical tests, as is known in the art.

As discussed herein, differentially expressed genes/proteins, or differential epigenetic elements may be differentially expressed on a single cell level, or may be differentially expressed on a cell population level. Preferably, the differentially expressed genes/proteins or epigenetic elements as discussed herein, such as constituting the gene signatures as discussed herein, when as to the cell population level, refer to genes that are differentially expressed in all or substantially all cells of the population (such as at least 80%, preferably at least 90%, such as at least 95% of the individual cells). This allows one to define a particular subpopulation of tumor cells. As referred to herein, a "subpopulation" of cells preferably refers to a particular subset of cells of a particular cell type which can be distinguished or are uniquely identifiable and set apart from other cells of this cell type. The cell subpopulation may be phenotypically characterized, and is preferably characterized by the signature as discussed herein. A cell (sub)population as referred to herein may constitute of a (sub)population of cells of a particular cell type characterized by a specific cell state.

When referring to induction, or alternatively suppression of a particular signature, preferable is meant induction or alternatively suppression (or upregulation or downregulation) of at least one gene/protein and/or epigenetic element of the signature, such as for instance at least to, at least three, at least four, at least five, at least six, or all genes/proteins and/or epigenetic elements of the signature.

Signatures may be functionally validated as being uniquely associated with a particular immune responder phenotype. Induction or suppression of a particular signature may consequentially be associated with or causally drive a particular immune responder phenotype.

Various aspects and embodiments of the invention may involve analyzing gene signatures, protein signature, and/or other genetic or epigenetic signature based on single cell analyses (e.g. single cell RNA sequencing) or alternatively based on cell population analyses, as is defined herein elsewhere.

In further aspects, the invention relates to gene signatures, protein signature, and/or other genetic or epigenetic signature of particular tumor cell subpopulations, as defined herein elsewhere. The invention hereto also further relates to particular tumor cell subpopulations, which may be identified based on the methods according to the invention as discussed herein; as well as methods to obtain such cell (sub)populations and screening methods to identify agents capable of inducing or suppressing particular tumor cell (sub)populations.

The invention further relates to various uses of the gene signatures, protein signature, and/or other genetic or epigenetic signature as defined herein, as well as various uses of the tumor cells or tumor cell (sub)populations as defined herein. Particular advantageous uses include methods for identifying agents capable of inducing or suppressing particular tumor cell (sub)populations based on the gene signatures, protein signature, and/or other genetic or epigenetic signature as defined herein. The invention further relates to agents capable of inducing or suppressing particular tumor cell (sub)populations based on the gene signatures, protein signature, and/or other genetic or epigenetic signature as defined herein, as well as their use for modulating, such as inducing or repressing, a particular gene signature, protein signature, and/or other genetic or epigenetic signature. In one embodiment, genes in one population of cells may be activated or suppressed in order to affect the cells of another population. In related aspects, modulating, such as inducing or repressing, a particular a particular gene signature, protein signature, and/or other genetic or epigenetic signature may modify overall tumor composition, such as tumor cell composition, such as tumor cell subpopulation composition or distribution, or functionality.

By means of additional guidance, when a cell is said to be positive for or to express or comprise expression of a given marker, such as a given gene or gene product, a skilled person would conclude the presence or evidence of a distinct signal for the marker when carrying out a measurement capable of detecting or quantifying the marker in or on the cell. Suitably, the presence or evidence of the distinct signal for the marker would be concluded based on a comparison of the measurement result obtained for the cell to a result of the same measurement carried out for a negative control (for example, a cell known to not express the marker) and/or a positive control (for example, a cell known to express the marker). Where the measurement method allows for a quantitative assessment of the marker, a positive cell may generate a signal for the marker that is at least 1.5-fold higher than a signal generated for the marker by a negative control cell or than an average signal generated for the marker by a population of negative control cells, e.g., at least 2-fold, at least 4-fold, at least 10-fold, at least 20-fold, at least 30-fold, at least 40-fold, at least 50-fold higher or even higher. Further, a positive cell may generate a signal for the marker that is 3.0 or more standard deviations, e.g., 3.5 or more, 4.0 or more, 4.5 or more, or 5.0 or more standard deviations, higher than an average signal generated for the marker by a population of negative control cells. The upregulation and/or downregulation of gene or gene product, including the amount, may be included as part of the gene signature or expression profile.

A "deviation" of a first value from a second value may generally encompass any direction (e.g., increase: first value>second value; or decrease: first value<second value) and any extent of alteration.

For example, a deviation may encompass a decrease in a first value by, without limitation, at least about 10% (about 0.9-fold or less), or by at least about 20% (about 0.8-fold or less), or by at least about 30% (about 0.7-fold or less), or by at least about 40% (about 0.6-fold or less), or by at least about 50% (about 0.5-fold or less), or by at least about 60% (about 0.4-fold or less), or by at least about 70% (about 0.3-fold or less), or by at least about 80% (about 0.2-fold or less), or by at least about 90% (about 0.1-fold or less), relative to a second value with which a comparison is being made.

For example, a deviation may encompass an increase of a first value by, without limitation, at least about 10% (about 1.1-fold or more), or by at least about 20% (about 1.2-fold or more), or by at least about 30% (about 1.3-fold or more), or by at least about 40% (about 1.4-fold or more), or by at least about 50% (about 1.5-fold or more), or by at least about 60% (about 1.6-fold or more), or by at least about 70% (about 1.7-fold or more), or by at least about 80% (about 1.8-fold or more), or by at least about 90% (about 1.9-fold or more), or by at least about 100% (about 2-fold or more), or by at least about 150% (about 2.5-fold or more), or by at least about 200% (about 3-fold or more), or by at least about 500% (about 6-fold or more), or by at least about 700% (about 8-fold or more), or like, relative to a second value with which a comparison is being made.

Preferably, a deviation may refer to a statistically significant observed alteration. For example, a deviation may refer to an observed alteration which falls outside of error margins of reference values in a given population (as expressed, for example, by standard deviation or standard error, or by a predetermined multiple thereof, e.g., 1×SD or ±2×SD or ±3×SD, or 1×SE or ±2×SE or ±3×SE). Deviation may also refer to a value falling outside of a reference range defined by values in a given population (for example, outside of a range which comprises ≥40%, ≥50%, ≥60%, ≥70%, ≥75% or ≥80% or ≥85% or ≥90% or ≥95% or even ≥100% of values in said population).

In a further embodiment, a deviation may be concluded if an observed alteration is beyond a given threshold or cut-off. Such threshold or cut-off may be selected as generally known in the art to provide for a chosen sensitivity and/or specificity of the prediction methods, e.g., sensitivity and/or specificity of at least 50%, or at least 60%, or at least 70%, or at least 80%, or at least 85%, or at least 90%, or at least 95%.

For example, receiver-operating characteristic (ROC) curve analysis can be used to select an optimal cut-off value of the quantity of a given immune cell population, biomarker or gene or gene product signatures, for clinical use of the present diagnostic tests, based on acceptable sensitivity and specificity, or related performance measures which are well-known per se, such as positive predictive value (PPV), negative predictive value (NPV), positive likelihood ratio (LR+), negative likelihood ratio (LR−), Youden index, or similar.

The signature genes of the present invention were discovered by analysis of expression profiles of single-cells within a population of cells from freshly isolated tumors, thus allowing the discovery of novel cell subtypes that were previously invisible in a population of cells within a tumor. The presence of subtypes may be determined by subtype specific signature genes. The presence of these specific cell types may be determined by applying the signature genes to bulk sequencing data in a patient tumor. Not being bound by a theory, a tumor is a conglomeration of many cells that make up a tumor microenvironment, whereby the cells communicate and affect each other in specific ways. As such, specific cell types within this microenvironment may express signature genes specific for this microenvironment. Not being bound by a theory the signature genes of the present invention may be microenvironment specific, such as their expression in a tumor. Not being bound by a theory, signature genes determined in single cells that originated in a tumor are specific to other tumors. Not being bound by a theory, a combination of cell subtypes in a tumor may indicate an outcome. Not being bound by a theory, the signature genes can be used to deconvolute the network of cells present in a tumor based on comparing them to data from bulk analysis of a tumor sample. Not being bound by a theory the presence of specific cells and cell subtypes may be indicative of tumor growth, invasiveness and resistance to treatment. The signature gene may indicate the presence of one particular cell type. In one embodiment, the signature genes may indicate that tumor infiltrating T-cells are present. The presence of cell types within a tumor may indicate that the tumor will be resistant to a treatment. In one embodiment, the signature genes of the present invention are applied to bulk sequencing data from a tumor sample obtained from a subject, such that information relating to disease outcome and personalized treatments is determined. In one embodiment, the novel signature genes are used to detect multiple cell states that occur in a subpopulation of tumor cells that are linked to resistance to targeted therapies and progressive tumor growth.

In one embodiment, the signature genes are detected by immunofluorescence, immunohistochemistry, fluorescence activated cell sorting (FACS), mass cytometry (CyTOF), drop-seq, RNA-seq, single cell qPCR, MERFISH (multiplex (in situ) RNA FISH) and/or by in situ hybridization. Other methods including absorbance assays and colorimetric assays are known in the art and may be used herein.

In one embodiment, tumor cells are stained for cell subtype specific signature genes. In one embodiment, the cells are fixed. In another embodiment, the cells are formalin fixed and paraffin embedded. Not being bound by a theory, the presence of the cell subtypes in a tumor indicate outcome and personalized treatments. Not being bound by a theory, the cell subtypes may be quantitated in a section of a tumor and the number of cells indicates an outcome and personalized treatment.

Diagnostic Methods

Methods as disclosed herein are also directed to methods of diagnosing a cell or tissue in a subject comprising AML. In methods of diagnosing, the method comprises the step of detecting a gene expression profile in one or more cells or tissues associated with AML. The order of steps provided herein is exemplary, certain steps may be carried out simultaneously or in a different order.

Diagnosis is commonplace and well-understood in medical practice. By means of further explanation and without limitation the term "diagnosis" generally refers to the process or act of recognizing, deciding on or concluding on a disease or condition in a subject on the basis of symptoms and signs and/or from results of various diagnostic procedures (such as, for example, from knowing the presence, absence and/or quantity of one or more biomarkers characteristic of the diagnosed disease or condition). Identifying a disease state, disease progression, or other abnormal condition, based upon symptoms, signs, and other physiological and anatomical parameters are also encompassed in diagnosis. In certain instances, diagnosis comprises detecting a gene expression profile of a sample, host tissue, cell or cell subpopulation.

The terms "prognosing" or "prognosis" generally refer to an anticipation on the progression of a disease or condition and the prospect (e.g., the probability, duration, and/or extent) of recovery. A good prognosis of the diseases or conditions taught herein may generally encompass anticipation of a satisfactory partial or complete recovery from the diseases or conditions, preferably within an acceptable time period. A good prognosis of such may more commonly encompass anticipation of not further worsening or aggravating of such, preferably within a given time period. A poor prognosis of the diseases or conditions as taught herein may generally encompass anticipation of a substandard recovery and/or unsatisfactorily slow recovery, or to substantially no recovery or even further worsening of such.

In certain embodiments, signature genes and biomarkers related to AML may be identified by comparing single cell expression profiles obtained from healthy or normal cells and AML cells.

In one particular embodiment, signature genes and biomarkers related to AML may be identified by comparing single cell expression profiles obtained from uninfected cells and cells containing AML.

Various aspects and embodiments of the invention may involve analyzing gene signatures, protein signature, and/or other genetic or epigenetic signature based on single cell analyses (e.g. single cell RNA sequencing) or alternatively based on cell population analyses, as is defined herein elsewhere.

A gene profile can be a gene signature, or expression profile. In one aspect, the gene expression profile measures upregulation or down regulation of particular genes or pathways. In particular instances, the gene expression profile comprises one or more genes from Table 2.

In some embodiments the gene signature is derived from a T cell, or a B cell. In some embodiments a TCR, a BCR, or a CAR-T cell. In some instances, the methods target variable regions of a transcript of interest. In some instances, the gene of interest is in a cancer cell. In some instances, it is an AML cell. In some instances, the cell can be characterized by the highly expressed genes comprised with in a cell, and may be characterized as a GMP HSC/progenitor like cell or a myeloid cell.

AML genes of interest for use in the current methods and gene signatures may comprise any gene of interest in Table 2. In some instances, the gene of interest is PRTN3, MPO, CALR, CLEC5A, ELANE, POU4F1, TRH, TSPOAP1, CEBPE, LINC01835, NUCB2, CSF3R, RUNX1T1, CD38, PLPPR3, IGFBP2, PRRT4, SNHG5, FABP5, LOC100419170, CLEC11A, SERPINB1, AZU1, FBN2, HNRNPDL, HSPB1, RNA5-8S, THSD7A, C12orf57, FGFR1, LPO, MGST1, C1QTNF4, HMGN1, SIPA1L2, DDOST, PTGIR, GATM, VAMP8, FAM46A, VAMP5, STAR, ANKRD18A, TM7SF3, CCND1, ROBO1, GFI1, DEFA4, CERS6; and the HSC signature genes may comprise SPINK2, ANGPT1, GUCY1A3, FAM30A, MMRN1, TPT1, GAS5, RAB27B, TPM4, MSI2, GCSAML, SOCS2, EEF1A1, NRIP1, HOPX, CD34, TFPI, TPSD1, PDZRN4, PCNP, PTPRCAP, FLT3, SMIM24, SELENOP, DAPK1, SMYD3, ADGRG6, PIM1, MECOM, CEP70, XIRP2, SPAG6, TAPT1-AS1, GNA15, DSE, TPSAB1, TPSB2, H2AFY, SCHIP1, LINC02470, NPR3, KMT2A, CD200, MACF1, GBP4, ABCC1, PROM1, TMEM70, FAM110A, TMEM123.

A method of detecting malignant AML cells in a sample is provided using the methods disclosed herein for detection. In some embodiments, the steps include selecting HSC/Prog-like cells in the sample, In some instances, malignancy may comprise detecting downregulated expression of one or more genes comprising MSI2, MEIS1 and EGR1 relative to a normal HSC/Prog-like.cell; and/or detecting upregulated expression of one or more GMP and cell cycles genes such as AZU1, TOP2A, MKI67 and CENPF relative to a normal HSC/Prog-like.cell; wherein the detecting of the upregulated and downregulated genes in the sample is indicative of a malignant AML cell.

TCRs for Use in Adoptive Cell Transfer (ACT)

In certain embodiments, T cell receptor (TCR) pairs are used in constructing cells for adoptive cell transfer. In certain embodiments, TCRs that are clonal or specific to an antigen are identified. As used herein, "ACT", "adoptive cell therapy" and "adoptive cell transfer" may be used interchangeably. In certain embodiments, Adoptive cell therapy (ACT) can refer to the transfer of cells to a patient with the goal of transferring the functionality and characteristics into the new host by engraftment of the cells (see, e.g., Mettananda et al., Editing an α-globin enhancer in primary human hematopoietic stem cells as a treatment for β-thalassemia, Nat Commun. 2017 Sep. 4; 8(1):424). As used herein, the term "engraft" or "engraftment" refers to the process of cell incorporation into a tissue of interest in vivo through contact with existing cells of the tissue. Adoptive cell therapy (ACT) can refer to the transfer of cells, most commonly immune-derived cells, back into the same patient or into a new recipient host with the goal of transferring the immunologic functionality and characteristics into the new host. If possible, use of autologous cells helps the recipient by minimizing GVHD issues. The adoptive transfer of autologous tumor infiltrating lymphocytes (TIL) (Besser et al., (2010) Clin. Cancer Res 16 (9) 2646-55; Dudley et al., (2002) Science 298 (5594): 850-4; and Dudley et al., (2005) Journal of Clinical Oncology 23 (10): 2346-57.) or genetically re-directed peripheral blood mononuclear cells (Johnson et al., (2009) Blood 114 (3): 535-46; and Morgan et al., (2006) Science 314(5796) 126-9) has been used to successfully treat patients with advanced solid tumors, including melanoma and colorectal carcinoma, as well as patients with CD19-expressing hematologic malignancies (Kalos et al., (2011) Science Translational Medicine 3 (95): 95ra73). In certain embodiments, allogenic cells immune cells are transferred (see, e.g., Ren et al., (2017) Clin Cancer Res 23 (9) 2255-2266). As described further herein, allogenic cells can be edited to reduce alloreactivity and prevent graft-versus-host disease. Thus, use of allogeneic cells allows for cells to be obtained from healthy donors and prepared for use in patients as opposed to preparing autologous cells from a patient after diagnosis.

Aspects of the invention involve the adoptive transfer of immune system cells, such as T cells, specific for selected antigens, such as tumor associated antigens or tumor specific neoantigens (see, e.g., Maus et al., 2014, Adoptive Immunotherapy for Cancer or Viruses, Annual Review of Immunology, Vol. 32: 189-225; Rosenberg and Restifo, 2015, Adoptive cell transfer as personalized immunotherapy for human cancer, Science Vol. 348 no. 6230 pp. 62-68; Restifo et al., 2015, Adoptive immunotherapy for cancer: harnessing the T cell response. Nat. Rev. Immunol. 12(4): 269-281; and Jenson and Riddell, 2014, Design and implementation of adoptive therapy with chimeric antigen receptor-modified T cells. Immunol Rev. 257(1): 127-144; and Rajasagi et al., 2014, Systematic identification of personal tumor-specific neoantigens in chronic lymphocytic leukemia. Blood. 2014 Jul. 17; 124(3):453-62).

Various strategies may for example be employed to genetically modify T cells by altering the specificity of the T cell receptor (TCR) for example by introducing new TCR a and R chains with selected peptide specificity (see U.S. Pat. No. 8,697,854; PCT Patent Publications: WO2003020763, WO2004033685, WO2004044004, WO2005114215, WO2006000830, WO2008038002, WO2008039818, WO2004074322, WO2005113595, WO2006125962, WO2013166321, WO2013039889, WO2014018863, WO2014083173; U.S. Pat. No. 8,088,379).

Chimeric Antigen Receptors (CARs)

As an alternative to, or addition to, TCR modifications, chimeric antigen receptors (CARs) may be used in order to generate immunoresponsive cells, such as T cells, specific for selected targets, such as malignant cells, with a wide variety of receptor chimera constructs having been described (see U.S. Pat. Nos. 5,843,728; 5,851,828; 5,912,170; 6,004,811; 6,284,240; 6,392,013; 6,410,014; 6,753,162; 8,211,422; and, PCT Publication WO9215322).

In general, CARs are comprised of an extracellular domain, a transmembrane domain, and an intracellular domain, wherein the extracellular domain comprises an antigen-binding domain that is specific for a predetermined target. While the antigen-binding domain of a CAR is often an antibody or antibody fragment (e.g., a single chain variable fragment, scFv), the binding domain is not particularly limited so long as it results in specific recognition of a target. For example, in some embodiments, the antigen-binding domain may comprise a receptor, such that the CAR is capable of binding to the ligand of the receptor. Alternatively, the antigen-binding domain may comprise a ligand, such that the CAR is capable of binding the endogenous receptor of that ligand. The antigen binding domain can include the CDRs from an identified TCR. Complementarity-determining regions (CDRs) are part of the variable chains in immunoglobulins (antibodies) and T cell receptors, generated by B-cells and T-cells respectively, where these molecules bind to their specific antigen.

The antigen-binding domain of a CAR is generally separated from the transmembrane domain by a hinge or spacer. The spacer is also not particularly limited, and it is designed to provide the CAR with flexibility. For example, a spacer domain may comprise a portion of a human Fc domain, including a portion of the CH3 domain, or the hinge region of any immunoglobulin, such as IgA, IgD, IgE, IgG, or IgM, or variants thereof. Furthermore, the hinge region may be modified so as to prevent off-target binding by FcRs or other potential interfering objects. For example, the hinge may comprise an IgG4 Fc domain with or without a S228P, L235E, and/or N297Q mutation (according to Kabat numbering) in order to decrease binding to FcRs. Additional spacers/hinges include, but are not limited to, CD4, CD8, and CD28 hinge regions.

The transmembrane domain of a CAR may be derived either from a natural or from a synthetic source. Where the source is natural, the domain may be derived from any membrane bound or transmembrane protein. Transmembrane regions of particular use in this disclosure may be derived from CD8, CD28, CD3, CD45, CD4, CD5, CDS, CD9, CD 16, CD22, CD33, CD37, CD64, CD80, CD86, CD 134, CD137, CD 154, TCR. Alternatively, the transmembrane domain may be synthetic, in which case it will comprise predominantly hydrophobic residues such as leucine and valine. Preferably a triplet of phenylalanine, tryptophan and valine will be found at each end of a synthetic transmembrane domain. Optionally, a short oligo- or polypeptide linker, preferably between 2 and 10 amino acids in length may form the linkage between the transmembrane domain and the cytoplasmic signaling domain of the CAR. A glycine-serine doublet provides a particularly suitable linker.

Alternative CAR constructs may be characterized as belonging to successive generations. First-generation CARs typically consist of a single-chain variable fragment of an antibody specific for an antigen, for example comprising a VL linked to a VH of a specific antibody, linked by a flexible linker, for example by a CD8α hinge domain and a CD8α transmembrane domain, to the transmembrane and intracellular signaling domains of either CD3ζ or FcRγ (scFv-CD3ζ or scFv-FcRγ; see U.S. Pat. Nos. 7,741,465; 5,912,172; U.S. Pat. No. 5,906,936). Second-generation CARs incorporate the intracellular domains of one or more costimulatory molecules, such as CD28, OX40 (CD134), or 4-1BB (CD137) within the endodomain (for example scFv-CD28/OX40/4-1BB-CD3ζ; see U.S. Pat. Nos. 8,911,993; 8,916,381; 8,975,071; 9,101,584; 9,102,760; 9,102,761). Third-generation CARs include a combination of costimulatory endodomains, such as a CD3ζ-chain, CD97, GDI la-CD18, CD2, ICOS, CD27, CD154, CDS, OX40, 4-1BB, CD2, CD7, LIGHT, LFA-1, NKG2C, B7-H3, CD30, CD40, PD-1, or CD28 signaling domains (for example scFv-CD28-4-1BB-CD3ζ or scFv-CD28-OX40-CD3ζ; see U.S. Pat. Nos. 8,906,682; 8,399,645; 5,686,281; PCT Publication No. WO2014134165; PCT Publication No. WO2012079000). In certain embodiments, the primary signaling domain comprises a functional signaling domain of a protein selected from the group consisting of CD3 zeta, CD3 gamma, CD3 delta, CD3 epsilon, common FcR gamma (FCERIG), FcR beta (Fc Epsilon Rib), CD79a, CD79b, Fc gamma RIIa, DAP10, and DAP12. In certain preferred embodiments, the primary signaling domain comprises a functional signaling domain of CD3ζ or FcRγ. In certain embodiments, the one or more costimulatory signaling domains comprise a functional signaling domain of a protein selected, each independently, from the group consisting of: CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, a ligand that specifically binds with CD83, CDS, ICAM-1, GITR, BAFFR, HVEM (LIGHTR), SLAMF7, NKp80 (KLRF1), CD160, CD19, CD4, CD8 alpha, CD8 beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, ITGB7, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Lyl08), SLAM (SLAMF1, CD150, IPO-3), BLAME (SLAMF8), SELPLG (CD162), LTBR, LAT, GADS, SLP-76, PAG/Cbp, NKp44, NKp30, NKp46, and NKG2D. In certain embodiments, the one or more costimulatory signaling domains comprise a functional signaling domain of a protein selected, each independently, from the group consisting of: 4-1BB, CD27, and CD28. In certain embodiments, a chimeric antigen receptor may have the design as described in U.S. Pat. No. 7,446,190, comprising an intracellular domain of CD3ζ chain (such as amino acid residues 52-163 of the human CD3 zeta chain, as shown in SEQ ID NO: 14 of U.S. Pat. No. 7,446,190), a signaling region from CD28 and an antigen-binding element (or portion or domain; such as scFv). The CD28 portion, when between the zeta chain portion and the antigen-binding element, may suitably include the transmembrane and signaling domains of CD28 (full sequence shown in SEQ ID NO: 6 of U.S. Pat. No. 7,446,190; these can include the following portion of CD28 as set forth in Genbank identifier NM_006139 (sequence version 1, 2 or 3. Alternatively, when the zeta sequence lies between the CD28 sequence and the antigen-binding element, intracellular domain of CD28 can be used alone (such as amino sequence set forth in SEQ ID NO: 9 of U.S. Pat. No. 7,446,190, incorporated herein by reference). Hence, certain embodiments employ a CAR comprising (a) a zeta chain portion comprising the intracellular domain of human CD3ζ chain, (b) a costimulatory signaling region, and (c) an antigen-binding element (or portion or domain), wherein the costimulatory signaling region comprises the amino acid sequence encoded by SEQ ID NO: 6 of U.S. Pat. No. 7,446,190.

Alternatively, costimulation may be orchestrated by expressing CARs in antigen-specific T cells, chosen so as to be activated and expanded following engagement of their native αβTCR, for example by antigen on professional antigen-presenting cells, with attendant costimulation. In addition, additional engineered receptors may be provided on the immunoresponsive cells, for example to improve targeting of a T-cell attack and/or minimize side effects.

By means of an example and without limitation, Kochenderfer et al., (2009) J Immunother. 32 (7): 689-702 described anti-CD19 chimeric antigen receptors (CAR). FMC63-28Z CAR contained a single chain variable region moiety (scFv) recognizing CD19 derived from the FMC63 mouse hybridoma (described in Nicholson et al., (1997) Molecular Immunology 34: 1157-1165), a portion of the human CD28 molecule, and the intracellular component of the human TCR-ζ molecule. FMC63-CD828BBZ CAR contained the FMC63 scFv, the hinge and transmembrane regions of the CD8 molecule, the cytoplasmic portions of CD28 and 4-1BB, and the cytoplasmic component of the TCR-ζ molecule. The exact sequence of the CD28 molecule included in the FMC63-28Z CAR corresponded to Genbank identifier NM_006139; the sequence included all amino acids starting with the amino acid sequence IEVMYPPPY and continuing all the way to the carboxy-terminus of the protein. To encode the anti-CD19 scFv component of the vector, the authors designed a DNA sequence which was based on a portion of a previously published CAR (Cooper et al., (2003) Blood 101: 1637-1644). This sequence encoded the following components in frame from the 5' end to the 3' end: an XhoI site, the human granulocyte-macrophage colony-stimulating factor (GM-CSF) receptor α-chain signal sequence, the FMC63 light chain variable region (as in Nicholson et al., supra), a linker peptide (as in Cooper et al., supra), the FMC63 heavy chain variable region (as in Nicholson et al., supra), and a NotI site. A plasmid encoding this sequence was digested with XhoI and NotI. To form the MSGV-FMC63-28Z retroviral vector, the XhoI and NotI-digested fragment encoding the FMC63 scFv was ligated into a second XhoI and NotI-digested fragment that encoded the MSGV retroviral backbone (as in Hughes et al., (2005) Human Gene Therapy 16: 457-472) as well as part of the extracellular portion of human CD28, the entire transmembrane and cytoplasmic portion of human CD28, and the cytoplasmic portion of the human TCR-ζ molecule (as in Maher et al., 2002) Nature Biotechnology 20: 70-75). The FMC63-28Z CAR is included in the KTE-C19 (axicabtagene ciloleucel) anti-CD19 CAR-T therapy product in development by Kite Pharma, Inc. for the treatment of inter alia patients with relapsed/refractory aggressive B-cell non-Hodgkin lymphoma (NHL). Accordingly, in certain embodiments, cells intended for adoptive cell therapies, more particularly immunoresponsive cells such as T cells, may express the FMC63-28Z CAR as described by Kochenderfer et al. (supra). Hence, in certain embodiments, cells intended for adoptive cell therapies, more particularly immunoresponsive cells such as T cells, may comprise a CAR comprising an extracellular antigen-binding element (or portion or domain; such as scFv) that specifically binds to an antigen, an intracellular signaling domain comprising an intracellular domain of a CD3ζ chain, and a costimulatory signaling region comprising a signaling domain of CD28. Preferably, the CD28 amino acid sequence is as set forth in Genbank identifier NM_006139 (sequence version 1, 2 or 3).

Various combinations of a signal sequence (human CD8-alpha or GM-CSF receptor), extracellular and transmembrane regions (human CD8-alpha) and intracellular T-cell signalling domains (CD28-CD3ζ; 4-1BB-CD3ζ; CD27-CD3ζ; CD28-CD27-CD3ζ, 4-1BB-CD27-CD3ζ; CD27-4-1BB-CD3ζ; CD28-CD27-FcεRI gamma chain; or CD28-FcεRI gamma chain) were disclosed. Hence, in certain embodiments, cells intended for adoptive cell therapies, more particularly immunoresponsive cells such as T cells, may comprise a CAR comprising an extracellular antigen-binding element that specifically binds to an antigen, an extracellular and transmembrane region as set forth in Table 1 of WO2015187528 and an intracellular T-cell signalling domain as set forth in Table 1 of WO2015187528.

In certain embodiments, the immune cell may, in addition to a CAR or exogenous TCR as described herein, further comprise a chimeric inhibitory receptor (inhibitory CAR) that specifically binds to a second target antigen and is capable of inducing an inhibitory or immunosuppressive or repressive signal to the cell upon recognition of the second target antigen. In certain embodiments, the chimeric inhibitory receptor comprises an extracellular antigen-binding element (or portion or domain) configured to specifically bind to a target antigen, a transmembrane domain, and an intracellular immunosuppressive or repressive signaling domain. In certain embodiments, the second target antigen is an antigen that is not expressed on the surface of a cancer cell or infected cell or the expression of which is downregulated on a cancer cell or an infected cell. In certain embodiments, the second target antigen is an MHC-class I molecule. In certain embodiments, the intracellular signaling domain comprises a functional signaling portion of an immune checkpoint molecule, such as for example PD-1 or CTLA4. Advantageously, the inclusion of such inhibitory CAR reduces the chance of the engineered immune cells attacking non-target (e.g., non-cancer) tissues.

Alternatively, T-cells expressing CARs may be further modified to reduce or eliminate expression of endogenous TCRs in order to reduce off-target effects. Reduction or elimination of endogenous TCRs can reduce off-target effects and increase the effectiveness of the T cells (U.S. Pat. No. 9,181,527). T cells stably lacking expression of a functional TCR may be produced using a variety of approaches. T cells internalize, sort, and degrade the entire T cell receptor as a complex, with a half-life of about 10 hours in resting T cells and 3 hours in stimulated T cells (von Essen, M. et al. 2004. J. Immunol. 173:384-393). Proper functioning of the TCR complex requires the proper stoichiometric ratio of the proteins that compose the TCR complex. TCR function also requires two functioning TCR zeta proteins with ITAM motifs. The activation of the TCR upon engagement of its MHC-peptide ligand requires the engagement of several TCRs on the same T cell, which all must signal properly. Thus, if a TCR complex is destabilized with proteins that do not associate properly or cannot signal optimally, the T cell will not become activated sufficiently to begin a cellular response.

Accordingly, in some embodiments, TCR expression may eliminated using RNA interference (e.g., shRNA, siRNA, miRNA, etc.), CRISPR, or other methods that target the nucleic acids encoding specific TCRs (e.g., TCR-α and TCR-β) and/or CD3 chains in primary T cells. By blocking expression of one or more of these proteins, the T cell will no longer produce one or more of the key components of the TCR complex, thereby destabilizing the TCR complex and preventing cell surface expression of a functional TCR.

In some instances, CAR may also comprise a switch mechanism for controlling expression and/or activation of the CAR. For example, a CAR may comprise an extracellular, transmembrane, and intracellular domain, in which the extracellular domain comprises a target-specific binding element that comprises a label, binding domain, or tag that is specific for a molecule other than the target antigen that is expressed on or by a target cell. In such embodiments, the specificity of the CAR is provided by a second construct that comprises a target antigen binding domain (e.g., an scFv or a bispecific antibody that is specific for both the target antigen and the label or tag on the CAR) and a domain that is recognized by or binds to the label, binding domain, or tag on the CAR. See, e.g., WO 2013/044225, WO 2016/000304, WO 2015/057834, WO 2015/057852, WO 2016/070061, U.S. Pat. No. 9,233,125, US 2016/0129109. In this way, a T-cell that expresses the CAR can be administered to a subject, but the CAR cannot bind its target antigen until the second composition comprising an antigen-specific binding domain is administered.

Alternative switch mechanisms include CARs that require multimerization in order to activate their signaling function (see, e.g., US 2015/0368342, US 2016/0175359, US 2015/0368360) and/or an exogenous signal, such as a small molecule drug (US 2016/0166613, Yung et al., Science, 2015), in order to elicit a T-cell response. Some CARs may also comprise a "suicide switch" to induce cell death of the CAR T-cells following treatment (Buddee et al., PLoS One, 2013) or to downregulate expression of the CAR following binding to the target antigen (WO 2016/011210).

Constructing Cells

Alternative techniques may be used to transform target immunoresponsive cells, such as protoplast fusion, lipofection, transfection or electroporation. A wide variety of vectors may be used, such as retroviral vectors, lentiviral vectors, adenoviral vectors, adeno-associated viral vectors, plasmids or transposons, such as a Sleeping Beauty transposon (see U.S. Pat. Nos. 6,489,458; 7,148,203; 7,160,682; 7,985,739; 8,227,432), may be used to introduce CARs, for example using 2nd generation antigen-specific CARs signaling through CD3ζ and either CD28 or CD137. Viral vectors may for example include vectors based on HIV, SV40, EBV, HSV or BPV.

Cells that are targeted for transformation may for example include T cells, Natural Killer (NK) cells, cytotoxic T lymphocytes (CTL), regulatory T cells, human embryonic stem cells, tumor-infiltrating lymphocytes (TIL) or a pluripotent stem cell from which lymphoid cells may be differentiated. T cells expressing a desired CAR may for example be selected through co-culture with γ-irradiated activating and propagating cells (AaPC), which co-express the cancer antigen and co-stimulatory molecules. The engineered CAR T-cells may be expanded, for example by co-culture on AaPC in presence of soluble factors, such as IL-2 and IL-21. This expansion may for example be carried out so as to provide memory CAR+ T cells (which may for example be assayed by non-enzymatic digital array and/or multi-panel flow cytometry). In this way, CAR T cells may be provided that have specific cytotoxic activity against antigen-bearing tumors (optionally in conjunction with production of desired chemokines such as interferon-γ). CAR T cells of this kind may for example be used in animal models, for example to treat tumor xenografts.

In certain embodiments, ACT includes co-transferring CD4+ Th1 cells and CD8+ CTLs to induce a synergistic antitumour response (see, e.g., Li et al., Adoptive cell therapy with CD4+ T helper 1 cells and CD8+ cytotoxic T cells enhances complete rejection of an established tumour, leading to generation of endogenous memory responses to non-targeted tumour epitopes. Clin Transl Immunology. 2017 October; 6(10): e160).

In certain embodiments, Th17 cells are transferred to a subject in need thereof. Th17 cells have been reported to directly eradicate melanoma tumors in mice to a greater extent than Th1 cells (Muranski P, et al., Tumor-specific Th17-polarized cells eradicate large established melanoma. Blood. 2008 Jul. 15; 112(2):362-73; and Martin-Orozco N, et al., T helper 17 cells promote cytotoxic T cell activation in tumor immunity. Immunity. 2009 Nov. 20; 31(5):787-98). Those studies involved an adoptive T cell transfer (ACT) therapy approach, which takes advantage of CD4$^+$ T cells that express a TCR recognizing tyrosinase tumor antigen. Exploitation of the TCR leads to rapid expansion of Th17 populations to large numbers ex vivo for reinfusion into the autologous tumor-bearing hosts.

In certain embodiments, ACT may include autologous iPSC-based vaccines, such as irradiated iPSCs in autologous anti-tumor vaccines (see e.g., Kooreman, Nigel G. et al., Autologous iPSC-Based Vaccines Elicit Anti-tumor Responses In Vivo, Cell Stem Cell 22, 1-13, 2018, doi.org/10.1016/j.stem.2018.01.016).

To guard against possible adverse reactions, engineered immunoresponsive cells may be equipped with a transgenic safety switch, in the form of a transgene that renders the cells vulnerable to exposure to a specific signal. For example, the herpes simplex viral thymidine kinase (TK) gene may be used in this way, for example by introduction into allogeneic T lymphocytes used as donor lymphocyte infusions following stem cell transplantation (Greco, et al., Improving the safety of cell therapy with the TK-suicide gene. Front. Pharmacol. 2015; 6: 95). In such cells, administration of a nucleoside prodrug such as ganciclovir or acyclovir causes cell death. Alternative safety switch constructs include inducible caspase 9, for example triggered by administration of a small-molecule dimerizer that brings together two nonfunctional icasp9 molecules to form the active enzyme. A wide variety of alternative approaches to implementing cellular proliferation controls have been described (see U.S. Patent Publication No. 20130071414; PCT Patent Publication WO2011146862; PCT Patent Publication WO2014011987; PCT Patent Publication WO2013040371; Zhou et al. BLOOD, 2014, 123/25:3895-3905; Di Stasi et al., The New England Journal of Medicine 2011; 365:1673-1683; Sadelain M, The New England Journal of Medicine 2011; 365:1735-173; Ramos et al., Stem Cells 28(6):1107-15 (2010)).

In certain embodiments, T cells comprising a CAR or an exogenous TCR, may be manufactured as described in WO2015120096, by a method comprising: enriching a population of lymphocytes obtained from a donor subject; stimulating the population of lymphocytes with one or more T-cell stimulating agents to produce a population of activated T cells, wherein the stimulation is performed in a closed system using serum-free culture medium; transducing the population of activated T cells with a viral vector comprising a nucleic acid molecule which encodes the CAR or TCR, using a single cycle transduction to produce a population of transduced T cells, wherein the transduction is performed in a closed system using serum-free culture medium; and expanding the population of transduced T cells for a predetermined time to produce a population of engineered T cells, wherein the expansion is performed in a closed system using serum-free culture medium. In certain embodiments, T cells comprising a CAR or an exogenous TCR, may be manufactured as described in WO2015120096, by a method comprising: obtaining a population of lymphocytes; stimulating the population of lymphocytes with one or more stimulating agents to produce a population of activated T cells, wherein the stimulation is performed in a closed system using serum-free culture medium; transducing the population of activated T cells with a viral vector comprising a nucleic acid molecule which encodes the CAR or TCR, using at least one cycle transduction to produce a population of transduced T cells, wherein the transduction is performed in a closed system using serum-free culture medium; and expanding the population of transduced T cells to produce a population of engineered T cells, wherein the expansion is performed in a closed system using serum-free culture medium. The predetermined time for expanding the population of transduced T cells may be 3 days. The time from enriching the population of lymphocytes to producing the engineered T cells may be 6 days. The closed system may be a closed bag system. Further provided is population of T cells comprising a CAR or an exogenous TCR obtainable or obtained by said method, and a pharmaceutical composition comprising such cells.

In certain embodiments, T cell maturation or differentiation in vitro may be delayed or inhibited by the method as described in WO2017070395, comprising contacting one or more T cells from a subject in need of a T cell therapy with an AKT inhibitor (such as, e.g., one or a combination of two or more AKT inhibitors disclosed in claim 8 of WO2017070395) and at least one of exogenous Interleukin-7 (IL-7) and exogenous Interleukin-15 (IL-15), wherein the resulting T cells exhibit delayed maturation or differentiation, and/or wherein the resulting T cells exhibit improved T cell function (such as, e.g., increased T cell proliferation; increased cytokine production; and/or increased cytolytic activity) relative to a T cell function of a T cell cultured in the absence of an AKT inhibitor.

Isolating T Cells

In certain embodiments, T cells are isolated from a subject. The T cell receptors may be identified according to the present invention. The TCRs may be present on any type of T cell, including, e.g., thymocytes, Th or Tc; Th1, Th2, Th17, Thαβ, CD4$^+$, CD8$^+$, effector Th, memory Th, regulatory Th, CD4$^+$/CD8$^+$ thymocytes, CD4−/CD8− thymocytes, γδ T cells, etc.

Immune cells may be obtained using any method known in the art. In one embodiment, allogenic T cells may be obtained from healthy subjects. In one embodiment T cells that have infiltrated a tumor are isolated. T cells may be removed during surgery. T cells may be isolated after removal of tumor tissue by biopsy. T cells may be isolated by any means known in the art. In one embodiment, T cells are obtained by apheresis. In one embodiment, the method may comprise obtaining a bulk population of T cells from a tumor sample by any suitable method known in the art. For example, a bulk population of T cells can be obtained from a tumor sample by dissociating the tumor sample into a cell suspension from which specific cell populations can be selected. Suitable methods of obtaining a bulk population of T cells may include, but are not limited to, any one or more of mechanically dissociating (e.g., mincing) the tumor, enzymatically dissociating (e.g., digesting) the tumor, and aspiration (e.g., as with a needle).

The bulk population of T cells obtained from a tumor sample may comprise any suitable type of T cell. Preferably, the bulk population of T cells obtained from a tumor sample comprises tumor infiltrating lymphocytes (TILs).

The tumor sample may be obtained from any mammal. Unless stated otherwise, as used herein, the term "mammal" refers to any mammal including, but not limited to, mammals of the order Lagomorpha, such as rabbits; the order Carnivora, including Felines (cats) and Canines (dogs); the order Artiodactyla, including Bovines (cows) and Swines (pigs); or of the order Perissodactyla, including Equines (horses). The mammals may be non-human primates, e.g., of the order Primates, Ceboids, or Simoids (monkeys) or of the order Anthropoids (humans and apes). In some embodiments, the mammal may be a mammal of the order Rodentia, such as mice and hamsters. Preferably, the mammal is a non-human primate or a human. An especially preferred mammal is the human.

T cells can be obtained from a number of sources, including peripheral blood mononuclear cells (PBMC), bone marrow, lymph node tissue, spleen tissue, and tumors. In certain embodiments of the present invention, T cells can be obtained from a unit of blood collected from a subject using any number of techniques known to the skilled artisan, such as Ficoll separation. In one preferred embodiment, cells from the circulating blood of an individual are obtained by apheresis or leukapheresis. The apheresis product typically contains lymphocytes, including T cells, monocytes, granulocytes, B cells, other nucleated white blood cells, red blood cells, and platelets. In one embodiment, the cells collected by apheresis may be washed to remove the plasma fraction and to place the cells in an appropriate buffer or media for subsequent processing steps. In one embodiment of the invention, the cells are washed with phosphate buffered saline (PBS). In an alternative embodiment, the wash solution lacks calcium and may lack magnesium or may lack many if not all divalent cations. Initial activation steps in the absence of calcium lead to magnified activation. As those of ordinary skill in the art would readily appreciate a washing step may be accomplished by methods known to those in the art, such as by using a semi-automated "flow-through" centrifuge (for example, the Cobe 2991 cell processor) according to the manufacturer's instructions. After washing, the cells may be resuspended in a variety of biocompatible buffers, such as, for example, Ca-free, Mg-free PBS. Alternatively, the undesirable components of the apheresis sample may be removed and the cells directly resuspended in culture media.

In another embodiment, T cells are isolated from peripheral blood lymphocytes by lysing the red blood cells and depleting the monocytes, for example, by centrifugation through a PERCOLL™ gradient. A specific subpopulation of T cells, such as CD28+, CD4+, CDC, CD45RA+, and CD45RO+ T cells, can be further isolated by positive or negative selection techniques. For example, in one preferred embodiment, T cells are isolated by incubation with anti-CD3/anti-CD28 (i.e., 3×28)-conjugated beads, such as DYNABEADS® M-450 CD3/CD28 T, or XCYTE DYNABEADS™ for a time period sufficient for positive selection of the desired T cells. In one embodiment, the time period is about 30 minutes. In a further embodiment, the time period ranges from 30 minutes to 36 hours or longer and all integer values there between. In a further embodiment, the time period is at least 1, 2, 3, 4, 5, or 6 hours. In yet another preferred embodiment, the time period is 10 to 24 hours. In one preferred embodiment, the incubation time period is 24 hours. For isolation of T cells from patients with leukemia, use of longer incubation times, such as 24 hours, can increase cell yield. Longer incubation times may be used to isolate T cells in any situation where there are few T cells as compared to other cell types, such in isolating tumor infiltrating lymphocytes (TIL) from tumor tissue or from immunocompromised individuals. Further, use of longer incubation times can increase the efficiency of capture of CD8+ T cells.

Enrichment of a T cell population by negative selection can be accomplished with a combination of antibodies directed to surface markers unique to the negatively selected cells. A preferred method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20, CD11b, CD16, HLA-DR, and CD8.

Further, monocyte populations (i.e., CD14+ cells) may be depleted from blood preparations by a variety of methodologies, including anti-CD14 coated beads or columns, or utilization of the phagocytotic activity of these cells to facilitate removal. Accordingly, in one embodiment, the invention uses paramagnetic particles of a size sufficient to be engulfed by phagocytotic monocytes. In certain embodiments, the paramagnetic particles are commercially available beads, for example, those produced by Life Technologies under the trade name Dynabeads™. In one embodiment, other non-specific cells are removed by coating the paramagnetic particles with "irrelevant" proteins (e.g., serum proteins or antibodies). Irrelevant proteins and antibodies include those proteins and antibodies or fragments thereof that do not specifically target the T cells to be isolated. In certain embodiments, the irrelevant beads include beads coated with sheep anti-mouse antibodies, goat anti-mouse antibodies, and human serum albumin.

In brief, such depletion of monocytes can be performed by preincubating T cells isolated from whole blood, apheresed peripheral blood, or tumors with one or more varieties of irrelevant or non-antibody coupled paramagnetic particles at any amount that allows for removal of monocytes (approximately a 20:1 bead:cell ratio) for about 30 minutes to 2 hours at 22 to 37 degrees C., followed by magnetic removal of cells which have attached to or engulfed the paramagnetic particles. Such separation can be performed using standard methods available in the art. For example, any magnetic separation methodology may be used including a variety of which are commercially available, (e.g., DYNAL® Magnetic Particle Concentrator (DYNAL MPC®)). Assurance of requisite depletion can be monitored by a variety of methodologies known to those of ordinary skill in the art, including flow cytometric analysis of CD14 positive cells, before and after depletion.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells, or from samples where there are many tumor cells present (i.e., leukemic blood, tumor tissue, etc). Such populations of cells may have therapeutic value and would be desirable to obtain. For example, using high concentration of cells allows more efficient selection of CD8+ T cells that normally have weaker CD28 expression.

In a related embodiment, it may be desirable to use lower concentrations of cells. By significantly diluting the mixture of T cells and surface (e.g., particles such as beads), interactions between the particles and cells is minimized. This selects for cells that express high amounts of desired antigens to be bound to the particles. For example, CD4+ T cells express higher levels of CD28 and are more efficiently captured than CD8+ T cells in dilute concentrations. In one embodiment, the concentration of cells used is $5\times10^6$/ml. In other embodiments, the concentration used can be from about $1\times10^5$/ml to $1\times10^6$/ml, and any integer value in between.

T cells can also be frozen. Wishing not to be bound by theory, the freeze and subsequent thaw step provides a more uniform product by removing granulocytes and to some extent monocytes in the cell population. After a washing step to remove plasma and platelets, the cells may be suspended in a freezing solution. While many freezing solutions and parameters are known in the art and will be useful in this context, one method involves using PBS containing 20% DMSO and 8% human serum albumin, or other suitable cell freezing media, the cells then are frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

T cells for use in the present invention may be antigen-specific T cells. For example, tumor-specific T cells can be used. In certain embodiments, antigen-specific T cells can be isolated from a patient of interest, such as a patient afflicted with a cancer or an infectious disease. In one embodiment, neoepitopes are determined for a subject and T cells specific to these antigens are isolated. Antigen-specific cells for use in expansion may also be generated in vitro using any number of methods known in the art, for example, as described in U.S. Patent Publication No. US 20040224402 entitled, Generation and Isolation of Antigen-Specific T Cells, or in U.S. Pat. No. 6,040,177. Antigen-specific cells for use in the present invention may also be generated using any number of methods known in the art, for example, as described in Current Protocols in Immunology, or Current Protocols in Cell Biology, both published by John Wiley & Sons, Inc., Boston, Mass.

In a related embodiment, it may be desirable to sort or otherwise positively select (e.g. via magnetic selection) the antigen specific cells prior to or following one or two rounds of expansion. Sorting or positively selecting antigen-specific cells can be carried out using peptide-MHIC tetramers (Altman, et al., Science. 1996 Oct. 4; 274(5284):94-6). In another embodiment, the adaptable tetramer technology approach is used (Andersen et al., 2012 Nat Protoc. 7:891-902). Tetramers are limited by the need to utilize predicted binding peptides based on prior hypotheses, and the restriction to specific HLAs. Peptide-MHC tetramers can be generated using techniques known in the art and can be made with any MHC molecule of interest and any antigen of interest as described herein. Specific epitopes to be used in this context can be identified using numerous assays known in the art. For example, the ability of a polypeptide to bind to MHC class I may be evaluated indirectly by monitoring the ability to promote incorporation of $^{125}$I labeled β2-microglobulin (β2m) into MHC class I/β2m/peptide heterotrimeric complexes (see Parker et al., J. Immunol. 152:163, 1994).

In one embodiment cells are directly labeled with an epitope-specific reagent for isolation by flow cytometry followed by characterization of phenotype and TCRs. In one embodiment, T cells are isolated by contacting with T cell specific antibodies. Sorting of antigen-specific T cells, or generally any cells of the present invention, can be carried out using any of a variety of commercially available cell sorters, including, but not limited to, MoFlo sorter (Dako-Cytomation, Fort Collins, Colo.), FACSAria™, FACSArray™, FACSVantage™, BD™ LSR II, and FACSCalibur™ (BD Biosciences, San Jose, Calif.).

In a preferred embodiment, the method comprises selecting cells that also express CD3. The method may comprise specifically selecting the cells in any suitable manner. Preferably, the selecting is carried out using flow cytometry. The flow cytometry may be carried out using any suitable method known in the art. The flow cytometry may employ any suitable antibodies and stains. Preferably, the antibody is chosen such that it specifically recognizes and binds to the particular biomarker being selected. For example, the specific selection of CD3, CD8, TIM-3, LAG-3, 4-1BB, or PD-1 may be carried out using anti-CD3, anti-CD8, anti-TIM-3, anti-LAG-3, anti-4-1BB, or anti-PD-1 antibodies, respectively. The antibody or antibodies may be conjugated to a bead (e.g., a magnetic bead) or to a fluorochrome. Preferably, the flow cytometry is fluorescence-activated cell sorting (FACS). TCRs expressed on T cells can be selected based on reactivity to autologous tumors. Additionally, T cells that are reactive to tumors can be selected for based on markers using the methods described in patent publication Nos. WO2014133567 and WO2014133568, herein incorporated by reference in their entirety. Additionally, activated T cells can be selected for based on surface expression of CD107a.

In one embodiment of the invention, the method further comprises expanding the numbers of T cells in the enriched cell population. Such methods are described in U.S. Pat. No. 8,637,307 and is herein incorporated by reference in its entirety. The numbers of T cells may be increased at least about 3-fold (or 4-, 5-, 6-, 7-, 8-, or 9-fold), more preferably at least about 10-fold (or 20-, 30-, 40-, 50-, 60-, 70-, 80-, or 90-fold), more preferably at least about 100-fold, more preferably at least about 1,000 fold, or most preferably at least about 100,000-fold. The numbers of T cells may be expanded using any suitable method known in the art. Exemplary methods of expanding the numbers of cells are described in patent publication No. WO 2003057171, U.S. Pat. No. 8,034,334, and U.S. Patent Application Publication No. 2012/0244133, each of which is incorporated herein by reference.

In one embodiment, ex vivo T cell expansion can be performed by isolation of T cells and subsequent stimulation or activation followed by further expansion. In one embodiment of the invention, the T cells may be stimulated or activated by a single agent. In another embodiment, T cells are stimulated or activated with two agents, one that induces a primary signal and a second that is a co-stimulatory signal. Ligands useful for stimulating a single signal or stimulating a primary signal and an accessory molecule that stimulates a second signal may be used in soluble form. Ligands may be attached to the surface of a cell, to an Engineered Multivalent Signaling Platform (EMSP), or immobilized on a surface. In a preferred embodiment both primary and secondary agents are co-immobilized on a surface, for example a bead or a cell. In one embodiment, the molecule providing the primary activation signal may be a CD3 ligand, and the co-stimulatory molecule may be a CD28 ligand or 4-1BB ligand.

Antigen Specific TCRs

In certain embodiments, TCRs are identified from a subject. In certain embodiments, the subject may have a disease associated with a specific immune response. The subject may have cancer, an infection, an autoimmune disease, or an inflammatory disease. The disease may be associated with an immune response against specific antigens. Thus, TCRs associated with an immune response can be identified according to the present invention.

As used herein "immune response" refers to a response by a cell of the immune system, such as a B cell, T cell (CD4$^+$ or CD8$^+$), regulatory T cell, antigen-presenting cell, dendritic cell, monocyte, macrophage, NKT cell, NK cell, basophil, eosinophil, or neutrophil, to a stimulus. In some embodiments, the response is specific for a particular antigen (an "antigen-specific response"), and refers to a response by a CD4 T cell, CD8 T cell, or B cell via their antigen-specific receptor. In some embodiments, an immune response is a T cell response, such as a CD4$^+$ response or a CD8$^+$ response. Such responses by these cells can include, for example, cytotoxicity, proliferation, cytokine or chemokine production, trafficking, or phagocytosis, and can be dependent on the nature of the immune cell undergoing the response.

T cell response refers more specifically to an immune response in which T cells directly or indirectly mediate or otherwise contribute to an immune response in a subject. T cell-mediated response may be associated with cell mediated effects, cytokine mediated effects, and even effects associated with B cells if the B cells are stimulated, for example, by cytokines secreted by T cells. By means of an example but without limitation, effector functions of NMC class I restricted Cytotoxic T lymphocytes (CTLs), may include cytokine and/or cytolytic capabilities, such as lysis of target cells presenting an antigen peptide recognized by the T cell receptor (naturally-occurring TCR or genetically engineered TCR, e.g., chimeric antigen receptor, CAR), secretion of cytokines, preferably IFN gamma, TNF alpha and/or or more immunostimulatory cytokines, such as IL-2, and/or antigen peptide-induced secretion of cytotoxic effector molecules, such as granzymes, perforins or granulysin. By means of example but without limitation, for NMC class II restricted T helper (Th) cells, effector functions may be antigen peptide-induced secretion of cytokines, preferably, IFN gamma, TNF alpha, IL-4, IL5, IL-10, and/or IL-2. By means of example but without limitation, for T regulatory (Treg) cells, effector functions may be antigen peptide-induced secretion of cytokines, preferably, IL-10, IL-35, and/or TGF-beta. B cell response refers more specifically to an immune response in which B cells directly or indirectly mediate or otherwise contribute to an immune response in a subject. Effector functions of B cells may include in particular production and secretion of antigen-specific antibodies by B cells (e.g., polyclonal B cell response to a plurality of the epitopes of an antigen (antigen-specific antibody response)), antigen presentation, and/or cytokine secretion.

During persistent immune activation, such as during uncontrolled tumor growth or chronic infections, subpopulations of immune cells, particularly of CD8+ or CD4+ T cells, become compromised to different extents with respect to their cytokine and/or cytolytic capabilities. Such immune cells, particularly CD8+ or CD4+ T cells, are commonly referred to as "dysfunctional" or as "functionally exhausted" or "exhausted". As used herein, the term "dysfunctional" or "functional exhaustion" refer to a state of a cell where the cell does not perform its usual function or activity in response to normal input signals, and includes refractivity of immune cells to stimulation, such as stimulation via an activating receptor or a cytokine. Such a function or activity includes, but is not limited to, proliferation (e.g., in response to a cytokine, such as IFN-gamma) or cell division, entrance into the cell cycle, cytokine production, cytotoxicity, migration and trafficking, phagocytotic activity, or any combination thereof. Normal input signals can include, but are not limited to, stimulation via a receptor (e.g., T cell receptor, B cell receptor, co-stimulatory receptor). Unresponsive immune cells can have a reduction of at least 10%, 20%, 30%, 40%, 50%, 60%, 70%, 80%, 90%, 95%, or even 100% in cytotoxic activity, cytokine production, proliferation, trafficking, phagocytotic activity, or any combination thereof, relative to a corresponding control immune cell of the same type. In some particular embodiments of the aspects described herein, a cell that is dysfunctional is a CD8+ T cell that expresses the CD8+ cell surface marker. Such CD8+ cells normally proliferate and produce cell killing enzymes, e.g., they can release the cytotoxins perforin, granzymes, and granulysin. However, exhausted/dysfunctional T cells do not respond adequately to TCR stimulation, and display poor effector function, sustained expression of inhibitory receptors and a transcriptional state distinct from that of functional effector or memory T cells. Dysfunction/exhaustion of T cells thus prevents optimal control of infection and tumors. Exhausted/dysfunctional immune cells, such as T cells, such as CD8+ T cells, may produce reduced amounts of IFN-gamma, TNF-alpha and/or one or more immunostimulatory cytokines, such as IL-2, compared to functional immune cells. Exhausted/dysfunctional immune cells, such as T cells, such as CD8+ T cells, may further produce (increased amounts of) one or more immunosuppressive transcription factors or cytokines, such as IL-10 and/or Foxp3, compared to functional immune cells, thereby contributing to local immunosuppression. Dysfunctional CD8+ T cells can be both protective and detrimental against disease control.

CD8+ T cell function is associated with their cytokine profiles. It has been reported that effector CD8+ T cells with the ability to simultaneously produce multiple cytokines (polyfunctional CD8+ T cells) are associated with protective immunity in patients with controlled chronic viral infections as well as cancer patients responsive to immune therapy (Spranger et al., 2014, J. Immunother. Cancer, vol. 2, 3). In the presence of persistent antigen CD8+ T cells were found to have lost cytolytic activity completely over time (Moskophidis et al., 1993, Nature, vol. 362, 758-761). It was subsequently found that dysfunctional T cells can differentially produce IL-2, TNFa and IFNg in a hierarchical order (Wherry et al., 2003, J. Virol., vol. 77, 4911-4927). Decoupled dysfunctional and activated CD8+ cell states have also been described (see, e.g., Singer, et al. (2016). A Distinct Gene Module for Dysfunction Uncoupled from Activation in Tumor-Infiltrating T Cells. Cell 166, 1500-1511 e1509; and WO/2017/075478).

TCRs associated with T cell balance may be identified, such as the balance between T cell types, e.g., between Th17 and other T cell types, for example, regulatory T cells (Tregs). For example, the level of and/or balance between Th17 activity and inflammatory potential. As used herein, terms such as "Th17 cell" and/or "Th17 phenotype" and all grammatical variations thereof refer to a differentiated T helper cell that expresses one or more cytokines selected from the group the consisting of interleukin 17A (IL-17A), interleukin 17F (IL-17F), and interleukin 17A/F heterodimer (IL17-AF). As used herein, terms such as "Th1 cell" and/or "Th1 phenotype" and all grammatical variations thereof refer to a differentiated T helper cell that expresses interferon gamma (IFNγ). As used herein, terms such as "Th2 cell" and/or "Th2 phenotype" and all grammatical variations thereof refer to a differentiated T helper cell that expresses one or more cytokines selected from the group the consisting of interleukin 4 (IL-4), interleukin 5 (IL-5) and interleukin 13 (IL-13). As used herein, terms such as "Treg cell" and/or "Treg phenotype" and all grammatical variations thereof refer to a differentiated T cell that expresses Foxp3.

As used herein, terms such as "pathogenic Th17 cell" and/or "pathogenic Th17 phenotype" and all grammatical variations thereof refer to Th17 cells that, when induced in the presence of TGF-β3, express an elevated level of one or more genes selected from Cxcl3, IL22, IL3, Ccl4, Gzmb, Lrmp, Ccl5, Casp1, Csf2, Ccl3, Tbx21, Icos, IL17r, Stat4, Lgals3 and Lag, as compared to the level of expression in a TGF-03-induced Th17 cells. As used herein, terms such as "non-pathogenic Th17 cell" and/or "non-pathogenic Th17 phenotype" and all grammatical variations thereof refer to Th17 cells that, when induced in the presence of TGF-β3, express a decreased level of one or more genes selected from IL6st, IL1rn, Ikzf3, Maf, Ahr, IL9 and IL10, as compared to the level of expression in a TGF-β3-induced Th17 cells.

Depending on the cytokines used for differentiation, in vitro polarized Th17 cells can either cause severe autoimmune responses upon adoptive transfer ('pathogenic Th17 cells') or have little or no effect in inducing autoimmune disease ('non-pathogenic cells') (Ghoreschi et al., 2010; Lee et al., 2012). In vitro differentiation of naïve CD4 T cells in the presence of TGF-β1+IL-6 induces an IL-17A and IL-10 producing population of Th17 cells, that are generally non-pathogenic, whereas activation of naïve T cells in the presence IL-1β+IL-6+IL-23 induces a T cell population that produces IL-17A and IFN-γ, and are potent inducers of autoimmune disease induction (Ghoreschi et al., 2010).

A dynamic regulatory network controls Th17 differentiation (See e.g., Yosef et al., Dynamic regulatory network controlling Th17 cell differentiation, Nature, vol. 496: 461-468 (2013); Wang et al., CD5L/AIM Regulates Lipid Biosynthesis and Restrains Th17 Cell Pathogenicity, Cell Volume 163, Issue 6, p1413-1427, 3 Dec. 2015; Gaublomme et al., Single-Cell Genomics Unveils Critical Regulators of Th17 Cell Pathogenicity, Cell Volume 163, Issue 6, p1400-1412, 3 Dec. 2015; and International publication numbers WO2016138488A2, WO2015130968, WO/2012/048265, WO/2014/145631 and WO/2014/134351, the contents of which are hereby incorporated by reference in their entirety).

The CD8+ T cell response within the tumor microenvironment (TME) is functionally (Sakuishi et al., 2010; Williams et al., 2017; Woo et al., 2012; Xu et al., 2015) and transcriptionally (Singer et al., 2016; Tirosh et al., 2016; Zheng et al., 2017) heterogeneous. At one end of the functional spectrum are CD8+ tumor-infiltrating lymphocytes (TILs) that lack the expression of co-inhibitory or immune checkpoint receptors (eg. CTLA-4 and PD-1) and exhibit effector potential, while at the opposite end are CD8+ TILs that co-express multiple checkpoint receptors and exhibit an "exhausted" or dysfunctional phenotype.

In certain embodiments, the presence of antigen specific immune cells may be used to detect an immune state. The term "antigen" as used throughout this specification refers to a molecule or a portion of a molecule capable of being bound by an antibody, or by a T cell receptor (TCR) when presented by MHC molecules. At the molecular level, an antigen is characterized by its ability to be bound at the antigen-binding site of an antibody. The specific binding denotes that the antigen will be bound in a highly selective manner by its cognate antibody and not by the multitude of other antibodies which may be evoked by other antigens. An antigen is additionally capable of being recognized by the immune system. In some instances, an antigen is capable of eliciting a humoral immune response in a subject. In some instances, an antigen is capable of eliciting a cellular immune response in a subject, leading to the activation of B- and/or T-lymphocytes. In some instances, an antigen is capable of eliciting a humoral and cellular immune response in a subject. Hence, an antigen may be preferably antigenic and immunogenic. Alternatively, an antigen may be antigenic and not immunogenic. Typically, an antigen may be a peptide, polypeptide, protein, nucleic acid, an oligo- or polysaccharide, or a lipid, or any combination thereof, a glycoprotein, proteoglycan, glycolipid, etc. In certain embodiments, an antigen may be a peptide, polypeptide, or protein. An antigen may have one or more than one epitope. The terms "antigenic determinant" or "epitope" generally refer to the region or part of an antigen that specifically reacts with or is recognized by the immune system, specifically by antibodies, B cells, or T cells.

In certain embodiments, TCRs are identified that recognize a tumor antigen. The term "tumor antigen" as used throughout this specification refers to an antigen that is uniquely or differentially expressed by a tumor cell, whether intracellular or on the tumor cell surface (preferably on the tumor cell surface), compared to a normal or non-neoplastic cell. By means of example, a tumor antigen may be present in or on a tumor cell and not typically in or on normal cells or non-neoplastic cells (e.g., only expressed by a restricted number of normal tissues, such as testis and/or placenta), or a tumor antigen may be present in or on a tumor cell in greater amounts than in or on normal or non-neoplastic cells, or a tumor antigen may be present in or on tumor cells in a different form than that found in or on normal or non-neoplastic cells. The term thus includes tumor-specific antigens (TSA), including tumor-specific membrane antigens, tumor-associated antigens (TAA), including tumor-associated membrane antigens, embryonic antigens on tumors, growth factor receptors, growth factor ligands, etc. Examples of tumor antigens include, without limitation, B cell maturation antigen (BCMA) (see, e.g., Friedman et al., Effective Targeting of Multiple BCMA-Expressing Hematological Malignancies by Anti-BCMA CAR T Cells, Hum Gene Ther. 2018 Mar. 8; Berdeja J G, et al. Durable clinical responses in heavily pretreated patients with relapsed/refractory multiple myeloma: updated results from a multicenter study of bb2121 anti-Bcma CAR T cell therapy. Blood. 2017; 130:740; and Mouhieddine and Ghobrial, Immunotherapy in Multiple Myeloma: The Era of CAR T Cell Therapy, Hematologist, May-June 2018, Volume 15, issue 3); PSA (prostate-specific antigen); prostate-specific membrane antigen (PSMA); PSCA (Prostate stem cell antigen); Tyrosine-protein kinase transmembrane receptor ROR1; fibroblast activation protein (FAP); Tumor-associated glycoprotein 72 (TAG72); Carcinoembryonic antigen (CEA); Epithelial cell adhesion molecule (EPCAM); Mesothelin; Human Epidermal growth factor Receptor 2 (ERBB2 (Her2/neu)); Prostase; Prostatic acid phosphatase (PAP); elongation factor 2 mutant (ELF2M); Insulin-like growth factor 1 receptor (IGF-1R); gplOO; BCR-ABL (breakpoint cluster region-Abelson); tyrosinase; New York esophageal squamous cell carcinoma 1 (NY-ESO-1); κ-light chain, LAGE (L antigen); MAGE (melanoma antigen); Melanoma-associated antigen 1 (MAGE-A1); MAGE A3; MAGE A6; legumain; Human papillomavirus (HPV) E6; HPV E7; prostein; survivin; PCTA1 (Galectin 8); Melan-A/MART-1; Ras mutant; TRP-1 (tyrosinase related protein 1, or gp75); Tyrosinase-related Protein 2 (TRP2); TRP-2/INT2 (TRP-2/intron 2); RAGE (renal antigen); receptor for advanced glycation end products 1 (RAGE1); Renal ubiquitous 1, 2 (RU1, RU2); intestinal carboxyl esterase (iCE); Heat shock protein 70-2 (HSP70-2) mutant; thyroid stimulating hormone receptor (TSHR); CD123; CD171; CD19; CD20; CD22; CD26; CD30; CD33; CD44v7/8 (cluster of differentiation 44, exons 7/8); CD53; CD92; CD100; CD148; CD150; CD200; CD261; CD262; CD362; CS-1 (CD2 subset 1, CRACC, SLAMF7, CD319, and 19A24); C-type lectin-like molecule-1 (CLL-1); ganglioside GD3 (aNeu5Ac(2-8)aNeu5Ac(2-3)bDGalp(1-4)bDGlcp(1-1)Cer); Tn antigen (Tn Ag); Fms-Like Tyrosine Kinase 3 (FLT3); CD38; CD138; CD44v6; B7H3 (CD276); KIT (CD 117); Interleukin-13 receptor subunit alpha-2 (IL-13Ra2); Interleukin 11 receptor alpha (IL-11Ra); prostate stem cell antigen (PSCA); Protease Serine 21 (PRSS21); vascular endothelial growth factor receptor 2 (VEGFR2); Lewis(Y) antigen; CD24; Platelet-derived growth factor receptor beta (PDGFR-beta); stage-specific embryonic antigen-4 (SSEA-4); Mucin 1, cell surface associated (MUC1); Mucin 16 (MUC16); epidermal growth factor receptor (EGFR); epidermal growth factor receptor variant III (EGFRvIII); neural cell adhesion molecule (NCAM); carbonic anhydrase IX (CAIX); Proteasome (Prosome, Macropain) Subunit, Beta Type, 9 (LMP2); ephrin type-A receptor 2 (EphA2); Ephrin B2; Fucosyl GM1; sialyl Lewis adhesion molecule (sLe); ganglioside GM3 (aNeu5Ac(2-3)bDGalp(1-4)bDGlcp(1-1)Cer); TGS5; high molecular weight-melanoma-associated antigen (HMWMAA); o-acetyl-GD2 ganglioside (OAcGD2); Folate receptor alpha; Folate receptor beta; tumor endothelial marker 1 (TEM1/CD248); tumor endothelial marker 7-related (TEM7R); claudin 6 (CLDN6); G protein-coupled receptor class C group 5, member D (GPRC5D); chromosome X open reading frame 61 (CXORF61); CD97; CD179a; anaplastic lymphoma kinase (ALK); Polysialic acid; placenta-specific 1 (PLAC1); hexasaccharide portion of globoH glycoceramide (GloboH); mammary gland differentiation antigen (NY-BR-1); uroplakin 2 (UPK2); Hepatitis A virus cellular receptor 1 (HAVCR1); adrenoceptor beta 3 (ADRB3); pannexin 3 (PANX3); G protein-coupled receptor 20 (GPR20); lymphocyte antigen 6 complex, locus K 9 (LY6K); Olfactory receptor 51E2 (OR51E2); TCR Gamma Alternate Reading Frame Protein (TARP); Wilms tumor protein (WT1); ETS translocation-variant gene 6, located on chromosome 12p (ETV6-AML); sperm protein 17 (SPA17); X Antigen Family, Member 1A (XAGE1); angiopoietin-binding cell surface receptor 2 (Tie 2); CT (cancer/testis (antigen)); melanoma cancer testis antigen-1 (MAD-CT-1); melanoma cancer testis antigen-2 (MAD-CT-2); Fos-related antigen 1; p53; p53 mutant; human Telomerase reverse transcriptase (hTERT); sarcoma translocation breakpoints; melanoma inhibitor of apoptosis (ML-IAP); ERG (transmembrane protease, serine 2 (TMPRSS2) ETS fusion gene); N-Acetyl glucosaminyltransferase V (NA17); paired box protein Pax-3 (PAX3); Androgen receptor; Cyclin B1; Cyclin Di; v-myc avian myelocytomatosis viral oncogene neuroblastoma derived homolog (MYCN); Ras Homolog Family Member C (RhoC); Cytochrome P450 1B1 (CYP1B1); CCCTC-Binding Factor (Zinc Finger Protein)-Like (BORIS); Squamous Cell Carcinoma Antigen Recognized By T Cells-1 or 3 (SART1, SART3); Paired box protein Pax-5 (PAX5); proacrosin binding protein sp32 (OY-TES1); lymphocyte-specific protein tyrosine kinase (LCK); A kinase anchor protein 4 (AKAP-4); synovial sarcoma, X breakpoint-1, -2, -3 or -4 (SSX1, SSX2, SSX3, SSX4); CD79a; CD79b; CD72; Leukocyte-associated immunoglobulin-like receptor 1 (LAIR1); Fc fragment of IgA receptor (FCAR); Leukocyte immunoglobulin-like receptor subfamily A member 2 (LILRA2); CD300 molecule-like family member f (CD300LF); C-type lectin domain family 12 member A (CLEC12A); bone marrow stromal cell antigen 2 (BST2); EGF-like module-containing mucin-like hormone receptor-like 2 (EMR2); lymphocyte antigen 75 (LY75); Glypican-3 (GPC3); Fc receptor-like 5 (FCRL5); mouse double minute 2 homolog (MDM2); livin; alphafetoprotein (AFP); transmembrane activator and CAML Interactor (TACI); B-cell activating factor receptor (BAFF-R); V-Ki-ras2 Kirsten rat sarcoma viral oncogene homolog (KRAS); immunoglobulin lambda-like polypeptide 1 (IGLL1); 707-AP (707 alanine proline); ART-4 (adenocarcinoma antigen recognized by T4 cells); BAGE (B antigen; b-catenin/m, b-catenin/mutated); CAMEL (CTL-recognized antigen on melanoma); CAP1 (carcinoembryonic antigen peptide 1); CASP-8 (caspase-8); CDC27m (cell-division cycle 27 mutated); CDK4/m (cyclin-dependent kinase 4 mutated); Cyp-B (cyclophilin B); DAM (differentiation antigen melanoma); EGP-2 (epithelial glycoprotein 2); EGP-40 (epithelial glycoprotein 40); Erbb2, 3, 4 (erythroblastic leukemia viral oncogene homolog-2, -3, 4); FBP (folate binding protein); fAchR (Fetal acetylcholine receptor); G250 (glycoprotein 250); GAGE (G antigen); GnT-V (N-acetylglucosaminyltransferase V); HAGE (helicase antigen); ULA-A (human leukocyte antigen-A); HST2 (human signet ring tumor 2); KIAA0205; KDR (kinase insert domain receptor); LDLR/FUT (low density lipid receptor/GDP L-fucose: b-D-galactosidase 2-a-L fucosyltransferase); L1CAM (L1 cell adhesion molecule); MC1R (melanocortin 1 receptor); Myosin/m (myosin mutated); MUM-1, -2, -3 (melanoma ubiquitous mutated 1, 2, 3); NA88-A (NA cDNA clone of patient M88); KG2D (Natural killer group 2, member D) ligands; oncofetal antigen (h5T4); p190 minor bcr-abl (protein of 190KD bcr-abl); Pml/RARa (promyelocytic leukaemia/retinoic acid receptor a); PRAME (preferentially expressed antigen of melanoma); SAGE (sarcoma antigen); TEL/AML1 (translocation Ets-family leukemia/acute myeloid leukemia 1); TPI/m (triose-phosphate isomerase mutated); and CD70.

In certain embodiments, a TCR is identified for a antigen to be targeted in adoptive cell therapy (such as particularly CAR or TCR T-cell therapy) of an universal tumor antigen.

In certain preferred embodiments, the universal tumor antigen is selected from the group consisting of: a human telomerase reverse transcriptase (hTERT), survivin, mouse double minute 2 homolog (MDM2), cytochrome P450 1B 1 (CYP1B), HER2/neu, Wilms' tumor gene 1 (WT1), livin, alphafetoprotein (AFP), carcinoembryonic antigen (CEA), mucin 16 (MUC16), MUC1, prostate-specific membrane antigen (PSMA), p53, cyclin (Dl), and any combinations thereof.

Administration of Cells

The administration of cells or population of cells, such as immune system cells expressing an endogenous TCR or CAR, as disclosed herein may be carried out in any convenient manner, including by aerosol inhalation, injection, ingestion, transfusion, implantation or transplantation. The cells or population of cells may be administered to a patient subcutaneously, intradermally, intratumorally, intranodally, intramedullary, intramuscularly, intrathecally, by intravenous or intralymphatic injection, or intraperitoneally. In some embodiments, the disclosed CARs may be delivered or administered into a cavity formed by the resection of tumor tissue (i.e. intracavity delivery) or directly into a tumor prior to resection (i.e. intratumoral delivery). In one embodiment, the cell compositions of the present invention are preferably administered by intravenous injection.

The administration of the cells or population of cells can consist of the administration of $10^4$-$10^9$ cells per kg body weight, preferably $10^5$ to $10^6$ cells/kg body weight including all integer values of cell numbers within those ranges. Dosing in CAR T cell therapies may for example involve administration of from $10^6$ to $10^9$ cells/kg, with or without a course of lymphodepletion, for example with cyclophosphamide. The cells or population of cells can be administrated in one or more doses. In another embodiment, the effective amount of cells are administrated as a single dose. In another embodiment, the effective amount of cells are administrated as more than one dose over a period time. Timing of administration is within the judgment of managing physician and depends on the clinical condition of the patient. The cells or population of cells may be obtained from any source, such as a blood bank or a donor. While individual needs vary, determination of optimal ranges of effective amounts of a given cell type for a particular disease or conditions are within the skill of one in the art. An effective amount means an amount which provides a therapeutic or prophylactic benefit. The dosage administrated will be dependent upon the age, health and weight of the recipient, kind of concurrent treatment, if any, frequency of treatment and the nature of the effect desired.

In another embodiment, the effective amount of cells or composition comprising those cells are administrated parenterally. The administration can be an intravenous administration. The administration can be directly done by injection within a tumor.

In certain embodiments, a patient in need of a T cell therapy may be conditioned by a method as described in WO2016191756 comprising administering to the patient a dose of cyclophosphamide between 200 mg/m²/day and 2000 mg/m²/day and a dose of fludarabine between 20 mg/m2/day and 900 mg/m²/day.

The present invention will be further described in the following Examples which are given for illustration purposes only and which do not limit the scope of the invention described in the claims.

EXAMPLES

Example 1: General Experimental Design of PCR-Based Methods

FIG. 1 provides a graphical summary and a detailed protocol is provided in Example 3 of an exemplary experimental design.

The primer that is used to amplify the region of interest from the WTA library needs to be biotinylated to allow for purification of the PCR product of interest. This is necessary because the WTA libraries are flanked with SMART sequences on both ends so the vast majority of the first product will be amplification of the entire WTA library. Advantageously, the SMART sequence covers any designed sequences orthogonal (without homology) to host genetic material. Without this innovation, the enrichment of the region of interest would be insufficient to efficiently and confidently call genetic mutations.

Gene-specific primers can be mixed for simultaneous detection of multiple mutations.

WTA libraries can be mixed for simultaneous detection of mutations in multiple samples. One of ordinary skill in the art will recognize that mixing primers to detect multiple mutations in the same gene should be avoided, since only the shortest fragment (the mutation closest to the polyA tail) would be detected.

The streptavidin bead kilobaseBINDER kit (Thermo Fisher, 60101) allows for isolation of large biotinylated DNA fragments, which will improve detection of mutations that are further from the polyA tail.

One of ordinary skill in the art will also recognize that single-cell RNA-seq and PCR libraries from the same WTA libraries should not be included in the same sequencing run, since the genes amplified by PCR may contribute to artefactually high detection of gene expression in the single-cell RNA-seq data if the library barcode is misread.

Example 2: Primer Design

Four exemplary primer designs for performing the two PCR amplification steps are described below.

Biotin-NEXT-GENE-for: Biotinylation enables purification of the desired first PCR product. NEXT creates a binding site so that the second PCR can be performed, as well as a partial primer binding site for standard Illumina sequencing kits. GENE is a sequence complementary to the WTA, designed to amplify a specific region of interest (usually an exon).

SMART-rev: The SMART sequence is used in Drop-seq and Seq-Well to generate WTA libraries. Because the polyT-unique molecular identifier-unique cellular barcode (polyT-UMI-CB) sequence is followed by the SMART sequence, and the template switching oligo (TSO) (labeled TSO in Table 4) also contains the SMART sequence, WTA libraries have the SMART sequence as a PCR initiation site on both the 5' and the 3' end.

P7-INDEX-NEXTERA: The P7 sequence allows fragments to bind the Illumina flowcell. The INDEX allows multiple sequencing libraries to be sequenced simultaneously (and demultiplexed using Illumina's bcl2fastq command). The NEXTERA sequence provides a primer binding site for Illumina's standard Read2 sequencing primer mix.

SMART-CR1P-P5: The SMART sequence is the same as in SMART-rev. CRIP is a Custom Read1 Primer binding site that is used for Drop-Seq and Seq-Well library sequencing. The P5 sequence allows fragments to bind the Illumina flowcell. Note that the primer design can be modified to extend compatibility. For example, the SMART sequence may be modified for compatibility with single-cell RNA-seq technologies used by 10× Genomics, Fluidigm, InDrop, or 1Cell Bio. The NEXTERA and CRIP sequences may be modified for compatibility with additional Illumina platforms or SeqLL.

Example 3: Detailed Protocol for an Exemplary PCR-Based Method

The protocol involves calling genetic variation from single-cell transcriptomes. Exemplary protocols are provided in this working example, but it is understood that one of ordinary skill in the art will readily be able to adapt such protocols to specific materials and reagents.

Exemplary commercially available reagents that may be used with the methods of the invention are AMPure XP (SPRI) beads (Beckman Coulter, A63881), Dynabeads' kilobaseBINDER™ kit (ThermoFisher, 60101), KAPA HiFi HotstartReadymix (Fisher Scientific, KK2602), PfuUltra II Hotstart PCR Master Mix (Agilent, 600852), Qubit dsDNA HS Assay kit (ThermoFisher, Q32854), BioA High Sensitivity DNA kit (Agilent, 5067-4626), Plasmid-Safe ATP-Dependent DNase (Lucigen E3101K) and USER Enzyme (NEB M5505S).

Oligonucleotides can readily be designed to serve as primers in this system, such as the primers listed in Table 4 under other primers, in combination with a custom biotinylated forward primer for mutation detection used in the first PCR amplification. In this example, Next_DNMT3A_2982 primer was used.

To prepare WTA mixes, the WTA from one PCR amplification can be used, or the WTA of multiple PCR amplifications can be mixed. The final amount of WTA DNA used as template 10 ng per PCR reaction in a total volume of 10 μl. For example, if the WTA from four PCR amplifications is used as an input, 2.5 ng may be taken from each WTA, and water added to make a total volume of 10 μl.

The reaction mixture to generate the first PCR product was:
- 10 ng cDNA+water to make a final volume of 10 μL
- 2.5 μL primer mix (of a 10× stock, 3 μM Next_DNMT3A_2982 primer/5Biosg/GTCTCGTGGGCTCGGAGATGTGTATAAGA-GACAGACTGACGTCTCCAACATG AGC (SEQ ID NO:8) and 3 μM CA_SMART_Rev primer)
- 12.5 μL of 2×KAPA HiFi hotstart readymix
- For a total volume of 25 μL.

The thermocycle program for performing the PCR was: 95° C. for 3 minutes, followed by twelve cycles of: 98° C. for 20 seconds, 65° C. for 15 seconds, and 72° C. for 3 minutes, and at the end of the twelfth cycle, 72° C. for 5 minutes. The samples were stored at 4° C. prior to further processing.

SPRI bead cleanup was performed to remove primer dimers (1 hour). To 25 μl PCR mix, 75 μl H$_2$O and 70 μl SPRI beads are added for a 0.7× cleanup, followed by incubation for 10 minutes, and magnetization for 5 minutes. The mixture was washed twice with freshly made 70% ethanol and magnetized for 1 minute. After 5 minutes of drying, the nucleic acids were eluted in 21 μl H$_2$O and 1 μl was measured on Qubit.

Streptavidin bead cleanup (kilobaseBINDER kit, 3.5 hours) was performed using the following steps. First, the Dynabeads® were thoroughly resuspended in the vial (vortex>30 sec or tilt and rotate for 5 min). Then 5 μl (50 μg) resuspended beads were transferred to a 1.5 mL microcentrifuge tube and magnetized for 2 min. The supernatant was removed and the beads resuspended in 20 μl Binding Solution, avoiding foaming. The beads were magnetized for 2 min, after which the supernatant was removed and the beads resuspended in 20 μl Binding Solution. 20 μl beads were added to 20 μl biotinylated DNA-fragments and mixed carefully to avoid foaming of the solution. Samples were incubated at room temperature for 3 hours on a roller to keep the beads in suspension and subsequently magnetized samples the supernatant removed. The Dynabeads®/DNA-complex was washed twice in 40 μl Washing Solution and once in 100 μl distilled water, followed by resuspension in 23 μl H$_2$O or TE. The entire reaction was used for the second PCR step.

The reaction mixture to generate the second PCR product was:
- 23.0 μL template (from above, maximum of 75 μg streptavidin beads)
- 2.0 μL primer mix (5 μM Seq-Well_SMART_P5_Hybrid primer and 5 μM N700_BC01 primer)
- 25.0 μL PfuUltra II HS 2× Master mix
- For a total volume of 50 μL.

The thermocycle program for performing the PCR was: 95° C. for 2 minutes, followed by four cycles of: 95° C. for 20 seconds, 65° C. for 20 seconds, and 72° C. for 2 minutes; followed by ten cycles of 95° C. for 20 seconds, 72° C. for 2 minutes 20 seconds, and, at the end of the 10$^{th}$ cycle, 72° C. for 5 minutes. Samples were stored at 4° C. prior to further processing.

After the second PCR reaction, the beads are magnetized and the supernatant is collected. The volume is measured, and to it are added 0.7×SPRI beads. For example, if volume is 48 μl, 33.6 μl beads would be added. The SPRI beads are cleaned as before and eluted in 20 μl TE. The concentration is measured on Qubit and run BioA.

Figure 2:
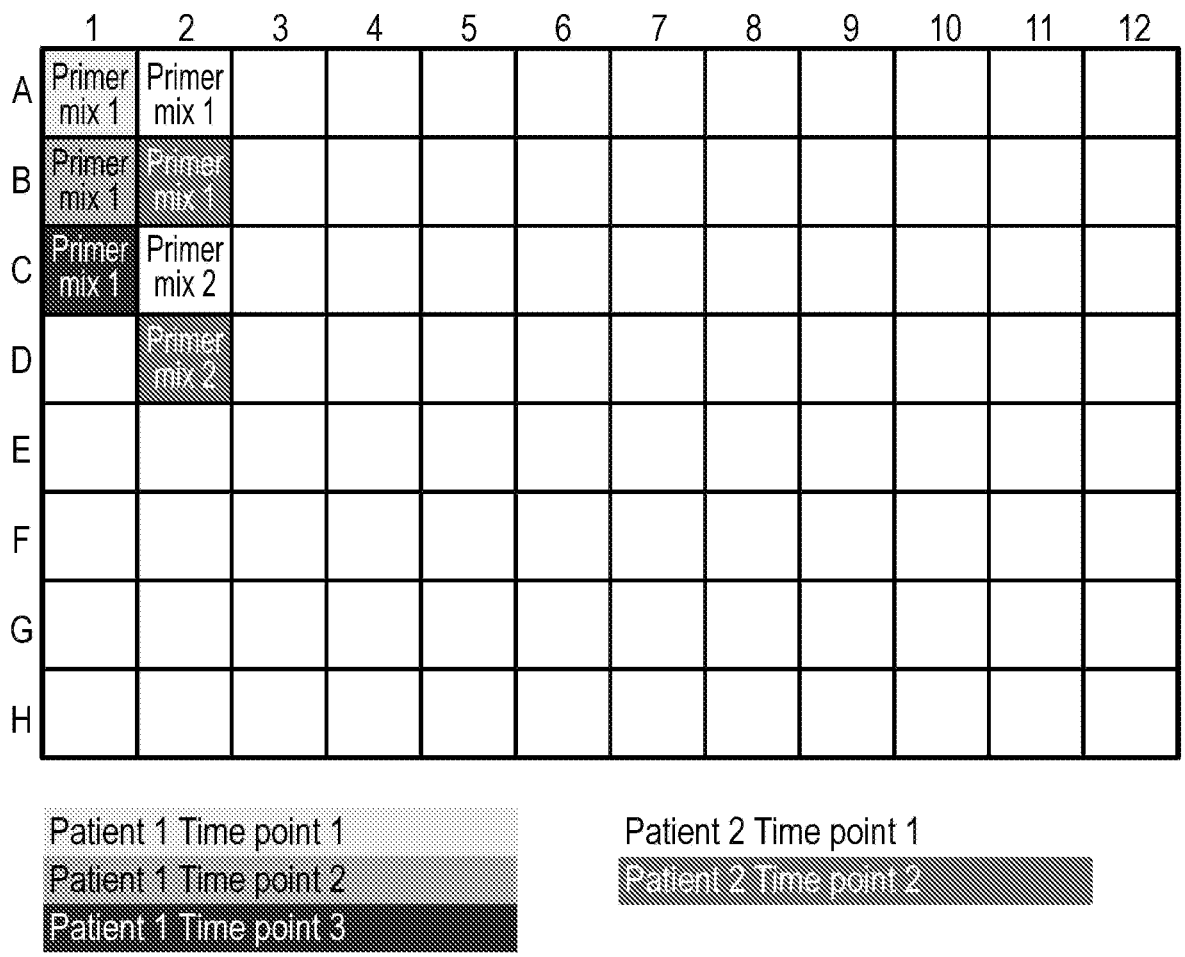
FIG. 2 depicts a schematic example of a 96 well plate for the first PCR reaction when employing the PCR-based approach described herein. There are five samples (three time points for patient 1, and two time points for patient 2). For Patient 1, there is one custom primer mix. For Patient 2, there are two custom primer mixes.
Figure 3:
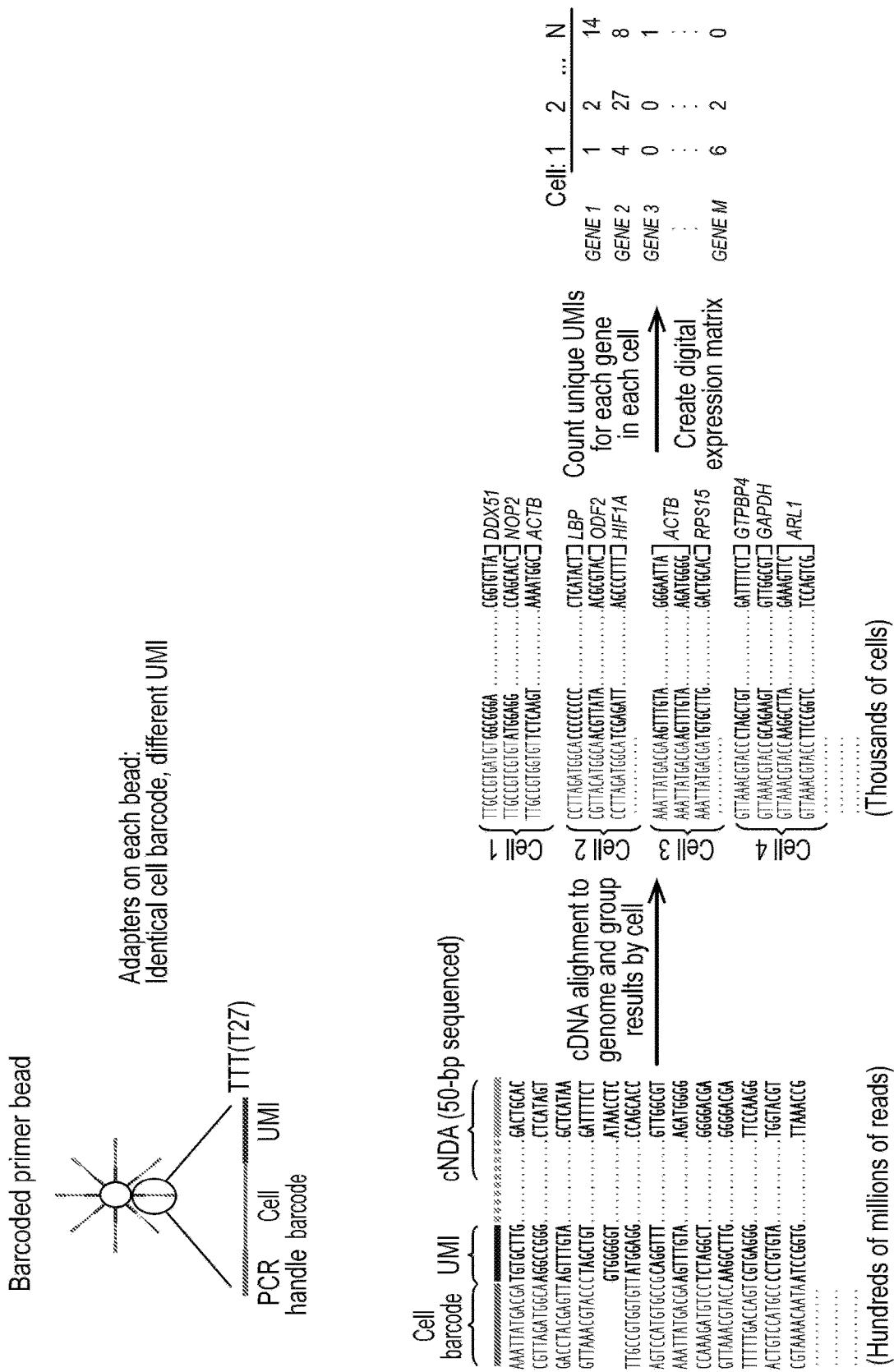
FIG. 3 depicts the workflow of basic data processing of the invention where the digital expression matrix shows the number of unique molecular identifiers (UMIs) per cell and gene.
Figure 4:
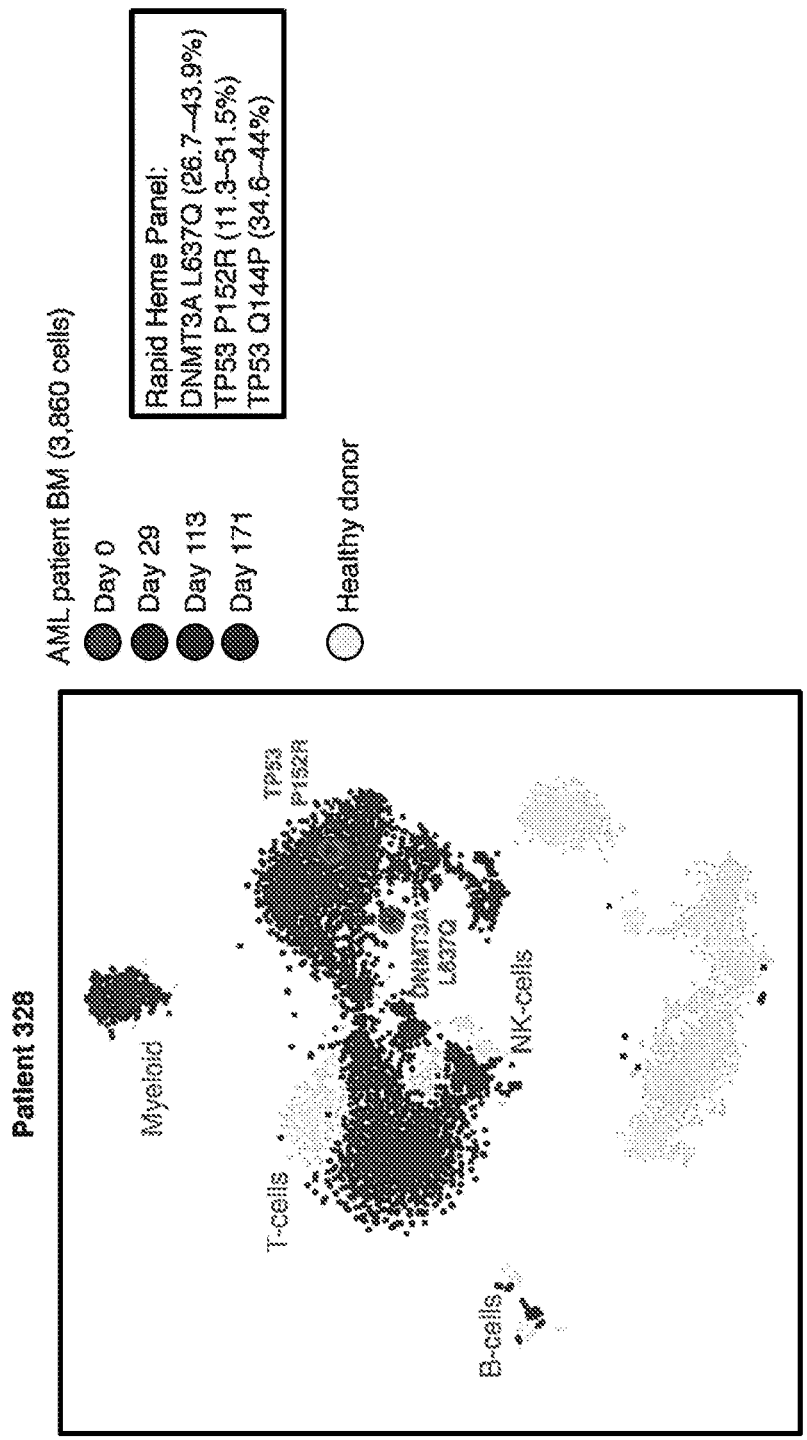
FIG. 4 depicts the results of experiments detecting mutations in patient tissue from Seq-well data.
Figure 5:
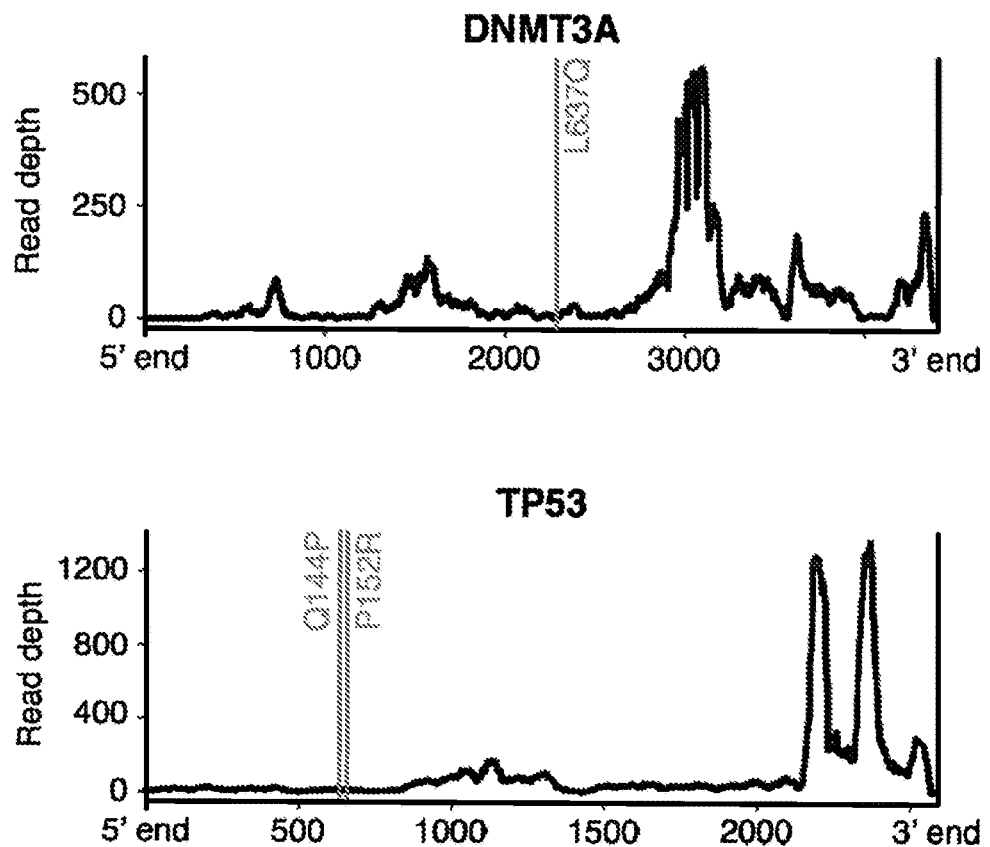
FIG. 5 provides graphs illustrating the 3' bias of typical Seq-well transcript data.

An example of a 96 well plate for the first PCR reaction is depicted in FIG. 2. There are five samples (three time points for patient 1, two time points for patient 2). For Patient 1, there is one custom primer mix. For Patient 2, there are two custom primer mixes.

Example 4: V Primer Circularization TCR Protocol

Figure 11:
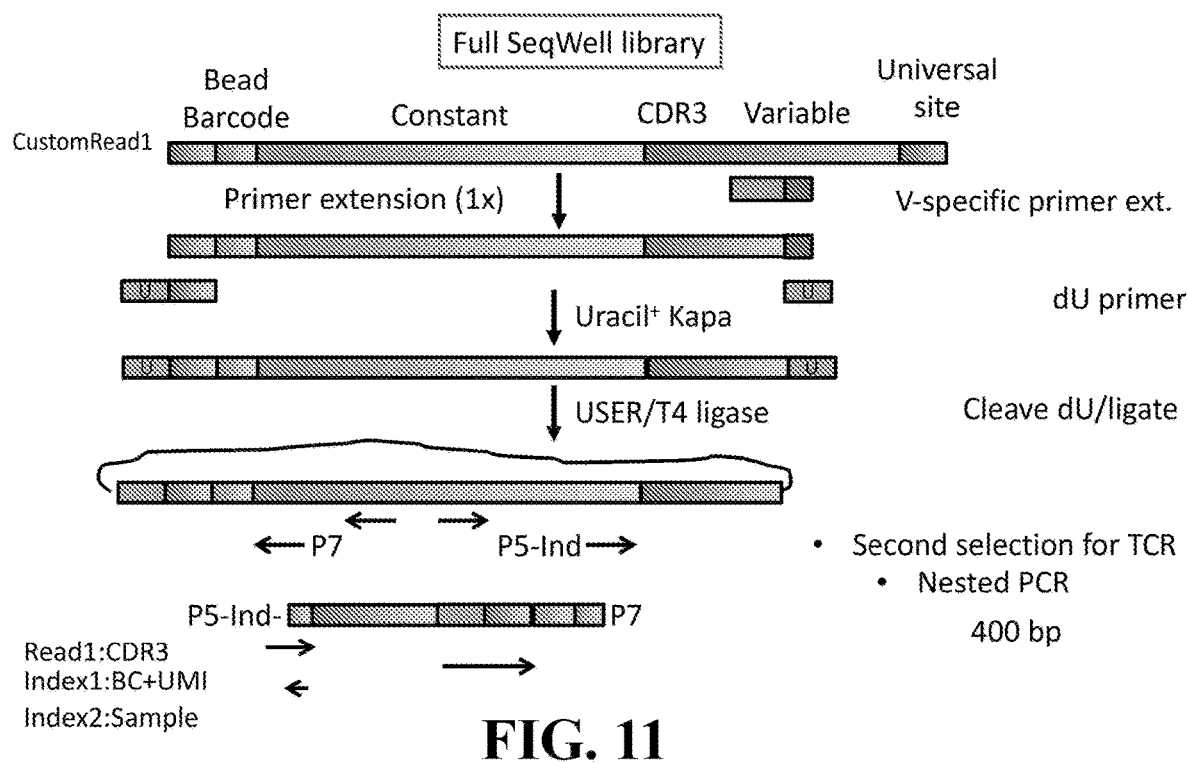
FIG. 11 depicts an exemplary T cell receptor (TCR) protocol using V (Variable) primer circularization.
Figure 12:
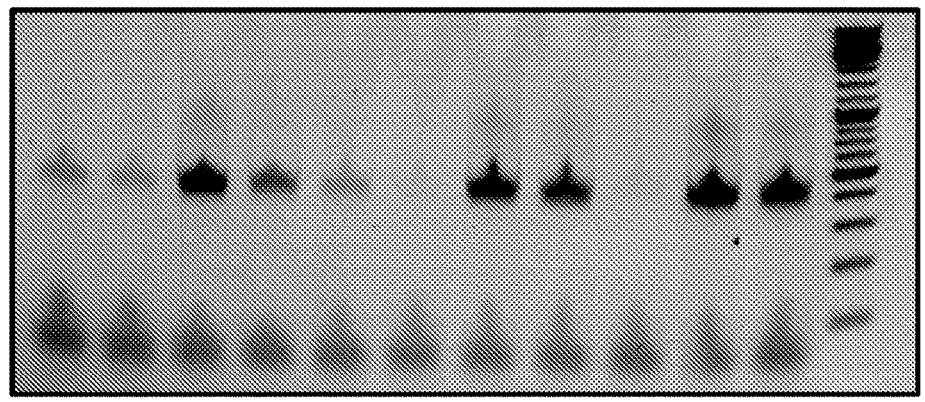
FIG. 12 depicts results of the V-primer circularization protocol in 11 human skin clinical samples. The expected product was present in 11/11 samples, with results achieved 1 day after receiving samples.
Figure 13:
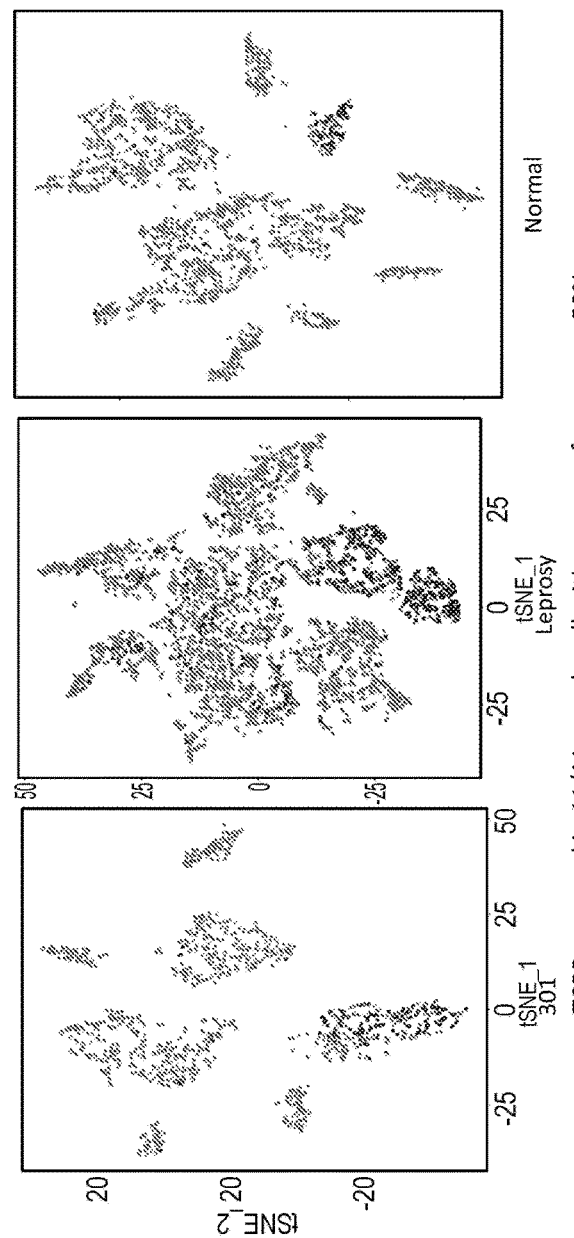
FIG. 13 depicts the results of experiments indicating TCRs map to T cell cluster in each sample, with TCRBs mapped in 11/11 samples with recovery frequency of ~50%.
Figure 14:
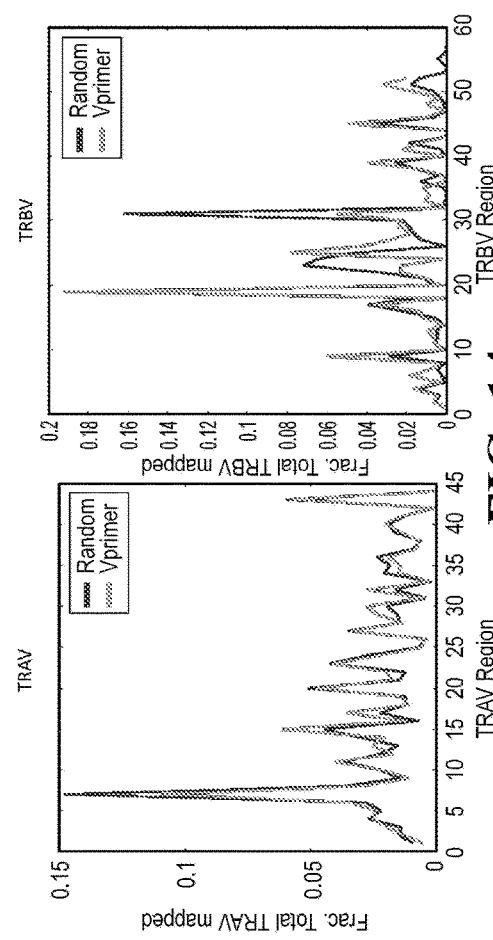
FIG. 14 provides graphs illustrating the same library sequences by tagmentation and V-primer protocol, indicating that combining protocols enables validation of V-primers.
Figure 15:
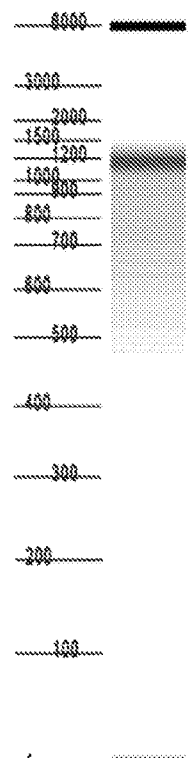
FIG. 15 depicts results from use of TCRB V-primers in the TCR-enriched/V primer protocol.
Figure 16:
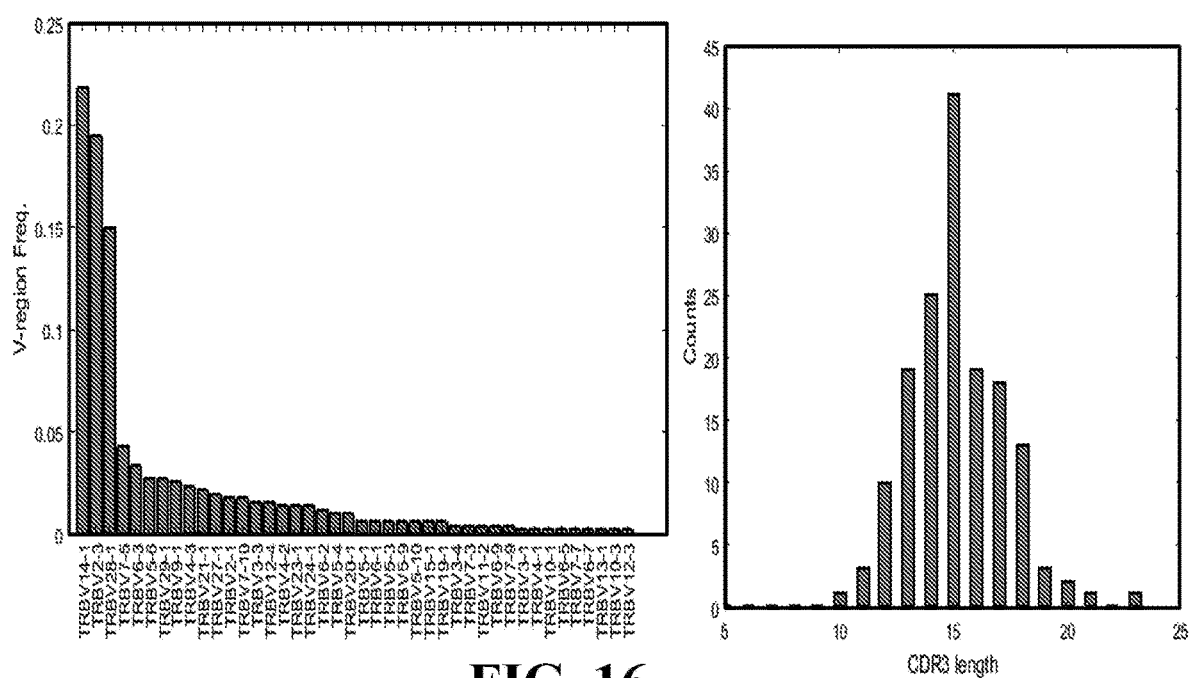
FIG. 16 provides sequencing results from TCRB full length circularization protocol.

As provided in FIG. 11, the V-primer circularization TCR protocol eliminates need for enrichment. The V-primer circularization TCR protocol allows extraction of TCRs from SeqWell libraries. A key challenge for matching TCR/BCR sequence to single cell transcriptomes using Seq Well has been enrichment while maintaining cell barcode as the variable region is on the opposite end of the transcript from the cell barcode. Three main goals need to be achieved to enable targeting any portion of a specific transcript—efficient selection of the desired transcript/transcripts, placing the sequencing reads in the desired location within the transcript and most challenging, making the total length of the sequencing library<1 kb so it can be efficiently sequenced on Illumina flowcells. The final goal is especially challenging when the desired sequence is natively>1 kb away from the 3'-end of the transcript where the cell barcode is located (which must be included in the sequencing construct to maintain linkage to cell identity).

The protocol utilizes a library, such as a full SeqWell library of 3' barcoded single cell TCRs. (FIG. 11) along with a pool of primers targeting all known V (variable) regions of TCR, termed V-specific primers, in a primer extension reaction thereby setting the 5' edge of the transcript sequence in a final sequencing construct. The V-specific primers are each tagged with a universal primer sequence shared by all transcripts from the library. Universal primers are then utilized to subsequently amplify the transcripts replicated in the primer extension reaction. Complementary sequences in the 5' ends of the universal primers are followed by a deoxy-uracil residue, although amplification can be effected in various ways.

Circularization is then achieved in a ligation reaction, in this instance by cleaving the dU residue by addition of a uracil-specific excision reagent ("USER®") enzyme/T4 ligase to generate long complementary sticky ends to mediate efficient circularization and ligation, which now places the barcode and the 5' edge of the transcript sequence set in the primer extension in close proximity, thereby bringing the cell barcode within 100 bases of any desired sequence in the transcript. Upon circularization, the cell barcode is linked on both sides to the transcript. Accordingly, a universal primer is not needed to maintain the cell barcode in a PCR reaction such that use of two transcript specific primers can be used to select for the transcript of interest from the ligation reaction. The method can then include one or more PCR steps with transcript specific primers, that can include adaptor sequences, and preferably uses nested PCR reactions where the final PCR reaction sets the 3' edge of the transcript sequence of the final sequencing construct. The final sequencing library can now be utilized in several ways, including sequencing of the transcript sequence, or at some desired location in the transcript sequence.

The protocol involves calling genetic variation from single-cell transcriptomes. Exemplary protocols are provided in this working example, but it is understood that one of ordinary skill in the art will readily be able to adapt such protocols.

Example 5: Single-Cell RNA-Seq Reveals AML Cellular Hierarchies Relevant to Disease Progression and Immunity The example provides a method for combined single-cell RNA-sequencing and genotyping to profile 38,410 cells from 40 bone marrow aspirates, including 16 AML patients at diagnosis or after treatment, and 5 healthy donors. A machine learning classifier was then applied to distinguish malignant from normal cells. We found that malignant progenitors co-express transcriptional programs associated with stemness and myeloid priming, which are normally exclusive. the analyses also revealed a spectrum of malignant cell types whose abundances varied between patients. By integrating our data with a large cohort of expression profiles, we associated these cell type abundances with prototypic genetic lesions and patient outcomes. Finally, we identified a population of AML-derived, monocyte-like cells that suppresses T-cell activity in vitro. As discussed herein, the results provide insight into malignant progenitors, differentiation hierarchies and immunosuppressive monocyte-like cells in the AML tumor ecosystem.

Nanowell-based sequencing technology (Gierahn et al., 2017) is adapted to measure transcriptomes and genetic mutations in thousands of single cells from BM aspirates. We profiled 30,712 cells from 16 AML patients at diagnosis or during treatment, and 7,698 cells from 5 healthy donors. We integrated the data into a machine learning classifier that distinguished malignant from normal cells, and identified six distinct malignant AML cell types that project along the HSC-myeloid differentiation axis. AML progenitors are shown to co-express stemness and myeloid priming gene expression programs, and that these progenitor programs and overall cell type abundances vary markedly between tumors. We use this foundational resource to evaluate properties and prognostic significance of primitive AML cells, to relate cell type compositions to genetic lesions, and to investigate determinants of the anti-tumor immunity.

Methods

Patient Cohort

All patients consented to an excess sample banking and sequencing protocol that covered all study procedures and was approved by the Institutional Review Board of the Dana-Farber Cancer Institute. Demographic and clinical details are provided in Table 3.

Cell Preparation

All normal BM and AML patient samples were processed using density gradient centrifugation to isolate mononuclear cells, viably frozen with 10% DMSO and stored in liquid nitrogen (only BM5 was not frozen). Note that these procedures may select against mature granulocytes, megakaryocytes and erythroid cells. Frozen cells were thawed using standard procedures, and viable cells were enriched using magnetic removal of dead cells (MACS 130-090-101) or flow cytometry to sort propidium iodide-negative cells.

Targeted DNA Sequencing

Targeted sequencing of genetic mutations of was performed using the Rapid Heme Panel platform, which is a service by the Center for Advanced Molecular Diagnostics of Brigham and Women's Hospital (Kluk et al., 2016). Briefly, hotspots in 95 genes that are recurrently mutated in hematological malignancies are amplified and sequenced at average 1500× coverage. Single nucleotide variants and small insertions/deletions are detected at allele frequencies of ≥5%. This platform was used for every AML patient at diagnosis, some patients at later time points (Table 3) and sorted $CD14^+$ cells (FIG. 29D).

Seq-Well

Seq-Well was performed as described (Gierahn et al., 2017), with the following changes: we did 18 PCR cycles for whole transcriptome amplification (WTA), and we used a template switching oligo with an LNA-modification of the last guanine (Table 4). Briefly, an array with ~90,000 nanowells is loaded with barcoded mRNA capture beads (Chemgenes NC0927472) and 200 μL of single cell suspension containing 10,000 cells. The size of the beads relative to the wells of the array ensures that only one bead will occupy each well. A partially permeable polycarbonate membrane (Sterlitech Custom Order) is used to seal the surface of the array, which allows buffers to pass through but traps the bead and the cell. Cells are lysed with a lysis buffer and mRNA binds to the bead contained in the same well. Following a bead removal process, the bead-bound mRNA is reverse transcribed to produce cDNA which is then used for whole-transcriptome amplification (WTA) PCR. Sequencing libraries are prepared using Nextera reagents (Illumina FC-131-1096). An Illumina NextSeq 500 instrument was used for sequencing according to manufacturer's instructions, with the following adjustments: (1) libraries were loaded at 2.5 μM, (2) a Custom Read 1 Primer (CR1P, Table 4) was used by diluting 6.6 μl of CR1P (100 μM) to 2.2 ml with HT1 buffer, (3) We did not use PhiX because it would be incompatible with CR1P. Read length was 20 cycles for Read 1, 8 cycles for the library index, and 50 or 64 cycles for Read 2 (64 cycles used for single-cell genotyping, all single-cell Seq-Well reads were shortened to 50 bp for comparability). Cell type frequencies vary between healthy individuals; the variability shown in FIG. 1C is within the expected range (Burel et al., 2017; Stemcell Technologies, 2017). Reproducibility of the Seq-Well protocol was supported by similar results for BM1 (processed Apr. 11, 2017), BM2 (processed Apr. 24, 2017), and BM4 (processed Jun. 10, 2017) and BM3 (processed Jul. 24, 2017).

Single-Cell Genotyping

Figure 25A:
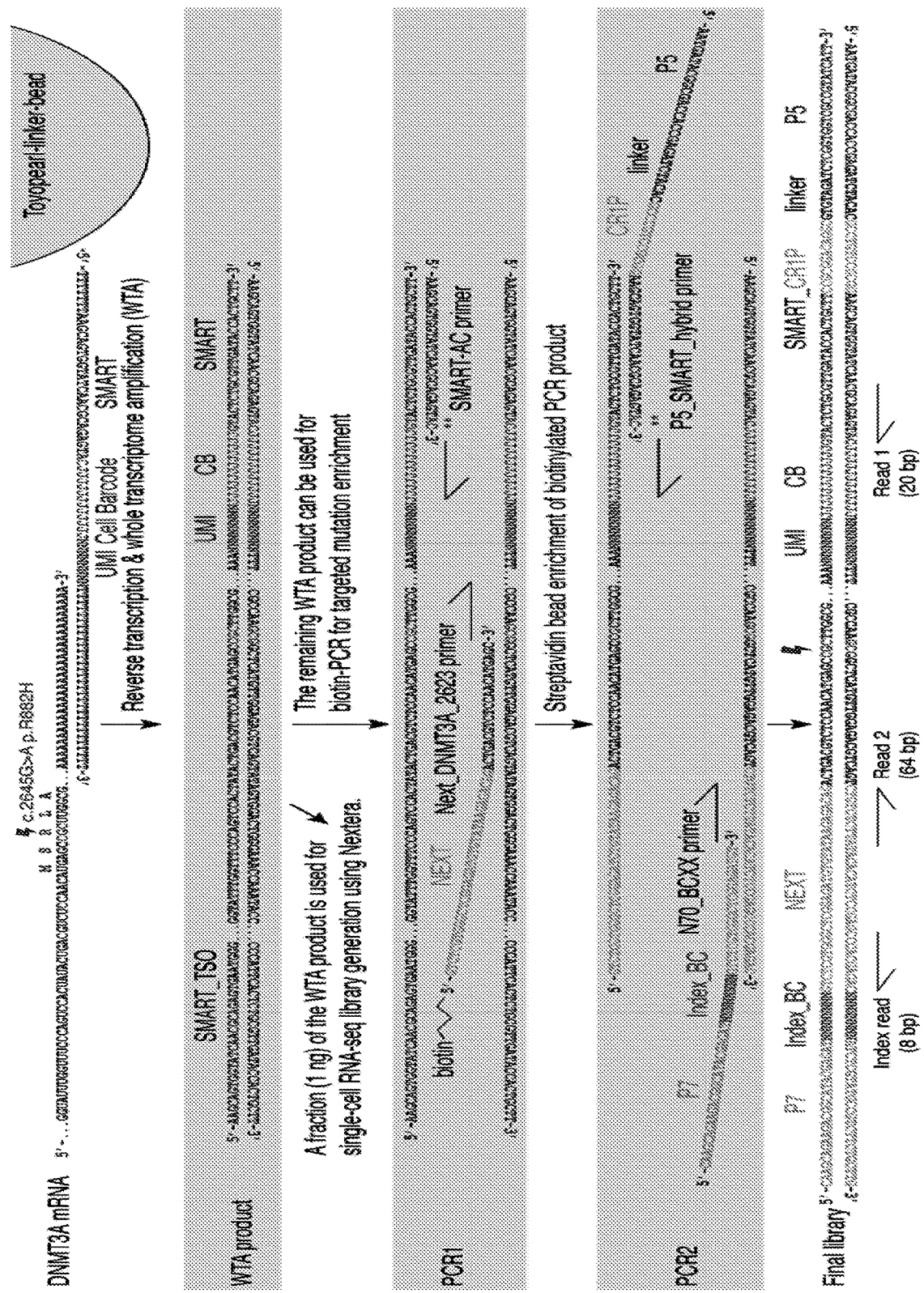
FIG. 25A-25D Single-cell genotyping overview and blast count correlation FIG. 25A. Overview depicts single-cell genotyping strategy to determine genetic variants of interest. In this example, a DNMT3A mRNA molecule is captured by a Seq-Well bead, reverse transcribed and the cDNA is amplified during the Seq-Well whole transcriptome amplification (WTA). The WTA product contains cDNAs with a cell barcode (CB), a unique molecular identifier (UMI) to detect unique mRNA molecules, and SMART primer binding sites on both ends, with SMART-PCR primer used for WTA (SMART-PCR in Table 4) PCR1 is performed using a SMART-AC primer (SMART AC in Table 4]. and a second biotinylated primer that binds just upstream of the DNMT3A.2645G>A (R882H) mutation. The second primer also adds a NEXT primer binding site (PvG1060-Next_DNMT3A_2623 in Table 4). Since the SMART primer binding sequence is present on both ends of Seq-Well WTA fragments, PCR1 amplifies the whole transcriptome, but only the DNMT3A fragments of interest are biotinylated. Following streptavidin bead enrichment of the fragments of interest, PCR2 is used to add (1) P5 (P5 SMART Hybrid) and P7 (SEQ ID NO: 4) sequences for Illumina flowcell binding and cluster generation, (2) an index barcode (Index BC) to identify the sequencing library, and (3) a Custom Read 1 Primer binding sequence (CRIP, which is also used for scRNA-seq libraries), the CRIP (CRIP in Table 4). An exemplary sequence is N70_BC01. Following paired-end sequencing, Read 1 (20 bp starting from CRIP) will contain the CB and UMI, and Read 2 (64 bp starting from NEXT) will contain the transcript sequence with the mutation site. See Table 4 for all primer characteristics.

We designed an adaptation of the Seq-Well method for targeted amplification of known mutations from the WTA product (FIG. 25A). The starting material for this single-cell genotyping method is the product of the Seq-Well WTA reaction (only a fraction of which is used for scRNA-seq). The method consists of two PCR reactions with a streptavidin bead enrichment in between. The first PCR reaction serves to add a biotin tag and Nextera adapter (NEXT) to the mutation of interest while retaining the UMI and cell barcode (CB) of the transcripts. Prior to setting up this reaction, we first designed biotinylated primers to detect specific mutations (Table 4), that were known because every patient underwent targeted DNA sequencing (see below). For every AML sample, a primer mix is created containing the SMART-AC primer at 3 µM, which is common to all initial reactions, and one or more mutation-specific primers (such as Next_DNMT3A_2623) at a combined concentration of 3 µM.

To prepare the template for the single-cell genotyping reaction, WTA products from an AML sample are pooled and diluted to be used at 10 ng in a total volume of 10 µL (every AML sample is split into several WTA reactions during the Seq-Well protocol). Next, 2.5 µL of primer mix and 12.5 µL of KAPA HiFi Hotstart ReadyMix (Fisher Scientific KK2602) are added to the template and PCR is performed using the following conditions: initial denaturation at 95° C. for 3 minutes, followed by 12 cycles of 90° C. for 20 seconds, 65° C. for 15 seconds, and 72° C. for 3 minutes, and final extension at 72° C. for 5 minutes. Following amplification, the PCR product is purified with 0.7×AMPure XP beads to remove primers (Beckman Coulter A63881). Since the SMART-AC primer is nearly complementary to both ends of the WTA product, this first PCR yields many unintended fragments. Using Streptavidin-coupled Dynabeads, only biotinylated fragments containing the mutation of interest are captured (following manufacturer's instructions, ThermoFisher 60101). Dynabeads/DNA-complex is eluted in 23 µL $H_2O$.

To add Illumina adapters, index barcodes, and custom read primer binding sequence to the fragments, a second PCR is performed using 23 µL of streptavidin-bound product as template, with 2 µL of 0.5 µM primer mix (P5_SMART_Hybrid and N70_BCXX, Table 4) and 25 µL PFU Ultra II HS 2× Master Mix (ThermoFisher Q32854). The parameters used for PCR2 are an initial denaturation at 95° C. for 2 minutes, then 4 cycles of 95° C. for 20 seconds, 65° C. for 20 seconds, and 72° C. for 2 minutes, followed by 10 cycles of 95° C. for 20 seconds and 72° C. for 2 minutes and 20 seconds, and then final extension at 72° C. for 5 minutes.

After PCR, the streptavidin beads are magnetized and the supernatant is saved and then purified with 0.7×AMPure XP beads. After eluting in 20 µL of TE, the beads are magnetized and the supernatant is saved for sequencing. The resulting libraries are similar to Seq-Well scRNA-seq libraries but with targeted integration of the NEXT sequencing primer binding site adjacent to the mutation of interest. The libraries were generally 0.5-30 ng/µl and 200-800 bp in size. Single-cell genotyping libraries can be sequenced together with Seq-Well scRNA-seq libraries.

Tissue Culture

MUTZ-3 cells were purchased from DSMZ (ACC-295), 5637 cells were purchased from ATCC (HTB-9), OCI-AML3 cells were received from Dr. Mark Minden. Cell line verification by Short Tandem Repeat profiling was performed upon receipt and every six months (ATCC 135-XV). OCI-AML3, THP-1 cells and 5637 cells were cultured in RPMI-1640 with Glutamax (Thermo 61870-036) with 10% heat-inactivated FBS (Peak Serum PS-FB1) and P/S (RPMI+). MUTZ-3 cells were cultured in MEM-alpha (Thermo 12571-063) with 20% heat-inactivated FBS (Peak Serum PS-FB1), P/S, and 10% 5637-conditioned medium containing several cytokines (Quentmeier et al., 1996).

T-Cell Activation Bioassay

The T-cell activation bioassay was purchased from Promega (J1621) and carried out according to manufacturer's instructions. Briefly, 25 µl RPMI+ containing 100,000 Human T-Activator CD3/CD28 beads (Thermo Fisher 11131D) was combined with 25 µl RPMI+ containing 100,000 BM or AML cells and 25 µl RPMI+ containing 100,000 TCR/CD3 Effector Cells (total 75 µl/well). The TCR/CD3 Effector Cells are Jurkat cells with endogenous TCR, CD3, CD4 and CD28 expression and luciferase driven by an NFAT-response element (NFAT-RE). Engagement of the TCR/CD3 with an appropriate ligand results in NFAT-RE mediated luminescence. The beads and cells were incubated at 37° C. for 6 hours followed by reading out luciferase using Bio-Glo (Promega G7941) on a BioTek SYNERGY HT machine. Positive control wells contained Human T-Activator CD3/CD28 beads and TCR/CD3 Effector cells (no BM/AML cells, 100% luminescence). Background control wells contained 75 µl RPMI+, and never exceeded 1% of positive controls. Negative controls wells contained TCR/CD3 Effector cells±BM/AML cells (no beads), and never exceeded background levels. Luminescence was calculated by subtracting background and shown as a percentage of positive control wells.

CD14+ and CD34+ cells were sorted using Miltenyi Biotec magnetic enrichment microbeads (130-050-201 and 130-046-702) according to manufacturer's instructions. Briefly, MUTZ-3 cells or freshly thawed primary samples were resuspended in PBS with 2% FBS (Peak Serum PS-FB1) and incubated with antibody-conjugated magnetic beads. Cells were applied to an MS column (Miltenyi Biotec 130-042-201) on a magnet followed by collection of negative (flow-through) and positive fractions.

Of note, monocytes could conceivably phagocytose CD3/CD28 Dynabeads, thus inhibiting T-cell activation in our assay without engaging the T-cells (Gu et al., 2014; Whyte et al., 2000). To control for this possibility, we added 100,000 AML cells and 100,000 CD3/CD28 together. Using THP-1 cells as a positive control, we indeed observed CD3/CD28 Dynabead phagocytosis after 6 hours at 37° C. (Lloyd et al., 2017). However, OCI-AML3 and MUTZ-3 cells showed very limited bead phagocytosis (<1% of beads), indicating that MUTZ-3 cells directly inhibit T-cell activation.

To test the involvement GAL9, neutralizing antibody (Millipore MABT834, clone 9S2-1) was added at 10 µg/ml. To test the involvement of HLA-DR, blocking antibody L243 (Abcam ab136320) was added at 11.5 µg/ml (van Luijn et al., 2010).

Cell Barcode Processing

All sequencing data was first assessed by looking at general quality metrics such as cluster density, total yield, and per-cycle base quality. Sequencing libraries were then split by library barcodes using bcl2fastq version 2.15.0.4 and default settings, except for allowing for 2 mismatches to library barcode sequences when appropriate. Read 1, containing a 12 bp cell barcode and an 8 bp unique molecular identifier (UMI), yielded 20 bp reads. Read 2, containing part of the transcript, yielded 50 bp reads. For some of the sequencing runs Read 2 was sequenced for up to 64 cycles. The extra bases were used only for single-cell genotyping analysis. All downstream analyses were performed using the R programming language (version 3.4), unless otherwise noted (R Core Team, 2016). We made extensive use of the data.table and Rsamtools packages (Dowle, 2016; Morgan M, 2018).

To analyze our single-cell sequencing data, we employed an approach to annotate sequencing reads by cell barcode before sequence alignment and quantification. First, we counted all unique 12 bp cell barcodes for each library. We excluded cell barcodes occurring less than 100 times, and filtered barcodes containing stretches of eight identical nucleotides. Next, we excluded cell barcodes that were associated with non-random UMIs. At every position in the UMI, we checked that the frequency of each nucleotide did not exceed 90%. The majority of reads filtered this way contained part of the Tn5 binding sequence, i.e. reflected events in which the transposase integrated within the cell barcode/UMI, yielding very short fragments.

We noticed that a number of cell barcodes (5-20%, depending on the batch of barcoded beads) were associated with UMIs that contained a Thymine as the last nucleotide. These sequences often represent cell barcodes in which a single nucleotide is missing due to errors in the split-pool synthesis. In this case cell barcodes are only 11bp long and the last base of the UMI reflects the first base of the poly-T sequence that hybridizes to the poly-A tail of captured mRNAs. Also, the last base of the cell barcode reflects the first base of the UMI, causing a single cell to produce four different single-cell transcriptomes. We corrected these barcodes if in fact four different cell barcodes were detected with a similar number of total reads that were variable in their last base. The UMI was also corrected accordingly.

To filter out cell barcodes that likely resulted from sequencing errors, we ranked all cell barcodes according to their number of reads (requiring at least 1,000 reads). We filtered out all cell barcodes that had a higher ranked cell barcode that was different in only one position (hamming distance 1).

This final list of cell barcodes was then used to generate a fastq file containing the Read 2 sequences of the remaining cells. The library barcode, the cell barcode, and the UMI were appended to the read identifier. For some of the sequencing runs we noticed a higher number of reads that were excluded because the library barcode was not detected accurately. We rescued these reads if their cell barcode matched uniquely to one of the libraries that were sequenced together in the respective run.

Sequence Alignment and Gene Quantification

Sequencing reads were aligned to the human genome (hg38) using STAR version 2.5.2b and default parameters. Alignments were guided by using RefSeq gene annotations. Transcripts were quantified using the "--quantMode TranscriptomeSAM" option. This resulted in two alignment files, one in which reads were aligned to the genome, and one in which contained pseudo-alignments to the transcriptome.

The transcriptome alignments were used to quantify gene expression. For every read all the unique gene names of the transcripts the read aligned to were recorded. Some reads aligned to multiple genes, which often reflected a primary gene and additionally one or more pseudo-, antisense-, or readthrough-genes. We checked if one of the gene names was contained in all the other gene names, with a "-" before or after (antisense- and readthrough-genes), or followed by "P" and a digit (pseudo-genes). If this was the case, we only kept the primary gene. Reads that still mapped to multiple genes were filtered. In a second step, all reads that mapped to the same gene and had an identical UMI were collapsed. This yielded a digital expression matrix consisting of the UMI counts for each cell and gene.

For all downstream analysis we required cells to have at least 1,000 UMIs (gene counts, indicative of the number of captured transcripts) mapping to at least 500 unique genes. We additionally excluded cells for which more than 20% of the gene counts reflected either mitochondrial genes or ribosomal RNAs, as these likely reflected poor quality cells. For each cell, we then normalized gene counts to a total of 10,000.

Single-Cell Genotyping Analysis

Sequencing reads from libraries of the single-cell genotyping protocol were processed using the final list of cells barcodes detected from the regular Seq-Well protocol. This ensured detection of fragments even if there were only few reads for a given cell barcode. All genotyping reads were aligned to a short reference index consisting only of the expected transcripts using BWA mem and default mapping parameters (Li, 2013).

For each mutational site and sample, we then determined the expected read sequence for both the wildtype and the mutant allele. These were identical to the most frequent detected read sequences for most of the sites. For some primers we observed unspecific amplification of other transcripts. This however did not affect our interpretation of the targeted site if it was detected by a sufficient number of reads. We only retained reads that contained the exact mutant or wildtype sequence at the expected position. In case of short insertions and deletions (indel, e.g. NPM1 internal tandem duplication), we required the exact sequence of the indel to be detected. We allowed for one mismatch to the reference transcript in the remaining read sequence.

We then counted the number of reads supporting the mutant or wild-type transcript for each cell barcode and UMI. Since most were detected hundreds of times, we required at least 10 sequencing reads per cell barcode and UMI. For each mutant transcript we frequently also detected the wild-type transcript at a much lower frequency (0.1-1%), and vice versa. This is consistent with a low background sequencing error rate. These transcripts were filtered out. For each cell and mutational site, we then counted the number of UMIs supporting the mutant and the wild-type allele and used these annotations throughout the study.

BackSPIN Clustering

Cells were clustered into cell types using BackSPIN (ref). BackSPIN employs a bi-clustering algorithm which iteratively splits both cells and genes, until a predetermined number of splits is reached. For clustering, we first determined the most variably expressed genes in the dataset. We performed a linear fit of the log-transformed average expression values and the log-transformed coefficients of variation (standard deviation divided by the average expression). Variably expressed genes were determined as genes associated with a residual larger than two times the standard deviation of all residuals. From these genes we excluded a set of genes that were associated with cell cycle (ASPM, CENPE, CENPF, DLGAP5, MKI67, NUSAP1, PCLAF, STMN1, TOP2A, TUBB). This yielded in the order of 1,000 to 2,000 variably expressed genes depending on the set of cells. Expression values were log-transformed (after addition of 1) before performing BackSPIN clustering. We used default settings and a maximum splitting depth of 5. In the healthy bone marrow data this yielded a final set of 31 clusters.

In a first post-processing step we calculated the average expression level of each gene for each cluster. If a single cell correlated higher to another cluster than the cluster it was part of, we reassigned it to the cluster it was most highly correlated to. For the healthy bone marrow data, we merged clusters if their average gene expression profiles were highly correlated and if they were characterized by similar cell type-specific marker genes. This yielded 15 cell types across the undifferentiated compartment and the three main lineages (erythroid, lymphoid, and myeloid).

Two-Dimensional Visualizations of Cell-Cell Similarities

Figure 6:
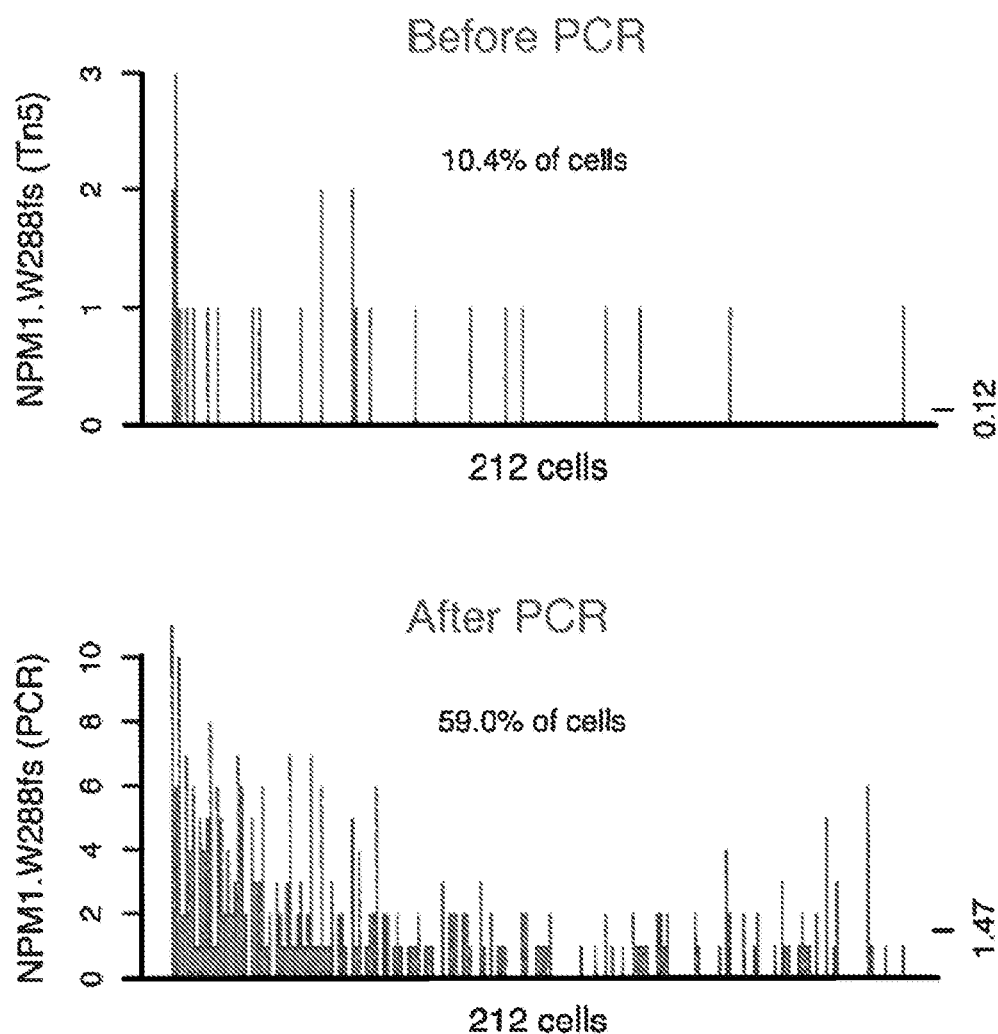
FIG. 6 depicts the results of experiments to detect cancer driver mutations in single cells in an OCI-AML3 cell line, with (bottom panel) and without (top panel) employment of a PCR-based amplification method of the invention.
Figure 7:
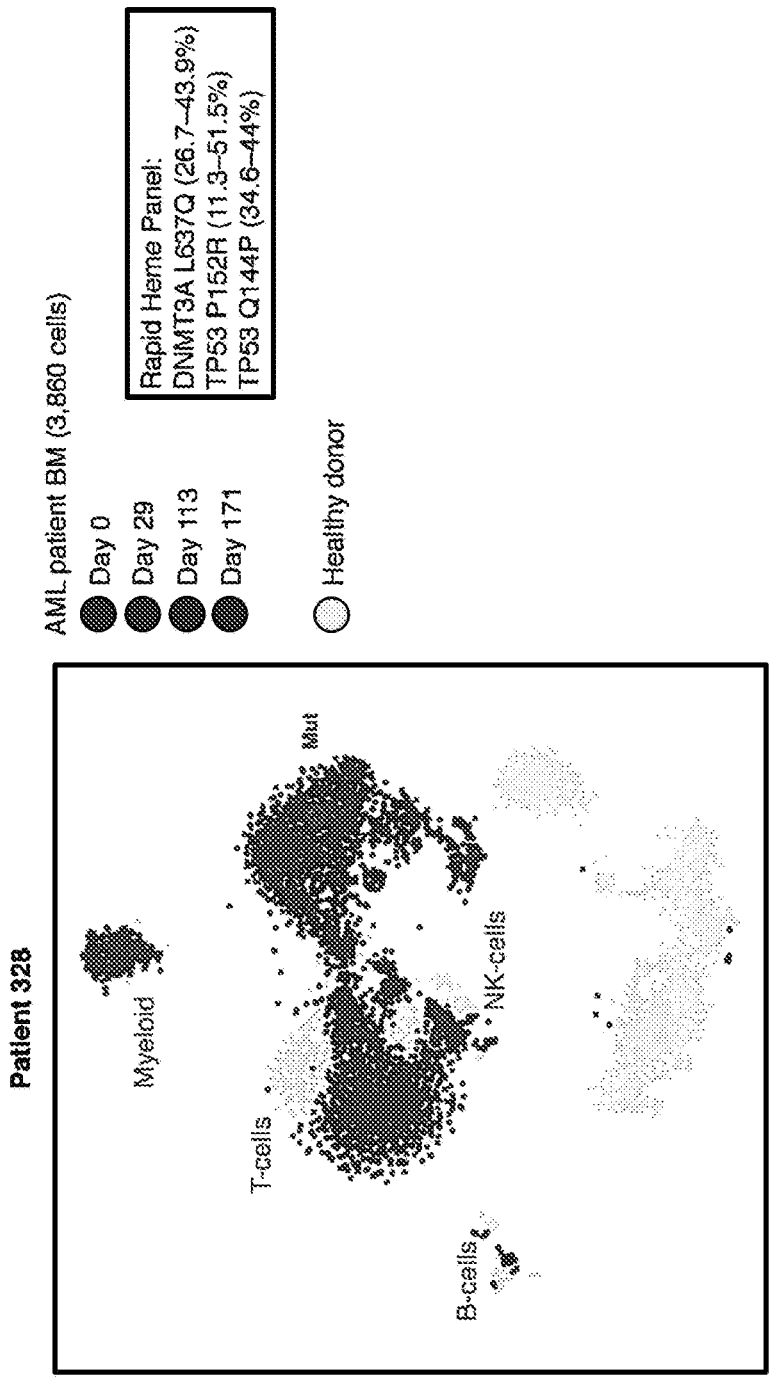
FIG. 7 depicts detection of mutations from Seq-well data from a single AML patient tissue sample without the enrichment techniques of the invention.
Figure 8:
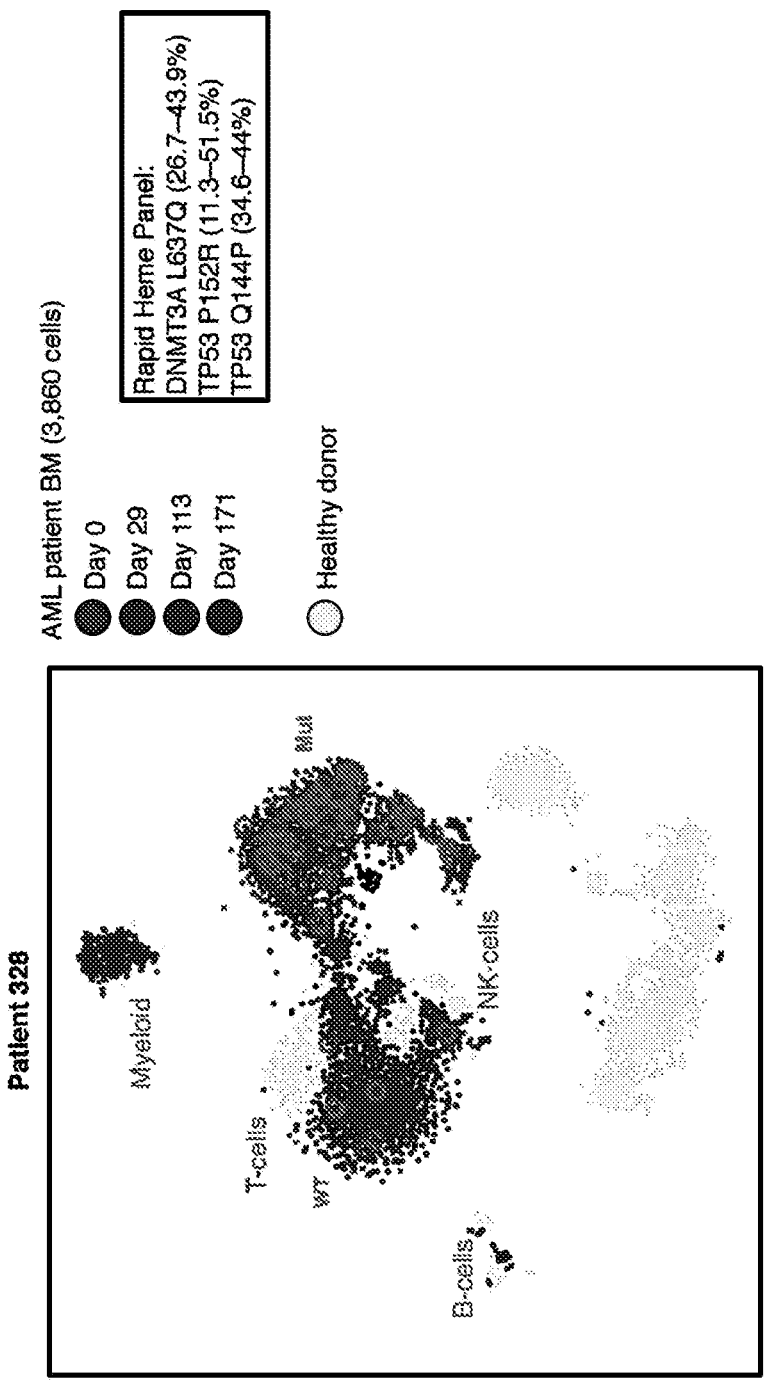
FIG. 8 depicts detection of mutations from Seq-well data from the same AML patient in FIG. 7, using the PCR enrichment method disclosed herein.
Figure 9:
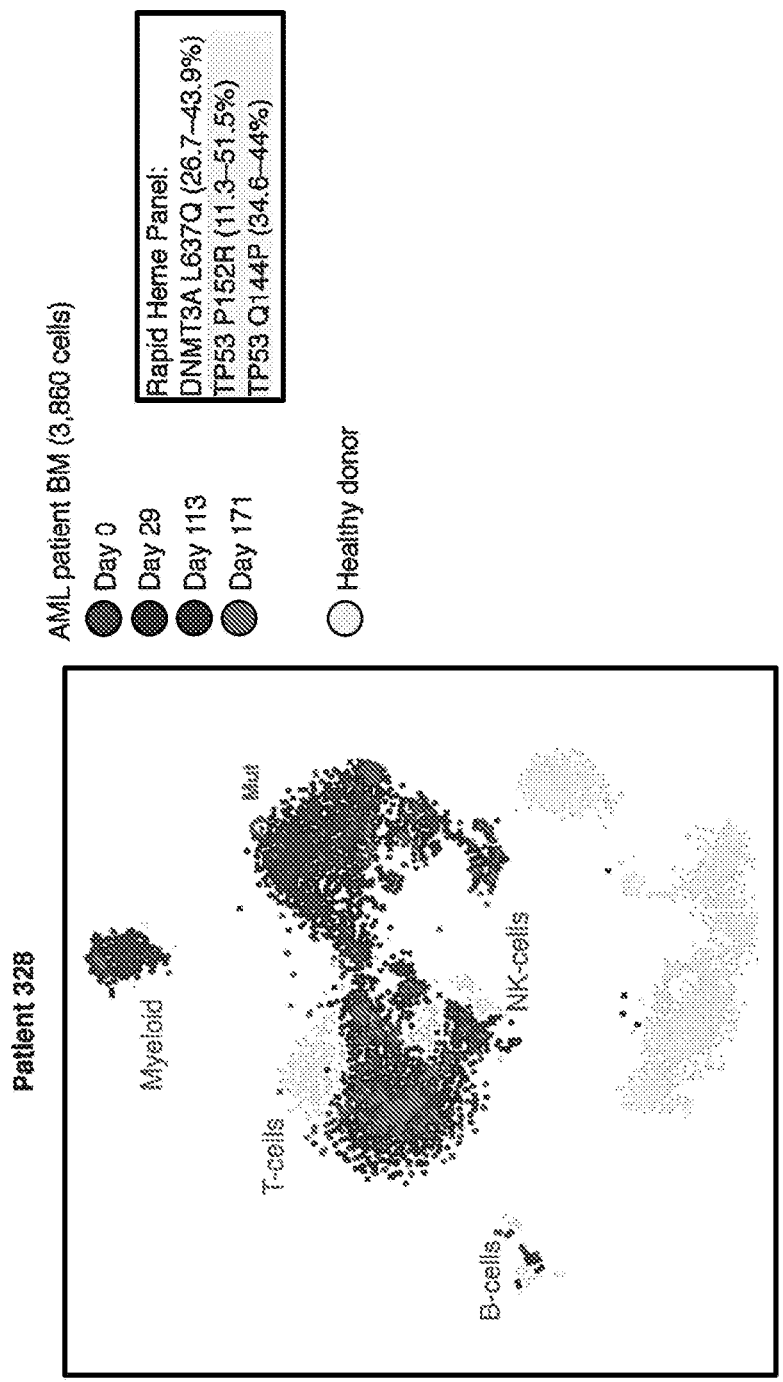
FIG. 9 depicts mutation detection in residual tumor cells from the same AML patient, using the PCR enrichment methods of the invention.
Figure 10:
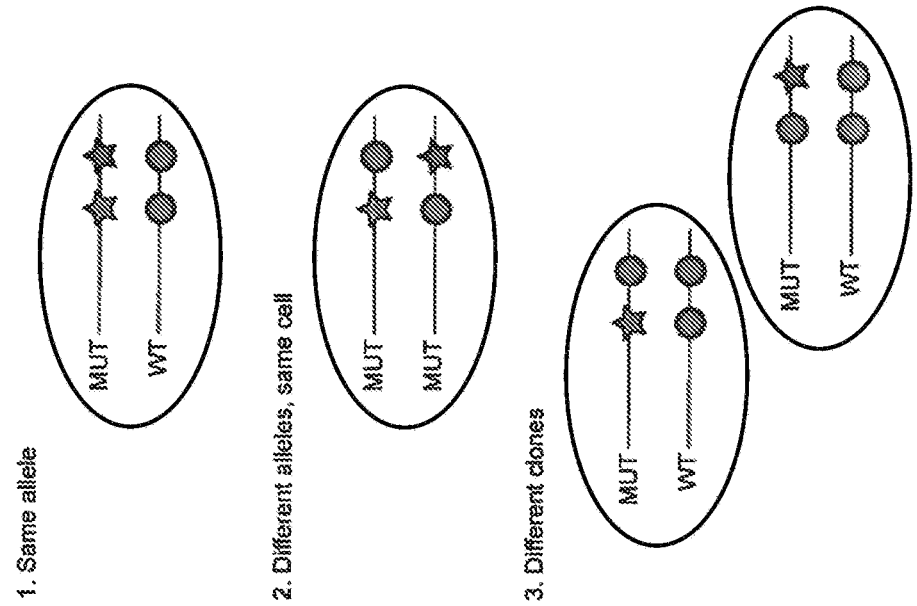
FIG. 10 depicts identification of the mutational status of TP53 across both alleles using the methods of the invention in residual cells from the same patient as above.
Figure 10:
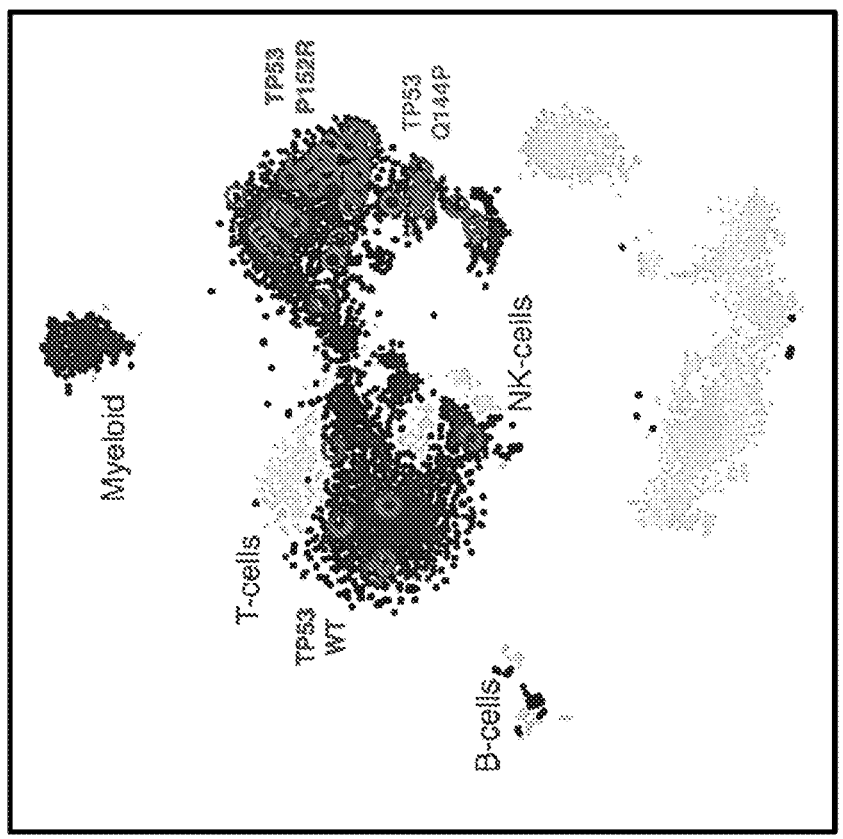

We employed two different methods for visualizing similarities between cells in two-dimensional space: Visualization of k-nearest-neighbor (KNN) graphs and t-distributed stochastic neighbor embedding (t-SNE) (Krijthe, 2015; van der Maaten, 2014; Weinreb et al., 2018). For both methods we started with the same set of variable genes as for the BackSPIN clustering. For KNN visualization we calculated pairwise correlation coefficients between single cells. Then we constructed a graph by connected each cell to its five most highly correlated neighbors. This graph was visualized using SPRING, an interactive tool that uses force-directed graph drawing. For t-SNE visualization we used the Rtsne implementation in R and default parameters, except setting the maximum number of iterations to 2,000 (5,000 for the healthy bone marrow data). Throughout the manuscript only two different KNN visualizations (healthy bone marrow and T and NK cells, FIG. 1 and FIG. 6, respectively) and two different t-SNE visualizations (AML556 and AML707B, FIG. 2) are shown. These visualizations are reused in other figures to highlight additional cell parameters, such as sample-of-origin, mutation status, and gene expression levels.

Random Forest-Based Classification

The Random forest algorithm is a machine learning approach that uses a large number of binary decision trees that are learned from random subsets of a training set (Breiman, 2001). These trees (the forest) can then be applied to a given sample to generate a class probability that reflects its similarity to a given class of the training set. If a single class prediction is required, the class with the highest probability score is used (majority vote). Random forest classifiers are particularly well suited if the dataset contains many different classes, many samples and many features. In our case samples represent single-cell expression profiles, features represent genes, and classes represent different cell types. For our analysis we used the randomForest R package version 4.6-14 (Liaw, 2002).

Figure 26A:
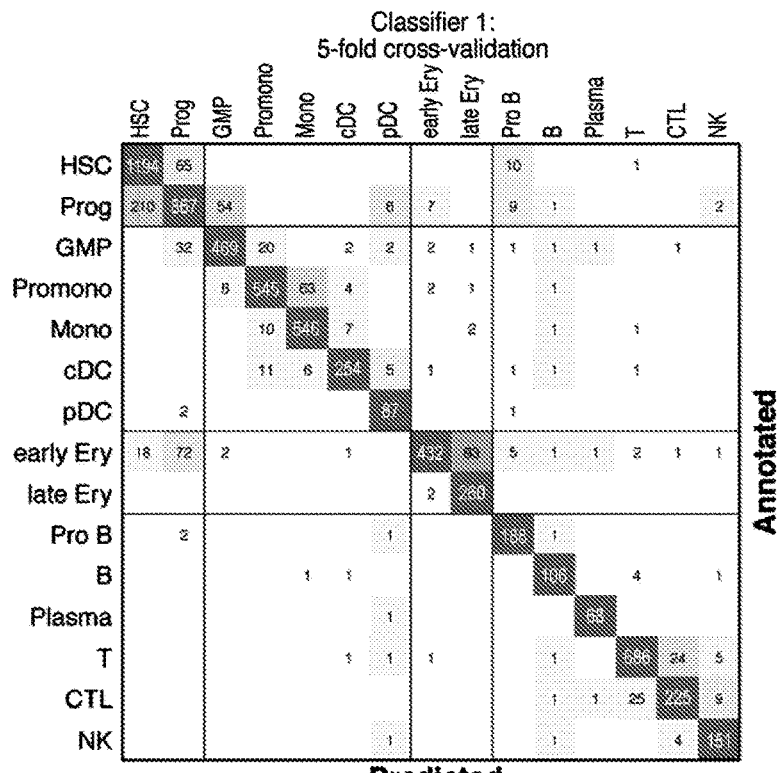
FIG. 26A-26J Classifier distinguishes normal from malignant cells by transcriptional and genetic data.
Figure 26B:
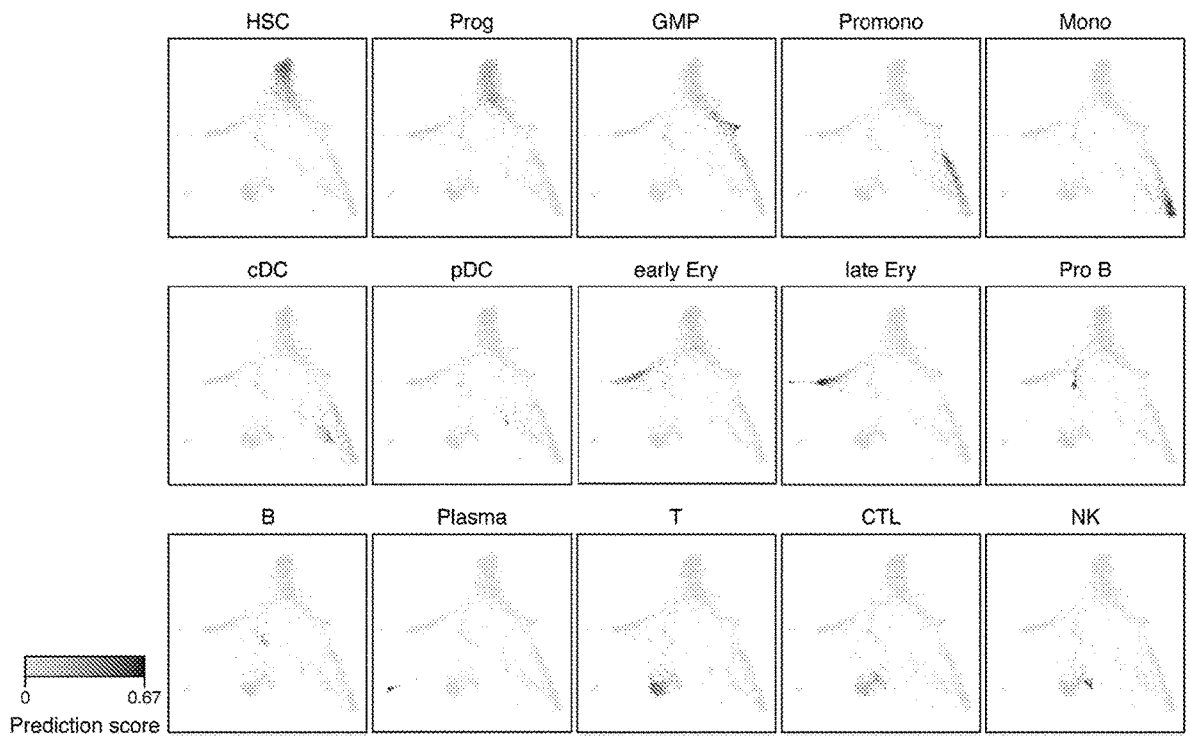
Figure 26C:
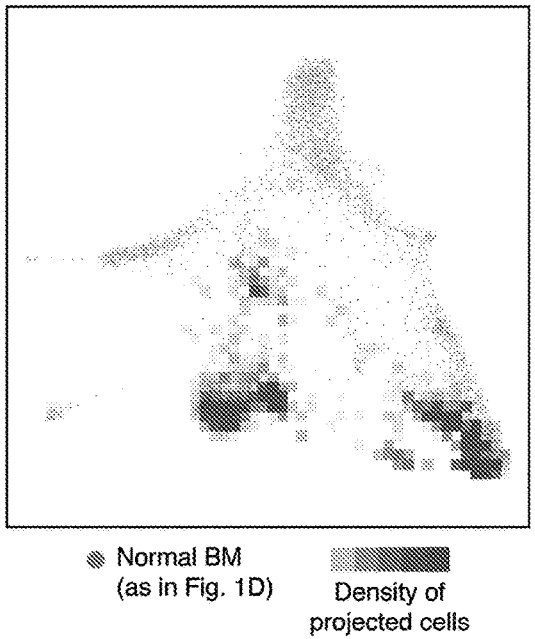

We used Random forest-based classification for two different purposes: To predict similarity of single cells to the 15 different cell types detected in healthy bone marrow (classifier 1), and to predict if a single from a tumor sample is malignant or normal (classifier 2). To train the first classifier, we first performed a feature selection step that selected the most informative genes from all 14,554 expressed genes in the dataset (average expression>0.01). We trained 1,000 trees and used a random subset of 50 cells from each cell type for each tree. We then selected the 1,000 most informative genes based on the overall importance. We then generated the final classifier based only on those genes, using the same parameters as before. This classifier was evaluated using 5-fold cross-validation by splitting the training dataset into five equally sized parts. In each iteration of the cross-validation, four of these parts were used to generate a classifier that was then used for predicting class probabilities of the remaining part. Results of this analysis are provided in FIG. 26A.

The second classifier is used for determining if a cell for which we did not detect a mutant transcript is malignant or normal, based on its similarity to normal and high-confidence malignant cells (cells from healthy bone marrow and cells from tumor samples for which we detected mutant transcripts). We first attempted to use a classifier that distinguishes between just these two classes. However, we achieved much better results by using all 15 normal and six malignant cell types in a combined training set (21 classes), presumably because a malignant monocyte-like cell is more similar to a normal monocyte than to a malignant HSC-like cell. For malignant cells we used cell type annotations as predicted by the first classifier, with the following exceptions: To have at least 65 HSC-like cells, we reclassified 23 cells initially classified as Progenitor-like as HSC-like cells. We also reclassified 29 cells that were initially classified as early Erythroid progenitors as Progenitor-like cells, if their prediction score for the Progenitor cell type was higher than the late Erythroid cell type. The second classifier was then generated using the same parameters as for the first classifier, and also evaluated using 5-fold cross-validation. Results of this analysis are provided in FIG. 26E.

When applying both classifiers to single cells from tumor samples, we first determined from the second classifier if the prediction score was highest for a malignant or normal cell type. If a cell was classified as malignant, we then used the highest prediction score of the HSC-to-myeloid cell types from the first classifier for cell type assignment. For normal cells we just used the predictions from the first classifier. We evaluated normal and malignant cell predictions by performing unsupervised BackSPIN clustering of all cells that were predicted as one six HSC-to-myeloid cell types. This analysis was performed for each patient separately. We included 500 normal cells of each cell type from healthy bone marrow samples in this clustering. For some samples we identified cells for which we could make a better judgement by considering the additional evidence at hand (e.g. mutated transcripts, targeted DNA sequencing results). We then refined these cells as malignant or normal. In total 578 cells were refined as malignant (1.9% of cells), and 573 cells were refined as normal (1.9%). We also identified seven samples from four different patients for which we were not confident about the classification results (AML314, AML371, AML722B and AML997, 3.7% of cells). These samples were of poor quality and had fewer detected cells, and were excluded from downstream analyses of malignant cells.

Note that T/NK-cell quantification shown in FIG. 2G was done based on tSNE coordinates rather than the classifier (which yielded nearly identical results for T/NK cells). Exemplary Resources used in this Example is provided in Table 1.

TABLE 1

| REAGENT or RESOURCE | SOURCE | IDENTIFIER |
| --- | --- | --- |
| Antibodies | | |
| Mouse CD15-V450, clone MMA | BD Biosciences | Cat# 642917, RRID: AB_1645751 |
| Monoclonal mouse CD34-FITC, clone 8G12 | BD Biosciences | Cat# 348053, RRID: AB_2228982 |

TABLE 1-continued

| REAGENT or RESOURCE | SOURCE | IDENTIFIER |
|---|---|---|
| Monoclonal mouse HLA-DR-PE-Cy7, clone G46-6 | BD Biosciences | Cat# 560651, RRID: AB_1727528 |
| Mouse CD14-APC, clone RMO52 | Beckman Coulter | Cat# IM2580U |
| Monoclonal mouse CD11b-APC-Cy7, clone ICRF44 | BD Biosciences | Cat# 557754, RRID: AB_396860 |
| Monoclonal mouse HLA-DR, clone L243 | Abcam | Cat# ab136320 |
| Chemicals, Peptides, and Recombinant Proteins | | |
| (3-Aminopropyl)triethoxysilane (APTES) | Sigma | Cat# A3648-100ML |
| p-Phenylene diisothiocyanate (PDITC) | Sigma | Cat# 258555-5G |
| Pyridine | Sigma | Cat# 270970-1L |
| N,N-Dimethylformamide (DMF) | Sigma | Cat# 227056-2L |
| Chitosan | Sigma | Cat# C3646-100G |
| Poly(L-glutamic) acid sodium solution | Sigma | Cat# P4761-100MG |
| Sodium Carbonate ReagentPlus | Sigma | Cat# S2127-500G |
| Guanidine Thiocyanate (GITC) | Sigma | Cat# G9277-500g |
| Sarkosyl (10%, 500 ml) | Fisher Scientific | Cat# 50-843-132 |
| Maxima H Minus Reverse Transcriptase | ThermoFisher | Cat# EP0753 |
| 20% Ficoll PM-400 | Sigma | Cat# F5415-50mL |
| Betaine | Sigma | Cat# B0300-5VL |
| 1M MgCl2 | Sigma | Cat# 63069-100ML |
| 1M Tris-HCl pH 8.0 | Boston BioProducts | Cat# BBT-80 |
| 10 mM dNTPs | New England BioLabs | Cat# N0447L |
| RNAse Inhibitor | ThermoFisher | Cat# AM2696 |
| Exonuclease I | New England Biolabs | Cat# M0293S |
| Poly(ethylene glycol) (PEG) Mn 400 | Sigma | Cat# 202398-250G |
| Poly(ethylene glycol) (PEG) BioUltra 8,000 | Sigma | Cat# 89510-250G-F |
| Acetone | Avantor | Cat# 2440-10 |
| BSA | Sigma | Cat# A9418-100G |
| 2-Mercaptoethanol | Fisher Scientific | Cat# NC0753648 |
| Tween-20 | Fisher Scientific | Cat# 65-520-4100ML |
| EDTA (0.5M, pH 8.0) | Boston Bioproducts | Cat# BM-150 |
| Sodium Chloride | Fisher Chemical | Cat# S671-3 |
| UltraPure Distilled Water | ThermoFisher | Cat# 10977023 |
| Sodium hydroxide | Sigma | Cat# S8045-500G |
| AMPure XP (SPRI) beads | Beckman Coulter | Cat# A63881 |
| Critical Commercial Assays | | |
| KAPA HiFi Hotstart Readymix PCR Kit | Kapa Biosystems | Cat# KK2602 |
| Nextera XT DNA Library Preparation Kit | Illumina | Cat# FC-131-1096 |
| Hybridization Chamber Kit - SureHyb enabled | Agilent | Cat# G2534A |
| MACOSKO-2011-10 mRNA Capture Beads | Chemgenes | Cat# NC0927472 |
| Dynabeads ™ kilobaseBINDER ™ Kit | ThermoFisher | Cat# 60101 |
| PfuUltra II Hotstart PCR Master Mix | Agilent | Cat# 600852 |
| Qubit dsDNA HS Assay Kit | ThermoFisher | Cat# Q32854 |
| BioA High Sensitivity DNA Kit | Agilent | Cat# 5067-4626 |
| High Sensitivity D5000 ScreenTape | Agilent | Cat# 5067-5592 |
| Bio-Glo ™ Luciferase Assay System | Promega | Cat# G7941 |
| Jurkat NFAT reporter cells | Promega | Cat# J1621 |
| Dynabeads ® Human T-Activator CD3/CD28 | Gibco | Cat# 11131D |
| Deposited Data | | |
| Jurkat RNA-seq data | ENCODE Project Consortium | link |
| Experimental Models: Cell Lines | | |
| MUTZ-3 | DSMZ | Cat# ACC-295, RRID: CVCL_1433 |
| OCI-AML3 | Dr. Mark Minden, University of Toronto | |
| Software and Algorithms | | |
| FlowJo version 10.4.2 | Tree Star | https://www.flowjo.com |
| Prism 7 | GraphPad Software | https://www.graphpad.com/scientific-software/prism/ |
| Integrative Genomics Viewer (IGV version 2.4.8) | | http://software.broadinstitute.org/software/igv/download |

Gene Signatures

We generated cell type-specific gene signatures by correlating gene expression levels to cell type prediction scores, and then considering the most highly correlated genes. This analysis was performed for each cell type along the HSC-to-myeloid differentiation axis using, using either normal cells from healthy bone marrow (4,430 cells) or malignant cells from AML patient samples at diagnosis (11,641cells). We determined the most highly correlated genes for each cell type by subtracting the highest correlation coefficient from all other cell types. This ensures that a gene is specific to certain cell type. For this analysis we included correlation coefficients of all 15 cell types. This prevents genes that are more highly correlated to the erythroid and lymphoid cell types to be part of the HSC-to-myeloid signatures. We also included correlation coefficients of gene expression values to cell cycle signature scores, which prevents genes that are highly expressed in cycling cells to be associated with a certain cell type. As many genes were highly correlated to the HSC and Prog, and the Promono, Mono and cDC prediction scores, we also generated signatures by adding up the prediction scores for these classes to generate combined gene signatures. All gene signatures are provided in Table 2.

TABLE 2

| | Normal-derived, combined | | | Tumor-derived, combined | | | HSC |
|---|---|---|---|---|---|---|---|
| | HSC/Prog | GMP | Myeloid | HSC/Prog | GMP | Myeloid | |
| 1 | SPINK2 | CPA3 | VCAN | SPINK2 | PRTN3 | LYZ | NPTX2 |
| 2 | ZFAS1 | PRSS57 | S100A9 | ANGPT1 | MPO | S100A9 | H1F0 |
| 3 | NRIP1 | ELANE | S100A8 | GUCY1A3 | CALR | S100A8 | EMP1 |
| 4 | GAS5 | SUCNR1 | MNDA | FAM30A | CLEC5A | VCAN | MEIS1 |
| 5 | JUN | CALR | FCN1 | MMRN1 | ELANE | MNDA | CALCRL |
| 6 | MEIS1 | PRTN3 | LYZ | TPT1 | POU4F1 | CSTA | TPSD1 |
| 7 | HLF | AZU1 | THBS1 | GAS5 | TRH | SRGN | TPT1 |
| 8 | EGR1 | CST7 | CSTA | RAB27B | TSPOAP1 | FCN1 | CRHBP |
| 9 | CRHBP | NUCB2 | SAMSN1 | TPM4 | CEBPE | FTL | CLNK |
| 10 | NPR3 | CTSG | FGL2 | MSI2 | LINC01835 | MS4A6A | TSC22D1 |
| 11 | FAM30A | EREG | TYROBP | GCSAML | NUCB2 | PSAP | DST |
| 12 | MMRN1 | IGFBP2 | IFI30 | SOCS2 | CSF3R | IFI30 | NRIP1 |
| 13 | MSI2 | TRH | PLBD1 | EEF1A1 | RUNX1T1 | ANXA2 | ABCB1 |
| 14 | ANGPT1 | FAM46A | S100A12 | NRIP1 | CD38 | FGL2 | GABRA4 |
| 15 | EIF4A2 | SERPINB1 | ANXA2 | HOPX | PLPPR3 | S100A10 | ZBTB20 |
| 16 | TPT1 | C1QTNF4 | S100A10 | CD34 | IGFBP2 | LGALS3 | ABCA9 |
| 17 | COMMD6 | VAT1 | PSAP | TFPI | PRRT4 | CTSS | TPSB2 |
| 18 | EEF1A1 | CEACAM6 | FCER1G | TPSD1 | SNHG5 | ANXA1 | KMT2A |
| 19 | SNORD13 | CAT | SAMHD1 | PDZRN4 | FABP5 | ANXA5 | FAM30A |
| 20 | FAU | TSPOAP1 | LGALS1 | PCNP | LOC100419170 | AIF1 | MEF2C |
| 21 | FOS | SNHG25 | COTL1 | PTPRCAP | CLEC11A | NCF2 | TMEM74 |
| 22 | PHLDB2 | MPO | CTSH | FLT3 | SERPINB1 | LYST | PDZRN4 |
| 23 | MSRB3 | CLEC11A | CTSS | SMIM24 | AZU1 | FCER1G | ST3GAL1 |
| 24 | GUCY1A3 | SLC2A5 | S100A6 | SELENOP | FBN2 | CD68 | XIRP2 |
| 25 | C6orf48 | PRRT4 | ITGB2 | DAPK1 | HNRNPDL | TNFSF13B | RBPMS |
| 26 | GBP4 | ERLIN1 | FPR1 | SMYD3 | HSPB1 | VIM | TMEM25 |
| 27 | PCDH9 | PCOLCE2 | MEGF9 | ADGRG6 | RNA5-8S | IRS2 | C20orf203 |
| 28 | SNHG6 | NCOA4 | CD14 | PIM1 | THSD7A | GRN | GNG11 |
| 29 | RACK1 | CD38 | MS4A6A | MECOM | C12orf57 | TNFAIP2 | SLC6A13 |
| 30 | ADGRG6 | SPARC | FTL | CEP70 | FGFR1 | MCL1 | HOPX |
| 31 | PREX2 | VAMP8 | KCTD12 | XIRP2 | LPO | MS4A7 | CMTM2 |
| 32 | PRKG2 | OSTC | S100A4 | SPAG6 | MGST1 | CLEC12A | HIST1H2BK |
| 33 | HINT1 | LINC01268 | IGSF6 | TAPT1-AS1 | C1QTNF4 | S100A12 | NPDC1 |
| 34 | RNA5-8S | ANKRD18A | NCF2 | GNA15 | HMGN1 | MEGF9 | SCRN1 |
| 35 | NFKBIZ | HYOU1 | CLEC7A | DSE | SIPA1L2 | CFD | MECOM |
| 36 | MYCT1 | SLPI | S100A11 | TPSAB1 | DDOST | S100A6 | CXCL2 |
| 37 | TUBA1A | MANF | CST3 | TPSB2 | PTGIR | TLR4 | CCS |
| 38 | CD34 | CLDN10 | CEBPD | H2AFY | GATM | KLF4 | FAM74A4 |
| 39 | ZBTB20 | DPM3 | ARPC1B | SCHIP1 | VAMP8 | SERPINA1 | UMODL1-AS1 |
| 40 | TFPI | FDX1 | CD68 | LINC02470 | FAM46A | MAFB | CCDC18-AS1 |
| 41 | SNHG8 | HSPA5 | IFNGR1 | NPR3 | VAMP5 | CTSD | TTLL10 |
| 42 | AVP | CEBPA | PTPRE | KMT2A | STAR | TMEM170B | CFAP61 |
| 43 | CEP70 | TMEM258 | RAB31 | CD200 | ANKRD18A | NAMPT | PLCB4 |
| 44 | H3F3B | CDCA7 | GPR183 | MACF1 | TM7SF3 | C1orf162 | SPON1 |
| 45 | RNU4-2 | RNASEH2C | NAMPT | GBP4 | CCND1 | S100A11 | LINC01770 |
| 46 | HIST1H2BG | HGF | TSPO | ABCC1 | ROBO1 | CEBPD | CACNB4 |
| 47 | HOPX | LINC01835 | CD86 | PROM1 | GFI1 | ADA2 | CCDC144NL-AS1 |
| 48 | TSC22D1 | BEND6 | IRS2 | TMEM70 | DEFA4 | CD14 | RNF217 |
| 49 | LRRC70 | FAM201A | LRRK2 | FAM110A | CERS6 | IL17RA | ZPBP |
| 50 | PBX1 | CHRNB1 | GLIPR2 | TMEM123 | PTMA | DUSP1 | MPPED2 |
| | Shown in FIGS. 20E-F, 28C-D | | | Shown in FIGS. 21A-B, 28D, 29A-E | | | |

| | Tumor-derived, per cell-type | | | | |
|---|---|---|---|---|---|
| | Progenitor | GMP* | Pro mono | Monocyte | cDC |
| 1 | CDK6 | | DEFB1 | FCN1 | MRC1 |
| 2 | HSP90AB1 | | RNASE2 | S100A12 | HLA-DRB5 |
| 3 | SPINK2 | | MS4A3 | MAFB | CST3 |
| 4 | EEF1B2 | | SERPINB10 | VCAN | SAMHD1 |
| 5 | PCNP | | SESN3 | S100A9 | NAPSB |
| 6 | TAPT1-AS1 | | ZFR | PLBD1 | FCER1A |
| 7 | HINT1 | | MRPL33 | SERPINA1 | HLA-DRB1 |
| 8 | LRRC75A-AS1 | | CTSG | BCL2A1 | JAML |
| 9 | DSE | | SLC44A1 | THBS1 | PKIB |
| 10 | PEBP1 | | SLPI | PSAP | HLA-DRA |
| 11 | LOC107984974 | | FUT4 | S100A8 | HLA-DRB6 |
| 12 | H2AFY | | SRGN | FPR1 | CPVL |
| 13 | EEF1A1 | | CD70 | C5AR1 | HLA-DPB1 |
| 14 | SMIM24 | | PRLR | CD14 | HLA-DQA1 |
| 15 | PSME1 | | PLD3 | NAMPT | HLA-DPA1 |
| 16 | SOX4 | | LPL | VNN2 | CLEC4A |
| 17 | LINC01623 | | RETN | CTSS | TMSB10 |
| 18 | EEF1G | | TP53INP2 | DUSP1 | CAP1 |
| 19 | EBPL | | HSPA5 | CEBPB | HLA-DQB1 |
| 20 | EIF4B | | RNASE3 | CR1 | CRIP1 |

TABLE 2-continued

Figure 28A:
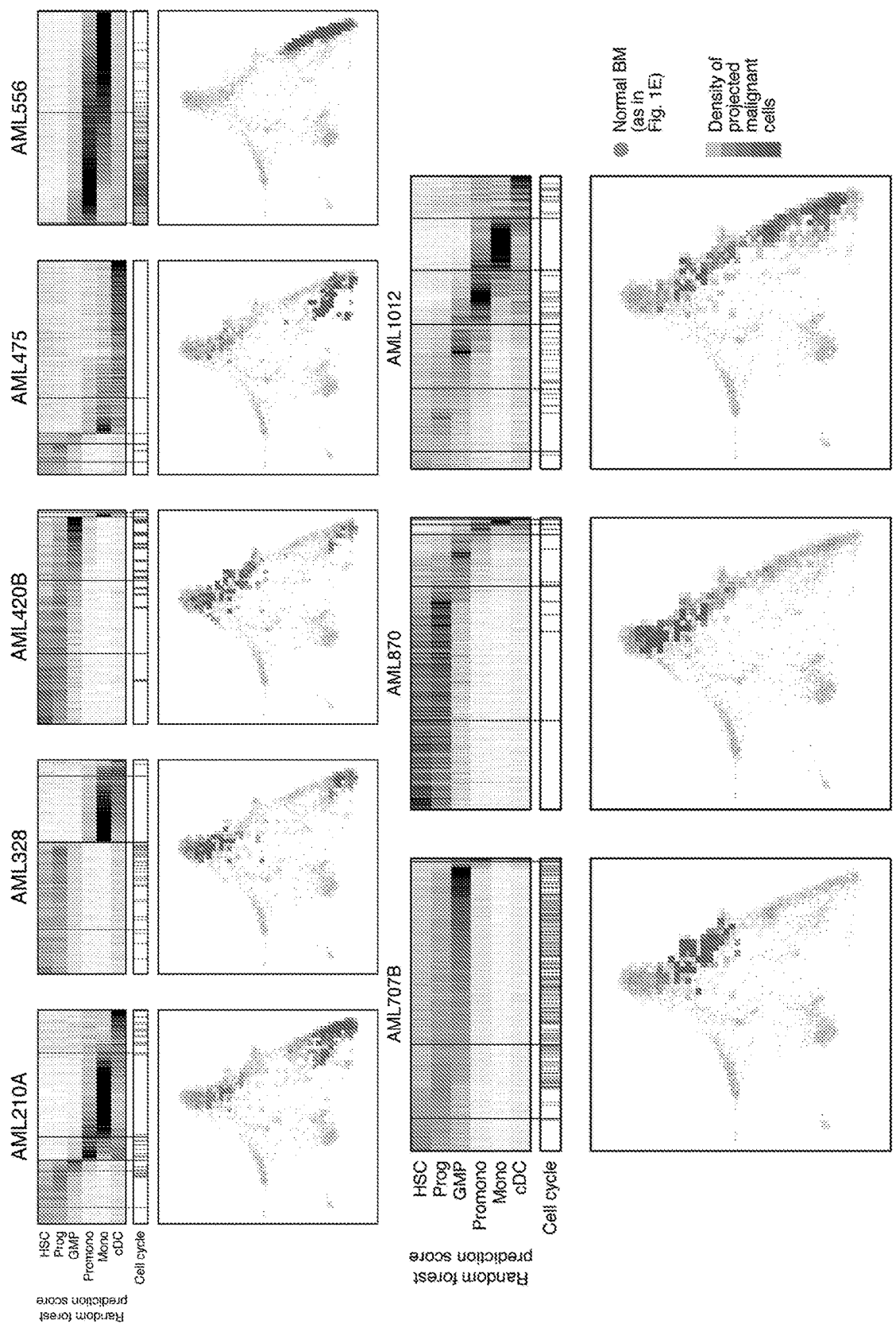
FIG. 28A-28D Intra-tumoral heterogeneity of malignant AML cells.

| | | | | |
|---|---|---|---|---|
| 21 | PARP1 | CCL23 | NFKBIA | CLEC10A |
| 22 | MEST | EMB | SLC11A1 | GPX1 |
| 23 | TMEM70 | ATP8B4 | LILRB3 | ITGB7 |
| 24 | TFDP2 | CLU | BCL6 | HLA-DQB2 |
| 25 | ATP5G2 | FAM107B | CYP1B1 | DBI |
| 26 | NAP1L1 | KBTBD11 | TNFAIP2 | FTH1P3 |
| 27 | MSI2 | CSTA | MS4A10 | ACTB |
| 28 | TPM4 | ANKRD28 | AQP9 | HLA-DQA2 |
| 29 | SPN | PIWIL4 | TLR4 | S100B |
| 30 | SELL | RNVU1-6 | APOBEC3A | ALDH2 |
| 31 | RACK1 | F13A1 | LRRK2 | GABARAP |
| 32 | CTSC | PROK2 | CD163 | LY86 |
| 33 | PRDX6 | IL31RA | LRP1 | IGSF6 |
| 34 | EGFL7 | PLAC8 | S100A10 | HLA-DPB2 |
| 35 | SNHG6 | ELF1 | CD68 | CD74 |
| 36 | NOP53 | EP400NL | MEGF9 | PAK1 |
| 37 | MRPL57 | EAF2 | NCF2 | LGALS2 |
| 38 | SELENOP | RFX8 | LOC643802 | CSF1R |
| 39 | CCDC152 | PTGFR | IFNGR1 | PALLD |
| 40 | SRSF6 | JUN | FTL | CCR2 |
| 41 | SNHG8 | FRMD3 | SLC24A4 | GPR183 |
| 42 | B4GALT6 | HOXB-AS3 | CD300E | GRB2 |
| 43 | HNRNPA1 | PHACTR3 | CXCL8 | EPS8 |
| 44 | KIF2A | AK2 | CLEC7A | COTL1 |
| 45 | HSH2D | ECRP | NEAT1 | DHRS9 |
| 46 | PTPRCAP | DDIT3 | CLEC4E | HLA-DMB |
| 47 | NACA2 | RFLNB | CRISPLD2 | HLA-DMA |
| 48 | PDLIM1 | FEZ1 | MEFV | PYCARD |
| 49 | CPA3 | SERPINB2 | ACSL1 | LOC644936 |
| 50 | GNPTAB | CDKN2A | NCF1 | SH3BGRL3 |
| | | Shown in FIGS. 21C, 28F | | |

*see combined signature

Bulk Expression Analysis

Bulk RNA-seq expression levels from the TCGA-LAML study were downloaded from the companion website of the original publication (Cancer Genome Atlas Research et al., 2013) (https://tcga-data.nci.nih.gov) We downloaded processed RPKM expression levels of 179 samples (laml.rnaseq.179_v1.0_gaf2.0_rpkm_matrix.txt.tcgaID.txt.gz). Information on cytogenetic alterations, genetic mutations and FAB classification was gathered from the updated supplementary table (SuppTable01.update.2013.05.13.xlsx). The most recent survival data was downloaded from the cBioPortal (Cerami et al., 2012; Gao et al., 2013).

We calculated expression scores of cell type-specific signatures in bulk profiles by using the top 30 most correlated genes that were part of both datasets. For each of those genes, we select the 100 genes with the smallest difference in average expression level as a background gene set. The average expression of the background gene set was then subtracted from the respective signature gene, and the average of the resulting values of all signature genes was kept as the signature score. A similar approach has been described before in other studies (Puram et al., 2017).

Results

Figure 24A:
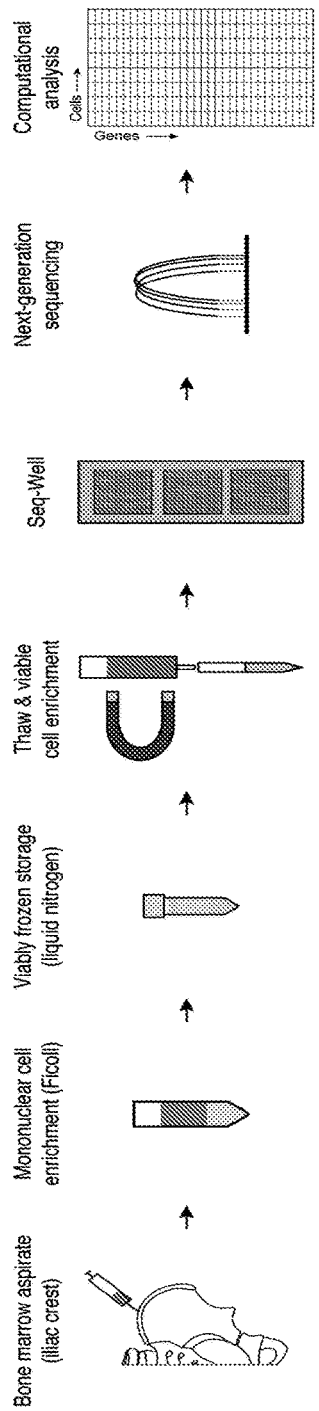

Identification of Cell Populations in Healthy BM Samples:

We first sought to characterize the baseline cellular diversity in BM of healthy individuals. To achieve comprehensive representation of cell types, we carried out scRNA-seq using a high-throughput nanowell-based protocol, termed Seq-Well (Gierahn et al., 2017). This workflow was optimized for cryopreserved hematopoietic cells, and included magnetic enrichment of viable cells (FIG. 24A, Methods). We profiled viably frozen cells from iliac crest aspirates from four healthy donors, as well as progenitor populations from one donor by sorting primitive cells (CD34$^+$ and CD34$^+$CD38$^-$) (FIG. 24B, Table 3). Barcoded sequencing reads were assigned to cells and aligned to the transcriptome, and individual mRNA molecules were counted using unique molecular identifiers (UMIs). We acquired high quality data for 7,698 healthy donor BM cells that passed initial QC (see Methods).

Figure 17A:
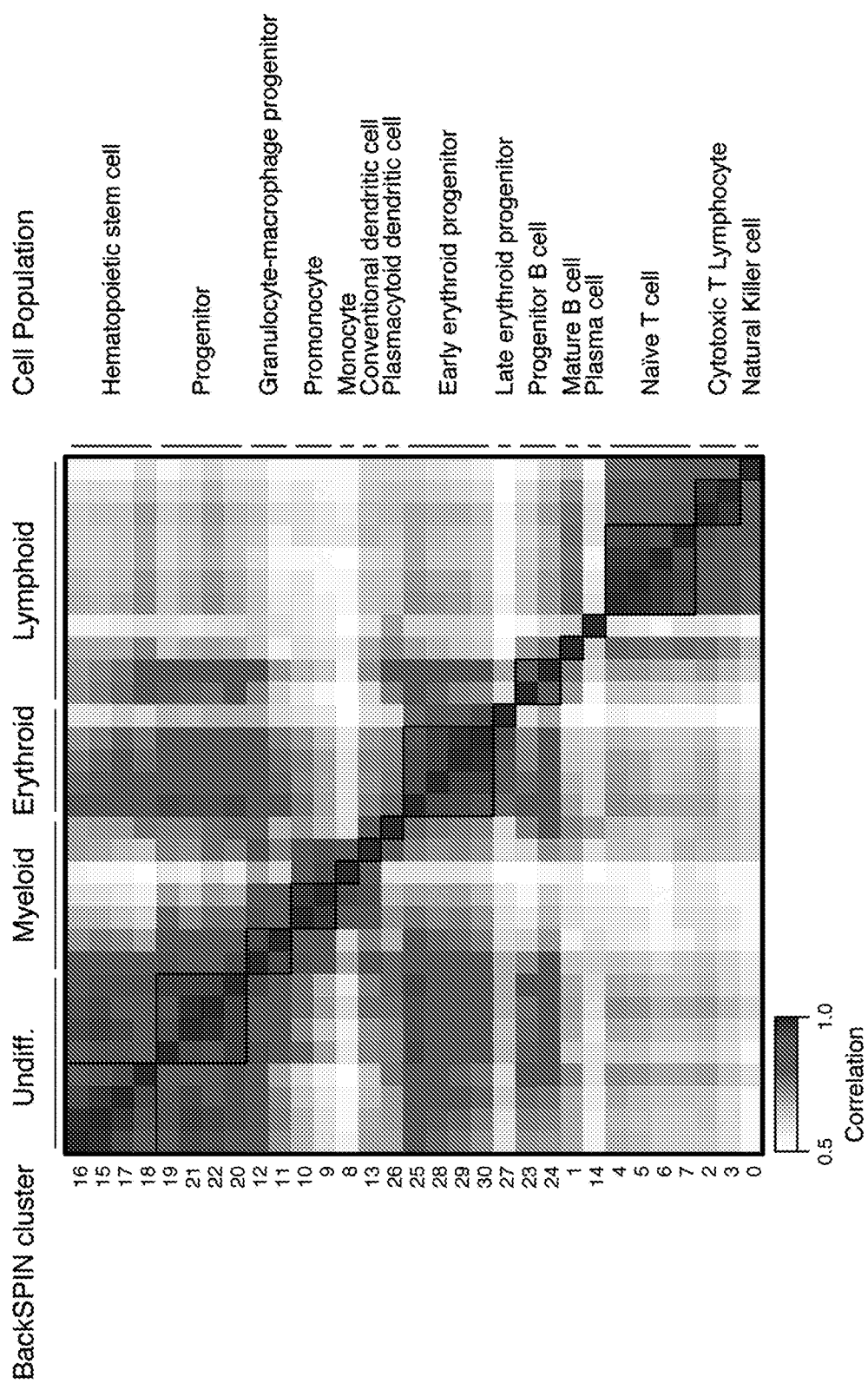
FIG. 17A-17D Identification of cell populations in healthy BM samples FIG. 17A. BackSPIN clustering of scRNA-seq data for 6,915 hematopoietic cells from normal BM identified 31 clusters of cells based on similarity of transcriptional states. Heatmap shows the pairwise correlation between the average expression profiles of these clusters (rows and columns). Clusters were merged into 15 cell populations based on marker gene expression (right).
Figure 17B:
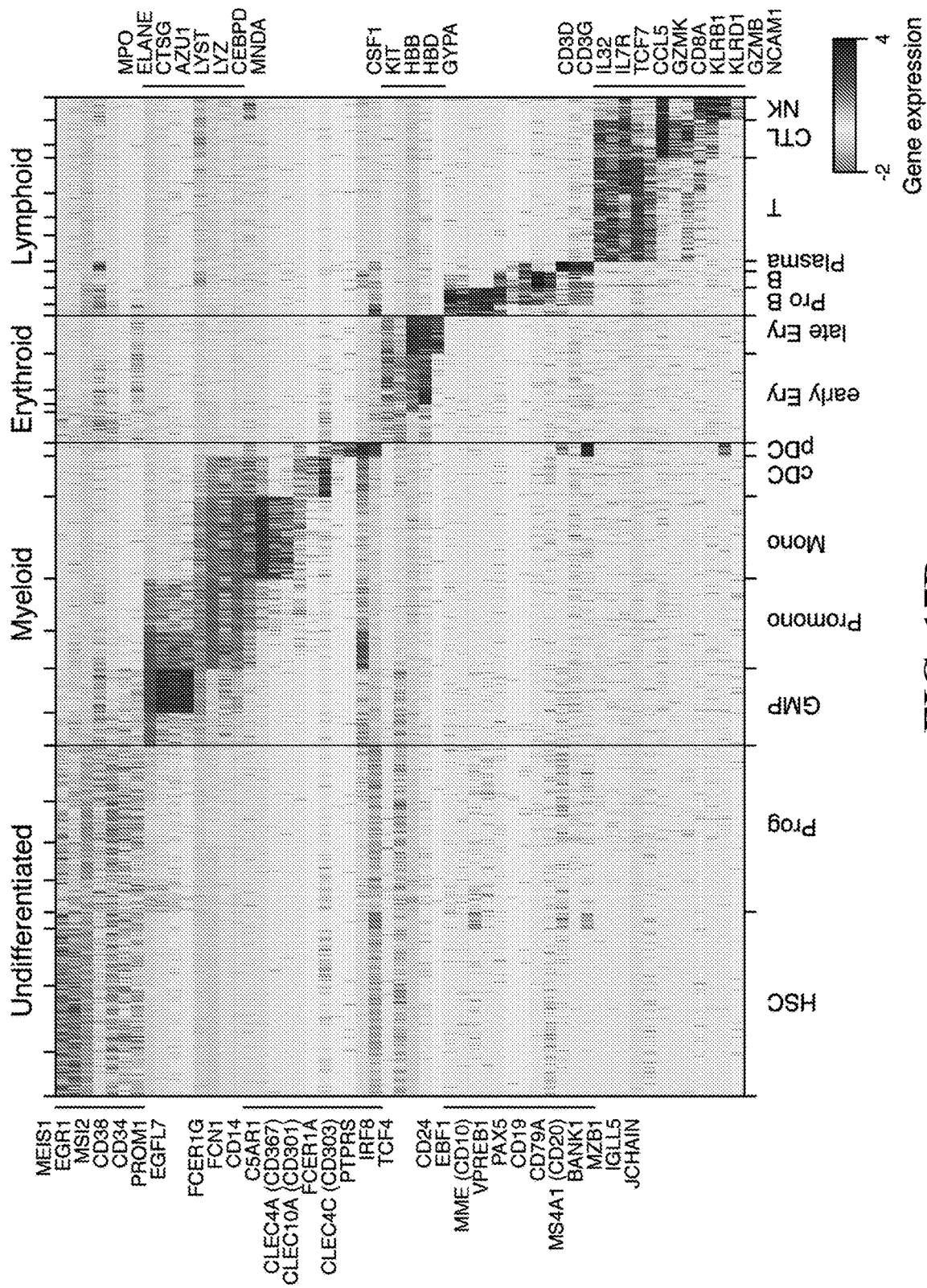
Figure 17C:
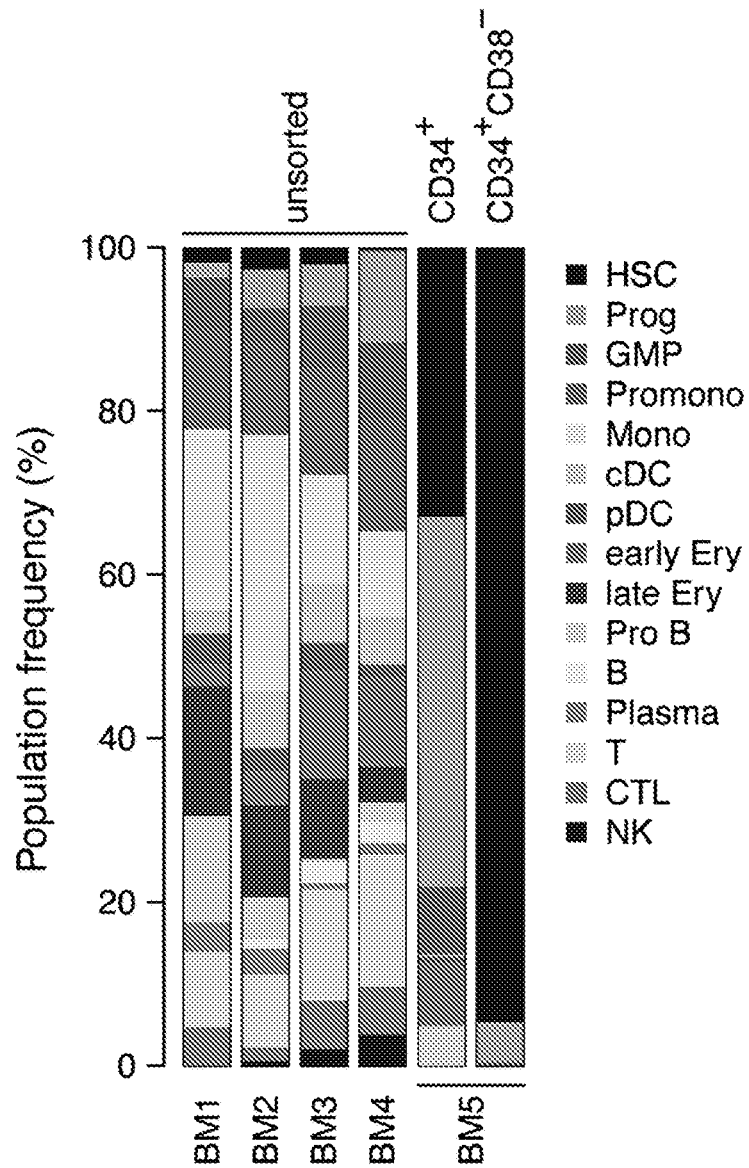
Figure 17D:
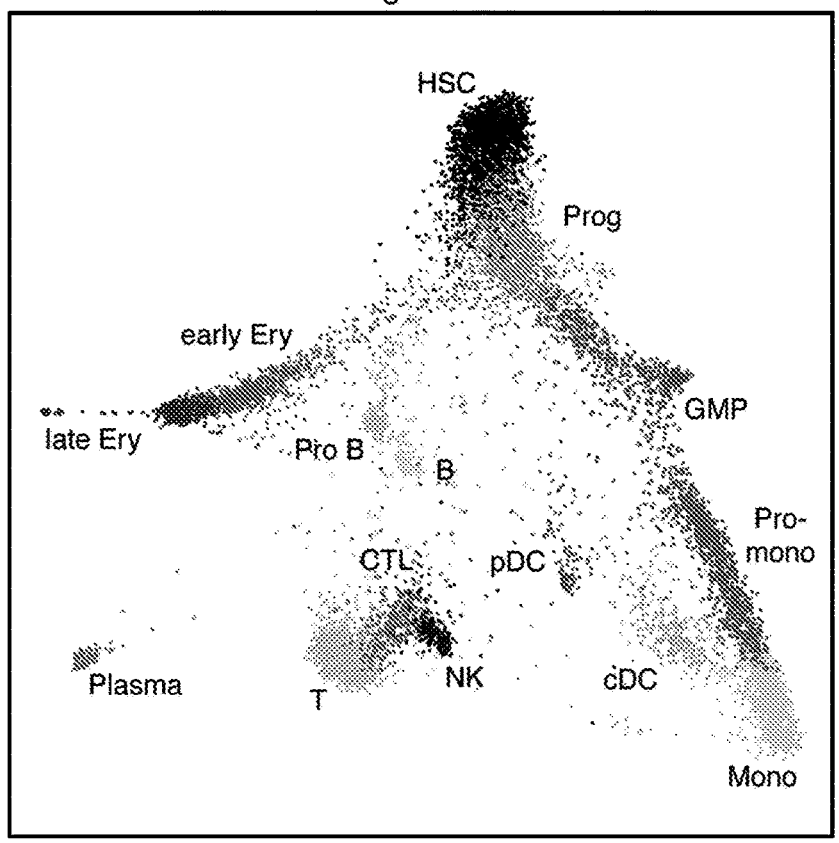
Figure 24C:
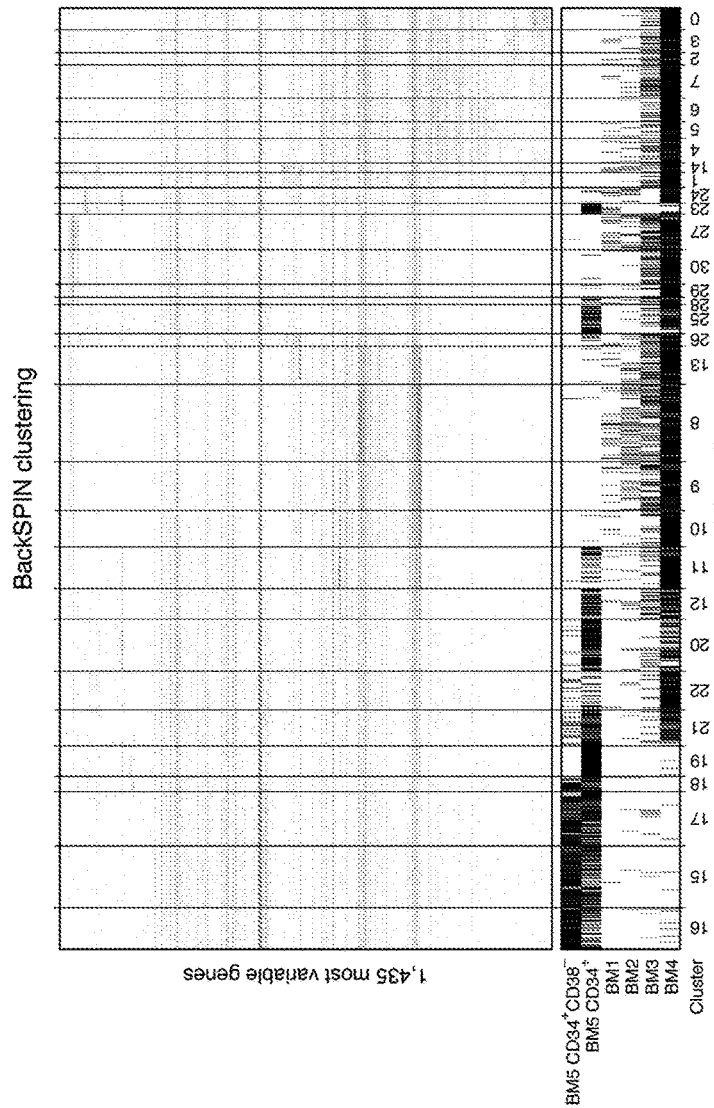
Figure 24B:
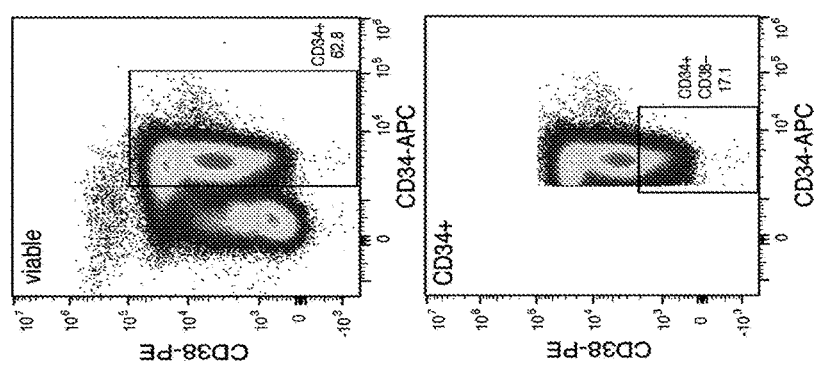
Figure 24G:
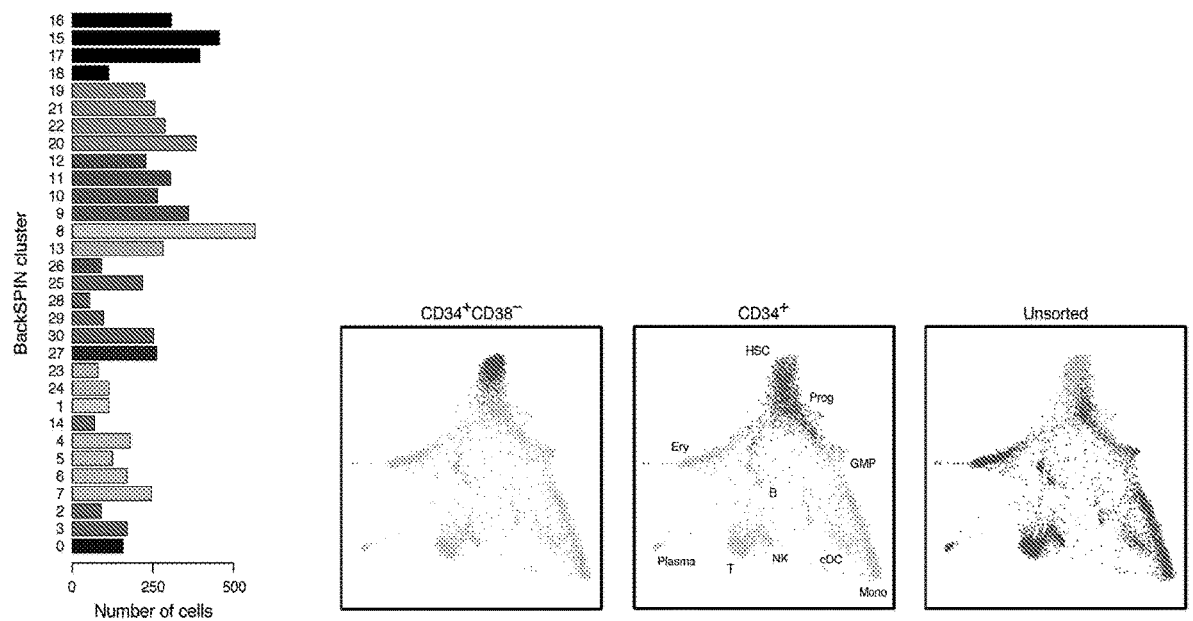
Figure 24G:
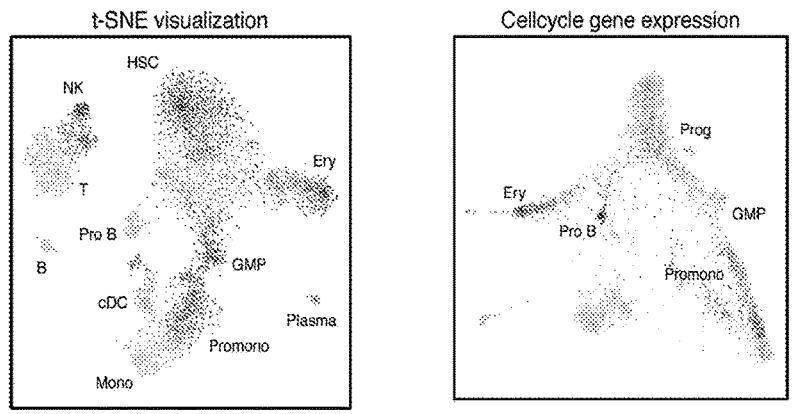
Figure 24G:
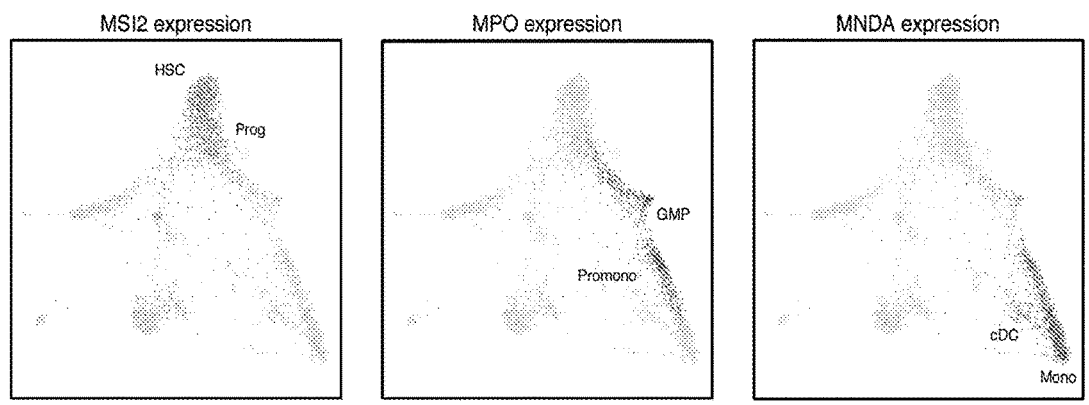

We distinguished cell types represented in the single-cell data by unsupervised clustering using BackSPIN (Zeisel et al., 2015), yielding 31 cell clusters (FIGS. 17A and 24C-24D). Clusters overlapped with well-established markers of hematopoietic cell populations, such as CD34 for HSC/Progenitor cells, CD14 for monocytes, CD3 for T-cells and CD56/NCAM1 for natural killer (NK) cells (Jaatinen et al., 2006; Laurenti et al., 2013; Novershtern et al., 2011) (FIG. 17B). This allowed us to merge the 31 clusters into 15 main cell populations (FIG. 17C). We captured a broad representation of cell types, including HSCs and progenitor cells, as well as multiple myeloid, erythroid and lymphoid populations.

We also compared cell type frequencies between donors to assess inter-individual variation and potential batch effects. All 15 cell types were reproducibly identified in at least three donors (FIG. 17C). The four unsorted BM samples contained similar proportions of the different cell types, with a degree of variability consistent with prior studies (Burel et al., 2017). The sorted CD34$^+$ cells were highly enriched for HSC and progenitor clusters, and also contained granulocyte-macrophage progenitors (GMP), early erythroid progenitors and progenitor B-cells, consistent with the established composition of CD34$^+$ cells (Karamitros et al., 2018; Laurenti et al., 2013; Velten et al., 2017). The sorted CD34$^+$CD38$^-$ cells were exclusively assigned to the HSC/progenitor clusters, consistent with the expected phenotypes. These results show that scRNA-seq from frozen BM aspirates captures expected cell types in proportions that are generally consistent with prior surveys based on surface markers.

We next explored the inter-relationships between these cell types using a tool for visualizing continuous gene expression topology (SPRING) (Weinreb et al., 2018). Two-dimensional K-nearest-neighbor (KNN) graphs were generated by connecting all single cells in our dataset to their five nearest neighbors in gene expression space (FIGS. 17D and 24E-24H). The resulting data reveal putative differentiation trajectories, including a continuum of cells from HSCs to monocytes. This continuum includes several intermediate states and gene expression gradients, such as MSI2, MPO and MNDA. In contrast, T- and NK cells form a discrete cluster. These cell types mature outside the BM, and our data correspondingly lack intermediate states between progenitors and these T/NK populations. Thus, scRNA-seq of normal BM reveals diverse hematopoietic cell types and implied differentiation trajectories consistent with current views of hematopoiesis.

Single-Cell Profiling of AML Tumor Ecosystems

Figure 18A:
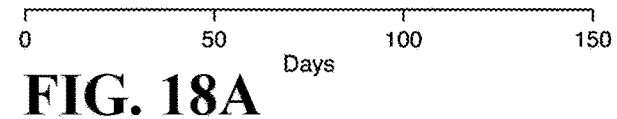
FIG. 18 Single-cell profiling of AML tumor ecosystems FIG. 18A provides an overview of AML patients and collection time points for BM aspirates profiled by scRNA-seq. Cell numbers reflect single-cell transcriptomes that passed quality thresholds. For each patient, pie charts indicate time of sample collections, relative to diagnosis and induction chemotherapy, and clinical blast count. Further details are listed in Table 3.
FIG. 18B includes a chart showing mutations in AML driver genes (gray) in the patient cohort. Recurrently mutated genes were assessed by targeted DNA sequencing (Kluk et al., 2016).
FIGS. 18C and 18D provides t-SNE plots visualizing 4,982 single cells from AML556
FIGS. 18E and 18F provides t-SNE plots for AML556 (FIG. 18E) or AML707B (FIG. 18F) with cells colored by their expression of marker genes for erythroid cells (HBB/HBD; hemoglobin), B-cells (MS4A1; CD20), plasma cells (JCHAIN), T-cells (CD3D/CD3G; CD3) and NK cells (NCAM1; CD56). Cells and clustering are the same as in (18C) and (18D).
FIG. 18G shows barplots of the frequency of T-cells at diagnosis and early time points after induction chemotherapy. D: Day.
Figure 18B:
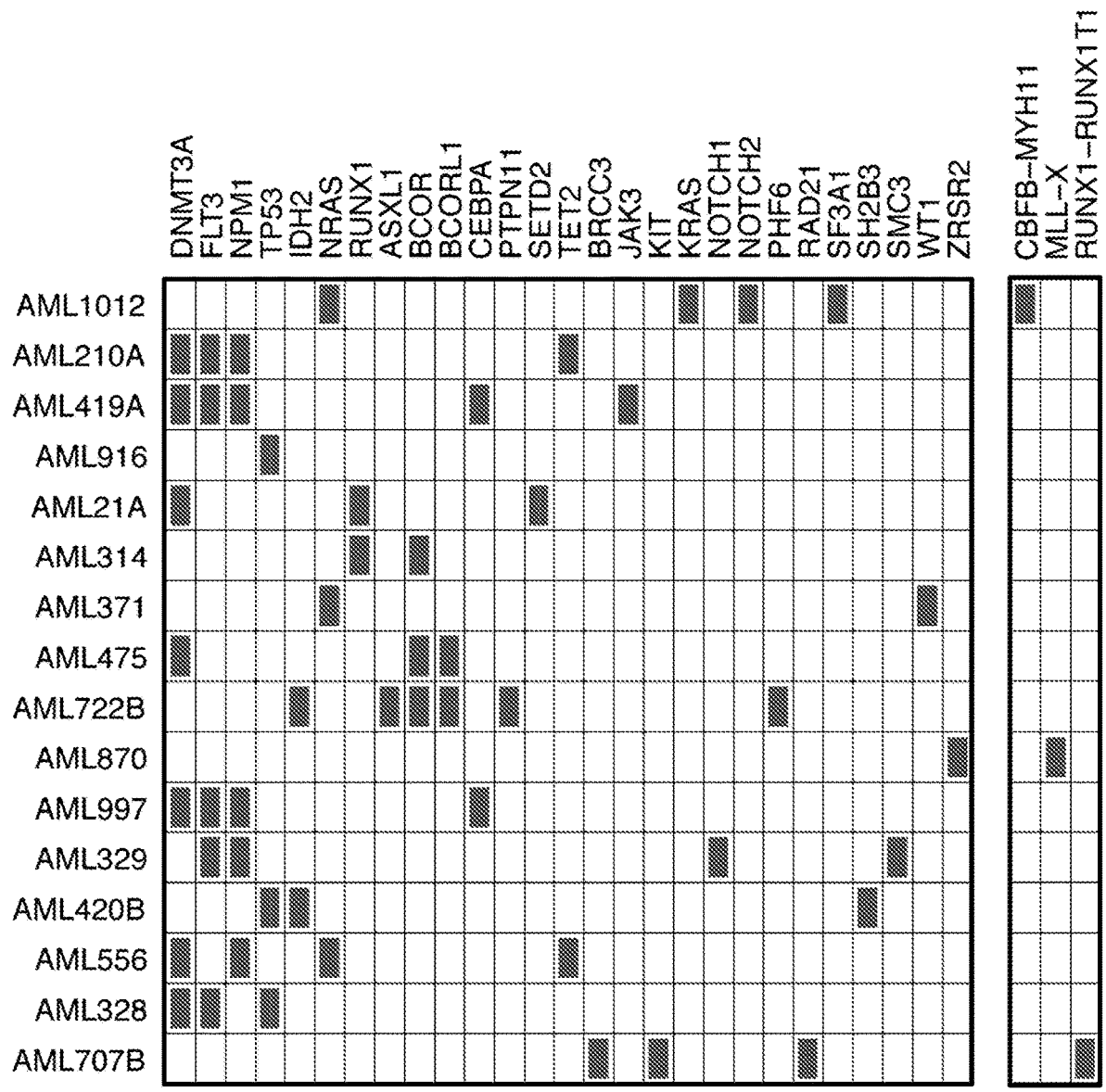

We next sought to explore the cellular diversity in AML patients at diagnosis and post treatment. We obtained 35 cryopreserved BM aspirates from 16 AML patients at diagnosis and at subsequent time points during treatment (FIG. 18A). This AML cohort spans different WHO subtypes and cytogenetic abnormalities (Table 3). Driver mutations for all tumors were assessed using a targeted DNA sequencing assay that covers 95 genes that are commonly mutated in hematological malignancies with a sensitivity of ~5% variant allele frequency (VAF) (Kluk et al., 2016). The most common driver mutations in our cohort were DNMT3A (44% of patients), FLT3 (38%), and NPM1 (31%), consistent with larger AML cohorts (FIG. 18B) (Cancer Genome Atlas Research et al., 2013). We performed scRNA-seq for these 35 samples without tumor cell enrichment to achieve a broad overview of the cell types in the AML tumor ecosystem.

Figure 18C:
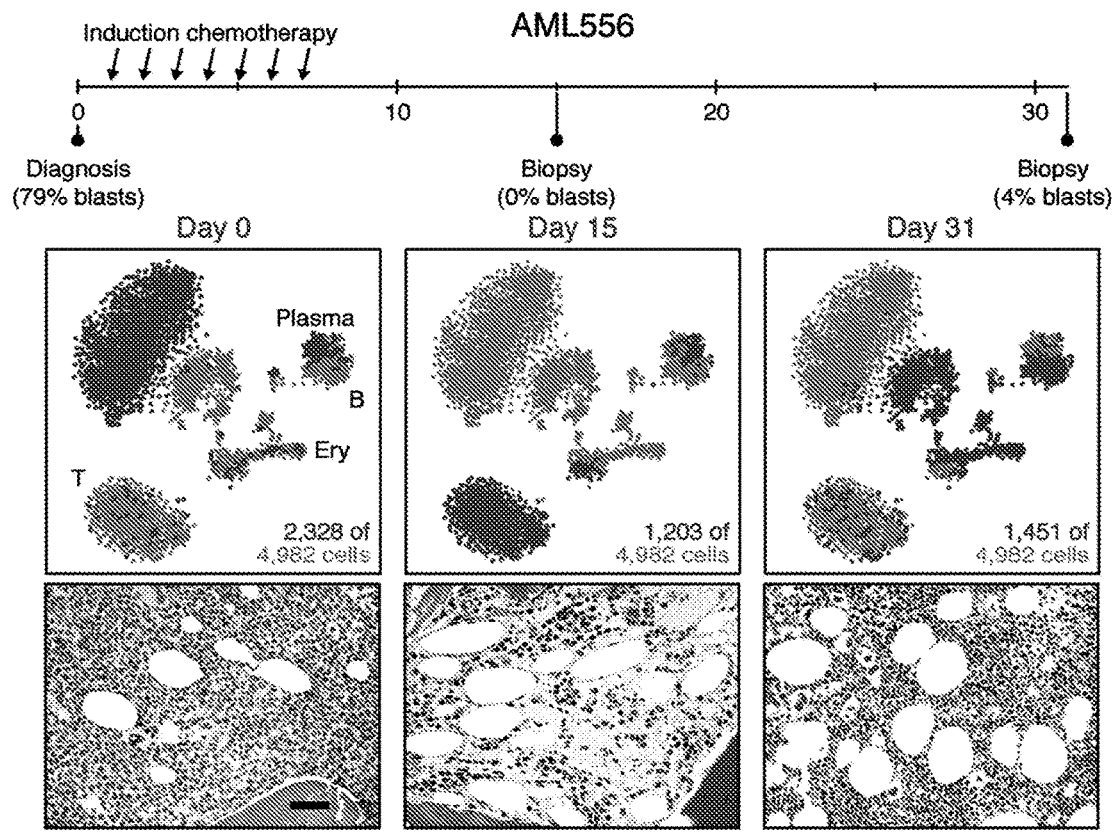
Figure 18D:
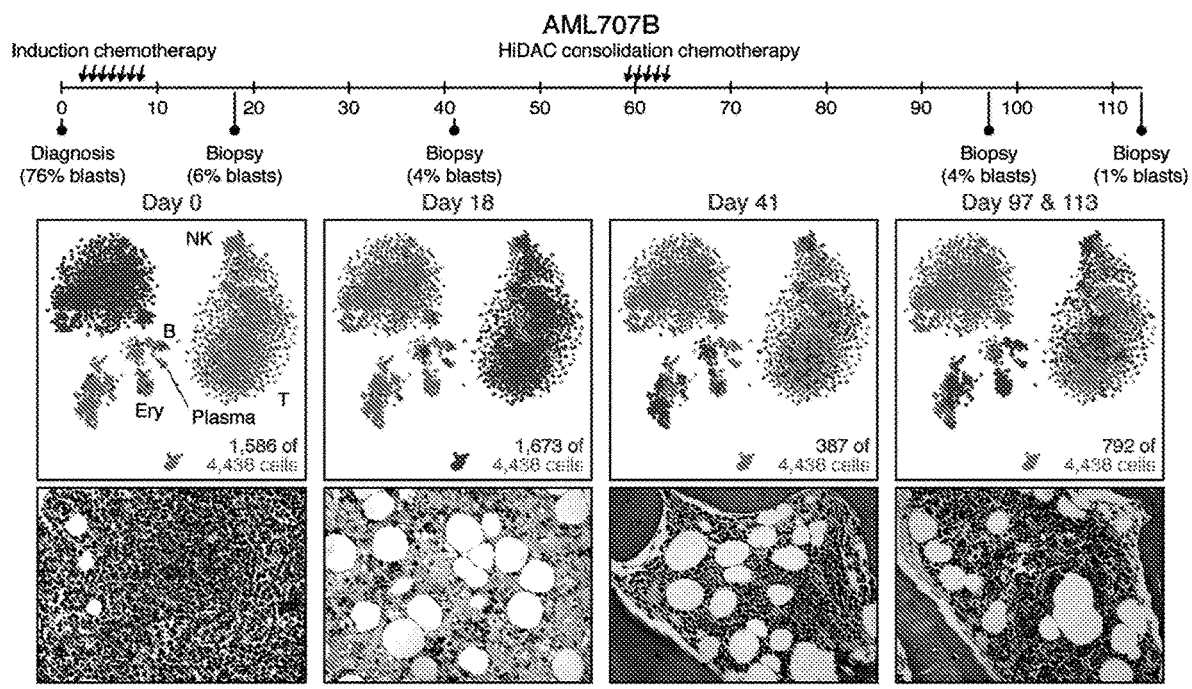
Figure 18E:
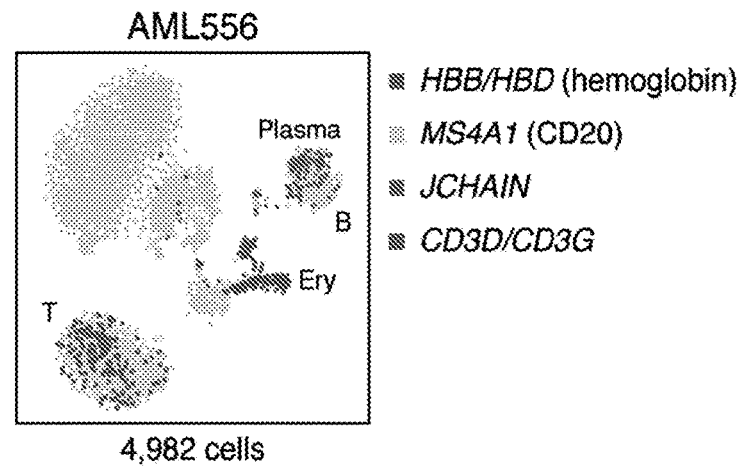
Figure 18F:
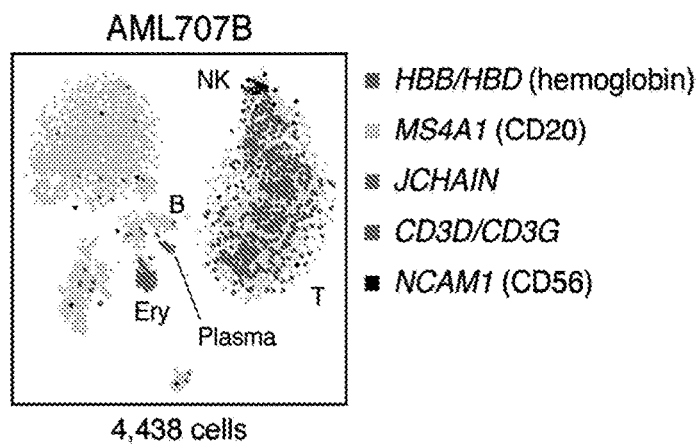
Figure 18G:
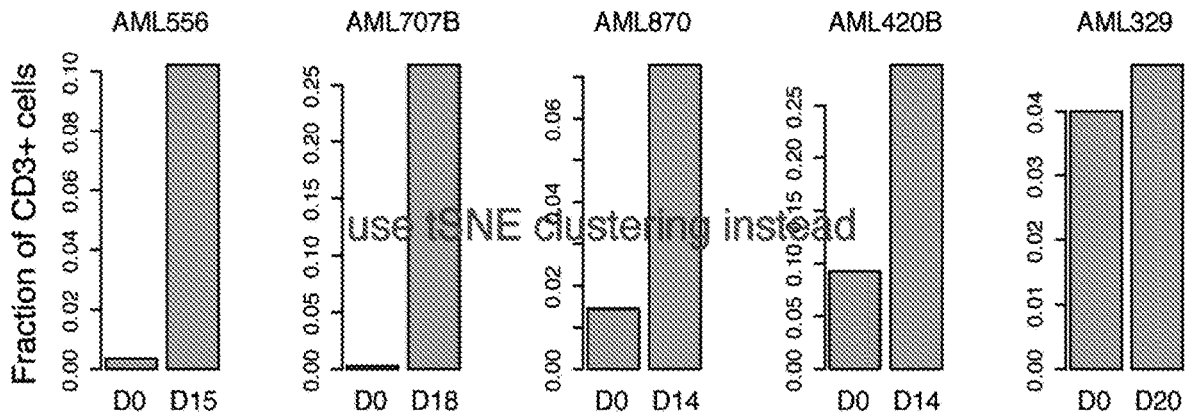

We acquired high quality transcriptomes for 30,712 cells from these AML aspirates. We used t-Distributed Stochastic Neighbor Embedding (t-SNE) to cluster cells for each patient across different time points. Visualization of these data revealed distinct cell types whose proportions changed markedly over the disease course (FIG. 18C-D). In addition to malignant cells, these data revealed presumed normal hematopoietic cell types in the tumor ecosystem that express marker genes, such as hemoglobin (erythroid cells) and CD3 (T-cells) (FIG. 18E-18F). There was a marked increase in the proportion of T-cells within 20 days after induction chemotherapy, consistent with the expected composition of the resulting hypo-cellular BM and with histological stains showing frequent small lymphocytes (FIG. 18G). Although other cell populations also expressed markers associated with specific hematopoietic cell types, their identity as normal or malignant could not be distinguished a priori from their expression programs. We therefore explored additional methods for distinguishing malignant AML cells.

Mutation-Specific Single-Cell Genotyping

Figure 19A:
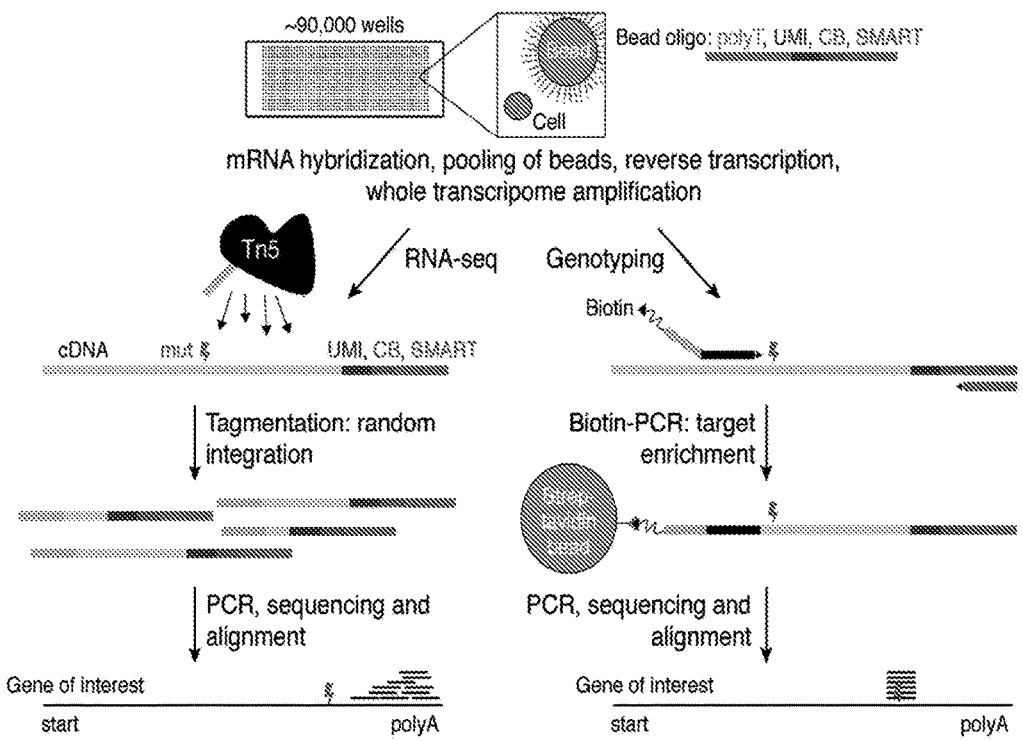

Prior scRNA-seq studies of tumors have distinguished malignant cells by gene mutations detected in full-length transcriptomic data and characteristic chromosomal abnormalities (Giustacchini et al., 2017; Puram et al., 2017). However, Seq-Well yields 3'-biased RNA data and, moreover, AMLs are frequently karyotypically normal. We therefore adapted the Seq-Well protocol to amplify and sequence portions of transcripts that contain mutations in AML (FIGS. 19A and 25A). Briefly, we took advantage of an intermediate whole transcriptome amplification (WTA) step in the protocol that yields full-length cDNAs with cell barcodes (CBs) appended to their 3' ends. We designed 43 primers adjacent to common AML driver mutations, and then amplified WTA product using sets of primers customized for each tumor. Finally, we enriched these target sequences by biotin-streptavidin pulldown. This procedure yielded amplicons containing the mutational sites appended to the CBs, enabling us to overlay mutational status onto our scRNA-seq data.

Figure 19B:
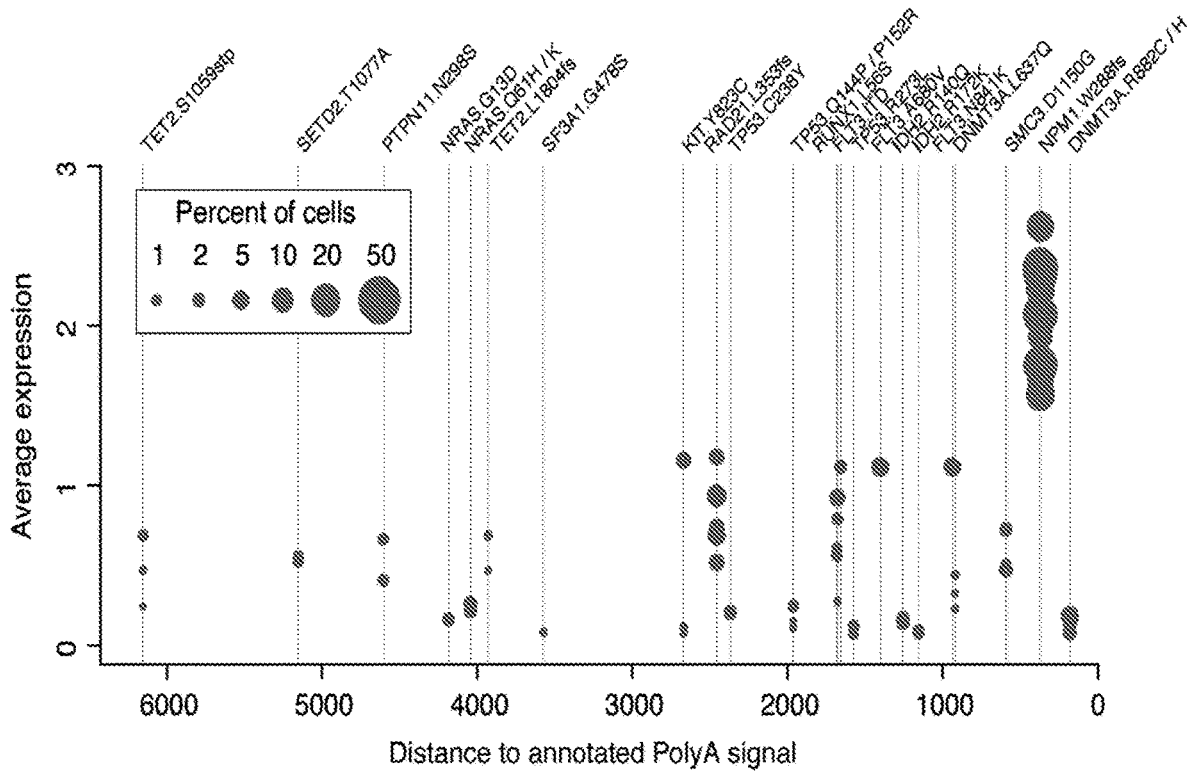
Figure 19C:
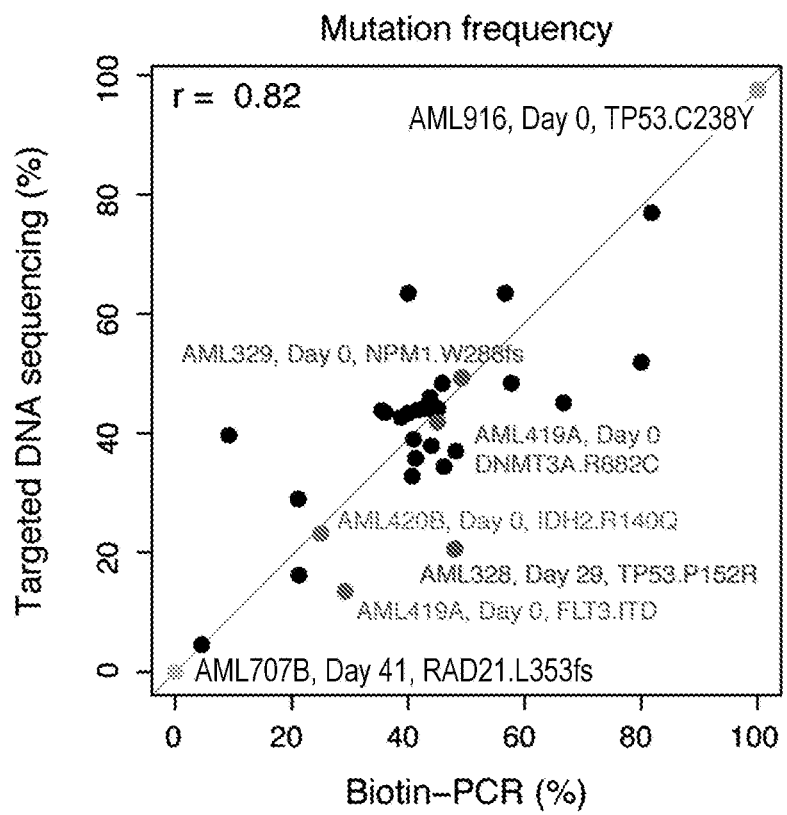
Figure 19D:
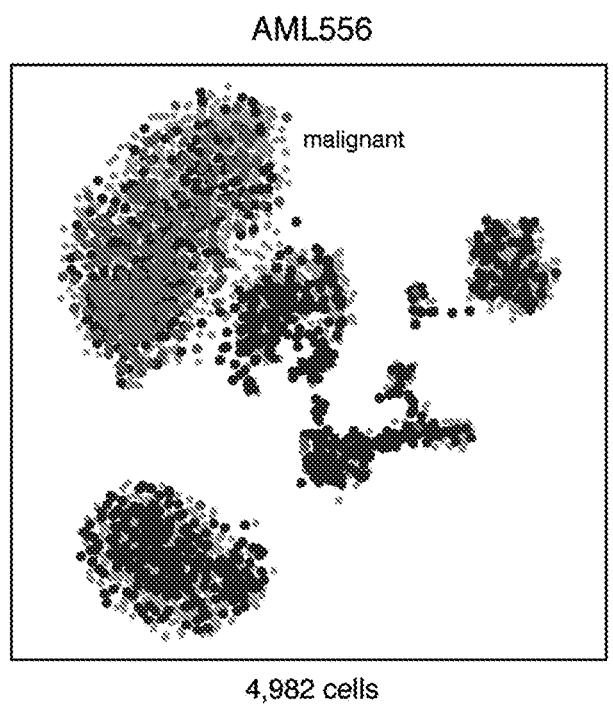
Figure 19E:
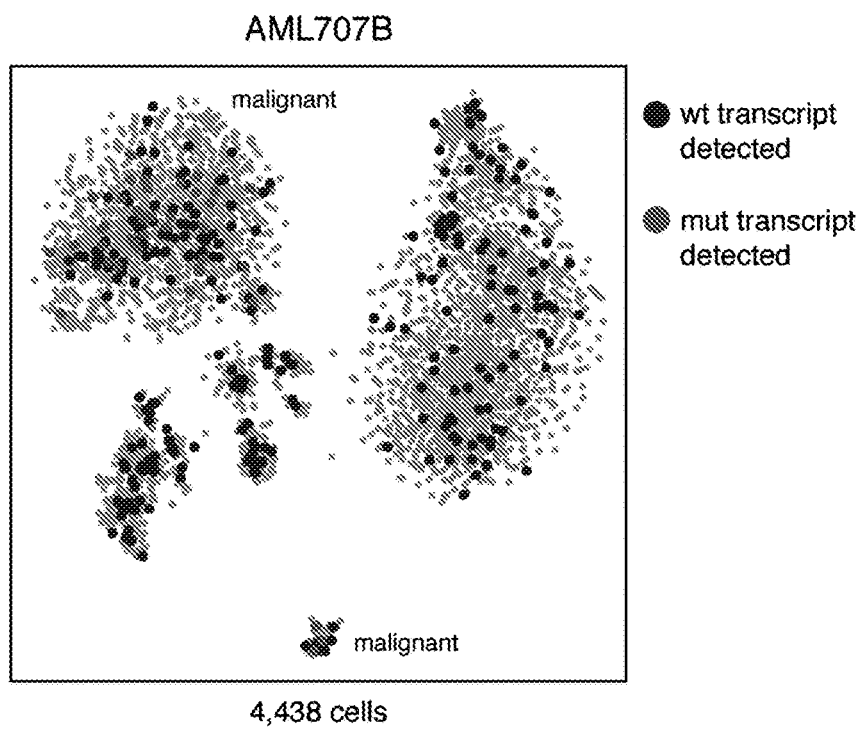
Figure 19F:
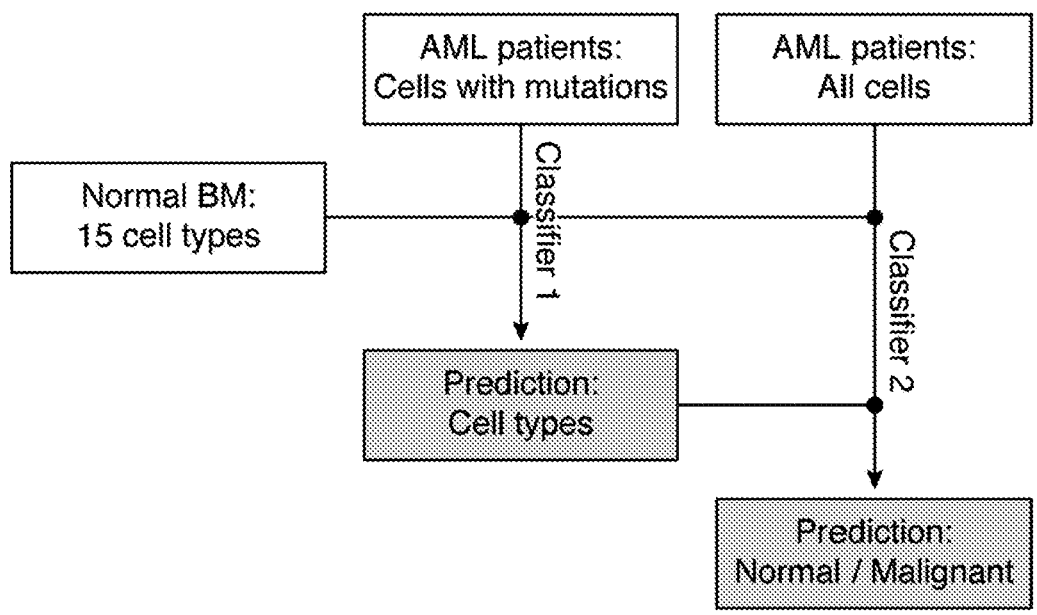
Figure 25B:
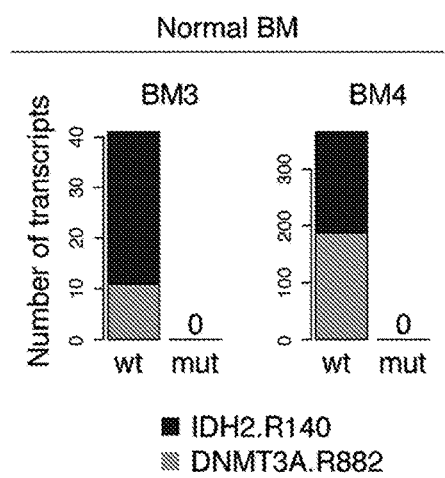
Figure 25C:
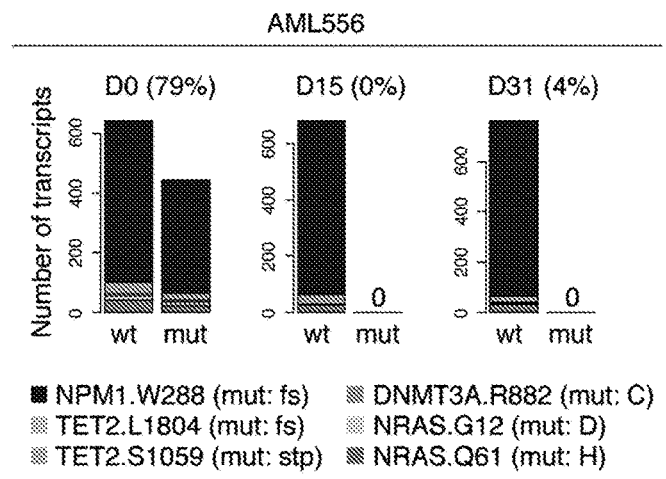
Figure 25D:
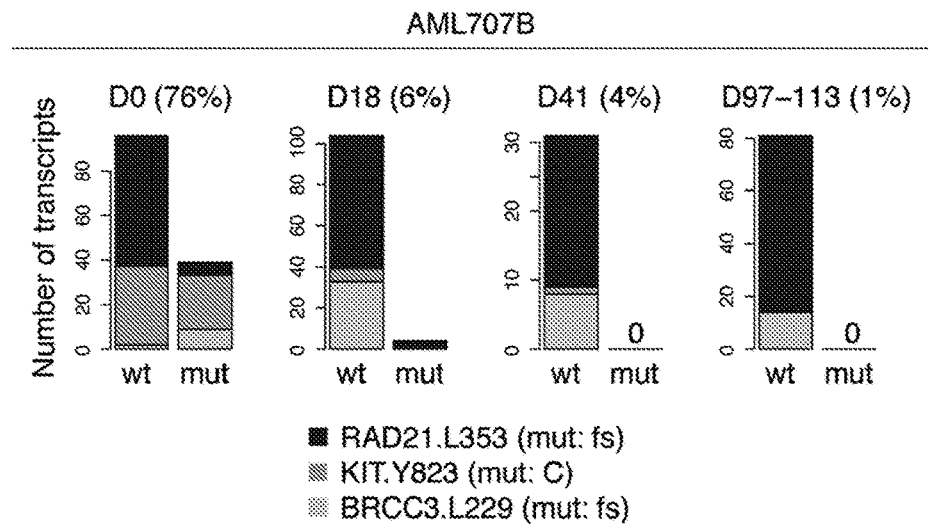

We applied mutation-specific single-cell genotyping to each of the 35 AML samples. Of the 43 mutational sites we targeted, we successfully detected wild-type and/or mutant transcripts at 27 sites (Table 4, Methods). We detected wild-type and mutant transcripts in 14 out of 16 patients, with an average of 349 transcripts mapping to 232 cells per patient. Efficiency of detection was correlated with expression level of the gene and proximity of the mutation to the 3' transcript ends (FIG. 19B). For example, NPM1 is highly expressed and W288fs is 342 bp from the nearest polyA signal, so a wild-type or mutant transcript was identified in 22% of the cells. DNMT3A.R882 mutations are only 161 bp from the nearest polyA signal, but expression is low, so a wild-type or mutant transcript was identified in 2.6% of the cells. We also captured some mutational sites located several thousand bases from 3' transcript ends, which likely reflects the ability of Illumina instruments to sequence paired-ends of relatively larger amplicons, as well as occasional internal priming in the initial reverse-transcription step. Mutations were not detected in healthy donor BM, and were markedly decreased in AML patients in clinical remission, supporting the specificity of mutation calling (FIG. 25B). Remarkably, when we compared our detected mutational frequencies to conventional targeted DNA sequencing data, we found a high correspondence between these orthogonal methods ($r=0.82$, FIG. 19C). Thus, our single-cell genotyping protocol faithfully captures mutations in AML driver genes at the single-cell level in a format that can be superimposed upon scRNA-seq data (FIG. 19D-19E).

Machine Learning Classifier Distinguishes Malignant from Normal Cells

Figure 26D:
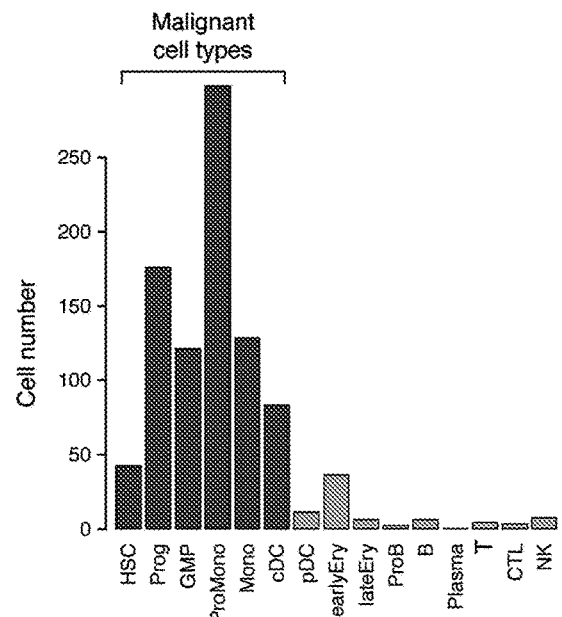

We next integrated single-cell transcriptomes and single-cell mutation calls for all patients, with the goal to distinguish malignant from non-malignant cells. Since informative genetic calls were acquired for only a subset of cells, we combined transcriptional and mutational information for this purpose. First, we selected all AML cells for which single-cell genotyping detected mutations in AML driver genes. We then used machine learning (Random Forest algorithm) to classify these putatively malignant cells according to their similarity to all 15 normal BM cell types (FIGS. 19F and 26A-26C). This classifier revealed that the vast majority of cells with genetic mutations resemble one of six normal cell types along the HSC to myeloid differentiation axis (HSC, progenitor, GMP, promonocyte, monocyte and cDC; FIGS. 19G and 26D). We therefore annotated all cells with AML driver mutations that were classified along the HSC-myeloid axis as high-confidence malignant cells (HSC-like, progenitor-like, GMP-like, promonocyte-like, monocyte-like or cDC-like). These malignant cell types were then incorporated as additional classes in a second classifier that was used to classify all AML cells in our dataset as malignant or normal (FIGS. 19F and 26A-C, Methods).

Figure 26E:
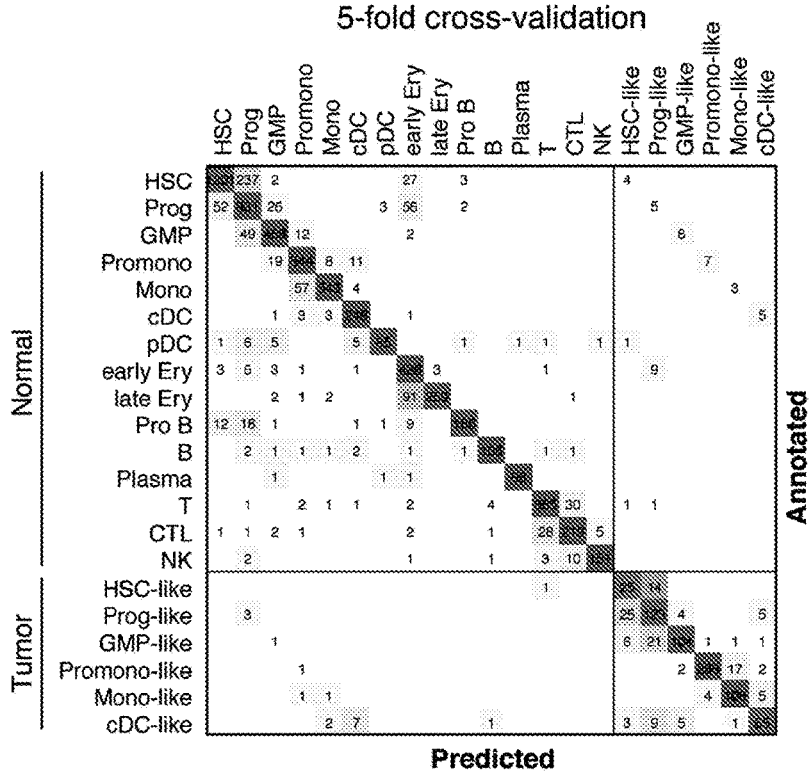
Figure 26F:
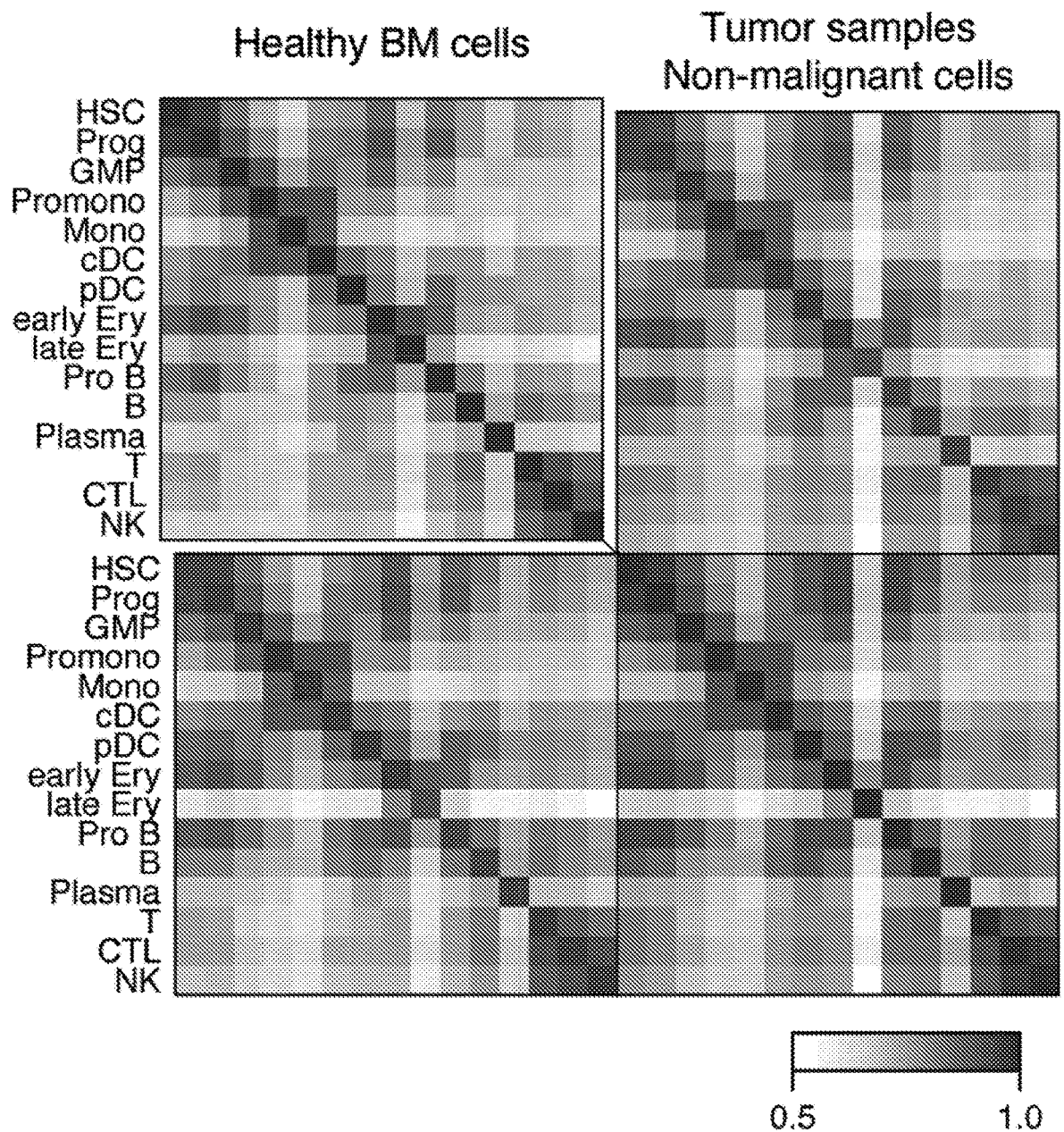
Figures 26G, 26H, 26I, 26J:
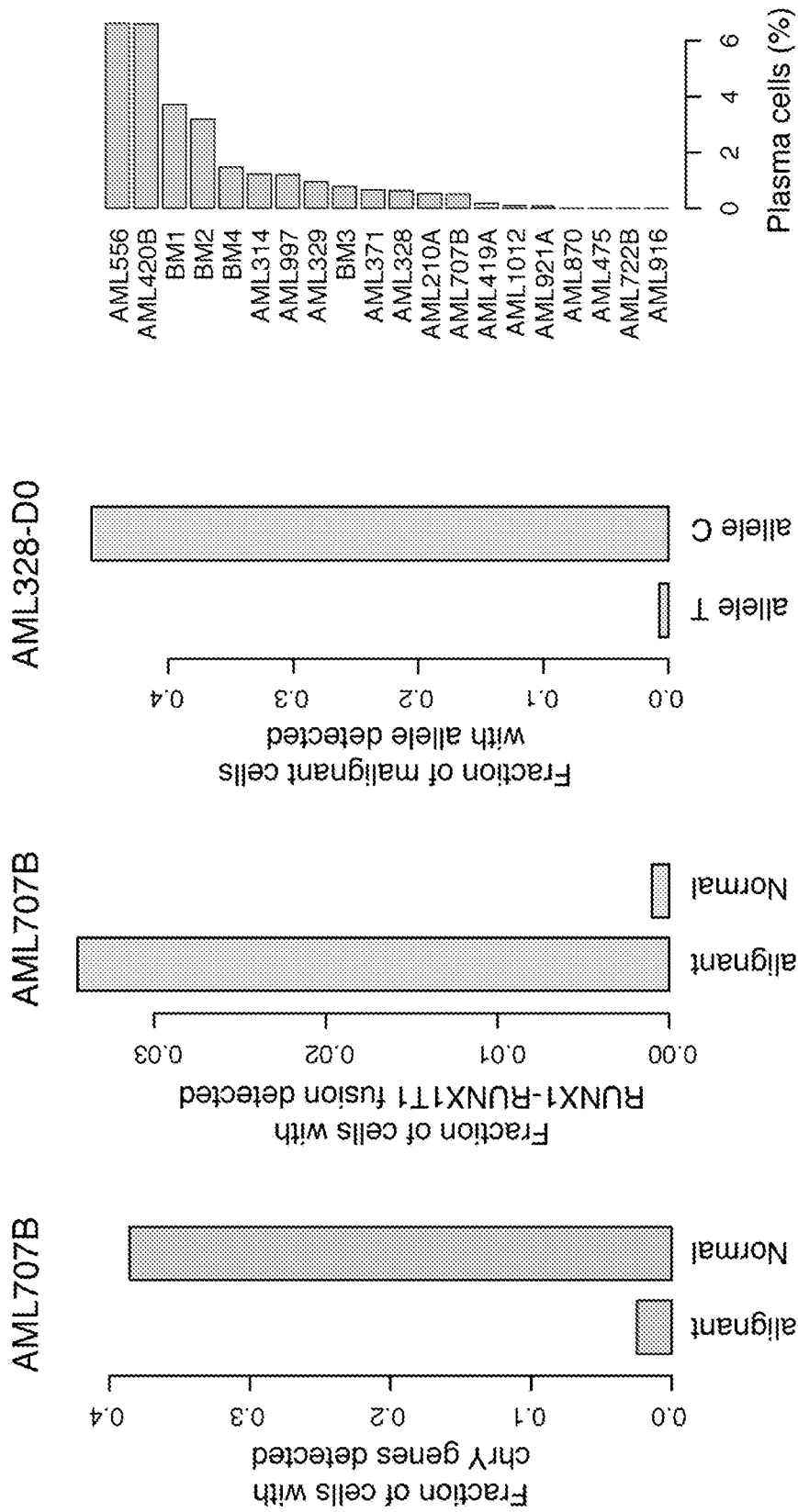

We validated our normal/malignant classifications and cell type annotations by several methods. First, we confirmed by 5-fold cross-validation that this second classifier distinguishes malignant cells with >95% sensitivity and >99% specificity (FIG. 26E). Second, we showed that non-malignant cells from the AML aspirates closely resemble counterparts from normal BM aspirates (FIG. 26D). Third, we leveraged independent genetic features present in two tumors to validate our malignant cell assignments. AML707B harbored a chromosome Y deletion and a RUNX1-RUNXT1 fusion identified by cytogenetics (Table 3). Consistently, Y-chromosome transcripts were only detected in normal cells from this patient (FIG. 26G). We were also able to detect the translocation based on common UMIs in both fusion partners in lxx malignant cells, but not in normal cells from this tumor (FIG. 26H). Additionally, AML328 harbored a chromosome 7 deletion, which we detected as loss-of-heterozygosity of a highly expressed SNP in the 3' UTR of ACTB in malignant cells (FIG. 26I).

Figure 27A:
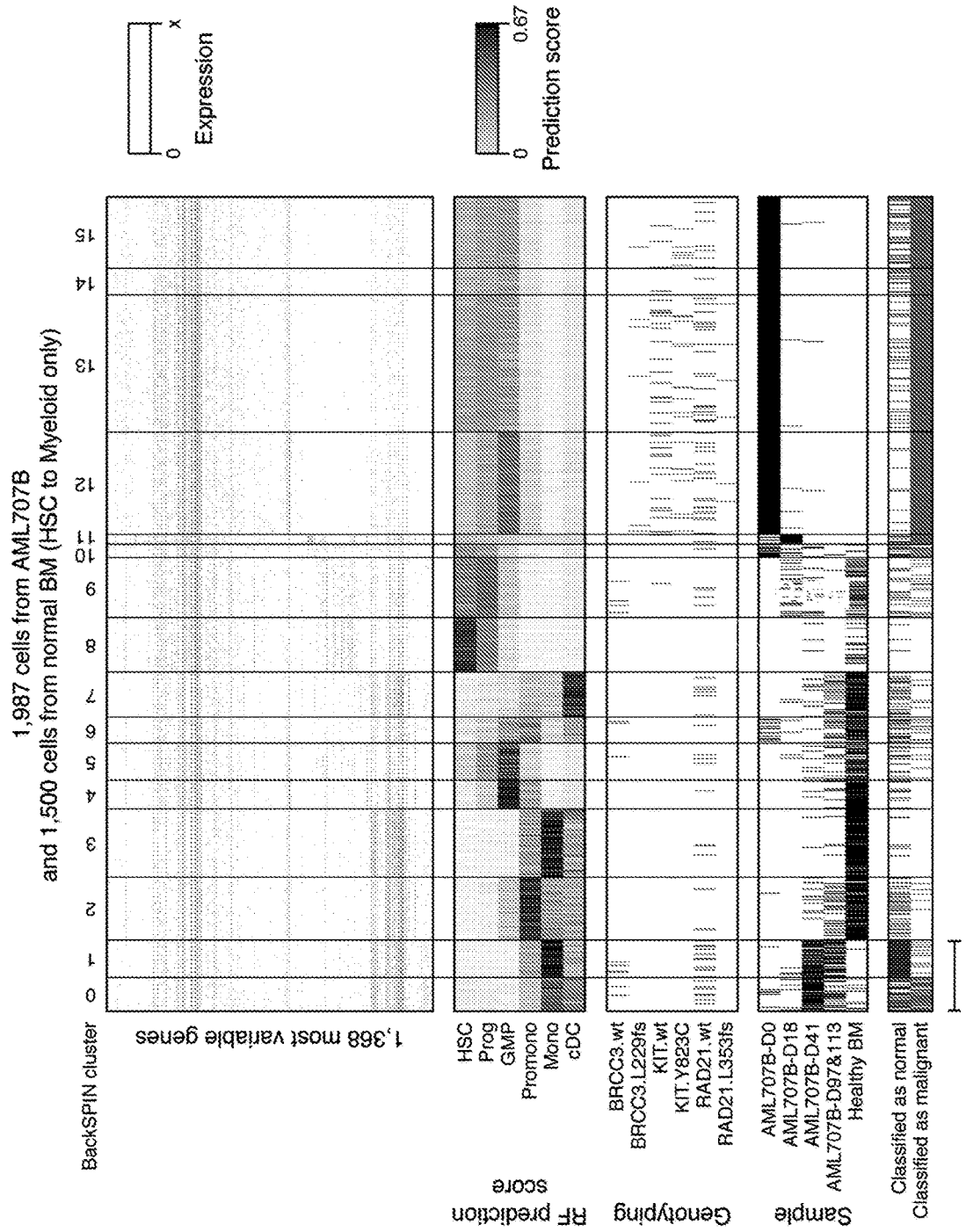
FIG. 27A-27C Evaluation of classification of malignant and normal cells FIG. 27A. Overview of AML707B single-cell data and annotations validates classification and refinement. Top heatmap shows the expression of the 1,368 most variable genes (rows) in 1,987 cells from AML707B and 1,500 cells from normal BM (columns, only cells classified as one of the six HSC-to-myeloid cell types are included). Combined BackSPIN clustering defined 16 clusters that are indicated on top. The second panel shows prediction scores of the first Random forest classifier for all cells (columns, same order as top). The third panel indicates cells in which wild-type and/or mutant transcripts were detected using single-cell genotyping. The fourth panel indicates the sample of origin for each cell. The bottom panel indicates if a cell was classified as normal or malignant by the second Random forest classifier. This analysis was performed to validate and refine the classification of malignant and normal cells. In AML707B, this confirms that the cells classified as malignant (predominantly in cluster 12 to 15) are transcriptionally distinct from normal cells (predominantly in cluster 2 to 9). Cluster 12 to 15 are also the clusters for which genetic mutations were detected using single-cell genotyping. Cluster 1 and 2, which are comprised mostly of cells from the Day 41, 97, and 113 timepoints, contained a number of cells that were classified as malignant monocytes and conventional dendritic cells. Based on the absence of genetic mutations and the presence of wild-type transcripts from the BRCC3 gene (located on chromosome X, AML707B is a male patient), these cells were refined as normal and treated accordingly in downstream analyses. A similar evaluation of the classification results was performed for each patient. Overall, 1.9% or malignant cells were refined as normal cells, and 1.9% of normal cells were refined as malignant cells. In four patients (AML314, AML371, AML722B and AML997), for which we detected few mutant transcripts and few high quality cells, we could not confidently assign malignant cells. We filtered these samples from downstream analyses of malignant cells.
Figure 27B:
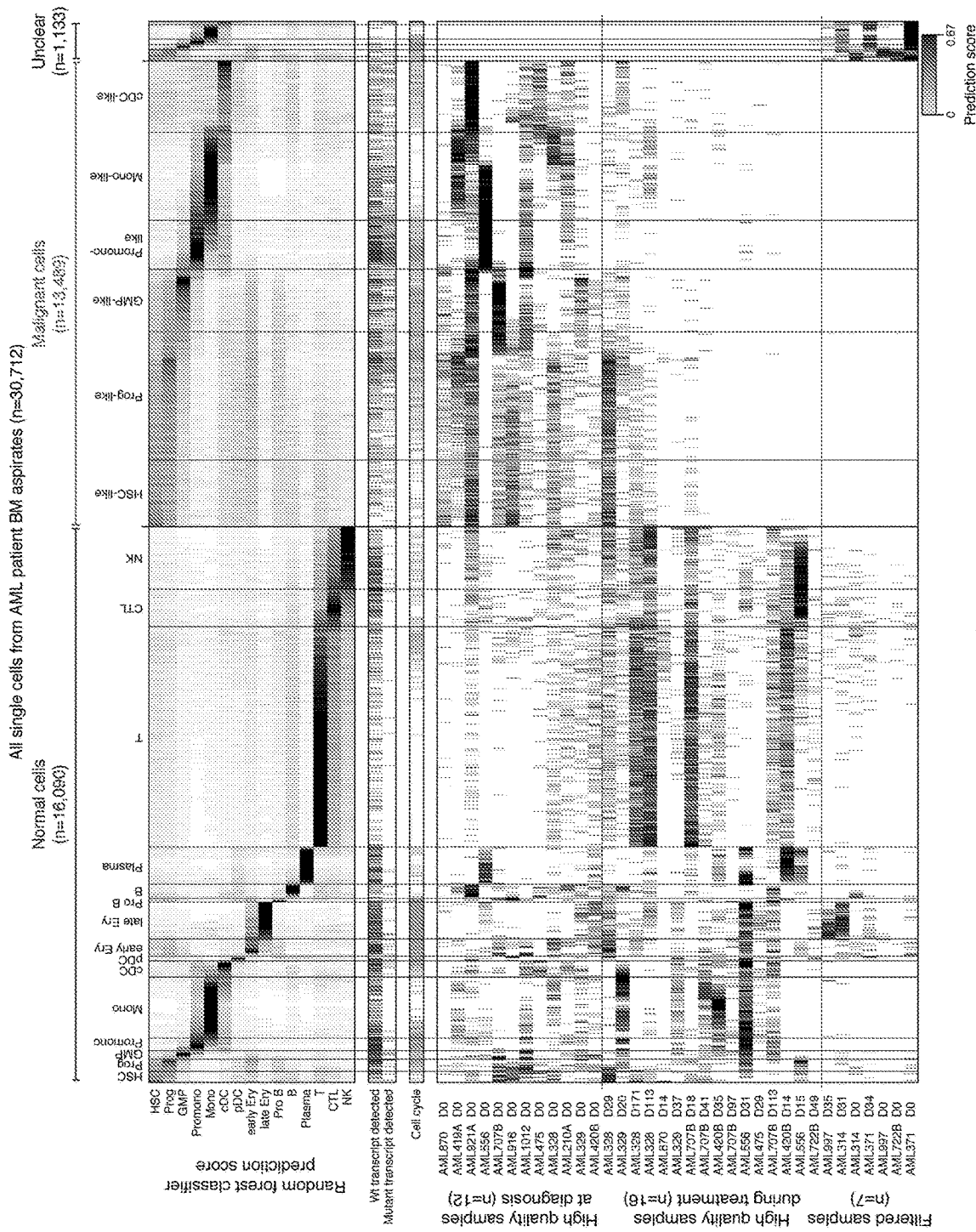
Figure 27C:
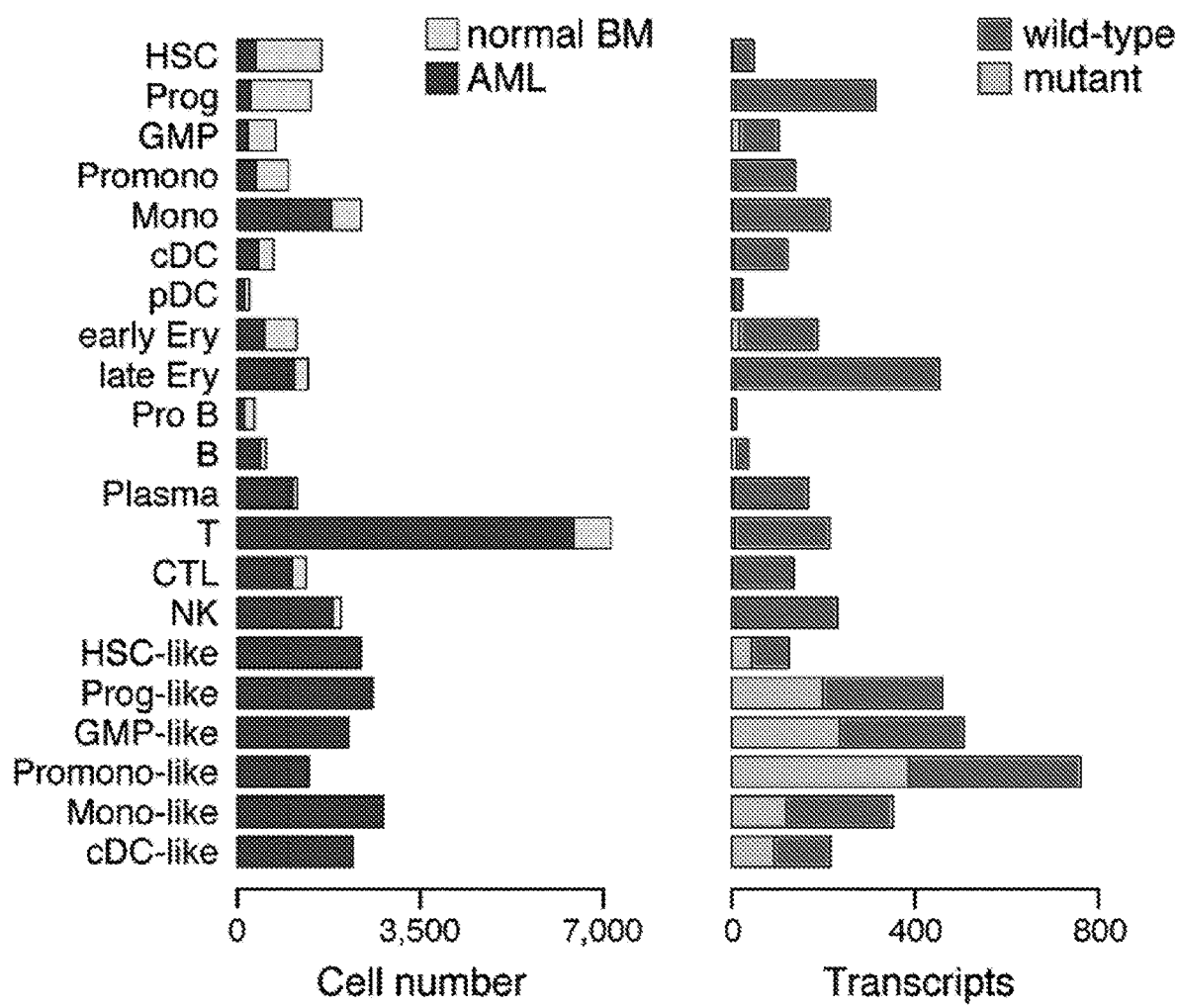

Overall, we detected 16,090 normal and 13,489 malignant cells in the AML BM aspirates (FIG. 27B-27C). The fraction of single cells classified as malignant for a given specimen strongly correlated with the clinical blast counts (r=0.90, FIG. 19H). Further correlates with clinical data included the identification of large numbers of plasma cells in scRNA-seq data for AML556 and AML420B, both of which had co-diagnoses of plasma cell neoplasms (FIG. 26H, Table 3). These plasma cells were classified as lymphoid cells and were therefore excluded from further analysis. In summary, integration of single-cell transcriptomics with driver mutations allowed us to distinguish normal from malignant cell types in the AML tumors.

TABLE 3

| # | Sample | Days from diagnosis | Tissue | Gender | Age | Blast count | RHP Mutations | Cytogenetics | Common translocation | Remarks | Cell # |
|---|---|---|---|---|---|---|---|---|---|---|---|
| 1 | BM1 | NA | Bone marrow | M | 52 | NA | NA | Unknown | NA | | 108 |
| 2 | BM2 | NA | Bone marrow | M | 21 | NA | NA | Unknown | NA | | 188 |
| 3 | BM3 | NA | Bone marrow | M | 56 | NA | NA | Unknown | NA | | 643 |
| 4 | BM4 | NA | Bone marrow | M | 23 | NA | NA | Unknown | NA | | 3738 |
| 5 | BM5-CD34+ | NA | Bone marrow | M | 45 | NA | NA | Unknown | NA | Not cryopreserved. | 1431 |
| 6 | BM5-CD34+ CD38- | NA | Bone marrow | M | 45 | NA | NA | Unknown | NA | Not cryopreserved. These cells were downsampled for clustering in FIG. 1. | 1590 |
| 7 | AML1012 | D0 | Bone marrow | F | 32 | 65% | KRAS NM_004985 c.38G > A p.G13D (4.6%) /// NRAS NM_002524 c.38G > A p.G13D (39.0%) /// NOTCH2 NM_024408 c.4238T > A p.L1413H (50.8%, VUS) /// SF3A1 NM_005877 c.1432G > A p.G478S (44.2%, VUS) | 46,XX,inv(16) (p13q22)[4]/48,idem, +8,+21[16] | CBFB-MYH11 | Newly diagnosed AML, pre-treatment. | 1136 |
| 8 | AML210A | D0 | Bone marrow | M | 67 | 83% | DNMT3A NM_175629 c.2644C > T p.R882C (43.4%) /// NPM1 NM_002520 c.859_860insTCTG p.W288fs* > 9 (42.7%) /// TET2 NM_001127208 c.1072A > G p.S358G (49.3%, VUS) /// FLT3-ITD NM_004119 c.1802_1802insTTGAAT | 46,XY[20] | NA | Newly diagnosed AML with myelomonocytic differentiation, pre-treatment. | 748 |

TABLE 3-continued

| # | Sample | Days from diagnosis | Tissue | Gender | Age | Blast count | RHP Mutations | Cytogenetics | Common trans- location | Remarks | Cell # |
|---|---|---|---|---|---|---|---|---|---|---|---|
| 9 | AML419A | D0 | Bone marrow | F | 54 | 60% | ATGATCTCAAATGGGAGTTT CCAAGAGAAATTTAGAGTT TG CEBPA NM_004364 c.118_118insC p.P39fs* (42.9%) /// DNMT3A NM_175629 c.2644C > T p.R882C (41.9%) /// NPM1 NM_002520 c.859_860insTCTG p.W288fs* > 9 (37.9%) /// FLT3 NM_004119 c.2039C > T p.A680V (29.0%) /// FLT3 NM_004119 c.2523C > A p.N841K (16.2%) /// FLT3-ITD NM_004119 c.1819_1819insTATGAT CTCAAATGGGAGTTTCCA (13.5%) /// JAK3 NM_000215 c.2773C > A p.R925S (55.1%, VUS) | 46,XX[20] | NA | Newly diagnosed AML with monocytic differentiation, pre-treatment. | 1189 |
| 10 | AML916 | D0 | Bone marrow | F | 57 | 75% | TP53 NM_000546 c.713G > A p.C238Y (97.6%) | 46,XX[20] | NA | Mixed phenotype acute leukemia expressing markers of stem cells (CD34, CD117), myeloid (CD64), T (CD3) and B (CD19) lineages by flow, pre-treatment. | 933 |
| 11 | AML921A | 1-D0 | Bone marrow | M | 42 | 70% | DNMT3A NM_175629 c.2645G > A p.R882H (44.2%) /// RUNX1 NM_001754 c.167T > C p.L56S (63.5%, VUS) /// | 46,XY | NA | Newly diagnosed AML, pre-treatment. | 3813 |

TABLE 3-continued

| # | Sample | Days from diagnosis | Tissue | Gender | Age | Blast count | RHP Mutations | Cytogenetics | Common trans-location | Remarks | Cell # |
|---|---|---|---|---|---|---|---|---|---|---|---|
| 12 | AML314 | D0 | Bone marrow | M | 54 | 28% | SETD2 NM_014159 c.3229A > G p.T1077A (48.4%, VUS) BCOR NM_001123385 c.2098delG p.K699fs* (36.4%) /// RUNX1 NM_001754 c.966_967delTC p.S322fs*160 (17.2%) | 46,XY | NA | Newly diagnosed AML,NOS, pre-treatment. | 162 |
| 13 | AML314 | D31 | Bone marrow | M | 54 | 1% | Not performed | 46,XY[20] | NA | Morphologic remission, post-induction chemotherapy | 346 |
| 14 | AML371 | D0 | Bone marrow | M | 51 | 16% | NRAS NM_002524 c.181C > A p.Q61K (37.9%) /// WT1 NM_024426 c.1130_1130insGTAGCC CCGA p.T309fs*11 (13.3%) | 46,XY,der(16)t (16;18)(p12?;p11.3) del(16)(q22q24),der (18)t(16;18) (p12;p11.3) [20].ishder(16) (18pter+,5'CBFB+), der(18)(pter-) | NA | Newly diagnosed AML with monocytic differentiation, pre-treatment. | 756 |
| 15 | AML371 | D34 | Bone marrow | M | 51 | 1% | None Detected | 46,XY | NA | Morphologic remission, post-induction chemotherapy | 204 |
| 16 | AML475 | D0 | Bone marrow | M | 70 | 1% (76% pro-mono-cytes) | DNMT3A NM_175629 c.2645G > A p.R882H (43.9%) /// BCOR NM_001123385 c.2926C > T p.R976* (83.0%) /// BCORL1 NM_021946 c.1942_1943insC p.T648fs* (13.3%) /// BCORL1 NM_021946 c.2996delC p.T999fs* (8.2%) /// BCORL1 NM_021946 c.3142C > T p.R1048* (50.0%) /// BCORL1 NM_021946 c.3586C > T p.R1196* (4.1%) | 46,XY | NA | Newly diagnosed AML with monocytic differentiation, pre-treatment. | 423 |

TABLE 3-continued

| # | Sample | Days from diagnosis | Tissue | Gender | Age | Blast count | RHP Mutations | Cytogenetics | Common translocation | Remarks | Cell # |
|---|---|---|---|---|---|---|---|---|---|---|---|
| 17 | AML475 | D29 | Bone marrow | M | 70 | 1% | Not performed | 46,XY[20] | NA | Morphologic remission, post-induction chemotherapy | 102 |
| 18 | AML722B | D0 | Bone marrow | F | 52 | 84% | BCORL1 NM_021946 c.1627delG p.D542fs* (7.2%) /// IDH2 NM_002168 c.515G > A p.R172K (42.3%) /// ASXL1 NM_015338 c.1231C > T p.R411C (45.3%, VUS) /// PHF6 NM_001015877 c.976T > C p.Y325H (38.2%, VUS) /// PTPN11 NM_002834 c.893A > G p.N298S (51.2%, VUS) | 46,XX,i(7)(p10) or add(7)(q11.2) [17]/47,XX,+8[3] | NA | Newly diagnosed AML, pre-treatment. | 79 |
| 19 | AML722B | D49 | Bone marrow | F | 52 | 3% | IDH2 NM_002168 c.515G > A p.R172K (0.5%) /// ASXL1 NM_015338 c.1231C > T p.R411C (46.7%, VUS) /// PTPN11 NM_002834 c.893A > G p.N298S (47.4%, VUS) | Unknown | NA | Post 7 + 3 induction and 2 + 5 re-induction chemotherapy. | 73 |
| 20 | AML870 | D0 | Bone marrow | M | 32 | 89% | ZRSR2 NM_005089 c.1147C > G p.P383A (99.6%, VUS) | 46,XY, t(9;11) (p21;q23) [8]·nucish(MLLx2) (5' MLLsep3' MLLx1) [91/100] | MLL-X | Newly diagnosed AML with recurrent genetic abnormalities, pre-treatment. | 345 |
| 21 | AML870 | D14 | Bone marrow | M | 32 | 1% | Not performed | Not performed | NA | Ablated, post-induction chemotherapy | 96 |
| 22 | AML997 | D0 | Bone marrow | M | 62 | 16% | DNMT3A NM_175629 c.2645G > A p.R882H (43%) /// NPM1 NM_002520 c.859_860insTCTG p.W288fs* > 9 (46%) /// | 46,XY | NA | Newly diagnosed AML with monocytic differentiation. | 83 |

TABLE 3-continued

| # | Sample | Days from diagnosis | Tissue | Gender | Age | Blast count | RHP Mutations | Cytogenetics | Common trans-location | Remarks | Cell # |
|---|---|---|---|---|---|---|---|---|---|---|---|
| 23 | AML997 | D35 | Bone marrow | M | 62 | 1% | CEBPA NM_004364 c.138insT p.A47fs (48%) /// FLT3-ITD (exon 14 ITD) | 46,XY[20] | NA | Morphologic remission, post-induction chemotherapy | 187 |
| 24 | AML329 | D0 | Bone marrow | F | 73 | 37% | Not performed | 46,XX[20] | NA | Newly diagnosed AML with monocytic differentiation, pre-treatment. | 525 |
| 25 | AML329 | D20 | Bone marrow | F | 73 | <1% | NPM1 NM_002520 c.859_860insTCTG p.W288fs* > 9 (49.3%) /// NOTCH1 NM_017617 c.5273G > A p.R1758H (67.9%, VUS) /// SMC3 NM_005445 c.3449A > G p.D1150G (45.1%, VUS) /// FLT3-ITD NM_004119 c.1800_1800insCTACGT TGATTCAGAGAATATGA | Unknown | NA | Post 7 + 3 induction chemotherapy, ablated marrow. | 953 |
| 26 | AML329 | D37 | Bone marrow | F | 73 | 3% | Unknown | Unknown | NA | Remission. | 224 |
| 27 | AML420B | D0 | Bone marrow | M | 58 | 29% | IDH2 NM_002168 c.419G > A p.R140Q (23.2%) /// TP53 NM_000546 c.818G > T p.R273L (16.0%) /// SH2B3 NM_005475 c.1655A > G p.D552G (55.7%, VUS) | 46,XY,add(1)(p36.1) [3]/46,XY[17] | NA | Newly diagnosed AML, pre-treatment. Possible plasma cell neoplasm in the background. | 485 |
| 28 | AML420B | D14 | Bone marrow | M | 58 | <5% | Unknown | Unknown | NA | Post 7 + 3 induction chemotherapy. | 1282 |

TABLE 3-continued

| # | Sample | Days from diagnosis | Tissue | Gender | Age | Blast count | RHP Mutations | Cytogenetics | Common trans-location | Remarks | Cell # |
|---|---|---|---|---|---|---|---|---|---|---|---|
| 29 | AML420B | D35 | Bone marrow | M | 58 | 1% | Unknown | 45,X,-Y,add(1)(p36.1)[1]/46,XY[19] | NA | | 743 |
| 30 | AML556 | D0 | Bone marrow | M | 70 | 79% | DNMT3A NM_175629 c.2644C > T p.R882C (43.5%) /// NPM1 NM_002520 c.859_860insTCTG p.W288fs* > 9 (35.8%) /// NRAS NM_002524 c.183A > T p.Q61H (43.8%) /// NRAS NM_002524 c.35G > A p.G12D (3.8%) /// TET2 NM_001127208 c.3176C > G p.S1059* (37.0%) /// TET2 NM_001127208 c.5412_5413insA p.L1804fs* (34.4%) /// ATM NM_000051 c.6067G > A p.G2023R (51.9%, VUS) | 46,XY | NA | Newly diagnosed AML with myelomonocytic differentiation, pre-treatment. Also diagnosed with smoldering myeloma at the same time. | 2328 |
| 31 | AML556 | D15 | Bone marrow | M | 70 | 0% | Not performed | Not performed | NA | Ablated, post-induction chemotherapy | 1203 |
| 32 | AML556 | D31 | Bone marrow | M | 70 | 4% | Not performed | 46,XY[20] | NA | Morphologic remission, post-induction chemotherapy | 1451 |
| 33 | AML328 | D0 | Bone marrow | F | 74 | 55% | DNMT3A NM_175629 c.1910T>A p.L637Q (43.9%) /// TP53 NM_000546 c.431A>C p.Q144P (38.7%, VUS) /// TP53 NM_000546 c.455C>G p.P152R (51.5%) /// FLT3-ITD NM_004119 c.1749_1752delCTCC insAGGTCAG p.584_585delSinGQ | 45,XXider(3)(q10)inv(3)(q21q26.2),add(5)(q13),-7,add(9)?dup(q13q22)[19]/46,XX[1].ishider(3)(RP11-669C7/RP11-637O11 sep,RP11-82C9,RP11-362K14+)x2[5] | NA | Newly diagnosed AML, pre-treatment. | 1094 |

TABLE 3-continued

| # | Sample | Days from diagnosis | Tissue | Gender | Age | Blast count | RHP Mutations | Cytogenetics | Common translocation | Remarks | Cell # |
|---|---|---|---|---|---|---|---|---|---|---|---|
| 34 | AML328 | D29 | Bone marrow | F | 74 | 20% | DNMT3A NM_175629 c.1910T > A p.L637Q (28.1%) /// TP53 NM_000546 c.431A > C p.Q144P (44.0%, VUS) /// TP53 NM_000546 c.455C > G p.P152R (20.6%) /// FLT3-ITD NM_004119 c.1749_1752delCTCC insAGGTCAG p.584_585delS1inGQ (9.5%) | 45,XXider(3)(q10)inv(3)(q21q26.2),add(5)(q13),-7,add(9)?dup(q13q22)[7]/45,idem,add(16)(q13)[cp3] | NA | Azacitidine + venetoclax, C1D27. | 1880 |
| 35 | AML328 | D113 | Bone marrow | F | 74 | 15% | DNMT3A NM_175629 c.1910T > A p.L637Q (26.7%) /// TP53 NM_000546 c.431A > C p.Q144P (34.6%, VUS) /// TP53 NM_000546 c.455C > G p.P152R (11.3%) /// FLT3-ITD NM_004119 c.1749_1752delCTCC insAGGTCAG p.584_585delS1inGQ (3.4%) | 45,XX,ider(3)(q10)inv(3)(q21q26.2),add(5)(q13),-7,dup(9)(q13q22)[1]/46,XX[1].nucish(D5S723/D5S721x2,EGR1x1)[5/100] | NA | Azacitidine + venetoclax, C4D23. | 2029 |
| 36 | AML328 | D171 | Bone marrow | F | 74 | 30% | Unknown | 45-46,XX,ider(3)(q10)inv(3)(q21q26.2),add(5)(q13),-7,add(9)?dup(9)(q13q22),add(17)(p11.2)[4],+mar[5][cp13]/43~44,idem,add(3)(q12)[2],der(9)t(9;9)(p22;q13),der(15;16)(q10;q10),-17,del(18)(q?21)[2],+mar[2][cp7] | NA | Azacitidine + venetoclax, C6D17. | 1402 |
| 37 | AML707B | D0 | Bone marrow | M | 26 | 76% | BRCC3 NM_024332 c.686_687insTGATGTCGCG p.L229fs* (77.0%) /// | 45,X,-Y,t(8;21)(q22;q22)[10]/45,idem,t(2;5)(p21;q31)[9]/46,XY[1] | RUNX1-RUNX1T1 | Newly diagnosed AML, pre-treatment. | 1586 |

TABLE 3-continued

| # | Sample | Days from diagnosis | Tissue | Gender | Age | Blast count | RHP Mutations | Cytogenetics | Common translocation | Remarks | Cell # |
|---|---|---|---|---|---|---|---|---|---|---|---|
| 38 | AML707B | D18 | Bone marrow | M | 26 | 6% | KIT NM_000222 c.2468A > G p.Y823C (32.8%) /// RAD21 NM006265 c.1058_1058insCC p.L353fs* (39.7%) | Unknown | NA | Day 17 post 7 + 3 induction chemotherapy. | 1673 |
| 39 | AML707B | D41 | Bone marrow | M | 26 | 4% | None Detected | 46,XY[20] | NA | Day 40 post 7 + 3 induction chemotherapy. | 387 |
| 40 | AML707B | D97 | Bone marrow | M | 26 | 4% | Unknown | 46,XY[20] | NA | Day 38 post high-dose Ara-C consolidation (HIDAC), C1D38 | 84 |
| 41 | AML707B | D113 | Bone marrow | M | 26 | 1% | Unknown | Unknown | NA | Day 54 post HIDAC, C1D54 | 708 |
| 42 | OCI-AML3 | NA | Cell line | M | 57 | NA | BCORL1 NM_021946 c.3714_3715insA p.G1238fs* (18.1%) /// DNMT3A NM_175629 c.2644C > T p.R882C (54.4%) /// NPM1 NM_002520 c.859_860insTCTG p.W288fs* > 9 (49.8%) /// NRAS NM_002524 c.182A > T p.Q61L (100.0%) /// RAD21 NM_006265 c.19_19insT p.F6fs* (6.7%) /// SMC3 NM_005445 c.864_882delAGAACAGCTTAGTGCTGAAinsGAAC p.289_294delEQLSAEinsKN | Hyperdiploid karyotype-48(45-50)<2n>X/XY,+1,+5,+8,der(1)t(1;18)(p11;q11),i(5p),del(13)(q13q21),dup(17)(q21q25)-sideline with r(Y)x1-2-hemizygous for RB1 | NA | | 1178 |

TABLE 3-continued

| # | Sample | Days from diagnosis | Tissue | Gender | Age | Blast count | RHP Mutations | Cytogenetics | Common translocation | Remarks | Cell # |
|---|---|---|---|---|---|---|---|---|---|---|---|
| | | | | | | | (20.1%) /// ATM NM_000051 c.2119T > C p.S707P (48.4%, VUS) /// SETD2 NM_014159 c.5666T > C p.M1889T (44.2%, VUS) | | | | |
| 44 | MUTZ-3 | NA | Cell line | M | 29 | NA | SF3B1 NM_012433 c.1998G > T p.K666N (45.4%) /// KRAS NM_004985 c.32_32insGAG p.G10_A11insG (24.2%) /// ASXL1 NM_015338 c.3306G > T p.E1102D (53.4%, VUS) /// GATA2 NM_032638 c.919C > T p.R307W (53.4%, VUS) /// IKZF1 NM_006060 c.476A > G p.N159S (52.6%, VUS) | Near-diploid karyotype with 6% tetraploidy-46(44-48)<2n>XY,t(1;3)(q43;q13)inv(3)(q21q26),t(2;7)(q36;q36)inv(7)(p15q36),t(12;22)(p13;q12)-carries t(12;22) recurrent in AML M4-also carries masked inv(3) associated with abnormal megakaryocytopoiesis | NA | | 1502 |

Intra-Tumoral Heteroegenity of Malignant AMVL Cells

Intra-tumoral heterogeneity of AML cell types has been extensively studied using cell surface markers (Dick, 2008; Meacham and Morrison, 2013). However, this approach relies on predefined markers genes that may not accurately represent underlying transcriptional programs and, moreover, may be expressed by both malignant and normal cells (Levine et al., 2015). We therefore explored the potential of our unbiased transcriptomic classification to yield new insights into the malignant cell subsets within AML tumors. The six malignant cell populations that we identified each show similarities to normal hematopoietic counterparts along the HSC-myeloid differentiation axis: HSCs, progenitors, GMPs, promonocytes, monocytes or cDCs (FIG. 20A). Each malignant cell type was represented by at least 1,000 cells in our dataset and identified in at least ten patients (FIG. 27B-27C).

Figures 20B, 20C:
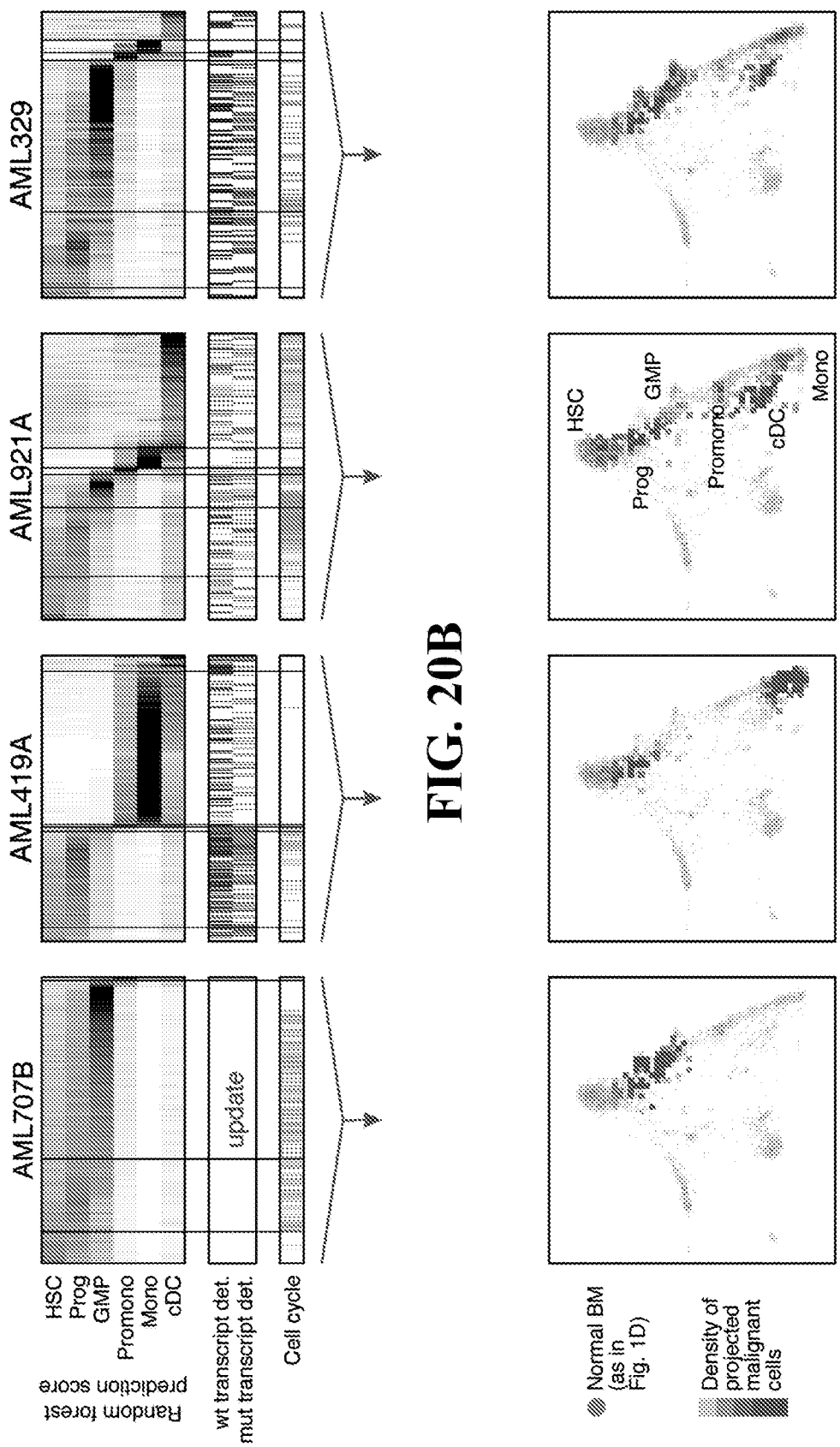
Figure 20D:
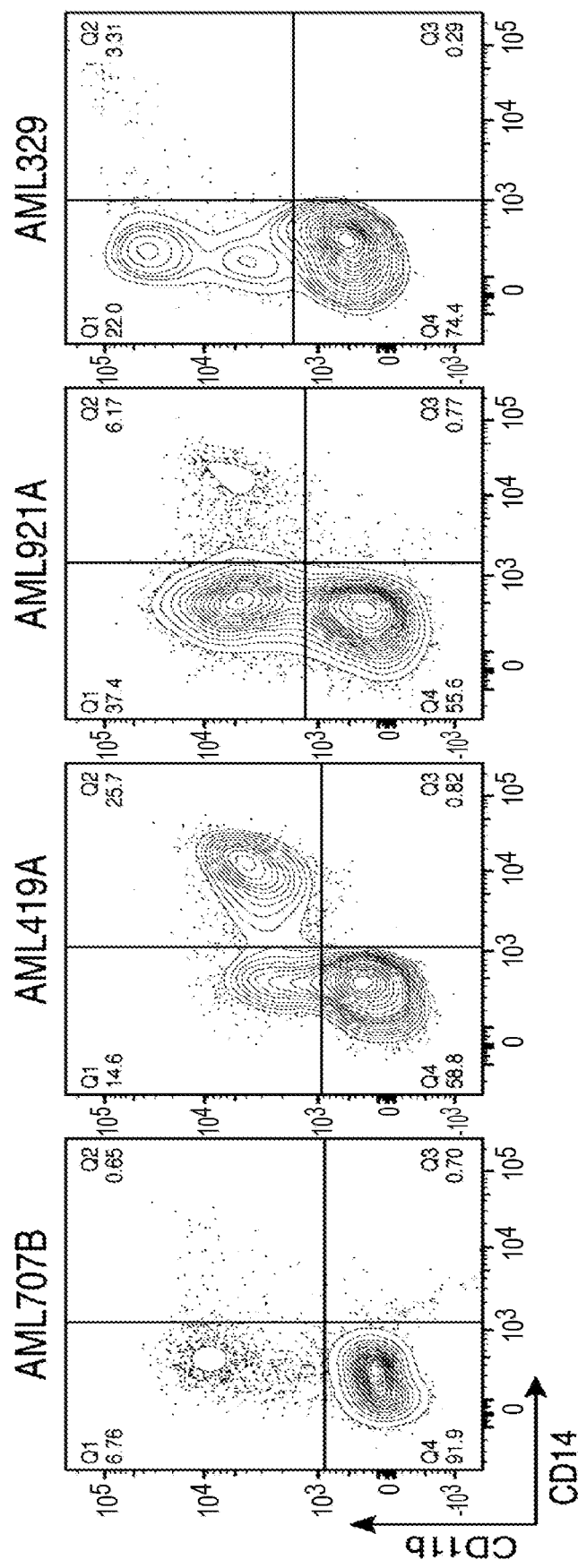
Figure 28B:
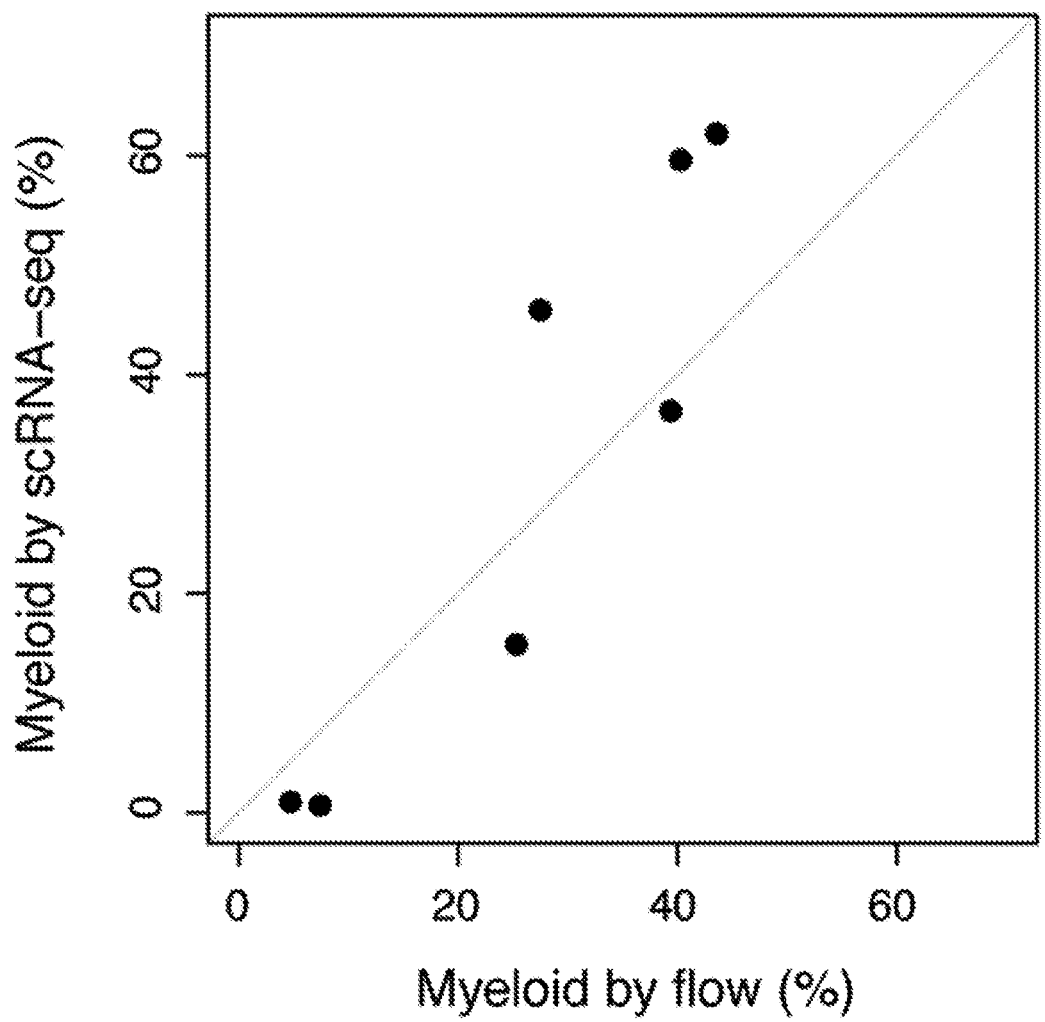

The relative proportions of primitive and differentiated AML cells varied markedly between patients (FIGS. 20B-20C and 28A), with some tumors consisting primarily of one or two cell types, and others comprising a spectrum of malignant cell types. The cell type abundances estimated by our classifier corresponded closely to clinical parameters determined by cell morphology and surface phenotypes. For example, AML707B had a high proportion of cells classified as GMP-like, consistent with flow cytometry showing low levels of myeloid differentiation markers. In contrast, AML419A had a higher proportion of cells classified as differentiated myeloid cells (60%), consistent with the clinical diagnosis as an AML with monocytic differentiation and with flow cytometry. Despite a strong overall correlation with clinical flow-based estimates of myeloid differentiation (FIG. 28B), the scRNA-seq data revealed more extensive malignant cell diversity than could be appreciated from a limited number of flow cytometry markers. For example, AML921A and AML329 had representation for all six malignant cell types including cDC-like cells (FIG. 20B-C). Thus, while consistent with clinical parameters, scRNA-seq provides more detailed information on AML cell types and differentiation states.

Malignant Progenitors Co-Express Stemness and Myeloid Priming Programs

Figure 20E:
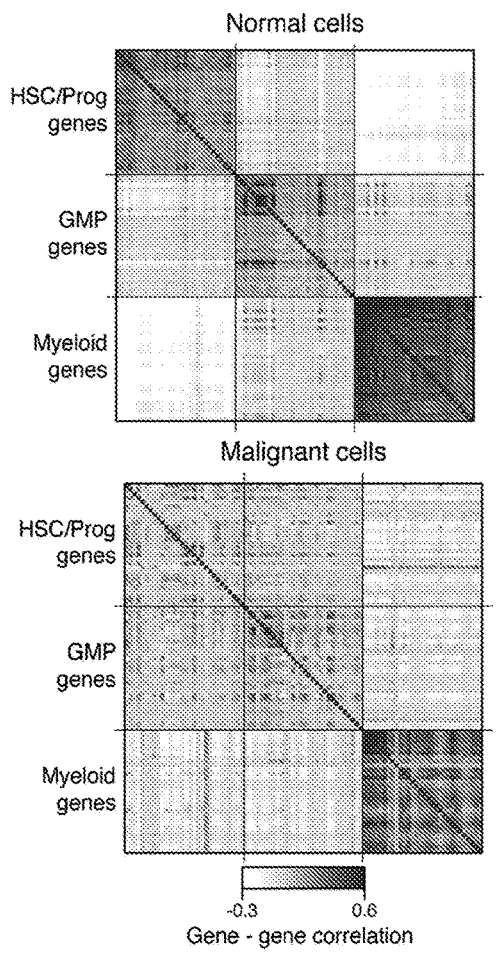
Figure 20F:
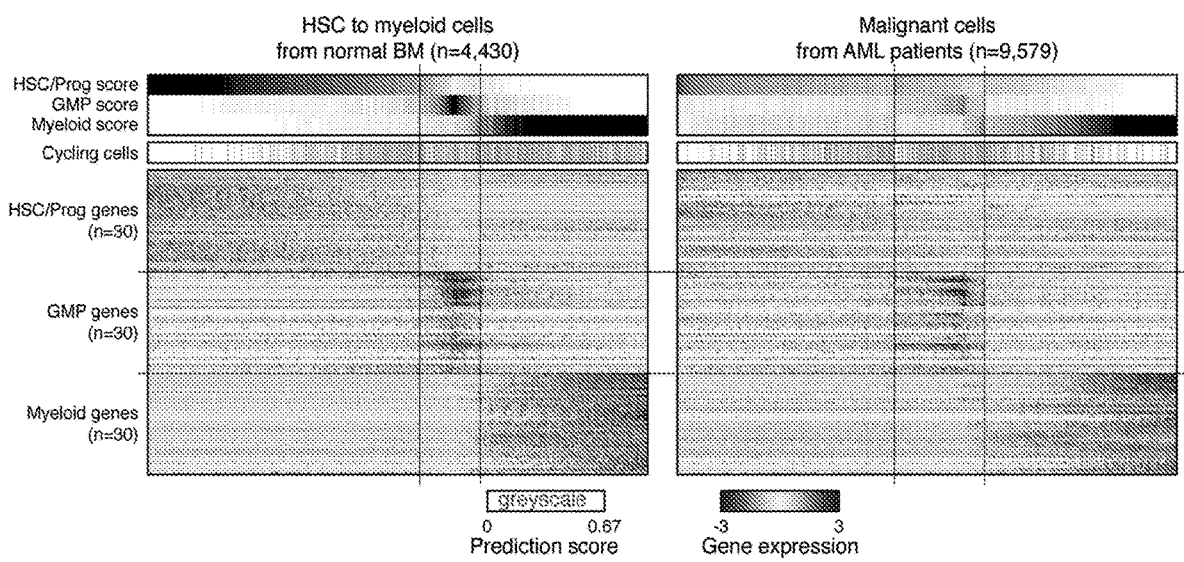
Figure 28C:
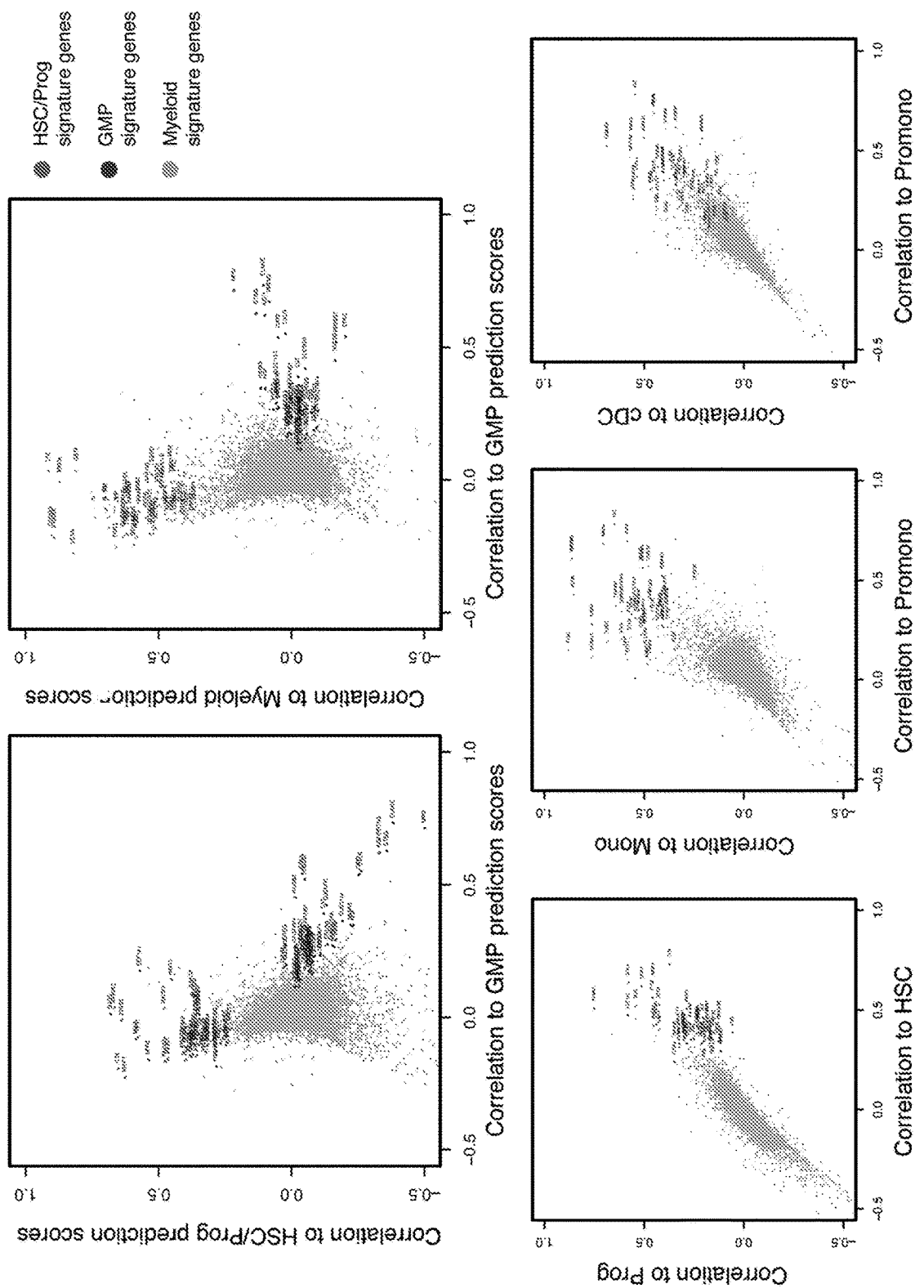
Figure 28D:
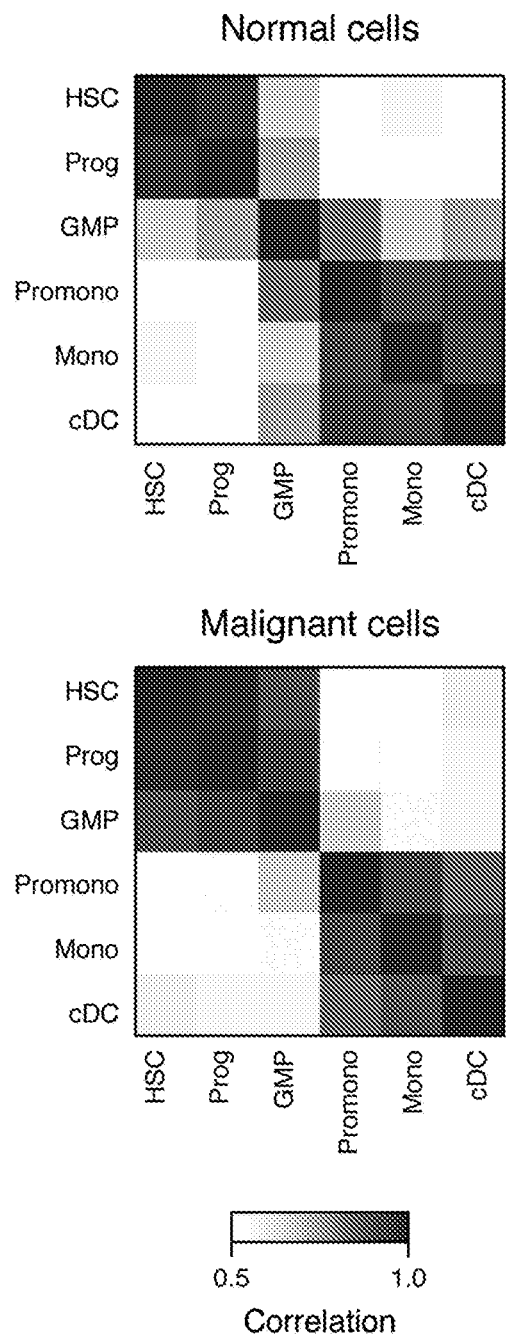

To better understand AML cell types, we compared their expression programs to normal counterparts. We generated gene signatures for the six normal cell types along the HSC-myeloid differentiation axis for which we had identified malignant counterparts (FIG. 17A and FIG. 20A). These signatures consisted of genes that are most highly correlated with prediction scores for each cell type (see Methods). Since the gene correlations for HSCs and Progenitors were similar, we combined them into a single signature for this analysis (FIG. 28C-28D). We also combined the differentiated cell types (promonocytes, monocytes, cDC) to generate a single myeloid signature. In contrast, the GMP signature primarily contained unique genes. These respective gene signatures included multiple known marker genes: MEIS1, MSI2, EGR1 for HSC/Progenitor; MPO, ELANE, AZU1 for GMP, and LYZ, MNDA, CD14 for myeloid (Table 2). As expected, application of these signatures to single cells from normal BMs clearly distinguished these three major cellular subsets (FIG. 20E-20F). Furthermore, genes within each signature were highly correlated, but were anti-correlated with genes in different signatures.

However, a distinct pattern emerged when we applied these signatures to malignant cells from the AML aspirates. Here, HSC/Progenitor signature genes were frequently co-expressed with GMP signature genes in the same malignant cells, contrasting markedly with their exclusivity in normal hematopoiesis (FIG. 20E-20F). For example, the surface marker genes CD38 and CD96 are positively correlated with malignant HSC/Prog-like cells, despite their negative correlation with normal HSC/Prog, consistent with earlier studies (Eppert et al., 2011; Hosen et al., 2007). Malignant HSC/Prog-like cells also express myeloid priming factors, such as MPO and ELANE, that are absent in normal HSC/Prog. More broadly, malignant HSC/Prog-like cells had lower expression of multiple HSC/Prog genes such as MSI2, MEIS1 and EGR1, and higher expression of multiple GMP and cell cycles genes such as AZU1, TOP2A, MKI67 and CENPF. Despite their perturbed state, primitive AML cells can differentiate into myeloid cells that closely recapitulate normal counterparts. Our findings extend earlier observations that LSCs can exhibit myeloid priming and proliferation (Krivtsov et al., 2006; Pollyea and Jordan, 2017) by revealing specific expression programs that coexist in these deranged cells and presumably underlie their unique capacity to self-renew, proliferate and recapitulate aspects of normal differentiation.

Figure 29A:
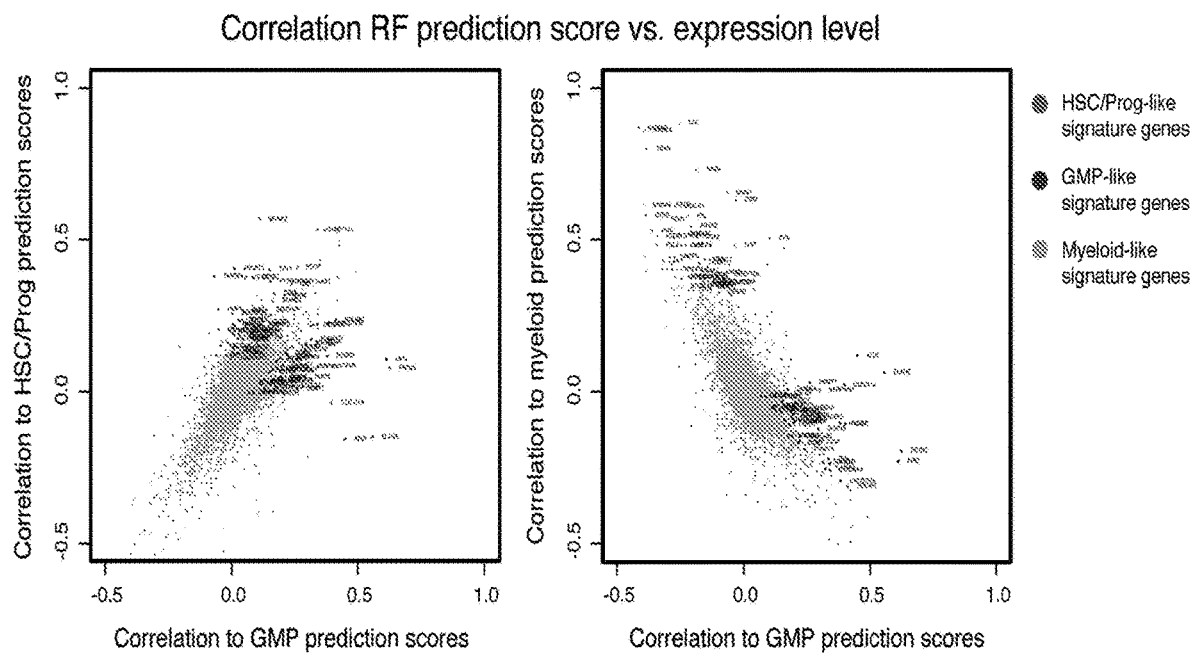
Figure 29B:
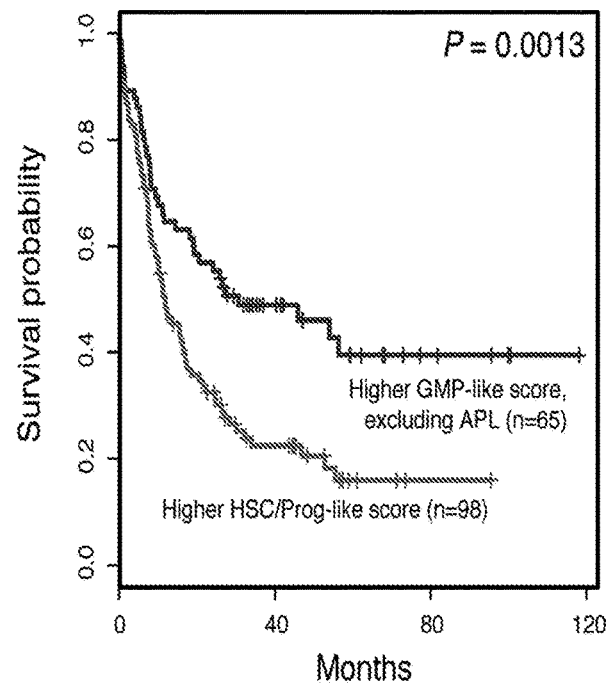

Finally, we considered the clinical implications of these deranged cellular programs. Our scRNA-seq data revealed that the relative abundances and the underlying expression states of HSC/Progenitor-like and GMP-like cells varied markedly among the tumors in our cohort. This prompted us to evaluate the generality and significance of these variations in a larger cohort of 179 diagnostic AMLs collected by the Cancer Genome Atlas (TCGA) (Cancer Genome Atlas Research et al., 2013). Although these samples were analyzed by bulk RNA-seq, we sought to use our single-cell-derived signatures to gain insight into the primitive cells within these tumors. Remarkably, we found that the HSC/Progenitor-like and GMP-like signatures were anti-correlated across these bulk expression profiles (FIG. 21A). This supported our observation that the transcriptional programs of primitive AML cells vary between tumors, and provided an opportunity to stratify patients. We partitioned the 179 AMLs into a group of tumors with relatively higher expression of HSC/Progenitor signature genes (n=98), and a group with higher expression of GMP signature genes (n=81). We found that patients with higher HSC/Progenitor expression, whose tumors presumably contain more primitive LSCs, had significantly poorer outcomes (FIG. 21B). This survival difference was maintained when we excluded acute promyelocytic leukemias (APL) cases defined by PML-RARA fusions (FIG. 29B). The significance of primitive cells was further supported by the observation that differentiated myeloid signature genes had no prognostic significance (FIG. 29C-29E). Our findings extend prior studies that have correlated features of sorted stem cell populations to AML outcome (Eppert et al., 2011; Gentles et al., 2010; Ng et al., 2016) by identifying primitive cell states and gene signatures that vary within and across tumors, with consequences for treatment response and outcomes.

AML Cellular Hierarchies Correlate to Genetics

We next expanded our analysis to consider the full repertoire of malignant cell types in AMLs. We found that the relative abundances of the six malignant cell types varied markedly across the 16 untreated AMLs that we profiled (FIGS. 20B and 28A), which prompted us to evaluate cell type composition across the larger cohort. To this effect, we used our scRNA-seq data to derive gene signatures for each of the six malignant cell types (FIG. 29A). Availability of the single-cell profiles enabled us to generate equally weighted and unbiased gene signatures for defined cell types and to exclude genes that are expressed in non-malignant cell types that can be prevalent in AML tumors. This distinguished our approach from prior studies that have stratified AML expression profiles by variable genes or signatures of sorted populations (Gentles et al., 2010; Ng et al., 2016; Valk et al., 2004; Verhaak et al., 2009).

We hierarchically clustered the 179 TCGA AML tumors by their expression of the six malignant cell type signatures. This revealed seven clusters of AML tumors with distinct expression patterns indicative of different malignant cell type compositions (FIG. 21C). Certain clusters include tumors with high relative abundances of specific cell types, such as GMP-like (cluster B), Progenitor-like (cluster D) or monocyte-like cells (cluster E). Others comprise tumors that contain a spectrum of malignant cell types along the HSC-myeloid axis (cluster G). These data extend prior marker- and histology-based studies by quantifying variations in cell type compositions and development hierarchies across a cohort of AMLs.

We next sought to relate these variable hierarchies to underlying genetic drivers. Remarkably, we found that the clusters derived from cell type abundances correspond closely to the genetics of the AMLs (FIG. 21D-E). For example, TCGA tumors with uniquely high GMP-like scores (cluster B) perfectly overlapped with RUNX1-RUNX1T1 fusions (P<0.001). Consistently, the one AML in our scRNA-seq dataset harboring this genetic alteration (AML707B) consists almost entirely of GMP-like cells (FIG. 29F). Moreover, TCGA tumors with high monocyte-like and cDC-like scores (cluster F) overlapped almost perfectly with CBFB-MYH11 fusions (P<001). Consistently, the one AML in our scRNA-seq dataset harboring this genetic alteration (AML1012) shows similarly high prevalence of these cell types (FIG. 29F). A third cluster of TCGA tumors with high GMP-like scores (cluster A) perfectly overlapped with APL cases. Two other clusters were enriched for cytogenetically complex tumors and those harboring CEBPA, RUNX1, and TP53 mutations (clusters C, G). These clusters have distinct malignant cell type compositions, with cluster C representing the most undifferentiated group of AMLs (enriched for FAB M0 subtype, FIG. 21F) and cluster G recapitulating a spectrum of differentiation (FIG. 29F).

The remaining two clusters (D, E) comprised mostly NPM1 mutant tumors. Cluster D is enriched for undifferentiated HSC/Progenitor-like cells (and FAB M1/2 subtypes), while cluster E is enriched for monocyte-like and cDC-like cells (and FAB M4/5 subtypes). Interestingly, the undifferentiated cluster is associated with FLT3 internal tandem duplications (ITD), while the differentiated cluster is associated with FLT3 tyrosine kinase domain (TKD) mutations (similar to AML210A, FIG. 29F). These respective FLT3 mutations in combination with NPM1 have been associated with distinct survival outcomes (Boddu et al., 2017). Our findings suggest that these distinct outcomes may relate to the high abundance of primitive AML cells in the relatively poor prognosis NPM1-FLT3-ITD tumors. These results convey a close connection between tumor genetics and developmental hierarchies, with prognostic relevance. They suggest the potential of scRNA-seq to guide the development of therapies that target the cellular contexts and programs manifest by specific genetic lesions.

T-Cell Signatures Moderated in AML Patients

Figure 22B:
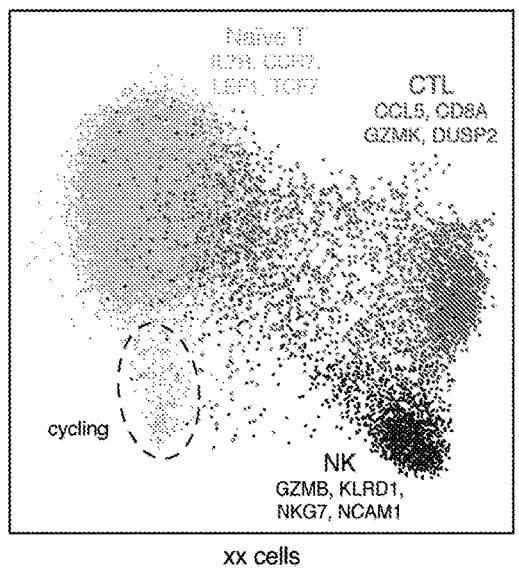

T-cells can in principle eliminate AML cells, as demonstrated by the potential of the graft-versus-leukemia effect to yield durable cures following stem cell transplantation (Bleakley and Riddell, 2004), but may be compromised in ANIL tumors (Austin et al., 2016; Ustun et al., 2011). We therefore examined the T-cells in our single-cell data for AMLs and healthy BMs (FIG. 22A). In the normal BM, we identified two T-cell subsets, naïve T-cells (IL7R, CCR7) and CTLs (CD8A, GZMK), and a population of NK cells (CD56/NCAM1, KLRD1) with related transcriptional programs (FIG. 17). In support, we consistently recovered the same three populations when we performed unsupervised clustering of all T- and NK cells from tumor and normal samples (FIG. 22B). Supervised analysis further distinguished a small subset of cells expressing Treg markers, but their limited numbers precluded further analysis.

Figure 22C:
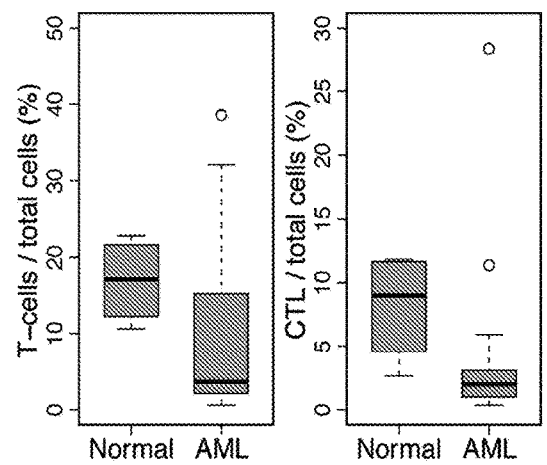
Figure 22D:
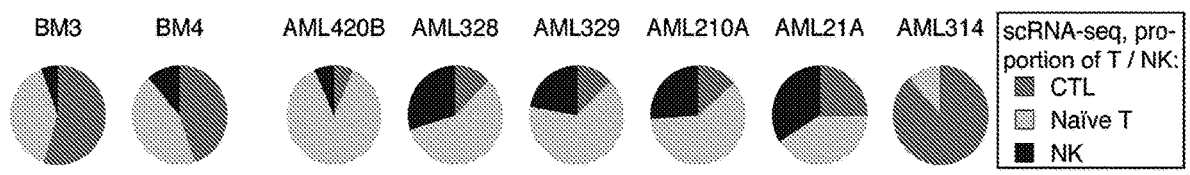
Figure 22E:
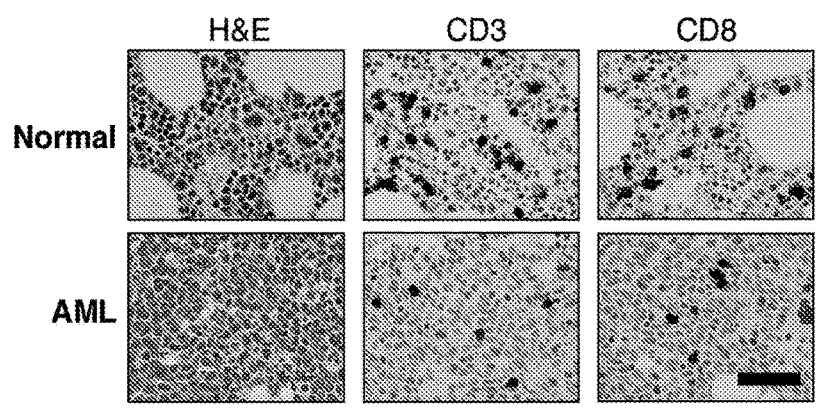
Figure 22F:
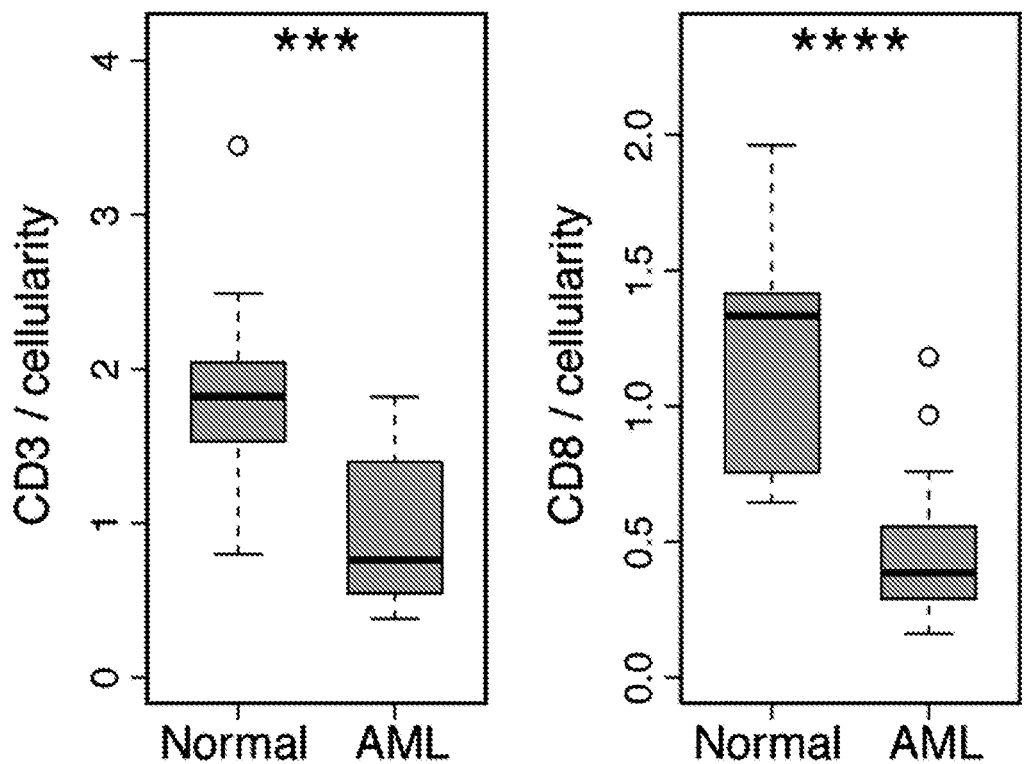
Figure 22G:
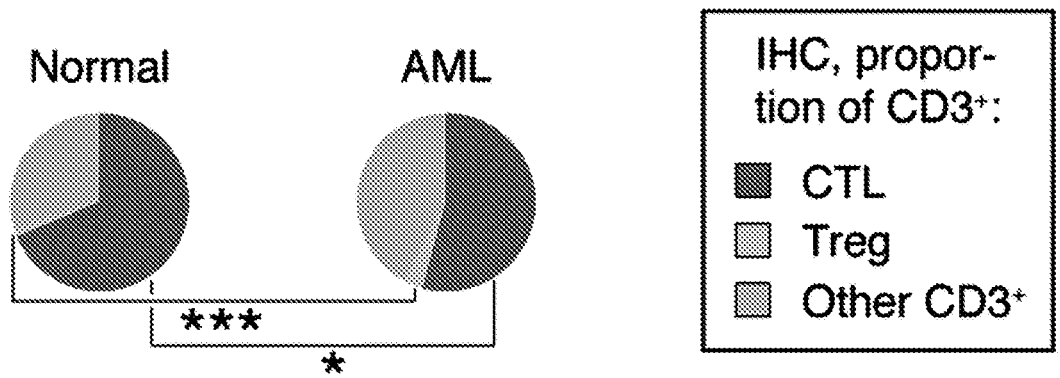

AMLs tended to have proportionally fewer T-cells and CTLs, compared to normal controls (FIG. 22C). CTL abundance as a proportion of T-/NK cells was reduced across five out of six tumors for which at least 50 T-/NK cells were identified, relative to normal controls (FIG. 22D). We also used immunohistochemistry (IHC) to co-stain CD3 (T-cells), CD8 (CTLs) and CD25+FOXP3 (Tregs) in an additional cohort of 15 newly diagnosed AMLs and 15 normal control BMs. We again found that the AMLs had significantly fewer T-cells and CTLs, and a reduced CTL: T-cell ratio, compared to normal controls (FIG. 22E-22G). Conversely, the tumors had relatively greater numbers of Tregs, consistent with prior reports that this suppressive subset is increased in AML (Ustun et al., 2011). Thus, scRNA-seq and IHC reveal consistent changes in T-cell numbers and composition, consistent with an immunosuppressive tumor environment (Austin et al., 2016).

Differentiated AML Cells Suppress T-Cell Activation In Vitro

Figure 23A:
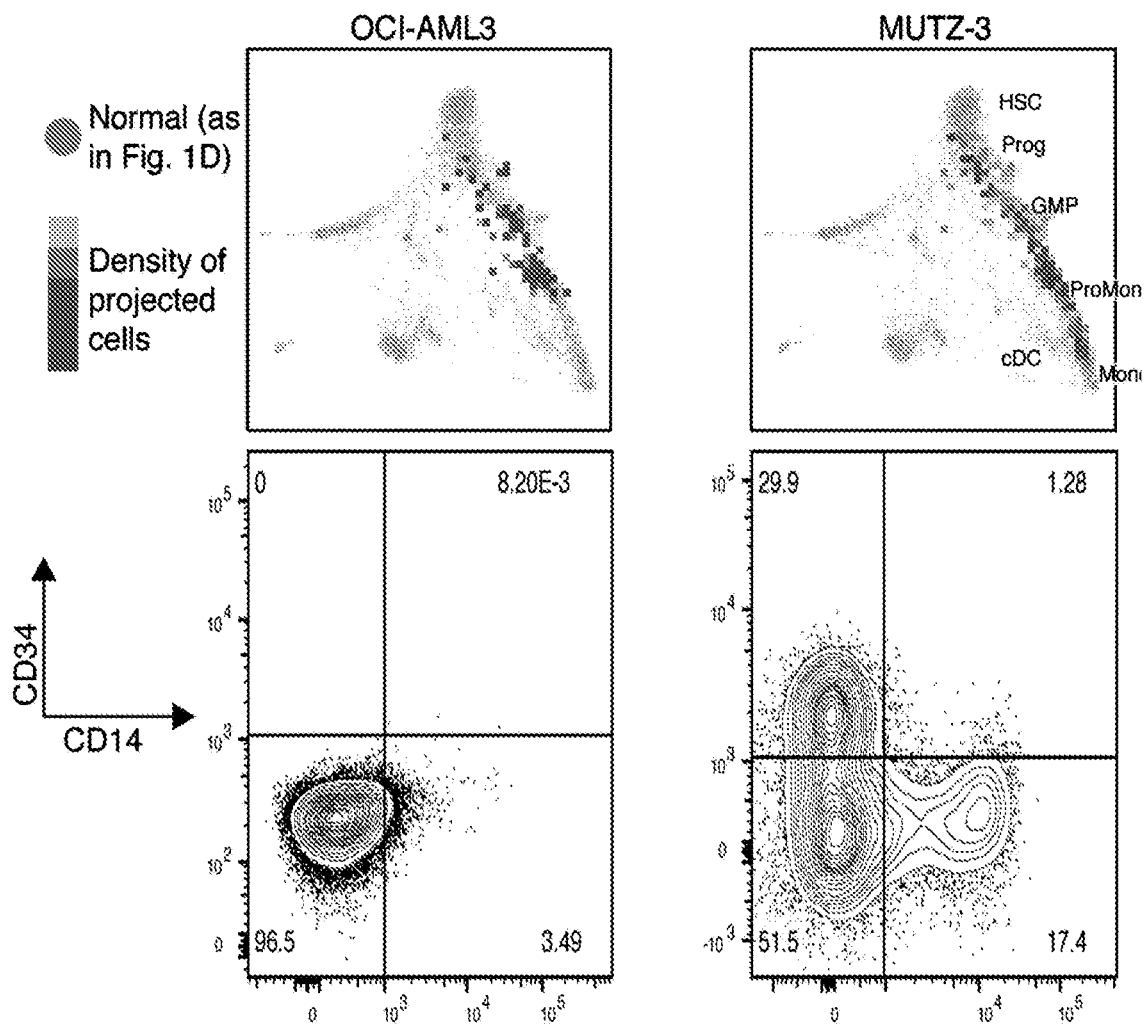
Figure 30A:
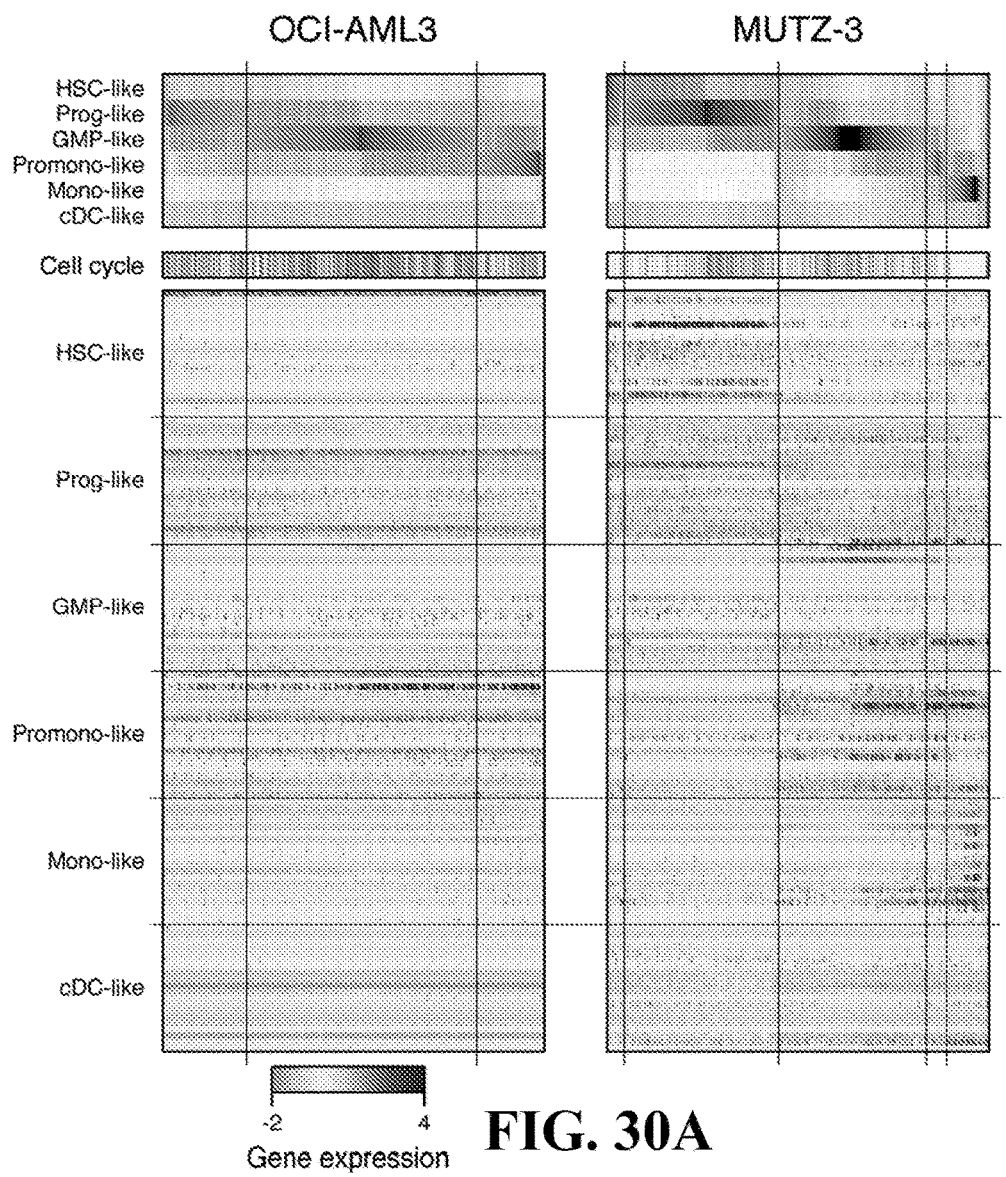
Figure 30B:
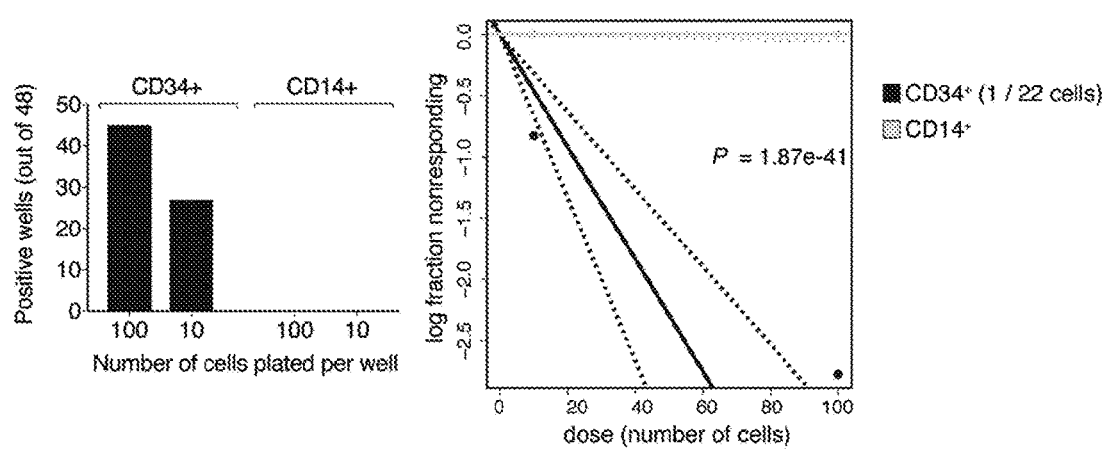

Finally, we considered whether specific malignant cell types might contribute to the relative T-cell suppression in the AMLs. To investigate this, we sought to identify an in vitro model that recapitulates the heterogeneous cell types in primary AMLs. We analyzed two AML cell lines by scRNA-seq and surface marker analysis (FIGS. 23A and 30A). We found that the MUTZ-3 line, derived from an acute myelomonocytic leukemia, recapitulates a spectrum of cell types, including HSC/Progenitor-like and monocyte-like cells. In contrast, the OCI-AML3 line is homogeneous and primarily composed of GMP-like cells. Further analysis confirmed that HSC/Progenitor-like, but not monocyte-like, MUTZ-3 cells could initiate new cultures, consistent with the in vivo biology of these cell types (FIG. 30B).

Figure 23B:
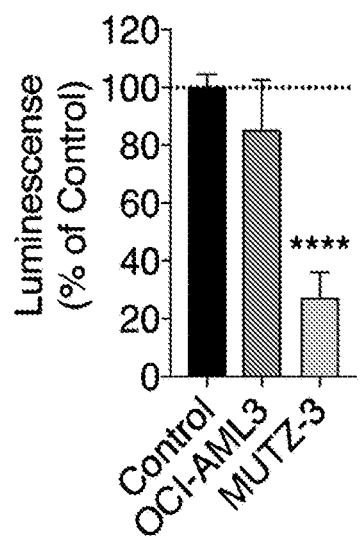
Figure 23C:
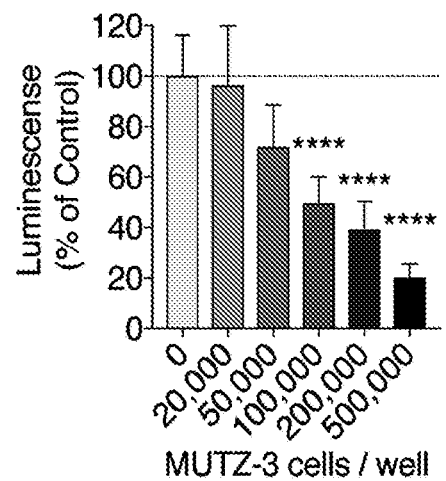
Figure 30C:
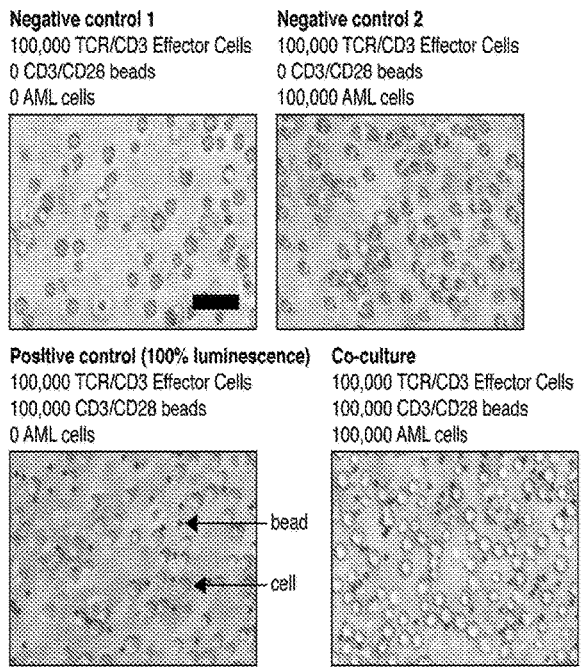

We tested these in vitro AML models in $CD4^+$ T-cell bioactivation assay that reports activation of Nuclear Factor of Activated T-cells (NFAT) (FIG. 30C, Methods). We co-cultured these T-cells with MUTZ-3 cells, stimulated them with CD3/CD28 beads, and measured T-cell activation. The MUTZ-3 cells exhibited a strong inhibitory effect, reducing T-cell activation by 3.7-fold in a 1:1 AML cell: T-cell ratio (FIG. 23B). OCI-AML3 cells had less potent inhibitory effects in this assay. Since AML cells vastly outnumber T-cells in AML tumors, we also increased the MUTZ-3 cell: T-cell ratio in the assay, which resulted in more potent inhibition (FIG. 23C). These results demonstrate that MUTZ-3 cells mediate a dose-dependent inhibition of T-cell activation in vitro.

Figure 30D:
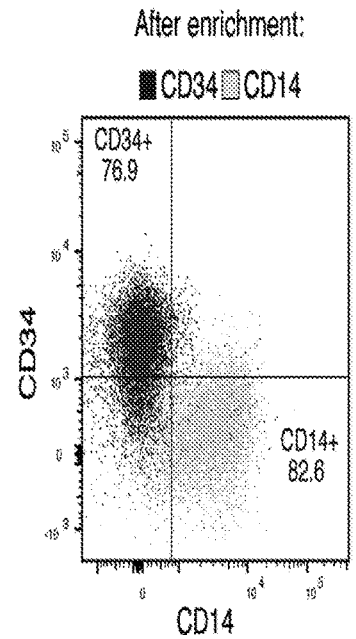
Figure 30E:
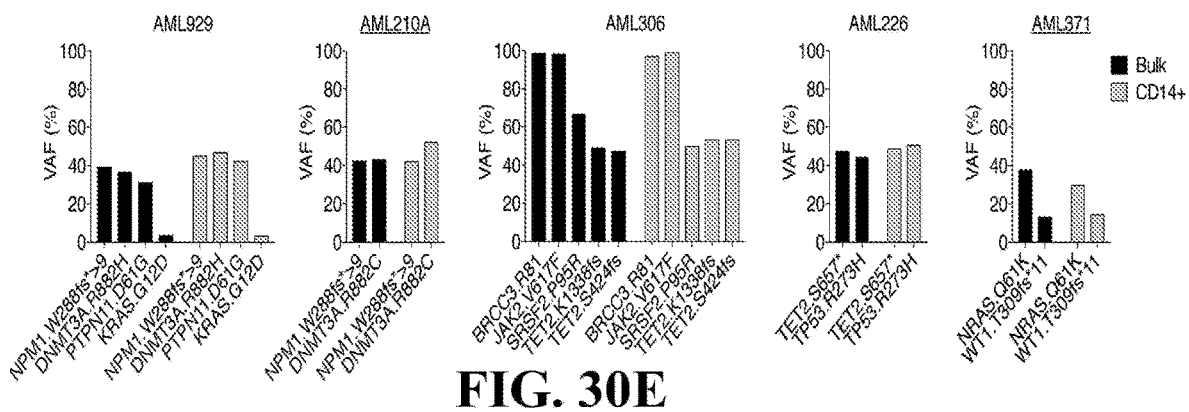

We next investigated whether the immunosuppressive properties of MUTZ-3 are mediated by specific sub-populations. We performed the co-culture assay with sorted HSC/Progenitor-like ($CD34^+$) or monocyte-like ($CD14^+$) MUTZ-3 cells (FIG. 30D). The $CD14^+$ cells reduced T-cell activation by 10-fold (P<0.0001, FIG. 23D), while the $CD34^+$ cells had little effect (1.3-fold). This prompted us to examine the immunosuppressive functions of monocyte-like cells from primary AMLs. We isolated $CD14^+$ and $CD14^-$ cells from five AML patients and six normal donors. The leukemic origin of the CD14+ AML cells was verified by targeted DNA sequencing of the sorted populations (FIG. 30E). We found that CD14+ cells from several of the AMLs strongly inhibited T-cell activation (1.3 to 5.3-fold), whereas CD14− cells had little or no effect (FIG. 23E). Notably, CD14+ cells from normal BM had only a subtle effect in this assay (1.4-fold, FIG. 23F). These results suggest that a subset of AMLs give rise to immunosuppressive CD14+ monocyte-like cells.

Figure 30F:
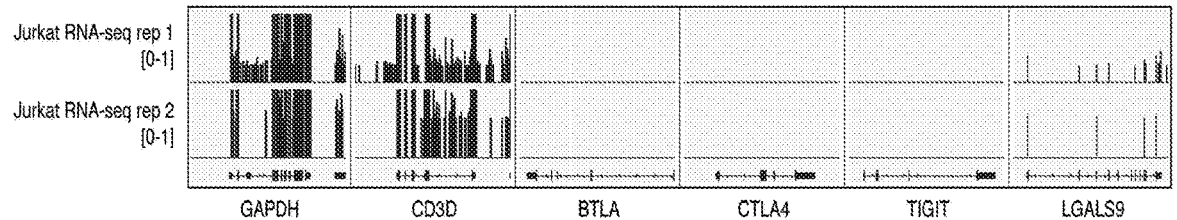

Finally, we considered the origin of the immunosuppressive signal provided by these AML cells. To test whether the effect is mediated by a soluble ligand, we performed the T-cell activation bioassay in the presence of MUTZ-3 conditioned medium. The conditioned medium had very little (1.1-fold) effect (FIG. 23G), suggesting that cell contact is required. Next, we examined our scRNA-seq data for primary AMLs to nominate surface ligands that could potentially interact with receptors on CD4+ T-cells (Austin et al., 2016; Wykes and Lewin, 2018). We did not detect PD-L1/CD274 or PD-L2/PDCD1LG2 in AML cells. However, the monocyte-like cells expressed other potentially immunosuppressive ligands, including TIM-3/HAVCR2, GAL9/LGALS9, CD86, CD155/PVR and HVEM/TNFRSF14, some of whose cognate receptors were expressed by the CD4+ T-cells in our assay (FIGS. 23H and 30F). Although these cells may relate to myeloid-derived suppressor cells, which have been described in AMLs, they express the MHC class II molecule HLA-DR, which is not typically associated with such populations (FIG. 23H, FIG. 30G) (Pyzer et al., 2017; Veglia et al., 2018). These collective results suggest that AMLs can differentiate into monocyte-like cells that suppress T-cell activation, and identify their expression programs and immune regulators, which bear further study.

TABLE 4

Primer sequences used in this study.

Mutation-specific primers for biotin-PCR

| Primer name | Mutations within sequenced region | Total # transcripts detected (≥10x) | Fraction of cells | Primer Sequence (5' to 3') | SEQ ID NO: |
|---|---|---|---|---|---|
| PvG1066-Next_NPM1_833 | NPM1.W288fs | 3316 | 22.0% | /5Biosg/GTCTCGTGG GCTCGGAGATGTGTATA AGAGACAGTGACTGACC AAGAGGCTATTCA | SEQ ID NO: 3 |
| PvG1075-Next_FLT3_2019 | FLT3.A680V | 71 | 5.7% | /5Biosg/GTCTCGTGG GCTCGGAGATGTGTATA AGAGACAGTATTGTGAA CCTGCTGGGGG | SEQ ID NO: 4 |
| PvG1062-Next_FLT3_2482 | FLT3.N841K | 66 | 5.4% | /5Biosg/GTCTCGTGG GCTCGGAGATGTGTATA AGAGACAGTGTGACTTT GGATTGGCTCGA | SEQ ID NO: 5 |
| PvG1099-Next_RAD21_1005 | RAD21.L353fs | 223 | 4.9% | /5Biosg/GTCTCGTGG GCTCGGAGATGTGTATA AGAGACAGGACAATTAG AGCCCAACTTAGTGA | SEQ ID NO: 6 |
| PvG1078-Next_KRAS_14 | KRAS.G13D | 44 | 3.8% | /5Biosg/GTCTCGTGG GCTCGGAGATGTGTATA AGAGACAGAACTTGTGG TAGTTGGAGCT | SEQ ID NO: 7 |
| PvG1060-Next_DNMT3A_2623 | DNMT3A.R882C, DNMT3A.R882H | 426 | 2.6% | /5Biosg/GTCTCGTGG GCTCGGAGATGTGTATA AGAGACAGACTGACGTC TCCAACATGAGC | SEQ ID NO: 8 |
| PvG1091-Next_TP53_683 | TP53.C238Y | 22 | 2.3% | /5Biosg/GTCTCGTGG GCTCGGAGATGTGTATA AGAGACAGACTGTACCA CCATCCACTACA | SEQ ID NO: 9 |
| PvG1068-Next_NRAS_151 | NRAS.Q61K, NRAS.Q61H | 134 | 2.1% | /5Biosg/GTCTCGTGG GCTCGGAGATGTGTATA AGAGACAGTGTTTGTTG GACATACTGGAT | SEQ ID NO: 10 |
| PvG1064-Next_IDH2_392 | IDH2.R140Q | 52 | 2.0% | /5Biosg/GTCTCGTGG GCTCGGAGATGTGTATA AGAGACAGTGTGGAAAA GTCCCAATGGAAC | SEQ ID NO: 11 |
| PvG1061-Next_FLT3_1740 | FLT3.ITD | 36 | 2.0% | /5Biosg/GTCTCGTGG GCTCGGAGATGTGTATA AGAGACAGGGTGACCGG CTCCTCAGATA | SEQ ID NO: 12 |

TABLE 4-continued

Primer sequences used in this study.

| | | | | | |
|---|---|---|---|---|---|
| PvG1105-Next_SMC3_3393 | SMC3.D1150G | 27 | 1.9% | /5Biosg/GTCTCGTGGGCTCGGAGATGTGTATAAGAGACAGTCAGAAATGTGACCCGGCTC | SEQ ID NO: 13 |
| PvG1065-Next_IDH2_491 | IDH2.R172K | 2 | 1.4% | /5Biosg/GTCTCGTGGGCTCGGAGATGTGTATAAGAGACAGGGACCAAGCCCATCACCATT | SEQ ID NO: 14 |
| PvG1103-Next_PTPN11_862 | PTPN11.N298S | 2 | 1.4% | /5Biosg/GTCTCGTGGGGCTCGGAGATGTGTATAAGAGACAGACCAGGGTTGTCCTACACGA | SEQ ID NO: 15 |
| PvG1097-Next_SETD2_3200 | SETD2.T1077A | 50 | 1.3% | /5Biosg/GTCTCGTGGGCTCGGAGATGTGTATAAGAGACAGAGTCTGTTGTGGTTGTGCCA | SEQ ID NO: 16 |
| PvG1096-Next_RUNX1_139 | RUNX1.L565 | 50 | 1.3% | /5Biosg/GTCTCGTGGGCTCGGAGATGTGTATAAGAGACAGCTGAGCCCAGGCAAGATGAG | SEQ ID NO: 17 |
| PvG1098-Next_BRCC3_666 | BRCC3.L229fs | 66 | 1.2% | /5Biosg/GTCTCGTGGGCTCGGAGATGTGTATAAGAGACAGCACTATCGGGAAAGTGTGCCT | SEQ ID NO: 18 |
| PvG1114-Next_TP53_794 | TP53.R273L | 23 | 1.1% | /5Biosg/GTCTCGTGGGCTCGGAGATGTGTATAAGAGACAGTGGGACGGAACAGCTTTGAG | SEQ ID NO: 19 |
| PvG1073-Next_FLT_1761 | FLT3.ITD | 24 | 1.0% | /5Biosg/GTCTCGTGGGCTCGGAGATGTGTATAAGAGACAGTGAGTACTTCTACGTTGATTTCAGAGA | SEQ ID NO: 20 |
| PvG1077-Next_KIT_2420 | KIT.Y823C | 66 | 0.9% | /5Biosg/GTCTCGTGGGCTCGGAGATGTGTATAAGAGACAGAGATTTGTGATTTTGGTCTAGCC | SEQ ID NO: 21 |
| PvG1111-Next_TET2_3139 | TET2.S1059stp | 35 | 0.6% | /5Biosg/GTCTCGTGGGCTCGGAGATGTGTATAAGAGACAGACTCTCAAATCACAGAAGCAAGT | SEQ ID NO: 22 |
| PvG1113-Next_ATM_6036 | ATM.G2023R | 24 | 0.5% | /5Biosg/GTCTCGTGGGCTCGGAGATGTGTATAAGAGACAGAGGGGAGCCAGATAGTTTGT | SEQ ID NO: 23 |
| PvG1067-Next_NRAS_11 | NRAS.G13D, NRAS.G12D | 22 | 0.5% | /5Biosg/GTCTCGTGGGCTCGGAGATGTGTATAAGAGACAGACAAACTGGTGGTGGTTGGA | SEQ ID NO: 24 |
| PvG1082-Next_TP53_405 | TP53.Q144P, TP53.P152R | 70 | 0.5% | /5Biosg/GTCTCGTGGGCTCGGAGATGTGTATAAGAGACAGCCAACTGGCCAAGACCTGC | SEQ ID NO: 25 |
| PvG1081-Next_SF3A1_1412 | SF3A1.G478S | 6 | 0.4% | /5Biosg/GTCTCGTGGGCTCGGAGATGTGTATAAGAGACAGAGCGGCGTACTGACATCTTC | SEQ ID NO: 26 |
| PvG1112-Next_TET2_5363 | TET2.L1804fs | 16 | 0.3% | /5Biosg/GTCTCGTGGGCTCGGAGATGTGTATAAGAGACAGACATGCTTTCCCACACAGCT | SEQ ID NO: 27 |

TABLE 4-continued

Primer sequences used in this study.

| | | | | | |
|---|---|---|---|---|---|
| PvG1071-Next_DNMT3A_1885 | DNMT3A.L637Q | 15 | 0.3% | /5Biosg/GTCTCGTGGGCTCGGAGATGTGTATAAGAGACAGGAGAAGAGGAAGCCCATCCG | SEQ ID NO: 28 |
| PvG1106-Next_BCOR_2881 | BCOR.R976stp | 2 | 0.3% | /5Biosg/GTCTCGTGGGCTCGGAGATGTGTATAAGAGACAGAAGCTGGCAAAGAGAATCGC | SEQ ID NO: 29 |
| PvG1072-Next_FLT3_1711 | FLT3.ITD | 0 | 0.0% | /5Biosg/GTCTCGTGGGCTCGGAGATGTGTATAAGAGACAGAGGTATGAAAGCCAGCTACAGA | SEQ ID NO: 30 |
| PvG1076-Next_JAK_2724 | JAK3.R925S | 0 | 0.0% | /5Biosg/GTCTCGTGGGCTCGGAGATGTGTATAAGAGACAGCTGCTTGCGCGACTTCCT | SEQ ID NO: 31 |
| PvG1079-Next_NOTCH2_4210 | NOTCH2.L1413H | 0 | 0.0% | /5Biosg/GTCTCGTGGGCTCGGAGATGTGTATAAGAGACAGCCACCATTCTCGGGTAGCC | SEQ ID NO: 32 |
| PvG1100-Next_BCORL1_1597 | BCORL1.D542fs | 0 | 0.0% | /5Biosg/GTCTCGTGGGCTCGGAGATGTGTATAAGAGACAGGGTAGCACCACCACCCAG | SEQ ID NO: 33 |
| PvG1101-Next_ASXL1_1204 | ASXL1.R411C | 0 | 0.0% | /5Biosg/GTCTCGTGGGCTCGGAGATGTGTATAAGAGACAGCGACAGCGAGATGGGCATTT | SEQ ID NO: 34 |
| PvG1102-Next_PHF6_938 | PHF6.Y325H | 0 | 0.0% | /5Biosg/GTCTCGTGGGCTCGGAGATGTGTATAAGAGACAGACATTGAAAATATGTCACGAGGA | SEQ ID NO: 35 |
| PvG1104-Next_NOTCH1_5253 | NOTCH1.R1758H | 0 | 0.0% | /5Biosg/GTCTCGTGGGCTCGGAGATGTGTATAAGAGACAGCTGCGGGGTGCTGCTGTC | SEQ ID NO: 36 |
| PvG1107-Next_BCORL1_1893 | BCORL1.T648fs | 0 | 0.0% | /5Biosg/GTCTCGTGGGCTCGGAGATGTGTATAAGAGACAGGAAGCTTCCATTGCCGAACC | SEQ ID NO: 37 |
| PvG1108-Next_BCORL1_2969 | BCORL1.T999fs | 0 | 0.0% | /5Biosg/GTCTCGTGGGCTCGGAGATGTGTATAAGAGACAGACATGTCCCATGAGCTGGTC | SEQ ID NO: 38 |
| PvG1109-Next_BCORL1_3103 | BCORL1.R1048 | 0 | 0.0% | /5Biosg/GTCTCGTGGGCTCGGAGATGTGTATAAGAGACAGACAGAGCGCCCACAGCTT | SEQ ID NO: 39 |
| PvG1110-Next_BCORL1_3557 | BCORL1.R1196 | 0 | 0.0% | /5Biosg/GTCTCGTGGGCTCGGAGATGTGTATAAGAGACAGCAAAGCCGGAGTCCCAGTC | SEQ ID NO: 40 |
| PvG1117-Next_SH2B3_1624 | SH2B3.D552G | 0 | 0.0% | /5Biosg/GTCTCGTGGGCTCGGAGATGTGTATAAGAGACAGCTGGAGCATGAGCCTGTGAA | SEQ ID NO: 41 |
| PvG1118-Next_RUNX1_926 | RUNX1.S322fs | 0 | 0.0% | /5Biosg/GTCTCGTGGGCTCGGAGATGTGTATAAAGAGCAGGCATGACAACCCTCTCTGCA | SEQ ID NO: 42 |

TABLE 4-continued

Primer sequences used in this study.

| Name | Note | | | Primer Sequence | |
|---|---|---|---|---|---|
| PvG1123-Next_BCOR_2063 | BCOR.K699fs | 0 | 0.0% | /5Biosg/GTCTCGTGGGCTCGGAGATGTGTATAAGAGACAGATGGCAGTCTGTTTCCTGGG | SEQ ID NO: 43 |
| PvG1124-Next_ZRSR2_1130 | ZRSR2.P383A | 0 | 0.0% | /5Biosg/GTCTCGTGGGCTCGGAGATGTGTATAAGAGACAGGCCACCACGACGACTACTAC | SEQ ID NO: 44 |
| PvG1125-Next_WT1_1093 | WT1.T309fs | 0 | 0.0% | /5Biosg/GTCTCGTGGGCTCGGAGATGTGTATAAGAGACAGATTCAGGATGTGCGACGTGT | SEQ ID NO: 45 |

Other primers

| Name | Note | Barcode | bcl2fastq | Primer Sequence (5' to 3') | |
|---|---|---|---|---|---|
| SMART-AC | Common to all biotin-PCR 1 reactions | — | — | AAGCAGTGGTATCAACGCAGAGT*A*C | SEQ ID NO: 46 |
| P5_SMART_Hybrid | Common to all biotin-PCR 2 reactions | — | — | AATGATACGGCGACCACCGAGATCTACACGCCTGTCCGCGGAAGCAGTGGTATCAACGCAGAGT*A*C | SEQ ID NO: 47 |
| N70_BC01 | Example 1 for barcoded biotin-PCR 2 | AACG CATT | AATG CGTT | CAAGCAGAAGACGGCATACGAGATAACGCATTGTCTCGTGGGCTCGGAGATGT | SEQ ID NO: 48 |
| N70_BC02 | Example 2 for barcoded biotin-PCR 2 | TTGT CTAT | ATAG ACAA | CAAGCAGAAGACGGCATACGAGATTTGTCTATGTCTCGTGGGCTCGGAGATGT | SEQ ID NO: 49 |
| N70_BC03 | Example 3 for barcoded biotin-PCR 2 | AAGA CACT | AGTG TCTT | CAAGCAGAAGACGGCATACGAGATAAGACACTGTCTCGTGGGCTCGGAGATGT | SEQ ID NO: 50 |
| N70_BC04 | Example 4 for barcoded biotin-PCR 2 | TTGA ATAG | CTAT TCAA | CAAGCAGAAGACGGCATACGAGATTTGAATAGGTCTCGTGGGCTCGGAGATGT | SEQ ID NO: 51 |
| SMART-PCR | Seq-Well whole transcriptome amplification | — | — | AAGCAGTGGTATCAACGCAGAGT | SEQ ID NO: 52 |
| CR1P | Seq-well Custom Read 1 Primer | — | — | GCCTGTCCGCGGAAGCAGTGGTATCAACGCAGAGTAC | SEQ ID NO: 53 |
| TSO | Seq-Well template switching oligo from Exiqon | — | — | AAGCAGTGGTATCAACGCAGAGTGAATrGrG+G | SEQ ID NO: 54 |

* = Phosphorothioate bond (IDT)
/5Biosg/ = 5' Biotin (IDT)

Discussion

Intratumoral heterogeneity in AML has been appreciated since the 1960s (Dick, 2008), but it has only recently become possible to study the complexity of tumors using high-dimensional single-cell analyses (Good et al., 2018; Levine et al., 2015; Muller and Diaz, 2017; Ziegenhain et al., 2017). Here, we applied technological innovations in scRNA-seq and genotyping to characterize the AML tumor ecosystem, to investigate developmental states of malignant cells as they relate to the normal hierarchy, and to evaluate interactions between tumor cells and the immune system.

To address unique challenges posed by the AML ecosystem, we adapted a nanowell-based method to measure transcriptomes and genotypes of single cells at high-throughput. Prior scRNA-seq studies of tumors have primarily relied on plate-based, full-length RNA sequencing protocols. These methods have insufficient throughput to parse complex AML tumors, which comprise diverse malignant and normal cell types represented at varying proportions. Whereas droplet-based approaches offer greater throughput, they yield 3'-biased RNA sequencing data that does not provide genotyping information needed to distinguish AML cells from normal counterparts. We therefore combined the Seq-Well protocol, which enables 3'-biased scRNA-seq profiling of thousands of cells per experiment, with single-cell genotyping of AML driver mutations (Gierahn et al., 2017). We profiled 38,410 cells from 35 AML biopsies and 5 normal bone marrows, vastly exceeding typical cell numbers from prior studies of human tumors (Giustacchini et al., 2017; Puram et al., 2017; Tirosh et al., 2016; Zheng et al., 2017a). We then developed a single-cell genotyping strategy to amplify AML mutational hotspots in conjunction with the cell barcodes, which allowed us to match genotyping information to single-cell transcriptomes. The underlying approach should in principle be compatible with other high-throughput scRNA-seq technologies (Macosko et al., 2015; Zheng et al., 2017b). Furthermore, it could be extended to query other expressed target sequences, including integrated expression constructs containing barcodes or guide RNAs (Kester and van Oudenaarden, 2018). We integrated these transcriptional and genotypic data in a machine learning classifier to assign each cell in our dataset as either malignant or normal. These innovations provided an essential foundation for our analysis of malignant and stromal diversity in AML.

AML cellular hierarchies have been the subject of extensive phenotypic and functional characterization. Flow cytometry studies suggest that the LSCs that fuel these tumors maintain major features of normal HSCs, but can also exhibit GMP characteristics, such as myeloid priming and proliferation (Goardon et al., 2011; Iwasaki et al., 2015; Krivtsov et al., 2006; Pollyea and Jordan, 2017). Recent technologies are also facilitating the study of single cell phenotypes and dynamics. Barcoded single-cell DNA sequencing is providing insight into the sub-clonal genetic architectures of AMLs (Hughes et al., 2014; Paguirigan et al., 2015), while mass cytometry is enabling high-dimensional phenotyping of single cells (Levine et al., 2015). However, our ability to acquire transcriptomic and genotypic information for the same single cells at high-throughput is a critical step forward as it allows unbiased and systematic assessment of cellular states in the malignant hierarchy, and their relationships to normal cells in the tumor microenvironment.

Our single-cell expression profiles demonstrate that transcriptional programs associated with stemness and myeloid priming are co-expressed in large numbers of individual HSC/Progenitor-like and GMP-like AML cells, despite their exclusivity during normal hematopoiesis. These deranged transcriptional programs may underlie the ability of the AML cells to combine properties of self-renewal and proliferation. The degree of transcriptional priming varied between individual progenitors in the same tumor, as well as between different AMLs in our cohort. We validated this inter-tumoral variability in a larger cohort (TCGA) by scoring bulk expression profiles for the HSC/Progenitor-like and GMP-like gene signatures derived from the scRNA-seq data. This analysis revealed that AML patients with relatively primitive and unprimed progenitors have considerably worse outcomes, potentially reflecting a capacity of more primitive HSC/Progenitor-like cells to persist through therapy and give rise to relapse.

Altogether, our scRNA-seq data revealed six major malignant AML cell types along a continuum that parallels the HSC to myeloid axis of normal hematopoiesis. The relative abundances of these different malignant cell types varied markedly between tumors (FIGS. 20C and 27C). We generalized this result by querying 179 bulk AML datasets with gene signatures for each cell type. Unbiased clustering identified seven groups of AMLs with distinct cell type compositions, each of which shows striking enrichment for different genetic lesions. Tumors with high HSC/Progenitor-like signature scores corresponded to high-risk molecular subtypes (cytogenetically complex/TP53), while tumors with high GMP-like or monocyte/cDC-like signature scores corresponded to low-risk subtypes (RUNX1-RUNX1T1 and CBFB-MYH11 fusions) (Lagunas-Rangel et al., 2017; Papaemmanuil et al., 2016). These data show that the molecular subtypes used for patient stratification are associated with specific malignant cell type compositions, and reinforce the link between primitive cells and poor outcomes (Eppert et al., 2011; Gentles et al., 2010; Lagunas-Rangel et al., 2017; Ng et al., 2016). Our results provide particular insight into the distinct outcomes for NPM1 mutant patients with weak (FLT3-TKD) or strong (FLT3-ITD) FLT3 gain-of-function mutations (Janke et al., 2014). The latter genotype has notably higher scores for HSC/Progenitor-like cells, potentially explaining its association with poorer outcomes (Boddu et al., 2017). Our study thus identifies specific cell type compositions and developmental hierarchies associated with different AML genotypes and patient outcomes. Primitive cell types and programs associated with a given genetic lesion are likely culprits for treatment failure, and thus represent targets for genotype-specific precision therapies.

In addition to these six malignant cell types, the AML ecosystem contains many normal hematopoietic cell types and immune cells. We focused in particular on T- and NK cells whose altered proportions in the AMLs are indicative of an immunosuppressive environment (Austin et al., 2016; Ustun et al., 2011). We hypothesized that this immune environment might be influenced by differentiated malignant AML cells that lack self-renewal capacity, but might otherwise impact tumor fitness. Consistently, we showed that HLA-DR$^+$ monocyte-like AML cells from an in vitro cell line and from a subset of primary tumors potently inhibit T-cell activation in vitro. Further study is needed to understand how these cells suppress T-cell activation, how they relate to previously described HLA-DR$^-$ myeloid-derived suppressor cells (Pyzer et al., 2017; Veglia et al., 2018). Regardless, the potential significance of these and other differentiated malignant populations to tumor immunity has clear implications for immunotherapy in AML (Lichtenegger et al., 2017).

In summary, we leveraged innovations in single-cell transcriptomics and driver mutation detection to parse the heterogeneous cellular ecosystem of AMLs. Our results provide insight into the aberrant regulatory programs that enable primitive AML cells to combine features of self-renewal and proliferation, reveal a striking correspondence between developmental hierarchies and underlying tumor genetics, and identify differentiated AML cell types with immunosuppressive properties. Our data and findings have potential to guide therapeutic strategies to target deranged AML progenitors or other malignant cell types associated with specific genetic lesions or immunosuppressive functions.

Example 6: Targeted Enrichment of KIAA1549:BRAF Fusion

Currently the resolution of single cell RNAseq allows for the detection of 8-10K unique genes at most. Many of the most informative genes used to determine important biological processes (cell identity, transcriptional responses to stimuli etc. . . . ) are not the most highly expressed genes. Here, we develop a new method to increase the level of detection for less highly expressed transcripts. This method will allow for increased resolution of low abundance transcripts, and enhanced resolution of isoform or allelic diversity from single cells. In theory this principle could be applied to both coding and non-coding RNAs.

Detailed in this example is a method to enrich for gene-specific low abundance mRNA transcripts from single cell cDNA libraries. This technology leverages a chimeric gene-specific primer with a universal adapter primer for reverse transcription during first strand cDNA synthesis. Gene or pathway specific gene enrichment kits could be sold in conjunction with single cell RNA extraction/synthesis kits. The ability to make "multi-plex" pathway kits would be especially valuable.

The design provided herein modified a reverse transcription primer to use instead of a SMART CDS primer that is designed to amplify all cellular mRNAs using polyA tails. The primer design is composed of two components: 1) a region that hybridizes with a gene of interest and 2) a region used as a universal adapter sequence for downstream PCR amplification of the target. Advantageously, primers can be multiplexed to target many regions of a single gene, or many genes simultaneously.

The current process uses the designed chimeric gene specific/universal adapter primer (FIG. 31) to update ultra low input cDNA synthesis processes. Design considerations include: Design gene specific primer to region complementary to 3' end of gene, usually designed to generate 1-2 kilobase, need to know target gene sequence, attach universal adapter sequence to 5' end of gene specific primer, Add primer during 1st strand reverse transcription step during SMARTseq2 protocol.

Figure 33:
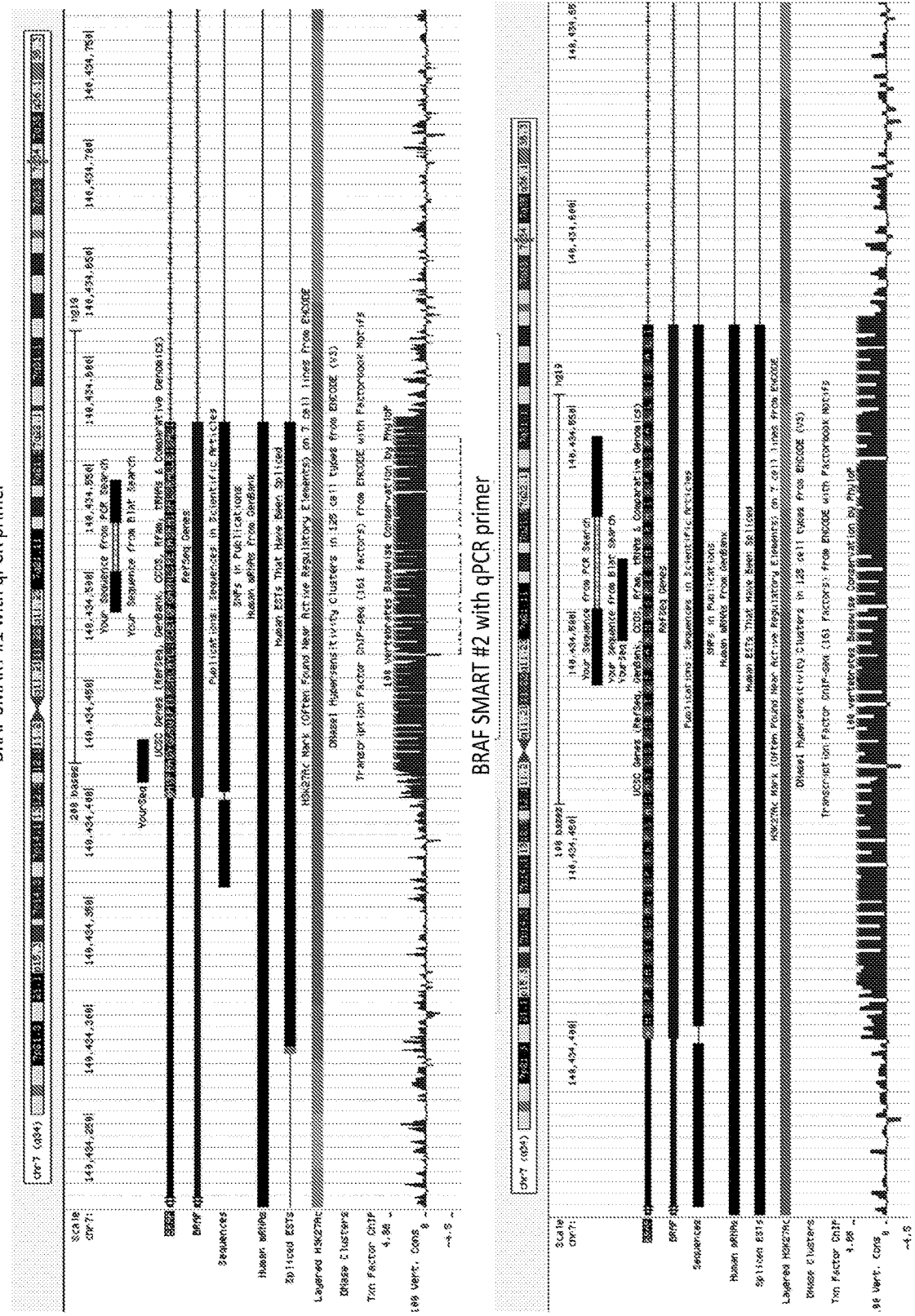
FIG. 33 depicts the locations of BRAF enrichment primers, BRAF SMART #1 upper panel, BRAF SMART #2 lower panel.
Figure 34:
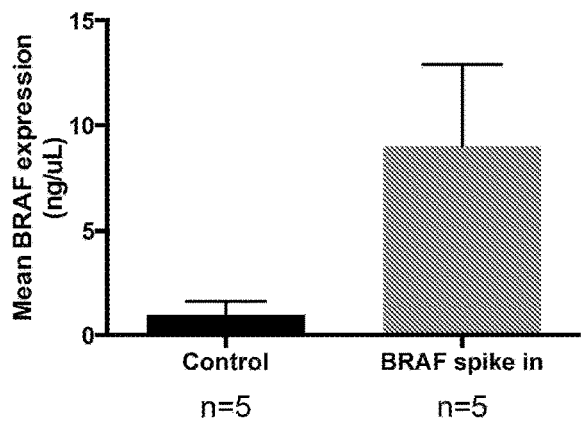
FIG. 34 charts the BRAF expression increase evaluated by qPCR when BRAF primer spike-in method used in single cells SMARTseq2 analysis.

As a proof of concept, targeted enrichment was performed of KIAA1549:BRAF fusion in neural stem cells and pediatric low grade gliomas. Locations of BRAF enrichment primers are provided in FIG. 33. As shown in FIG. 34, the BRAF primer spike-in increased BRAF expression in single cells by qPCR.

Figure 35:
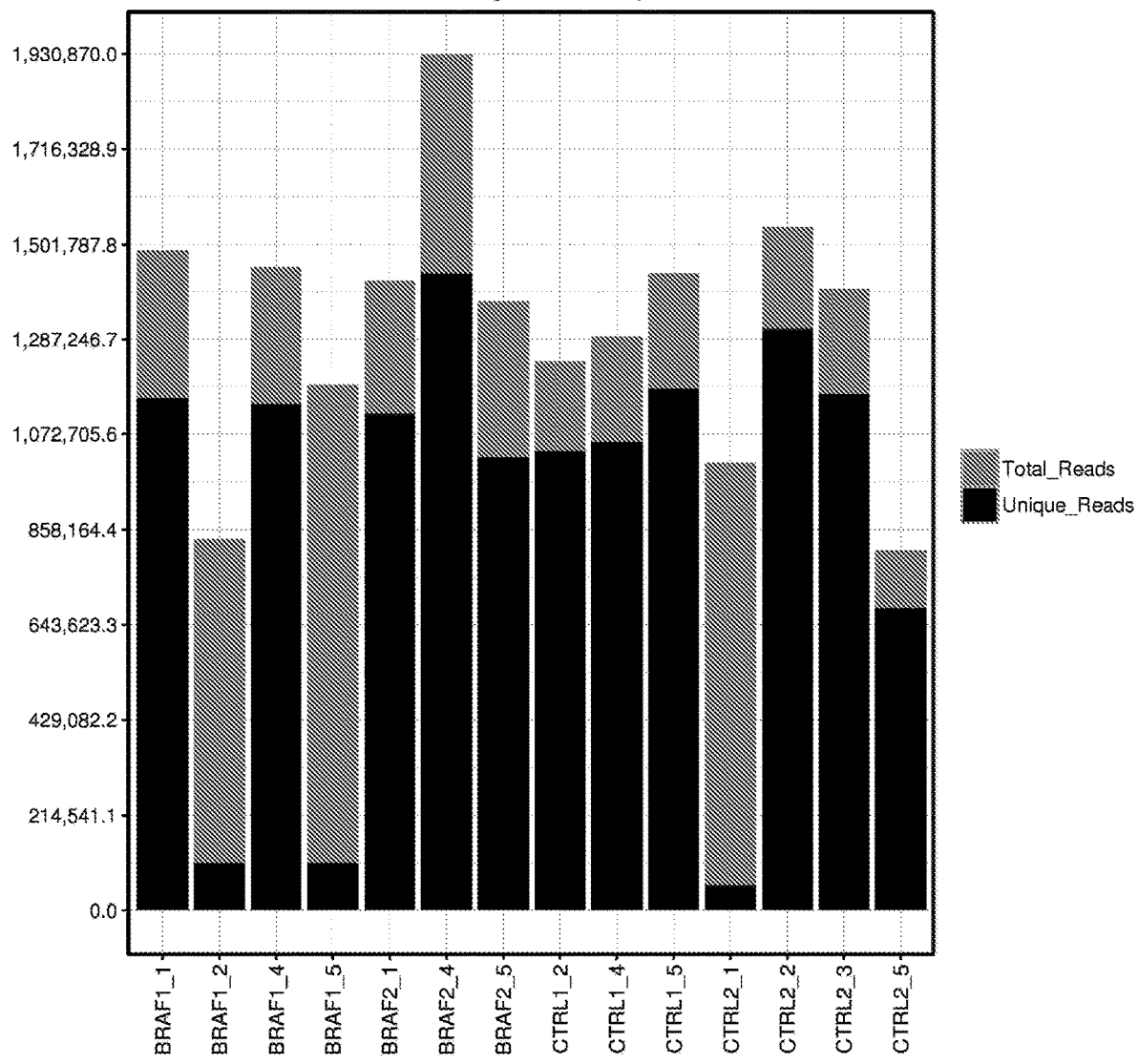
FIG. 35 charts a read alignment report showing that gene specific enrichment does not affect mapping quality.
Figure 38:
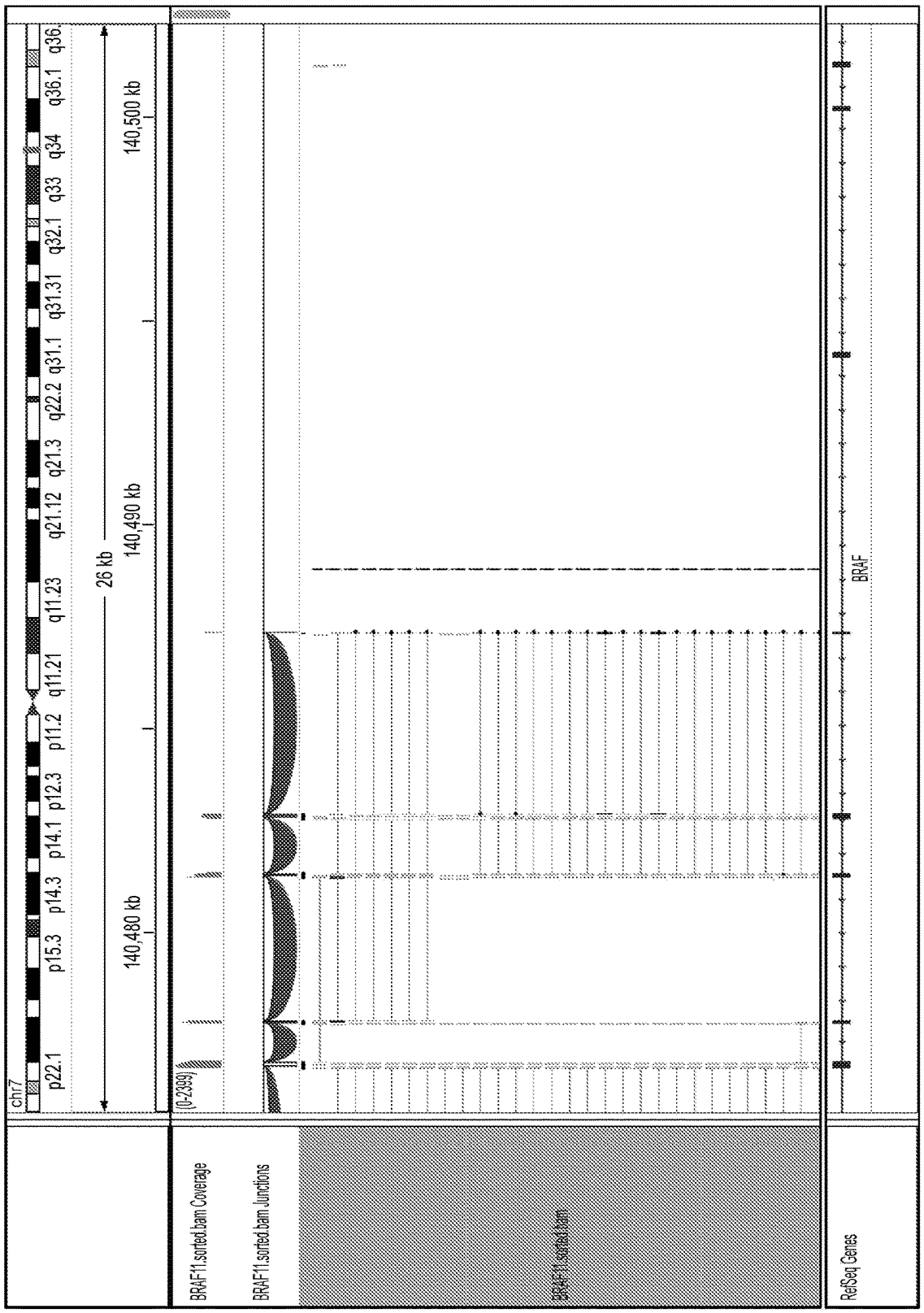
Figure 39:
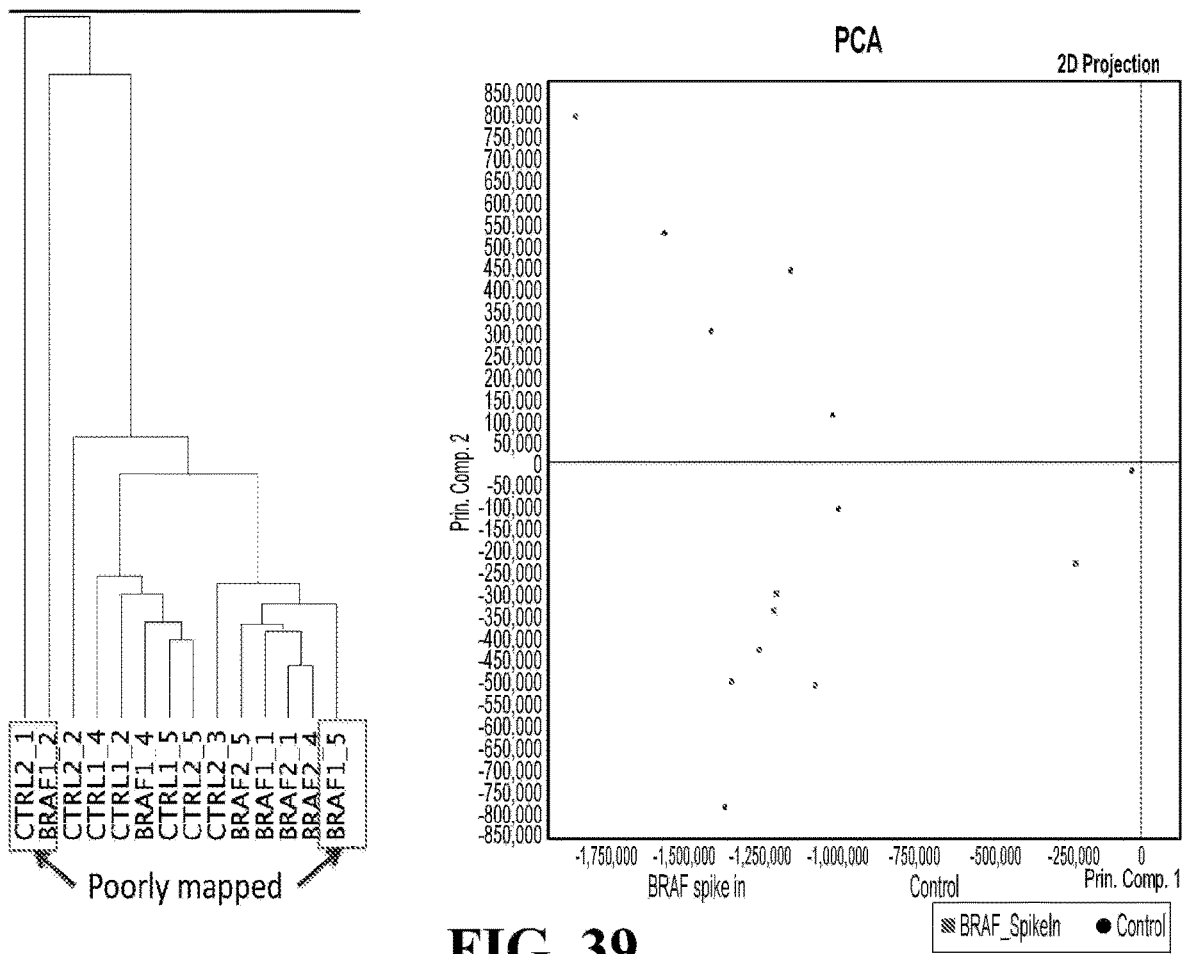
FIG. 39 provides hierarchical clustering, left and PCA, right, indicating BRAF spike-in does not systematically change transcriptomes.
Figure 40:
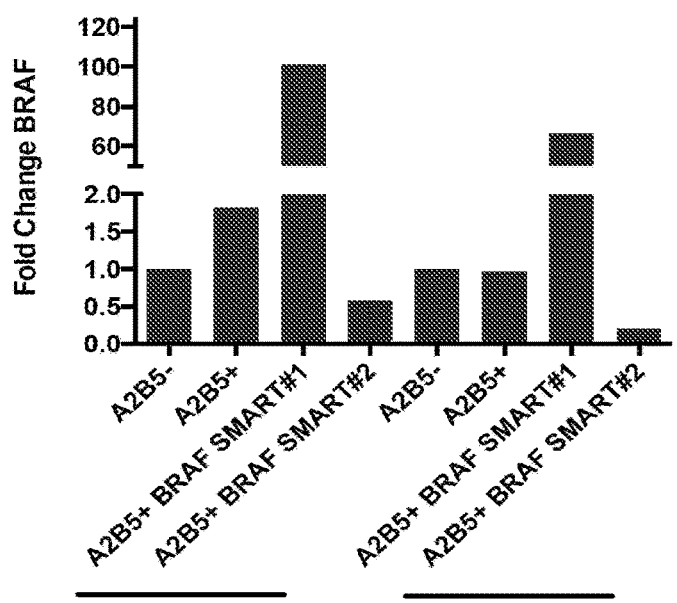
FIG. 40 charts how the spike-in approach works with SMARTseqv1 BRAF enrichment with BRAF targeting primer.

Design of RNA sequencing of BRAF spike in single cells is provided herein. First, Sequenced mNSCs pBabe-KIAA1549-BRAF (7 cells with primer, 7 w/out). 1.5 reads/cell (usually 0.5 million) was performed with sub sample reads for coverage. Align to both reference genomes (mouse and human for BRAF and KIAA1549 genes) was performed, with a read alignment report in FIG. 35. AS provided in the Read alignment report, the gene specific enrichment does not affect mapping quality, with increased BRAF and KIAA 1549 expression after gene specific priming (FIG. 36). The BRAF primer spike-in according to the methods provided in this example also increased reads spanning KIAA1549-BRAF fusion, and junction reads (FIG. 37A, 37B). STAR RNAseq fusion detector identified KIAA1549-BRAF, calling fusion in 6 of the 7 samples with primer spike in the sample. Fortunately, BRAF spike-in does not systematically change transcriptomes, as shown in FIG. 38. Additionally, the methods work on older chemistry too, including SMARTseq v1. FIG. 39 shows how SMARTseq v1 BRAF enrichment using BRAF targeting primer improves fold change of BRAF in samples using SMART seqv1.

This example provides approaches to enrich for gene-specific low abundance mRNA transcripts from single cell cDNA libraries. This technology leverages a chimeric gene-specific primer with a universal adapter primer for reverse transcription during first strand cDNA synthesis without systematic change of transcriptomes or affecting mapping quality.

The invention claimed is:

1. A method of distinguishing cells by genotype comprising:
   (a) constructing a library comprising a plurality of nucleic acids wherein each nucleic acid comprises a gene comprising a polyA tail, a unique molecular identifier (UMI) and a cell barcode (cell BC) flanked by sequencing adapters at the 5' and 3' end,
   (b) amplifying each nucleic acid in the library to create a first PCR product using a tagged 5' primer comprising a binding site for a second PCR product and a sequence complementary to a specific gene of interest and a 3' primer complementary to the adapter sequence at the 3' end of the nucleic acid thereby generating a first PCR product,
   (c) selectively enriching the first PCR product by binding to the tag introduced by the 5' primer or a targeted 3' capture with a bifunctional bead or targeted capture bead,
   (d) amplifying the tag-enriched first PCR product with a 5' primer comprising the binding site for the second PCR product and a 3' primer complementary to the adapter sequence at the 3' end of the nucleic acid thereby generating a second PCR product,
   (e) optionally amplifying the second PCR product with a 5' primer comprising the binding site for a third PCR product and a 3' primer complementary to the adapter sequence at the 3' end of the nucleic acid thereby generating the third PCR product, and
   (f) determining the genotype of the cell by identifying the UMI and cell BC, thereby distinguishing the cells by genotype.

2. The method of claim 1, further comprising size selecting a final product comprising the specific gene of interest.

3. The method of claim 1, wherein the sequencing adapters are switching mechanism at 5' end of RNA template (SMART) sequences at the 5' and 3' end.

4. The method of claim 1, wherein the binding site for the second PCR product is an oligomer comprising a primer binding site for sequencing.

5. The method of claim 1, wherein the amplifying the second PCR product is performed to generate a third PCR product, and further comprising sequencing the third PCR product by third generation sequencing.

6. The method of claim 5, further comprising sequencing the second PCR product by next generation sequencing.

7. The method of claim 4, wherein the binding site is an oligomer comprising a P7 sequence.

8. The method of claim 1, wherein the 5' primer comprising the binding site for the second PCR product to amplify the first PCR product further comprises a sequence to bind a flow cell.

9. The method of claim 8, wherein the 5' primer comprising the binding site for the second PCR product to amplify the first PCR product further comprises a sequence allowing multiple sequencing libraries to be sequenced simultaneously.

10. The method of claim 8, wherein the 5' primer comprising the binding site for the second PCR product to amplify the first PCR product further comprises a sequence providing an additional primer binding site.

11. The method of claim 8, wherein the sequence to bind a flow cell is a P7 sequence and the flow cell surface comprises oligos complementary to the P7 sequence.

12. The method of claim 9, wherein the sequence allowing multiple sequencing libraries to be sequenced simultaneously is a library barcode.

13. The method of claim 10, wherein the 5' primer comprising the binding site for the second PCR product to amplify the first PCR product further comprises a sequence comprising a primer binding site for a Read2 sequencing primer.

14. The method of claim 3, wherein the 3' primer complementary to the SMART sequence at the 3' end of the nucleic acid to amplify the first PCR product further comprises a sequence providing an additional primer binding site, optionally wherein the sequence providing an additional primer binding site is a custom read1 primer binding site (CR1P).

15. The method of claim 3, wherein the primer complementary to the SMART sequence at the 3' end of the nucleic acid to amplify the first PCR product further comprises a sequence to allow fragments to bind a flowcell, optionally wherein the sequence to allow fragments to bind a flowcell is a P5 sequence.

16. The method of claim 1, wherein the specific gene of interest comprises a mutation, deletion, insertion, translocation, single nucleotide polymorphism (SNP), splice variant or any combination thereof associated with a particular attribute in the specific gene of interest.

17. The method of claim 1, wherein the specific gene of interest is a cancer gene, a tumor protein P53 gene, a KIAA1549:BRAF fusion gene, or an acute myeloid leukemia (AML) gene.

18. The method of claim 17, wherein the AML gene is a DNA methyltransferase gene, optionally wherein the DNA methyltransferase is DNA 5-cytosine methyltransferase 3a (DNMT3A).

19. The method of claim 1, wherein the tagged 5' primer comprises a biotin tag.

20. The method of claim 1, wherein the tagged 5' primer and the 3' primer further comprise complementary sequences on 5' ends of the primers followed by a deoxyuracil residue, thereby generating a first PCR product comprising the complementary sequences,
and further comprising
   (a) treating the first PCR product with a uracil-specific excision reagent enzyme, (b) circularizing the first PCR product by sticky end ligation, and
(c) amplifying the tag-enriched circularized PCR product with a 5' primer complementary to the gene of interest and having a sequence adapter and a 3' primer having a polyA tail and another sequence adapter thereby generating the second PCR product.

21. The method of claim 16, wherein the mutation is within 1 kilobase of the polyA tail or wherein the mutation is anywhere in the gene.

* * * * *

UNITED STATES PATENT AND TRADEMARK OFFICE
CERTIFICATE OF CORRECTION

PATENT NO. : 11,732,257 B2
APPLICATION NO. : 16/758485
DATED : August 22, 2023
INVENTOR(S) : Peter van Galen et al.

It is certified that error appears in the above-identified patent and that said Letters Patent is hereby corrected as shown below:

In the Specification

In Column 2, Line 29, delete "AML," and insert -- AML --.

In Column 5, Line 4, delete "AIL;" and insert -- AML; --.

In Column 10, Line 13, delete "CD38-" and insert -- CD38⁻ --.

In Column 11, Line 6, delete "(CRIP," and insert -- (CR1P, --.

In Column 11, Line 7, delete "CRIP (CRIP" and insert -- CR1P (CR1P --.

In Column 11, Line 10, delete "CRIP)" and insert -- CR1P) --.

In Column 16, Line 19, delete ""a"" and insert -- "a", --.

In Column 31, Line 55, delete "p-glucosidase," and insert -- β-glucosidase, --.

In Column 43, Line 31, delete "("Tagman");" and insert -- ("Taqman"); --.

In Column 54, Line 36, delete "1×SD" and insert -- ±1×SD --.

In Column 54, Line 37, delete "1×SE" and insert -- ±1×SE --.

In Column 58, Line 7, delete "a and R" and insert -- α and β --.

In Column 59, Line 36, delete "Rib)," and insert -- R1b), --.

In Column 68, Line 5, delete "MHIC" and insert -- MHC --.

Signed and Sealed this
Twenty-sixth Day of March, 2024

Katherine Kelly Vidal
*Director of the United States Patent and Trademark Office*

CERTIFICATE OF CORRECTION (continued)
U.S. Pat. No. 11,732,257 B2

In Column 69, Line 54, delete "NMC" and insert -- MHC --.

In Column 69, Line 64, delete "NMC" and insert -- MHC --.

In Column 71, Line 39, delete "TGF-03" and insert -- TGF-β3 --.

In Column 73, Line 37, delete "(CD 117);" and insert -- (CD117); --.

In Column 74, Line 13, delete "Di;" and insert -- D1; --.

In Column 76, Line 65, delete "CRIP" and insert -- CR1P --.

In Column 77, Line 5, delete "CRIP" and insert -- CR1P --.

In Column 83, Line 30, delete "1lbp" and insert -- 11bp --.

In Column 87-88, Line 50 (Approx.), delete "Tree Star" and insert -- TreeStar --.

In Column 117, Line 67, delete "ANIL" and insert -- AML --.

SEQUENCE LISTING

```
<160> NUMBER OF SEQ ID NOS: 54

<210> SEQ ID NO 1
<211> LENGTH: 37
<212> TYPE: DNA
<213> ORGANISM: Artificial Sequence
<220> FEATURE:
<223> OTHER INFORMATION: Synthetic

<400> SEQUENCE: 1
gcctgtccgc ggaagcagtg gtatcaacgc agagtac                                37

<210> SEQ ID NO 2
<211> LENGTH: 55
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: /5Biosg/

<400> SEQUENCE: 2
gtctcgtggg ctcggagatg tgtataagag acagactgac gtctccaaca tgagc          55

<210> SEQ ID NO 3
<211> LENGTH: 56
<212> TYPE: DNA
```

```
<213> ORGANISM: Artificial Sequnce
<220> FEATURE:
<223> OTHER INFORMATION: Synthetic
<220> FEATURE:
<221> NAME/KEY: misc_feature
<222> LOCATION: (1)..(1)
<223> OTHER INFORMATION: /5Biosg/

<400> SEQUENCE: 3
gtctcgtggg ctcggagatg tgtataagag acagtgactg accaagaggc tattca        56

<210> SEQ ID NO 4
<211> LENGTH: 54
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: /5Biosg/

<400> SEQUENCE: 4
gtctcgtggg ctcggagatg tgtataagag acagtattgt gaacctgctg gggg          54

<210> SEQ ID NO 5
<211> LENGTH: 55
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: /5Biosg/

<400> SEQUENCE: 5
gtctcgtggg ctcggagatg tgtataagag acagtgtgac tttggattgg ctcga         55

<210> SEQ ID NO 6
<211> LENGTH: 58
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: /5Biosg/

<400> SEQUENCE: 6
gtctcgtggg ctcggagatg tgtataagag acaggacaat tagagcccaa cttagtga      58

<210> SEQ ID NO 7
<211> LENGTH: 54
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: /5Biosg/

<400> SEQUENCE: 7
gtctcgtggg ctcggagatg tgtataagag acagaacttg tggtagttgg agct          54

<210> SEQ ID NO 8
<211> LENGTH: 55
```

```
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: /5Biosg/

<400> SEQUENCE: 8
gtctcgtggg ctcggagatg tgtataagag acagactgac gtctccaaca tgagc        55

<210> SEQ ID NO 9
<211> LENGTH: 55
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: /5Biosg/

<400> SEQUENCE: 9
gtctcgtggg ctcggagatg tgtataagag acagactgta ccaccatcca ctaca        55

<210> SEQ ID NO 10
<211> LENGTH: 55
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: /5Biosg/

<400> SEQUENCE: 10
gtctcgtggg ctcggagatg tgtataagag acagtgtttg ttggacatac tggat        55

<210> SEQ ID NO 11
<211> LENGTH: 56
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: /5Biosg/

<400> SEQUENCE: 11
gtctcgtggg ctcggagatg tgtataagag acagtgtgga aaagtcccaa tggaac       56

<210> SEQ ID NO 12
<211> LENGTH: 54
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: /5Biosg/

<400> SEQUENCE: 12
gtctcgtggg ctcggagatg tgtataagag acagggtgac cggctcctca gata         54

<210> SEQ ID NO 13
```

```
<211> LENGTH: 54
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: /5Biosg/

<400> SEQUENCE: 13
gtctcgtggg ctcggagatg tgtataagag acagtcagaa atgtgacccg gctc       54

<210> SEQ ID NO 14
<211> LENGTH: 54
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: /5Biosg/

<400> SEQUENCE: 14
gtctcgtggg ctcggagatg tgtataagag acagggacca agcccatcac catt       54

<210> SEQ ID NO 15
<211> LENGTH: 54
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: /5Biosg/

<400> SEQUENCE: 15
gtctcgtggg ctcggagatg tgtataagag acagaccagg gttgtcctac acga       54

<210> SEQ ID NO 16
<211> LENGTH: 54
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: /5Biosg/

<400> SEQUENCE: 16
gtctcgtggg ctcggagatg tgtataagag acagagtctg ttgtggttgt gcca       54

<210> SEQ ID NO 17
<211> LENGTH: 54
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: /5Biosg/

<400> SEQUENCE: 17
gtctcgtggg ctcggagatg tgtataagag acagctgagc ccaggcaaga tgag       54
```

```
<210> SEQ ID NO 18
<211> LENGTH: 55
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: /5Biosg/

<400> SEQUENCE: 18
gtctcgtggg ctcggagatg tgtataagag acagcactat cgggaaagtg tgcct       55

<210> SEQ ID NO 19
<211> LENGTH: 54
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: /5Biosg/

<400> SEQUENCE: 19
gtctcgtggg ctcggagatg tgtataagag acagtgggac ggaacagctt tgag        54

<210> SEQ ID NO 20
<211> LENGTH: 61
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: /5Biosg/

<400> SEQUENCE: 20
gtctcgtggg ctcggagatg tgtataagag acagtgagta cttctacgtt gatttcagag  60
a                                                                  61

<210> SEQ ID NO 21
<211> LENGTH: 57
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: /5Biosg/

<400> SEQUENCE: 21
gtctcgtggg ctcggagatg tgtataagag acagagattt gtgattttgg tctagcc     57

<210> SEQ ID NO 22
<211> LENGTH: 57
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: /5Biosg/

<400> SEQUENCE: 22
```

```
gtctcgtggg ctcggagatg tgtataagag acagactctc aaatcacaga agcaagt        57
```

<210> SEQ ID NO 23
<211> LENGTH: 36
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: /5Biosg/

<400> SEQUENCE: 23

```
tgtgtataag agacagaggg gagccagata gtttgt                               36
```

<210> SEQ ID NO 24
<211> LENGTH: 54
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: /5Biosg/

<400> SEQUENCE: 24

```
gtctcgtggg ctcggagatg tgtataagag acagacaaac tggtggtggt tgga           54
```

<210> SEQ ID NO 25
<211> LENGTH: 53
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: /5Biosg/

<400> SEQUENCE: 25

```
gtctcgtggg ctcggagatg tgtataagag acagccaact ggccaagacc tgc            53
```

<210> SEQ ID NO 26
<211> LENGTH: 54
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: /5Biosg/

<400> SEQUENCE: 26

```
gtctcgtggg ctcggagatg tgtataagag acagagcggc gtactgacat cttc           54
```

<210> SEQ ID NO 27
<211> LENGTH: 54
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: /5Biosg/

<400> SEQUENCE: 27

-continued gtctcgtggg ctcggagatg tgtataagag acagacatgc tttcccacac agct         54

<210> SEQ ID NO 28
<211> LENGTH: 54
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: /5Biosg/

<400> SEQUENCE: 28
gtctcgtggg ctcggagatg tgtataagag acaggagaag aggaagccca tccg         54

<210> SEQ ID NO 29
<211> LENGTH: 36
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: /5Biosg/

<400> SEQUENCE: 29
tgtgtataag agacagaagc tggcaaagag aatcgc                             36

<210> SEQ ID NO 30
<211> LENGTH: 56
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: /5Biosg/

<400> SEQUENCE: 30
gtctcgtggg ctcggagatg tgtataagag acagaggtat gaaagccagc tacaga       56

<210> SEQ ID NO 31
<211> LENGTH: 52
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: /5Biosg/

<400> SEQUENCE: 31
gtctcgtggg ctcggagatg tgtataagag acagctgctt gcgcgacttc ct           52

<210> SEQ ID NO 32
<211> LENGTH: 53
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: /5Biosg/

-continued

<400> SEQUENCE: 32
gtctcgtggg ctcggagatg tgtataagag acagccacca ttctcgggta gcc    53

<210> SEQ ID NO 33
<211> LENGTH: 52
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: /5Biosg/

<400> SEQUENCE: 33
gtctcgtggg ctcggagatg tgtataagag acagggtagc accaccaccc ag    52

<210> SEQ ID NO 34
<211> LENGTH: 54
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: /5Biosg/

<400> SEQUENCE: 34
gtctcgtggg ctcggagatg tgtataagag acagcgacag cgagatgggc attt    54

<210> SEQ ID NO 35
<211> LENGTH: 57
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: /5Biosg/

<400> SEQUENCE: 35
gtctcgtggg ctcggagatg tgtataagag acagacattg aaaatatgtc acgagga    57

<210> SEQ ID NO 36
<211> LENGTH: 52
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: /5Biosg/

<400> SEQUENCE: 36
gtctcgtggg ctcggagatg tgtataagag acagctgcgg ggtgctgctg tc    52

<210> SEQ ID NO 37
<211> LENGTH: 54
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: /5Biosg/

```
<400> SEQUENCE: 37
gtctcgtggg ctcggagatg tgtataagag acaggaagct tccattgccg aacc      54

<210> SEQ ID NO 38
<211> LENGTH: 54
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: /5Biosg/

<400> SEQUENCE: 38
gtctcgtggg ctcggagatg tgtataagag acagacatgt cccatgagct ggtc      54

<210> SEQ ID NO 39
<211> LENGTH: 52
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: /5Biosg/

<400> SEQUENCE: 39
gtctcgtggg ctcggagatg tgtataagag acagacagag cgcccacagc tt        52

<210> SEQ ID NO 40
<211> LENGTH: 53
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: /5Biosg/

<400> SEQUENCE: 40
gtctcgtggg ctcggagatg tgtataagag acagcaaagc cggagtccca gtc       53

<210> SEQ ID NO 41
<211> LENGTH: 54
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: /5Biosg/

<400> SEQUENCE: 41
gtctcgtggg ctcggagatg tgtataagag acagctggag catgagcctg tgaa      54

<210> SEQ ID NO 42
<211> LENGTH: 54
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
```

<223> OTHER INFORMATION: /5Biosg/

<400> SEQUENCE: 42
gtctcgtggg ctcggagatg tgtataagag acaggcatga caaccctctc tgca          54

<210> SEQ ID NO 43
<211> LENGTH: 54
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: /5Biosg/

<400> SEQUENCE: 43
gtctcgtggg ctcggagatg tgtataagag acagatggca gtctgtttcc tggg          54

<210> SEQ ID NO 44
<211> LENGTH: 54
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: /5Biosg/

<400> SEQUENCE: 44
gtctcgtggg ctcggagatg tgtataagag acaggccacc acgacgacta ctac          54

<210> SEQ ID NO 45
<211> LENGTH: 54
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: /5Biosg/

<400> SEQUENCE: 45
gtctcgtggg ctcggagatg tgtataagag acagattcag gatgtgcgac gtgt          54

<210> SEQ ID NO 46
<211> LENGTH: 25
<212> TYPE: DNA
<213> ORGANISM: Artificial Sequence
<220> FEATURE:
<223> OTHER INFORMATION: Synthetic

<400> SEQUENCE: 46
aagcagtggt atcaacgcag agtac                                          25

<210> SEQ ID NO 47
<211> LENGTH: 66
<212> TYPE: DNA
<213> ORGANISM: Artificial Sequence
<220> FEATURE:
<223> OTHER INFORMATION: Synthetic

<400> SEQUENCE: 47
aatgatacgg cgaccaccga gatctacacg cctgtccgcg aagcagtgg tatcaacgca     60 gagtac                                                               66

<210> SEQ ID NO 48
<211> LENGTH: 53
<212> TYPE: DNA
<213> ORGANISM: Artificial Sequence
<220> FEATURE:
<223> OTHER INFORMATION: Synthetic

<400> SEQUENCE: 48
caagcagaag acggcatacg agataacgca ttgtctcgtg ggctcggaga tgt     53

<210> SEQ ID NO 49
<211> LENGTH: 53
<212> TYPE: DNA
<213> ORGANISM: Artificial Sequence
<220> FEATURE:
<223> OTHER INFORMATION: Synthetic

<400> SEQUENCE: 49
caagcagaag acggcatacg agatttgtct atgtctcgtg ggctcggaga tgt     53

<210> SEQ ID NO 50
<211> LENGTH: 53
<212> TYPE: DNA
<213> ORGANISM: Artificial Sequence
<220> FEATURE:
<223> OTHER INFORMATION: Synthetic

<400> SEQUENCE: 50
caagcagaag acggcatacg agataagaca ctgtctcgtg ggctcggaga tgt     53

<210> SEQ ID NO 51
<211> LENGTH: 53
<212> TYPE: DNA
<213> ORGANISM: Artificial Sequence
<220> FEATURE:
<223> OTHER INFORMATION: Synthetic

<400> SEQUENCE: 51
caagcagaag acggcatacg agatttgaat aggtctcgtg ggctcggaga tgt     53

<210> SEQ ID NO 52
<211> LENGTH: 23
<212> TYPE: DNA
<213> ORGANISM: Artificial Sequence
<220> FEATURE:
<223> OTHER INFORMATION: Synthetic

<400> SEQUENCE: 52
aagcagtggt atcaacgcag agt                                      23

<210> SEQ ID NO 53
<211> LENGTH: 37
<212> TYPE: DNA
<213> ORGANISM: Artificial Sequence
<220> FEATURE:
<223> OTHER INFORMATION: Synthetic

<400> SEQUENCE: 53
gcctgtccgc ggaagcagtg gtatcaacgc agagtac                       37

```
<210> SEQ ID NO 54
<211> LENGTH: 32
<212> TYPE: DNA
<213> ORGANISM: Artificial Sequence
<220> FEATURE:
<223> OTHER INFORMATION: Synthetic

<400> SEQUENCE: 54
aagcagtggt atcaacgcag agtgaatrgr gg                                    32
```